United States Patent
Mueller et al.

(10) Patent No.: US 9,422,565 B2
(45) Date of Patent: Aug. 23, 2016

(54) RECOMBINANT MICROORGANISMS COMPRISING NADPH DEPENDENT ENZYMES AND METHODS OF PRODUCTION THEREFOR

(71) Applicant: LanzaTech New Zealand Limited, Auckland (NZ)

(72) Inventors: Alexander Paul Mueller, Auckland (NZ); Michael Koepke, Auckland (NZ)

(73) Assignee: LANZATECH NEW ZEALAND LIMITED, Auckland (NZ)

( * ) Notice: Subject to any disclaimer, the term of this patent is extended or adjusted under 35 U.S.C. 154(b) by 0 days.

(21) Appl. No.: 14/168,810

(22) Filed: Jan. 30, 2014

(65) Prior Publication Data

US 2014/0212976 A1 Jul. 31, 2014

Related U.S. Application Data

(60) Provisional application No. 61/758,441, filed on Jan. 30, 2013, provisional application No. 61/828,675, filed on May 29, 2013.

(51) Int. Cl.
*C12N 15/52* (2006.01)
*C12N 9/02* (2006.01)

(52) U.S. Cl.
CPC .............. *C12N 15/52* (2013.01); *C12N 9/0036* (2013.01)

(58) Field of Classification Search
None
See application file for complete search history.

(56) References Cited

U.S. PATENT DOCUMENTS

| 8,039,239 B2 | 10/2011 | Reeves |
| 2009/0191599 A1 | 7/2009 | Devroe et al. |
| 2010/0151543 A1 | 6/2010 | Reeves |

FOREIGN PATENT DOCUMENTS

| WO | 2009111513 A1 | 9/2009 |
| WO | 2012088071 A2 | 12/2012 |

OTHER PUBLICATIONS

BRENDA information sheet on EC 1.1.1.36 (http://www.brenda-enzymes.org/enzyme.php?ecno=1.1.1.36, accessed Mar. 24, 2015).*
Walter et al. (J. Bacteriol., 174:7149-7158, 1992).*
Abrini, J., Naveau, H., & Nyns, E. J. (1994). *Clostridium autoethanogenum*, sp. nov., an anaerobic bacterium that produces ethanol from carbon monoxide. Archives of microbiology, 161(4), 345-351.
Bond-Watts, B. B., Bellerose, R. J., & Chang, M. C. Y. (2011). Enzyme mechanism as a kinetic control element for designing synthetic biofuel pathways. Nature chemical biology, 7(4), 222-7. doi:10.1038/nchembio.537.
Eppink, M. H., Overkamp, K. M., Schreuder, H. a, & Van Berkel, W. J. (1999). Switch of coenzyme specificity of p-hydroxybenzoate hydroxylase. Journal of molecular biology, 292(1), 87-96.
Hoffmeister, M., Piotrowski, M., Nowitzki, U., & Martin, W. (2005). Mitochondrial trans-2-enoyl-CoA reductase of wax ester fermentation from Euglena gracilis defines a new family of enzymes involved in lipid synthesis. The Journal of biological chemistry, 280(6), 4329-38.
Hu, K., Zhao, M., Zhang, T., Zha, M., Zhong, C., Jiang, Y., & Ding, J. (2012). Structures of trans-2-enoyl-CoA reductases from Clostridium acetobutulicum and Treponema denticola: insights into the substrate specificity and the catalytic mechanism. The Biochemical journal. doi:10.1042/BJ20120871.
Huang, H., Wang, S., Moll, J., & Thauer, R. K. (2012). Electron bifurcation involved in the energy metabolism of the acetogenic bacterium Moorella thermoacetica growing on glucose or H2 plus CO2. Journal of bacteriology, 194(14), 3689-99.
Ismaiel, a a, Zhu, C. X., Colby, G. D., & Chen, J. S. (1993). Purification and characterization of a primary-secondary alcohol dehydrogenase from two strains of Clostridium beijerinckii. Journal of bacteriology, 175(16), 5097-105.
Kita, A., Iwasaki, Y., Sakai, S., Okuto, S., Takaoka, K., Suzuki, T., Yano, S., et al. (2012). Development of genetic transformation and heterologous expression system in carboxydotrophic thermophilic acetogen Moorella thermoacetica. Journal of Bioscience and Bioengineering, xx(xx), 1-6. doi:10.1016/j.jbiosc.2012.10.013.
Köpke, M., Held, C., Hujer, S., Liesegang, H., Wiezer, A., Wollherr, A., Ehrenreich, A., et al. (2010). Clostridium ljungdahlii represents a microbial production platform based on syngas. Proceedings of the National Academy of Sciences of the United States of America, 107(29), 13087-92. doi:10.1073/pnas.1004716107.
Köpke, M., Mihalcea, C., Liew, F., Tizard, J. H., Ali, M. S., Conolly, J. J., Al-Sinawi, B., et al. (2011). 2,3-Butanediol Production by Acetogenic Bacteria, an Alternative Route to Chemical Synthesis, Using Industrial Waste Gas. Applied and environmental microbiology, 77(15), 5467-75. doi:10.1128/AEM.00355-11.
Leang, C., Ueki, T., & Lovley, D. R. (2011). Development of Genetic Systems for Clostridium ljungdahlii. Poster.
Li, F., Hinderberger, J., Seedorf, H., Zhang, J., Buckel, W., & Thauer, R. K. (2008). Coupled ferredoxin and crotonyl coenzyme A (CoA) reduction with NADH catalyzed by the butyryl-CoA dehydrogenase/Etf complex from Clostridium kluyveri. Journal of bacteriology, 190(3), 843-50. doi:10.1128/JB.01417-07.
Ma, C., Zhang, L., Dai, J., & Xiu, Z. (2010). Relaxing the coenzyme specificity of 1,3-propanediol oxidoreductase from Klebsiella pneumoniae by rational design. Journal of biotechnology, 146(4), 173-8. doi:10.1016/j.jbiotec.2010.02.005.

(Continued)

*Primary Examiner* — Brian J Gangle
(74) *Attorney, Agent, or Firm* — Andrea E. Schoen

(57) ABSTRACT

The invention provides a recombinant carboxydotrophic Clostridia microorganism with increased overall utilization of NADPH relative to a parent microorganism. Further, the invention provides a method of producing a recombinant carboxydotrophic Clostridia microorganism which exhibits increased NADPH utilization relative to a parental microorganism. In particular, the invention relates to increasing the overall utilization of NADPH in a recombinant carboxydotrophic Clostridia microorganism in order to increase the production of at least one fermentation product by the microorganism.

16 Claims, 8 Drawing Sheets

(56) References Cited

OTHER PUBLICATIONS

Ma, S. M., Garcia, D. E., Redding-Johanson, A. M., Friedland, G. D., Chan, R., Batth, T. S., Haliburton, J. R., et al. (2011). Optimization of a heterologous mevalonate pathway through the use of variant HMG-CoA reductases. Metabolic engineering, 13(5), 588-97. doi:10.1016/j.ymben.2011.07.001.

McKeever, B. M., Hawkins, B. K., Geissler, W. M., Wu, L., Sheridan, R. P., Mosley, R. T., & Andersson, S. (2002). Amino acid substitution of arginine 80 in 17β-hydroxysteroid dehydrogenase type 3 and its effect on NADPH cofactor binding and oxidation/reduction kinetics. Biochimica et Biophysica Acta (BBA)—Proteins and Proteomics, 1601(1), 29-37. doi:10.1016/S1570-9639(02)00434-X.

Miller, E N, Jarboe, L. R., Yomano, L. P., York, S. W., Shanmugam, K. T., & Ingram, L. O. (2009). Silencing of NADPH-dependent oxidoreductase genes (yqhD and dkgA) in furfural-resistant ethanologenic *Escherichia coli*. Applied and environmental microbiology, 75(13), 4315-23. doi:10.1128/AEM.00567-09.

Miller, Elliot N, Jarboe, L. R., Turner, P. C., Pharkya, P., Yomano, L. P., York, S. W., Nunn, D., et al. (2009). Furfural inhibits growth by limiting sulfur assimilation in ethanologenic *Escherichia coli* strain LY180. Applied and environmental microbiology, 75(19), 6132-41. doi:10.1128/AEM.01187-09.

Perez, J. M., Richter, H., Loftus, S. E., & Angenent, L. T. (2012). Biocatalytic reduction of short-chain carboxylic acids into their corresponding alcohols with syngas fermentation. Biotechnology and bioengineering, 1-30. doi:10.1002/bit.24786.

Poehlein, A., Schmidt, S., Kaster, A.-K., Goenrich, M., Vollmers, J., Thürmer, A., Bertsch, J., et al. (2012). An Ancient Pathway Combining Carbon Dioxide Fixation with the Generation and Utilization of a Sodium Ion Gradient for ATP Synthesis. (A. Driessen, Ed.)PLoS ONE, 7(3), e33439. doi:10.1371/journal.pone.0033439.

Rane, M. J., & Calvo, K. C. (1997). Reversal of the nucleotide specificity of ketol acid reductoisomerase by site-directed mutagenesis identifies the NADPH binding site. Archives of biochemistry and biophysics, 338(1), 83-9.

Scheer, M., Grote, A., Chang, A., Schomburg, I., Munaretto, C., Rother, M., Söhngen, C., et al. (2011). BRENDA, the enzyme information system in 2011. Nucleic acids research, 39(Database issue), D670-6.

Schuchmann, K., & Mueller, V. (2012). A bacterial electron bifurcating hydrogenase. The Journal of biological chemistry. doi:10.1074/jbc.M112.395038.

Schut, G. J., & Adams, M. W. W. (2009). The iron-hydrogenase of *Thermotoga maritima* utilizes ferredoxin and NADH synergistically: a new perspective on anaerobic hydrogen production. Journal of bacteriology, 191(13), 4451-7. doi:10.1128/JB.01582-08.

Tanner, R. S., Miller, L. M., & Yang, D. (1993). *Clostridium ljungdahlii* sp. nov., an acetogenic species in clostridial rRNA homology group I. International journal of systematic bacteriology, 43(2), 232.

Tyurin, M., & Kiriukhin, M. (2012). Electrofusion of cells of Acetogen *Clostridium* sp. MT 351 with erm (B) or cat in the chromosome. Journal of Biotech, 1-12.

Wang, G., & Wang, D. I. (1984). Elucidation of Growth Inhibition and Acetic Acid Production by *Clostridium thermoaceticum*. Applied and environmental microbiology, 47(2), 294-8.

Wang, S., Huang, H., Moll, J., & Thauer, R. K. (2010). NADP+ reduction with reduced ferredoxin and NADP+ reduction with NADH are coupled via an electron-bifurcating enzyme complex in *Clostridium kluyveri*. Journal of bacteriology, 192(19), 5115-23. doi:10.1128/JB.00612-10.

Vidal R., Lopez-Maury L., Guerrero M.G. and Florencio F.J. (2009). Characterization of an alcohol dehydrogenase from the Cyanobacterium *Synechocystis* sp. strain PCC 6803 that responds to environmental stress conditions via the Hik34-Rre1 two-component system. Journal of Bacteriology, 191, 4383-4391.

Erb T., Berg I. and Brecht V. (2007) Synthesis of C5-dicarboxylic acids from C2-units involving crotonyl-CoA carboxylase/reductase: the ethylmalonyl-CoA pathway. PNAS, USA 104, 1-6.

Linster C.L., Noel G., Stroobant V., Vertommen D., Vincent M.F., Bommer G.T., Veiga-da Cunha M. and Van Schaftingen E. (2011) Ethylmalonyl-CoA decarboxylase, a new enzyme involved in metabolite proofreading. Journal Biological Chemistry, 286, 42992-43003.

Yan R.T. and Chen J.S. Coenzyme A-acylating aldehyde dehydrogenase from *Clostridium berijerinckii* NRRL B592. Applied Environmental Microbiology, 56, 2591-2599 (1990).

Schiel-Bengelsdorf & Dürre, Pathway engineering and synthetic biology using acetogens, FEBS Lett. (May 2012), http://dx.doi.org/10.1016/j.febslet.2012.04.043.

Bennett GR, San K. 2009. Systems Biology and Biotechnology of *Escherichia coli*, Systems Biology and Biotechnology of *Escherichia coli*. Lee, SY (ed.),p. 351-376, Springer Netherlands, Dordrecht.

Bennett BD, Kimball EH, Gao M, Osterhout R, Van Dien SJ, Rabinowitz JD. Absolute metabolite concentrations and implied enzyme active site occupancy in *Escherichia coli*. Nat. Chem. Biol. 5:593-9(2009).

Chemler J a, Fowler ZL, McHugh KP, Koffas M a G. Improving NADPH availability for natural product biosynthesis in *Escherichia coli* by metabolic engineering. Metab. Eng. 12:96-104 (2010).

Peralta-Yahya PP, Keasling JD. Advanced biofuel production in microbes. Biotechnol. J. 5:147-62 (2010).

Auriol C, Bestel-Corre G, Claude J-B, Soucaille P, Meynial-Salles I. Stress-induced evolution of *Escherichia coli* points to original concepts in respiratory cofactor selectivity. Proc. Natl. Acad. Sci. U. S. A. 108:1278-83 (2011).

Dürre, Formation of solvents in Clostridia, In: Handbook on Clostridia, pp. 673-695, CRC Press, 2005.

Fisher, J Bacteriol, 175: 6959-6969, 1993.

Fontaine, J Bacteriol, 184: 821-830, 2002.

Herrmann, J Bacteriol, 190: 784-791, 2008.

International Search Report, PCT/US2014/013712, Nov. 21, 2014.

Nair, J Bacteriol, 176: 871-885, 1994.

Peterson, J Bacteriol, 173: 1831-1834, 1991.

UniProtKB P33744 (AdhE), integrated into UniProtKB Feb. 1, 1994.

UniProtKB Q04944 (BdhA), integrated into UniProtKB Feb. 1, 1994.

UniProtKB Q04945 (BdhB), integrated into UniProtKB Feb. 1, 1994.

Welch, Arch Biochem Biophys, 273: 309-318, 1989.

Hartmanis, Appl Environ Microbiol, 47: 1277-1283, 1984.

Inui, Appl Biotechnol, 77: 1305-1316, 2008.

Yoo, mBio, 6: e01808-15, 2015.

Schiel-Bengelsdorf, Pathway engineering and synthetic biology using acetogens, FEBS Letters, 586: 2191-2198, 2012.

Partial Supplementary European Search Report for EP14745530.7, European Patent Office, May 16, 2016.

* cited by examiner

RECOMBINANT MICROORGANISMS COMPRISING NADPH DEPENDENT ENZYMES AND METHODS OF PRODUCTION THEREFOR

FIELD OF INVENTION

The invention relates to methods of selecting enzymes to optimise production of desirable compounds by way of fermentation. More particularly, but not exclusively, the invention relates to co-factor balancing in fermentation pathways and metabolic engineering.

BACKGROUND

Reducing equivalents such as nicotinamide adenine dinucleotide (NADH) and nicotinamide adenine dinucleotide phosphate (NADPH) are important coenzymes for enzymatic redox reactions such as oxidoreducatase reactions and are found in all living cells. It is generally accepted that the NADPH pool is considerably smaller than the pool of NADH (G. N. Bennett & San, 2009). In *E. coli* grown on glucose sugar the pool of NADH is over 20 times larger than the NADPH pool (B. D. Bennett et al., 2009). This low NADPH availability limits many biosynthetic reactions and bioconversions especially in fermentation processes (R Poulsen et al., 2005). The preference of enzymes for NADPH can limit the production of a desired product (G. N. Bennett & San, 2009). This is a problem when engineering new reactions and pathways into a microorganism and is one of the major hurdles for the generation of efficient production platforms of compounds including biofuels, chemicals, amino acids or vitamins (Chemler, Fowler, McHugh, & Koffas, 2010).

Nevertheless, metabolic engineering has been successfully demonstrated for production of a wide range of fuels and chemicals (Peralta-Yahya & Keasling, 2010) by limiting, avoiding or bypassing NADPH dependent reactions where possible. Alternatively, energy-consuming transhydrogenases have been used that interconvert between NADH and NADPH pools. Another strategy to achieve successful metabolic engineering is elimination of competing NADPH dependent reactions. Despite these advances, such novel strategies are often pursued at the expense of production yields and/or growth rates (Auriol, Bestel-Corre, Claude, Soucaille, & Meynial-Salles, 2011). Further, they only become possible by extensive engineering work with multiple modifications (S. M. Ma et al., 2011). Thus these efforts have been limited only to genetically tractable organisms such as *Escherichia coli* and *Saccharomyces cerevisiae* (Peralta-Yahya & Keasling, 2010). These organisms are limited as they feed only on sugar. Accordingly, their commercial use and viability suffers from the significant drawbacks around land-use, food-security, volatility of supply and environmental issues.

Carboxydotrophic Clostridia offer an alternative to *E. coli* and *S. cerevisiae* and are able to grow on waste gases and syngas. There are a few examples of recombinant carboxydotrophic clostridia which have a limited number of modifications (Schiel-Bengelsdorf & Dürre, 2012). All known examples use NADH-dependent reactions.

It is an object of the invention to overcome or ameliorate one or more of the disadvantages of the prior art, or at least to provide the public with a useful choice.

SUMMARY OF THE INVENTION

In a first aspect, the invention provides a recombinant carboxydotrophic Clostridia microorganism adapted to express one or more exogenous NADPH-dependent enzymes, and/or adapted to over-express one or more endogenous NADPH-dependent enzymes, the enzymes selected such that when the exogenous enzyme is expressed, and/or the endogenous enzyme is overexpressed, the overall utilisation of NADPH by the microorganism is increased relative to a parental microorganism.

In a second aspect, the invention provides a method of producing a recombinant carboxydotrophic Clostridia microorganism which exhibits increased NADPH utilisation relative to a parental microorganism, the method comprising:
 a. selecting one or more exogenous and/or endogenous NADPH-dependent enzymes;
 b. transforming a parental microorganism to yield a recombinant microorganism which is adapted to express the one or more NADPH-dependent exogenous enzymes, and/or over-express the one or more NADPH-dependent endogenous enzymes. The expression or over-expression of any one or more of the NADPH-dependent enzymes in the microorganism results in an overall increase in the utilisation of NADPH relative to a parental microorganism.

The invention also provides a recombinant carboxydotrophic Clostridia made by a method of the second aspect.

In a particular embodiment of the first or second aspect, the one or more NADPH-dependent enzymes comprises hydrogenase (for example Seq.ID 6, 8, 10, 12, 14, 16, 18, 20, 22, 24, 26, 28, 30, 32, YP_003781016, YP_003781017, YP_003778879, YP_003779640, YP_003779893, YP_003780193 or a functionally equivalent variant of any one thereof), formate dehydrogenase (for example AEI90721, AEI90723, AEI90725, YP_003779063, YP_003778871, YP_003780168, AEI90722, AEI90724, AEI90726 or a functionally equivalent variant of any one thereof) or methylene-THF-dehydrogenase (for example AEI90753, YP_003781891, AEI90771 or a functionally equivalent variant of any one thereof).

In a particular embodiment of the first or second aspect, the one or more NADPH-dependent enzyme exists in NADH- and NADPH-dependent isoforms and the recombinant microorganism is adapted to express and/or overexpress the NADPH-dependent isoform.

In a particular embodiment, the microorganism is adapted to express and/or over-express an NADPH-dependent isoform while the expression of a corresponding NADH-dependent isoform is substantially unchanged, decreases, or exhibits a comparatively smaller increase when compared to the change in expression of the NADPH-dependent isoform. In one particular embodiment, the microorganism is adapted so expression of the one or more NADH-dependent isoforms is attenuated or knocked out compared to a parental microorganism. In one embodiment, the expression is attenuated or knocked out by modifying a nucleic acid encoding the one or more NADH-dependent enzyme or replacing one or more nucleic acid encoding an NADH-dependent isoform with one or more nucleic acid encoding an NADPH-dependent isoform.

In a particular embodiment of the first or second aspect, the increase in overall utilisation of NADPH comprises an increase in the NADPH flux through the pathway in which the one or more NADPH-dependent enzymes is active. In a particular embodiment, the flux is increased by at least 5%, at least 10%, at least 20%, at least 50%, at least 100%. Flux through the pathway can be measured by the level of metabolites and products (metabolomics) (Patti, Yanes, & Siuzdak, 2012) and/or labelling experiments as C13 (fluxomics) (Niittylae, Chaudhuri, Sauer, & Frommer, 2009; Tang et al., n.d.).

In one particular embodiment of the first or second aspect, the increase in overall utilisation of NADPH results, in use, in an increase in the efficiency of production of one or more products by the microorganism.

In one particular embodiment, the one or more enzymes existing in NADPH- and NADH-dependent isoforms is a hydroxymethylglutaryl-CoA (HMG-CoA) reductase, and comprises an NADPH-dependent isoform (EC 1.1.1.34; GO:0004420; e.g. *Saccharomyces cerevisiae*: DAA09822.1; BK006946.2:115734..118898 or a functionally equivalent variant of any one thereof) and an NADH-dependent isoform (EC1.1.1.88; GO:0042282; e.g. *Pseudomonas mevalonii*: P13702.1 or a functionally equivalent variant of any one thereof).

In one particular embodiment, the one or more enzymes existing in NADPH- and NADH-dependent isoforms is a hydroxybutyryl-CoA dehydrogenase/acetoacetyl-CoA reductase/3-hydroxybutyryl-CoA hydratase, and comprises an NADPH-dependent isoform phaB (EC:1.1.1.36; GO:0018454; e.g. from *Ralstonia eutropha*: YP_725942.1, GeneID:4249784 or a functionally equivalent variant of any one thereof), NADPH dependent phaJ (EC 4.2.1.119; e.g. from *Aeromonas punctata*: BAA21816.1) and a corresponding NADH-dependent isoform hbd (EC 1.1.1.157; GO:0008691; e.g. from *C. acetobutylicum*: NP_349314.1, GeneID:1118891 or a functionally equivalent variant of any one thereof).

In one particular embodiment, the one or more enzymes existing in NADPH- and NADH-dependent isoforms is a Crotonyl-CoA reductase/trans-2-enoyl-CoA reductase/butyryl-CoA dehydrogenase, and comprises an NADPH-dependent isoform ccr (EC 1.3.1.86; e.g. from *Streptomyces collinus* or a functionally equivalent variant of any one thereof) or ccr (EC 1.3.1.85; e.g. from *Rhodobacter sphaeroides*: YP_354044.1, Gene ID: 3720751) and a corresponding NADH-dependent isoform ter (EC 1.3.1.44; GO:0050343; e.g. from *Treponema denticola* or a functionally equivalent variant of any one thereof).

In a further embodiment, the enzyme exists in NADH and NADPH dependent isoforms and also exhibits multiple co-factor dependence. In one embodiment of the second aspect, the enzyme exhibiting multiple co-factor dependence may comprise a NADH/ferredoxin bifurcating enzyme or a NADH/NADPH co-dependent enzyme. In a particular embodiment, the enzyme exists in an NADH/NADPH bifurcating isoform and an NADH/Ferredoxin bifurcating isoform and the microorganism is adapted to express and/or overexpress the NADH/NADPH dependent isoform. In a particular embodiment, the NADH/NADPH dependent isoform is ter (EC 1.3.1.44; GO:0050343; e.g. from *Euglena gracilis*: AY741582.1 or a functionally equivalent variant of any one thereof). In a further embodiment, the NADH/Fd dependent isoform is NADH/ferredoxin bifurcating bcd-etfAB complex (EC 1.3.8.1; GO:0004085; e.g. from *C. acetobutylicum*: NP_349317.1; GeneID:1118894 or a functionally equivalent variant of any one thereof).

In a particular embodiment of the first or second aspects, the recombinant microorganism exhibits attenuated expression of one or more NADH-dependent enzymes. In this embodiment, an NADH-dependent isoform of an enzyme in a parental microorganism may have been replaced by an NADPH-dependent isoform of the enzyme in the recombinant microorganism.

In a particular embodiment of the first or second aspect, the microorganism exhibits increased efficiency during a fermentation reaction when compared to a parental microorganism.

In one particular embodiment of the first or second aspect, the parental microorganism is selected from the group of carboxydotrophic Clostridia comprising *Clostridium autoethanogenum*, *Clostridium ljungdahlii*, *Clostridium ragsdalei*, *Clostridium carboxidivorans*, *Clostridium drakei*, *Clostridium scatologenes*, *Clostridium aceticum*, *Clostridium formicoaceticum*, *Clostridium magnum*.

In one embodiment of the first or second aspect, the parental microorganism is *Clostridium autoethanogenum* or *Clostridium ljungdahlii*. In one particular embodiment, the microorganism is *Clostridium autoethanogenum* DSM23693 a derivate of strain DSM10061. In another particular embodiment, the microorganism is *Clostridium ljungdahlii* DSM13528 (or ATCC55383).

In a further embodiment of the first aspect, the one or more NADPH-dependent enzymes is modified to increase its NADPH co-factor specificity relative to its NADH co-factor specificity.

In a further embodiment of the second aspect, the method further comprises a step of increasing the NADPH co-factor specificity of the one or more NADPH-dependent enzymes relative to the NADH co-factor specificity of the enzyme(s). In one embodiment, this comprises modifying one or more nucleic acid encoding one or more NADPH-dependent enzymes.

In a particular embodiment, the one or more enzyme in which NADPH co-factor specificity is increased is an oxidoreductase enzyme, preferably selected from the group consisting of Crotonyl-CoA reductase/trans-2-enoyl-CoA reductase/butyryl-CoA dehydrogenase.

In a particular embodiment, the one or more exogenous or endogenous enzymes comprises a bifurcating NADP Fe-only hydrogenase, a bifurcating NADP formate dehydrogenase, and/or a formate-hydrogen lyase complex as described herein, or a functionally equivalent variant thereof.

In a further embodiment, the invention provides a recombinant microorganism according to the first aspect having one or more modifications as described in any of the aspects described herein.

In a further embodiment, the invention provides a method of producing a recombinant microorganism according to the second aspect having one or more modifications as described in any of the aspects described herein.

In a third aspect, the invention provides a method of producing one or more fermentation products, the method comprising anaerobically fermenting a substrate comprising CO in the presence of a carboxydotrophic microorganism wherein the carboxydotrophic microorganism is a recombinant microorganism as described in the first aspect or as produced by the second aspect.

In a particular embodiment, the one or more fermentation products comprises ethanol, butanol, isopropanol, isobutanol, higher alcohols, butanediol, succinate, isoprenoids, fatty acids and/or biopolymers.

In a particular embodiment, the substrate comprising CO is a gaseous substrate comprising CO. In one embodiment, the substrate comprises an industrial waste gas. In certain embodiments, the gas is steel mill waste gas or syngas.

In one embodiment, the substrate will typically contain a major proportion of CO, such as at least about 20% to about 100% CO by volume, from 20% to 70% CO by volume, from 30% to 60% CO by volume, and from 40% to 55% CO by volume. In particular embodiments, the substrate comprises about 25%, or about 30%, or about 35%, or about 40%, or about 45%, or about 50% CO, or about 55% CO, or about 60% CO by volume.

In a fourth aspect, the invention provides the use of a bifurcating NADP Fe-only hydrogenase, a bifurcating NADP formate dehydrogenase, and/or a formate-hydrogen lyase complex or a functionally equivalent variant thereof for the purpose of utilising multiple co-factors in a reaction. Preferably, the multiple co-factors comprise ferredoxin and NADPH.

In a particular embodiment, the bifurcating NADP formate dehydrogenase is selected from the group consisting of AEI90721, YP_003778871, AEI90722, and a functionally equivalent variant of any one or more thereof.

In a particular embodiment, the bifurcating NADP Fe-only hydrogenase is selected from the group consisting of SEQ ID NO:10, SEQ ID NO:26 and YP_003778879, and a functionally equivalent variant of any one or more thereof.

In a particular embodiment, the bifurcating formate-hydrogen lyase complex is encoded by any one of SEQ ID NOs:65 to 67 or a functionally equivalent variant thereof.

In a fifth aspect, the invention provides a recombinant microorganism wherein the microorganism is adapted to express an exogenous bifurcating NADP Fe-only hydrogenase, bifurcating NADP formate dehydrogenase, and/or formate-hydrogen lyase complex, and/or overexpress an endogenous bifurcating NADP Fe-only hydrogenase, bifurcating NADP formate dehydrogenase, and/or formate-hydrogen lyase complex such that the microorganism is adapted to utilize multiple cofactors in a reaction.

In a sixth aspect, the invention provides a method of making a recombinant microorganism which can utilize multiple cofactors in a reaction, the method comprising at least the steps of:
a) selecting one or more bifurcating NADP Fe-only hydrogenase, bifurcating NADP formate dehydrogenase, and/ or formate-hydrogen lyase complex
b) transforming a parental microorganism to yield a recombinant microorganism which is adapted to utilize multiple cofactors in a reaction.

In one embodiment of the fifth or sixth aspects, the multiple co-factors comprise ferredoxin and NADPH.

In one embodiment of the fifth or sixth aspects, the parental microorganism is a carboxydotrophic Clostridia. In one embodiment, the parental microorganism is selected from the group of carboxydotrophic Clostridia comprising *Clostridium autoethanogenum, Clostridium ljungdahlii, Clostridium ragsdalei, Clostridium carboxidivorans, Clostridium drakei, Clostridium scatologenes, Clostridium aceticum, Clostridium formicoaceticum, Clostridium magnum*. In one embodiment, the parental microorganism is *Clostridium autoethanogenum* or *Clostridium ljungdahlii*. In one particular embodiment, the microorganism is *Clostridium autoethanogenum* DSM23693 a derivate of strain DSM10061. In another particular embodiment, the microorganism is *Clostridium ljungdahlii* DSM13528 (or ATCC55383).

In one embodiment of the fifth or sixth aspects, the bifurcating NADP formate dehydrogenase is selected from the group consisting of AEI90721, YP_003778871, AEI90722, and a functionally equivalent variant of any one or more thereof.

In one embodiment of the fifth or sixth aspects, the bifurcating NADP Fe-only hydrogenase is selected from the group consisting of SEQ ID NO:10, SEQ ID NO:26 and YP_003778879, and a functionally equivalent variant of any one or more thereof.

In one embodiment of the fifth or sixth aspects, the bifurcating formate-hydrogen lyase complex is encoded by SEQ ID NO:65 to 67 or a functionally equivalent variant of thereof.

In a particular embodiment of the fifth or sixth aspects, the parental microorganism is transformed with one or more exogenous polynucleotides encoding a bifurcating NADP Fe-only hydrogenase, a bifurcating NADP formate dehydrogenase, and/or a formate-hydrogen lyase complex. In one particular embodiment, the parental microorganism is transformed with one or more exogenous polynucleotides selected from the group consisting of HQ876015, CLJU_c06990, AEI90722, SEQ ID NO:9, SEQ ID NO:25, CLJU_c07070, SEQ ID NO: SEQ ID Nos:65 to 67 and a functionally equivalent variant of any one or more thereof.

In a related aspect, the invention provides the use of a recombinant microorganism comprising a bifurcating NADP Fe-only hydrogenase, a bifurcating NADP formate dehydrogenase, and/or a formate-hydrogen lyase complex, for the purpose of utilising multiple co-factors in a reaction. Preferably, the multiple co-factors comprise ferredoxin and NADPH. In one embodiment, the a bifurcating NADP Fe-only hydrogenase, a bifurcating NADP formate dehydrogenase, and/or a formate-hydrogen lyase complex is as described in the fourth aspect.

In a seventh aspect, the invention provides a method of increasing the efficiency of a reaction, the method comprising the use of a bifurcating NADP Fe-only hydrogenase, a bifurcating NADP formate dehydrogenase, and/or a formate-hydrogen lyase complex and/or a polynucleotide encoding same, and/or a recombinant microorganism adapted to express and/or overexpress same. In a particular embodiment, the reaction is a fermentation of a substrate comprising CO. The efficiency is increased due to the bifurcating enzyme utilising both ferredoxin and NADPH rather than only NADPH. Without wishing to be bound by theory, the inventors believe that coupling the more negative redox potential of ferredoxin ($E_0'=-410$ mV) to NAD(P)H ($E_0'=-320$ mV) provides greater energetic potential and drives more exergonic reactions therefore increasing the reaction rate and CO substrate throughput.

In a particular embodiment, the bifurcating NADP Fe-only hydrogenase, bifurcating NADP formate dehydrogenase, and/or a formate-hydrogen lyase complex of the seventh aspect is as described in the fourth aspect.

In an eighth aspect, the invention provides the use of a recombinant microorganism to convert NADH to NADPH, wherein the recombinant microorganism is adapted to express and/or overexpress a single NADH-dependent reduced ferredoxin:NADP+ oxidoreductase (Nfn) enzyme. In a particular embodiment, the Nfn enzyme comprises the amino acid sequence of SEQ_ID No. 2, 4, YP_003781852.1, CLJU_c37240 or a functionally equivalent variant of any one thereof with at least 76%, 80%, 85%, 90%, 95%, or 99% sequence identity. The Nfn enzyme converts NADH to NADPH therefore when expressed in the presence of NADH and NADPH-dependent enzymes, enzyme efficiency is increased leading to a faster reaction rate and faster regeneration rate of NADPH.

In a particular embodiment, the microorganism comprises a carboxydotrophic Clostridia microorganism. In a further embodiment, the microorganism is selected from the group of carboxydotrophic Clostridia comprising *Clostridium autoethanogenum, Clostridium ljungdahlii, Clostridium ragsdalei*.

In a further embodiment, the invention provides the use as described in the eighth aspect wherein the recombinant microorganism comprises one or more modifications as described in the fifth aspect.

In a ninth aspect, the invention provides the use of a polypeptide to convert NADH to NADPH, wherein the polypeptide comprises a single NADH-dependent reduced ferredoxin:NADP+ oxidoreductase (Nfn) enzyme according to SEQ ID NO: 2, 4, YP_003781852.1, CLJU_c37240 or a functionally equivalent variant thereof with at least 76%, 80%, 85%, 90%, 95%, or 99% sequence identity.

In a particular embodiment, the single Nfn enzyme of the eighth or ninth aspect is encoded by a polynucleotide SEQ ID NO: 1, 3, the sequence encoding YP_003781852.1 or CLJU_c37240, or a functionally equivalent variant thereof with at least 83%, 85%, 90%, 95%, or 99% sequence identity.

In a tenth aspect, the invention provides a polynucleotide according to SEQ_ID NO. 1 or 3.

In an eleventh aspect, the invention provides a polypeptide according to SEQ_ID NO. 2 or 4.

In a twelfth aspect, the invention provides a vector comprising a polynucleotide according to the tenth aspect, or a polynucleotide which encodes a polypeptide according to the eleventh aspect.

In a thirteenth aspect, the invention provides a recombinant microorganism adapted to express a polynucleotide according to the tenth aspect, or a polypeptide according to the eleventh aspect.

The invention may also be said broadly to consist in the parts, elements and features referred to or indicated in the specification of the application, individually or collectively, in any or all combinations of two or more of said parts, elements or features, and where specific integers are mentioned herein which have known equivalents in the art to which the invention relates, such known equivalents are deemed to be incorporated herein as if individually set forth.

BRIEF DESCRIPTION OF THE DRAWINGS

Embodiments of the invention will now be described, by way of example only, with reference to the accompanying drawings in which.

DETAILED DESCRIPTION OF PREFERRED EMBODIMENTS

Definitions

Figure 1:
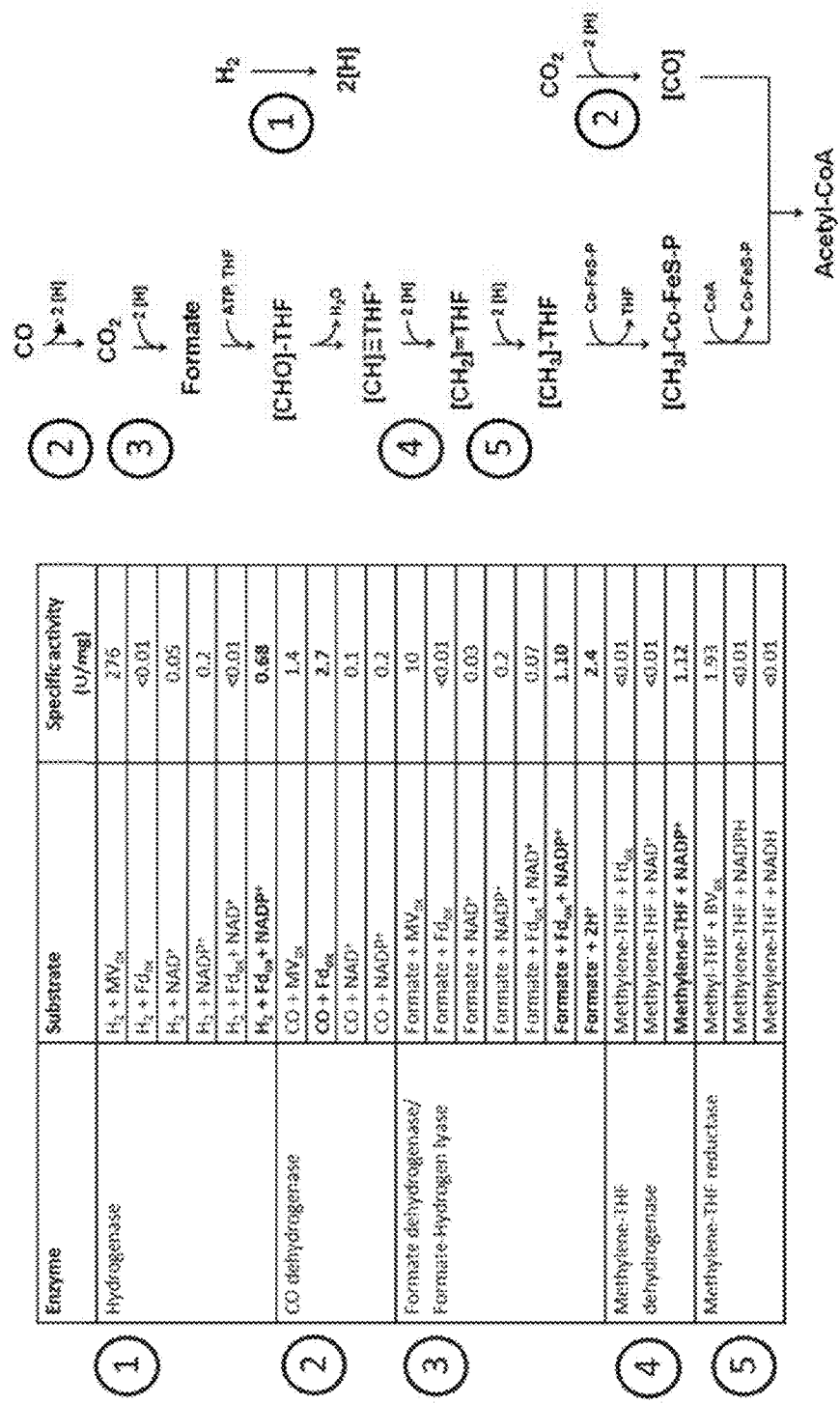
FIG. 1 shows the results of the enzyme assays for the oxidoreductase steps involved in the Wood Ljungdahl pathway to determine their co-factor specificities.

The term "nicotinamide adenine dinucleotide" (NADH) may refer to the redox couple of both NAD+ (oxidized form) and NADH+H+ (reduced form).

The term "nicotinamide adenine dinucleotide phosphate" (NADPH) may refer to the redox couple of both NADP+ (oxidized form) and NADPH+H+ (reduced form).

As referred to herein, an "NADPH dependent enzyme" predominantly (although not necessarily exclusively) uses NADPH as a co-factor to supply electrons to a reaction. Similarly, an NADH-dependent enzyme predominantly (although not necessarily exclusively) uses NADH as a co-factor to supply electrons to a reaction. It will also be appreciated by one of skill in the art that some enzymes are able to utilise NADPH and NADH and may be referred to as bifunctional NAD(P)H-dependent enzymes.

As referred to herein, the phrase "overall utilisation of NADPH by the microorganism is increased", or similar refers to an increase in the amount of NADPH co-factor binding to an enzyme in a particular time period. In particular embodiments, the increase is of at least 5%, at least 10%, at least 20%, at least 50%, or at least 100%. This increase may be measured according to the method used in example 3, or other methods known in the art, for example (S. Wang, Huang, Moll, & Thauer, 2010). The phrase may also be interpreted to mean that there is an increase in the NADPH flux through a pathway and the increase is of the same quanta as described above. NADPH flux may be measured by the level of metabolites and products (metaboliomics) and/or labelling experiments as C13 (fluxomics).

As used herein, "co-factor specificity" refers to the degree of affinity with which a co-factor binds to an enzyme during a reaction. It should not be taken to mean that an enzyme and a co-factor have absolute specificity, although this may be the case, and includes at least a preference for the binding between a particular enzyme and one co-factor over another co-factor.

As referred to herein, an "isoform" of an enzyme is any of two or more functionally similar proteins that are able to catalyse the same reaction and have a similar but not identical amino acid sequence.

As referred to herein, a "bifurcating enzyme" is an enzyme that is able to utilise multiple co-factors where one co-factor has a lower reaction potential (such as ferredoxin) and one has a higher reaction potential (such as NADH or NADPH) in a coupled reaction to catalyse a reaction that couldn't be catalysed, or where the reaction would proceed at a lower rate, by only the co-factor with the higher reaction potential (such as NADH or NADPH). In one embodiment a bifurcating enzyme may utilise multiple co-factors to increase the rate of a reaction. The bifurcating enzyme may be a complex, such as the formate hydrogen lyase complex described herein.

The term "adapted to" may be used herein to describe a recombinant microorganism of the invention; for example, the microorganism is "adapted to" express a particular enzyme. When used in relation to the expression of an enzyme, the term does not imply that the enzyme is continuously expressed, it is intended to cover situations where the enzyme may be expressed and such expression may be constitutive or induced.

As referred to herein, a "fermentation broth" is a culture medium comprising at least a nutrient media and bacterial cells.

The terms "increasing the efficiency", "increased efficiency" and the like, when used in relation to a fermentation process, include, but are not limited to, increasing one or more of the rate of growth of microorganisms catalysing the fermentation, the growth and/or product production rate at elevated product concentrations, the volume of desired product produced per volume of substrate consumed, the rate of production or level of production of the desired product, and the relative proportion of the desired product produced compared with other by-products of the fermentation.

The phrase "substrate comprising carbon monoxide" and like terms should be understood to include any substrate in which carbon monoxide is available to one or more strains of bacteria for growth and/or fermentation, for example.

The phrase "gaseous substrate comprising carbon monoxide" and like phrases and terms includes any gas which contains a level of carbon monoxide. In certain embodiments the substrate contains at least about 20% to about 100% CO by volume, from 20% to 70% CO by volume, from 30% to 60% CO by volume, and from 40% to 55% CO by volume. In particular embodiments, the substrate comprises about 25%, or about 30%, or about 35%, or about 40%, or about 45%, or about 50% CO, or about 55% CO, or about 60% CO by volume.

While it is not necessary for the substrate to contain any hydrogen, the presence of $H_2$ should not be detrimental to product formation in accordance with methods of the invention. In particular embodiments, the presence of hydrogen results in an improved overall efficiency of alcohol production. For example, in particular embodiments, the substrate may comprise an approx 2:1, or 1:1, or 1:2 ratio of $H_2$:CO. In one embodiment the substrate comprises about 30% or less $H_2$ by volume, 20% or less $H_2$ by volume, about 15% or less $H_2$ by volume or about 10% or less $H_2$ by volume. In other embodiments, the substrate stream comprises low concentrations of $H_2$, for example, less than 5%, or less than 4%, or less than 3%, or less than 2%, or less than 1%, or is substantially hydrogen free. The substrate may also contain some $CO_2$ for example, such as about 1% to about 80% $CO_2$ by volume, or 1% to about 30% $CO_2$ by volume. In one embodiment the substrate comprises less than or equal to about 20% $CO_2$ by volume. In particular embodiments the substrate comprises less than or equal to about 15% $CO_2$ by volume, less than or equal to about 10% $CO_2$ by volume, less than or equal to about 5% $CO_2$ by volume or substantially no $CO_2$.

In the description which follows, embodiments of the invention are described in terms of delivering and fermenting a "gaseous substrate containing CO". However, it should be appreciated that the gaseous substrate may be provided in alternative forms. For example, the gaseous substrate containing CO may be provided dissolved in a liquid. Essentially, a liquid is saturated with a carbon monoxide containing gas and then that liquid is added to the bioreactor. This may be achieved using standard methodology. By way of example, a microbubble dispersion generator (Hensirisak et. al. Scale-up of microbubble dispersion generator for aerobic fermentation; Applied Biochemistry and Biotechnology Volume 101, Number 3/October, 2002) could be used. By way of further example, the gaseous substrate containing CO may be adsorbed onto a solid support. Such alternative methods are encompassed by use of the term "substrate containing CO" and the like.

In particular embodiments of the invention, the CO-containing gaseous substrate is an industrial off or waste gas. "Industrial waste or off gases" should be taken broadly to include any gases comprising CO produced by an industrial process and include gases produced as a result of ferrous metal products manufacturing, non-ferrous products manufacturing, petroleum refining processes, gasification of coal, gasification of biomass, electric power production, carbon black production, and coke manufacturing. Further examples may be provided elsewhere herein.

Unless the context requires otherwise, the phrases "fermenting", "fermentation process" or "fermentation reaction" and the like, as used herein, are intended to encompass both the growth phase and product biosynthesis phase of the process. As will be described further herein, in some embodiments the bioreactor may comprise a first growth reactor and a second fermentation reactor. As such, the addition of metals or compositions to a fermentation reaction should be understood to include addition to either or both of these reactors.

The term "bioreactor" includes a fermentation device consisting of one or more vessels and/or towers or piping arrangement, which includes the Continuous Stirred Tank Reactor (CSTR), Immobilized Cell Reactor (ICR), Trickle Bed Reactor (TBR), Bubble Column, Gas Lift Fermenter, Static Mixer, or other vessel or other device suitable for gas-liquid contact. In some embodiments the bioreactor may comprise a first growth reactor and a second fermentation reactor. As such, when referring to the addition of substrate to the bioreactor or fermentation reaction it should be understood to include addition to either or both of these reactors where appropriate.

As referred to herein, a "shuttle microorganism" is a microorganism in which a methyltransferase enzyme is expressed and is distinct from the destination microorganism.

As referred to herein, a "destination microorganism" is a microorganism in which the genes included on an expression construct/vector are expressed and is distinct from the shuttle microorganism.

"Exogenous nucleic acids" are nucleic acids which originate outside of the microorganism to which they are introduced. Exogenous nucleic acids may be derived from any appropriate source, including, but not limited to, the microorganism to which they are to be introduced (for example a parental microorganism from which the recombinant microorganism is derived), strains or species of microorganisms which differ from the organism to which they are to be introduced, or they may be artificially or recombinantly created. In one embodiment, the exogenous nucleic acids represent nucleic acid sequences naturally present within the microorganism to which they are to be introduced, and they are introduced to increase expression of or over-express a particular gene (for example, by increasing the copy number of the sequence (for example a gene), or introducing a strong or constitutive promoter to increase expression). In another embodiment, the exogenous nucleic acids represent nucleic acid sequences not naturally present within the microorganism to which they are to be introduced and allow for the expression of a product not naturally present within the microorganism or increased expression of a gene native to the microorganism (for example in the case of introduction of a regulatory element such as a promoter). The exogenous nucleic acid may be adapted to integrate into the genome of the microorganism to which it is to be introduced or to remain in an extra-chromosomal state.

"Exogenous" may also be used to refer to proteins. This refers to a protein that is not present or is not capable of being expressed in a parental microorganism from which the recombinant microorganism is derived.

The term "endogenous" as used herein in relation to a recombinant microorganism and a nucleic acid refers to any nucleic acid that is present in a parental microorganism from which the recombinant microorganism is derived. When used to describe proteins, "endogenous" should be taken to refer to any protein that is present or capable of being expressed in a parental microorganism from which the recombinant microorganism is derived "Oxidoreductases" (also known as "dehydrogenases" or "oxidases") include enzymes that catalyze the transfer of electrons from one molecule—the reductant, also called the electron donor, to another molecule—the oxidant, also called the electron acceptor. Oxidoreductases are classified as EC 1 in the EC number classification of enzymes. This group of enzymes usually requires co-factors such as NADH, NADPH or ferredoxin.

An enzymatic "reaction" as referred to herein is the conversion of one or more molecules (substrates) into another one or more molecules (products) catalyzed by an enzyme.

It should be appreciated that the invention may be practised using nucleic acids whose sequence varies from the sequences specifically exemplified herein, provided they perform substantially the same function. For nucleic acid sequences that encode a protein or peptide this means that the encoded protein or peptide has substantially the same function. For nucleic acid sequences that represent promoter sequences, the variant sequence will have the ability to promote expression of one or more genes. Such nucleic acids may be referred to herein as "functionally equivalent variants". By way of example, functionally equivalent variants of a nucleic acid include allelic variants, fragments of a gene, genes which include mutations (deletion, insertion, nucleotide substitutions and the like) and/or polymorphisms and the like. Homologous genes from other microorganisms may also be considered as examples of functionally equivalent variants of the sequences specifically exemplified herein. These include homologous genes in species such as *Clostridium acetobutylicum, Clostridium beijerinckii, C. ljungdahlii* details of which are publicly available on websites such as Genbank or NCBI. The phrase "functionally equivalent variants" should also be taken to include nucleic acids whose sequence varies as a result of codon optimisation for a particular organism. Unless the context requires otherwise, "functionally equivalent variants" of a nucleic acid herein will preferably have at least approximately 70%, 72%, 75%, 80%, 85%, 90%, 95% or greater nucleic acid sequence identity with the nucleic acid identified.

It should also be appreciated that the invention may be practised using polypeptides whose sequence varies from the amino acid sequences specifically exemplified herein. These variants may be referred to herein as "functionally equivalent variants". Unless the context requires otherwise, a functionally equivalent variant of a protein or a peptide includes those proteins or peptides that share at least 40%, 50%, 60%, 70%, 72%, 75%, 80%, 85%, 90%, 95% or greater amino acid identity with the protein or peptide identified and has substantially the same function as the peptide or protein of interest. Such variants include within their scope fragments of a protein or peptide wherein the fragment comprises a truncated form of the polypeptide wherein deletions may be from 1 to 5, to 10, to 15, to 20, to 25 amino acids, and may extend from residue 1 through 25 at either terminus of the polypeptide, and wherein deletions may be of any length within the region; or may be at an internal location. Functionally equivalent variants of the specific polypeptides herein should also be taken to include polypeptides expressed by homologous genes in other species of bacteria, for example as exemplified in the previous paragraph.

"Substantially the same function" as used herein is intended to mean that the nucleic acid or polypeptide is able to perform the function of the nucleic acid or polypeptide of which it is a variant. For example, a variant of an enzyme of the invention will be able to catalyse the same reaction as that enzyme. However, it should not be taken to mean that the variant has the same level of activity as the polypeptide or nucleic acid of which it is a variant.

One may assess whether a functionally equivalent variant has substantially the same function as the nucleic acid or polypeptide of which it is a variant using methods known to one of skill in the art. However, by way of example, assays to test for hydrogenase, formate dehydrogenase or methylene-THF-dehydrogenase activity are described in (Huang, Wang, Moll, & Thauer, 2012).

"Over-express", "over expression" and like terms and phrases when used in relation to the invention should be taken broadly to include any increase in expression of one or more proteins (including expression of one or more nucleic acids encoding same) as compared to the expression level of the protein (including nucleic acids) of a parental microorganism under the same conditions. It should not be taken to mean that the protein (or nucleic acid) is expressed at any particular level.

"Attenuated expression" as referred to herein refers to the expression of a nucleic acid or protein that is decreased relative to its expression in a parental microorganism. In one embodiment, attenuated expression may include substantially no expression (or substantially "zero" expression). This may be achieved by any method known to one of skill in the art including, for example, RNA silencing, modification of the expression process (for example disruption of the promoter function), alteration or modification of a nucleic acid sequence (including deletion, addition and substitution of one or more nucleotide), or complete or partial removal of the nucleic acid encoding the enzyme from the genome. Where a gene is made inoperative it may be referred to herein as a "knock-out" or having been "knocked out" or like terms.

A "parental microorganism" is a microorganism used to generate a recombinant microorganism of the invention. The parental microorganism may be one that occurs in nature (i.e. a wild type microorganism) or one that has been previously modified but which does not express or over-express one or more of the enzymes the subject of the present invention. Accordingly, the recombinant microorganisms of the invention are modified to express or over-express one or more enzymes that were not expressed or over-expressed in the parental microorganism In one embodiment, the microorganism is selected from the group of acetogenic carboxydotrophic organisms comprising the species *Clostridium autoethanogenum, Clostridium ljungdahlii, Clostridium ragsdalei, Clostridium carboxidivorans, Clostridium drakei, Clostridium scatologenes, Clostridium aceticum, Clostridium formicoaceticum, Clostridium magnum, Acetobacterium woodii, Alkalibaculum bacchii, Moorella thermoacetica, Sporomusa ovate, Butyribacterium methylotrophicum, Blautia producta, Eubacterium limosum, Thermoanaerobacter kiuvi.*

These carboxydotrophic acetogens are defined by their ability to utilize and grow chemoautotrophically on gaseous one-carbon (C1) sources such as carbon monoxide (CO) and carbon dioxide ($CO_2$) with carbon monoxide (CO) and/or hydrogen (H2) as energy source under anaerobic conditions forming acetyl-CoA, acetate and other products. They share the same mode of fermentation, the Wood-Ljungdahl or reductive acetyl-CoA pathway, and are defined by the presence of the enzyme set consisting of Carbon monoxide dehydrogenase (CODH), Hydrogenase, Formate dehydrogenase, Formyl-tetrahydrofolate synthetase, Methylene-tetrahydrofolate dehydrogenase, Formyl-tetrahydrofolate cyclohydrolase, Methylene-tetrahydrofolate reductase, and Carbon monoxide dehydrogenase/Acetyl-CoA synthase (CODH/ACS), which combination is characteristic and unique to this type of bacteria (Drake, Küsel, Matthies, Wood, & Ljungdahl, 2006). In contrast to chemoheterotrophic growth of sugar-fermenting bacteria that convert the substrate into biomass, secondary metabolites and pyruvate from which products are formed (either via acetyl-CoA or directly), in acetogens the substrate is channelled directly into acetyl-CoA, from which products, biomass, and secondary metabolites are formed.

In a one embodiment, the microorganism is selected from a cluster of carboxydotrophic Clostridia comprising the species *C. autoethanogenum*, *C. ljungdahlii*, and "*C. ragsdalei*" and related isolates. These include but are not limited to strains *C. autoethanogenum* JAI-1$^T$ (DSM10061) (Abrini, Naveau, & Nyns, 1994), *C. autoethanogenum* LBS1560 (DSM19630) (WO/2009/064200), *C. autoethanogenum* LBS1561 (DSM23693), *C. ljungdahlii* PETC$^T$ (DSM13528=ATCC 55383) (Tanner, Miller, & Yang, 1993), *C. ljungdahlii* ERI-2 (ATCC 55380) (U.S. Pat. No. 5,593,886), *C. ljungdahlii* C-01 (ATCC 55988) (U.S. Pat. No. 6,368,819), *C. ljungdahlii* O-52 (ATCC 55989) (U.S. Pat. No. 6,368,819), or "*C. ragsdalei* P11$^T$" (ATCC BAA-622) (WO 2008/028055), and related isolates such as "*C. coskatii*" (US patent 2011/0229947), "*Clostridium* sp. MT351" (Tyurin & Kiriukhin, 2012), "*Clostridium* sp. MT 653" (Berzin, Kiriukhin, & Tyurin, 2012a), "*Clostridium* sp. MT683" (Berzin, 2012), "*Clostridium* sp. MT962" (Berzin, Kiriukhin, & Tyurin, 2013) "*Clostridium* sp. MT1121" (Berzin, Kiriukhin, & Tyurin, 2012b), "*Clostridium* sp. MT1230" (Kiriukhin & Tyurin, 2013), or "*Clostridium* sp. MT1962" (Berzin, Tyurin, & Kiriukhin, 2013), and mutant strains thereof such as *C. ljungdahlii* OTA-1 (Tirado-Acevedo O. Production of Bioethanol from Synthesis Gas Using *Clostridium ljungdahlii*. PhD thesis, North Carolina State University, 2010) or "*Clostridium* sp. MT896" (Berzin, Kiriukhin, & Tyurin, 2012c).

These strains form a subcluster within the Clostridial rRNA cluster I (Collins et al., 1994), having at least 99% identity on 16S rRNA gene level, although being distinct species as determined by DNA-DNA reassociation and DNA fingerprinting experiments (WO 2008/028055, US patent 2011/0229947).

The strains of this cluster are defined by common characteristics, having both a similar genotype and phenotype, and they all share the same mode of energy conservation and fermentative metabolism. The strains of this cluster lack cytochromes and conserve energy via an Rnf complex.

All strains of this cluster have a genome size of around 4.2 MBp (Kopke et al., 2010) and a GC composition of around 32% mol (Abrini et al., 1994; Kopke et al., 2010; Tanner et al., 1993) (WO 2008/028055; US patent 2011/0229947), and conserved essential key gene operons encoding for enzymes of Wood-Ljungdahl pathway (Carbon monoxide dehydrogenase, Formyl-tetrahydrofolate synthetase, Methylene-tetrahydrofolate dehydrogenase, Formyl-tetrahydrofolate cyclohydrolase, Methylene-tetrahydrofolate reductase, and Carbon monoxide dehydrogenase/Acetyl-CoA synthase), hydrogenase, formate dehydrogenase, Rnf complex (rnfCDGEAB), pyruvate:ferredoxin oxidoreductase, aldehyde:ferredoxin oxidoreductase (Kopke et al., 2010, 2011). The organization and number of Wood-Ljungdahl pathway genes, responsible for gas uptake, has been found to be the same in all species, despite differences in nucleic and amino acid sequences (Kopke et al., 2011).

The strains all have a similar morphology and size (logarithmic growing cells are between 0.5-0.7×3-5 μm), are mesophilic (optimal growth temperature between 30-37° C.) and strictly anaerobe (Abrini et al., 1994; Tanner et al., 1993) (WO 2008/028055). Moreover, they all share the same major phylogenetic traits, such as same pH range (pH 4-7.5, with an optimal initial pH of 5.5-6), strong autotrophic growth on CO containing gases with similar growth rates, and a metabolic profile with ethanol and acetic acid as main fermentation end product, with small amounts of 2,3-butanediol and lactic acid formed under certain conditions (Abrini et al., 1994; Köpke et al., 2011; Tanner et al., 1993)(WO differentiate in substrate utilization of various sugars (e.g. rhamnose, arabinose), acids (e.g. gluconate, citrate), amino acids (e.g. arginine, histidine), or other substrates (e.g. betaine, butanol). Some of the species were found to be auxotroph to certain vitamins (e.g. thiamine, biotin) while others were not. Reduction of carboxylic acids into their corresponding alcohols has been shown in a range of these organisms (Perez, Richter, Loftus, & Angenent, 2012).

The traits described are therefore not specific to one organism like *C. autoethanogenum* or *C. ljungdahlii*, but rather general traits for carboxydotrophic, ethanol-synthesizing Clostridia. Thus, the invention can be anticipated to work across these strains, although there may be differences in performance.

In certain embodiments, the parental microorganism is selected from the group comprising *Clostridium autoethanogenum, Clostridium ljungdahlii*, and *Clostridium ragsdalei*. In one embodiment, the group also comprises *Clostridium coskatii*. In one particular embodiment, the parental microorganism is *Clostridium autoethanogenum* DSM23693.

The terms nucleic acid "constructs" or "vectors" and like terms should be taken broadly to include any nucleic acid (including DNA and RNA) suitable for use as a vehicle to transfer genetic material into a cell. The terms should be taken to include plasmids, viruses (including bacteriophage), cosmids and artificial chromosomes, for example constructs or vectors may include one or more regulatory elements, an origin of replication, a multicloning site and/or a selectable marker. In one particular embodiment, the constructs or vectors are adapted to allow expression of one or more genes encoded by the construct or vector. Nucleic acid constructs or vectors include naked nucleic acids as well as nucleic acids formulated with one or more agents to facilitate delivery to a cell (for example, liposome-conjugated nucleic acid, an organism in which the nucleic acid is contained).

*Clostridium* autoethanogenum LZ1561 was deposited with Deutsche Sammlung von Mikroorganismen and Zellkulturen GmbH (DSMZ) located at Inhoffenstraß 7B, D-38124 Braunschwieg, Germany on Jun. 7, 2010 under the terms of the Budapest Treaty and accorded accession number DSM23693.

Figure 2:
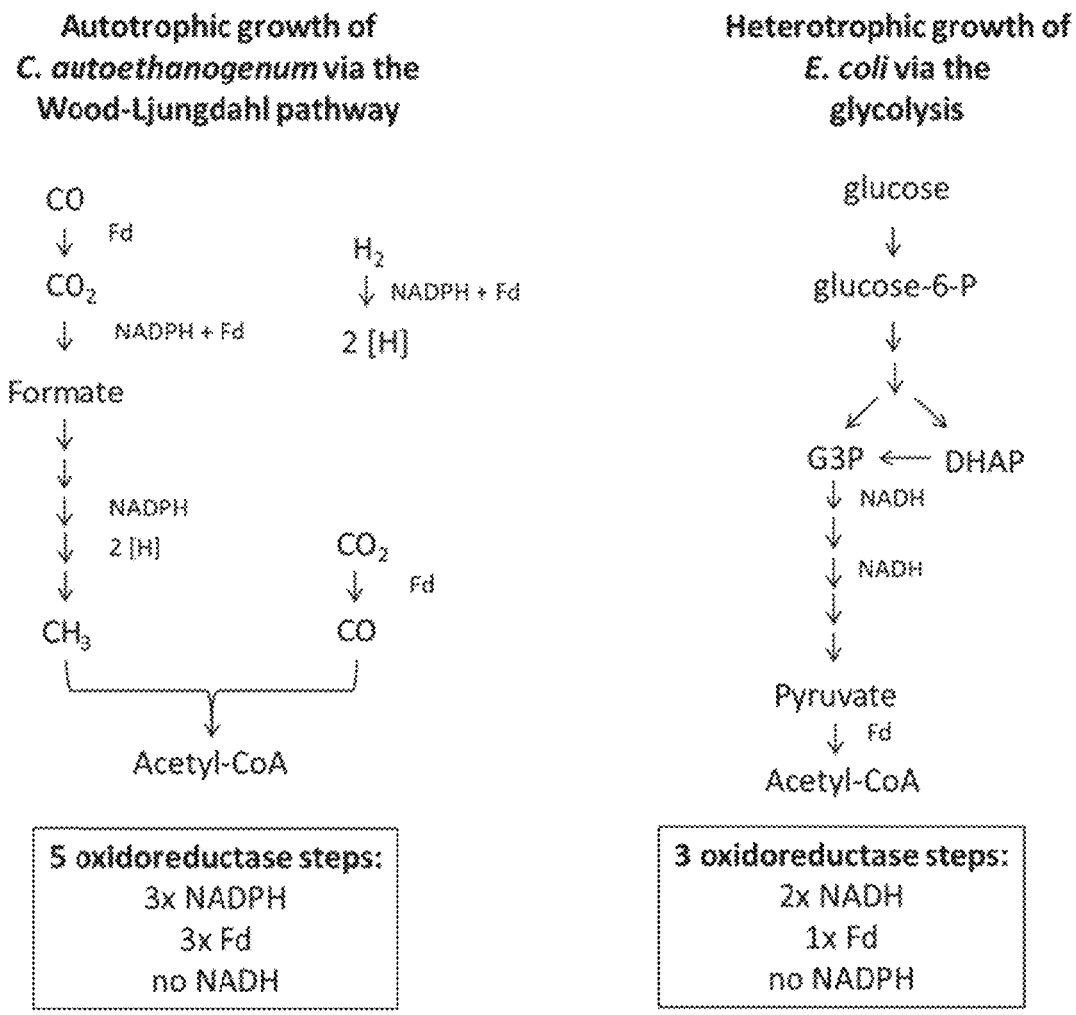
FIG. 2 shows the difference between glycolysis (e.g. in *E. coli*) and autotrophic growth via the Wood-Ljungdahl pathway in carboxydotrophic Clostridia (e.g. *C. autoethanogenum*) in respect of co-factor usage.

All known examples of carboxydotrophic Clostridia growing on waste gases and syngas use NADH-dependent reactions. The redox pair NADPH+H$^+$/NADP$^+$ has a more negative redox potential than the NADH+H+/NAD+ redox pair (Auriol et al., 2011). Under in vivo conditions the redox potential E' of the NAD+/NADH couple is about −280 mV (Eo'=−320 mV) whereas E' of the NADP+/NADPH couple is about −360 mV (Eo'=−320 mV). The inventors have surprisingly found that a number of enzymes involved in autotrophic growth for uptake and utilization of CO, $CO_2$, and $H_2$ gases (for example hydrogenase enzymes and Wood-Ljungdahl pathway enzymes) show a clear bias towards utilisation of NADPH over NADH. This is in complete contrast to for example glycolysis of sugar utilizing bacteria such as *E. coli* which serves as a model for most bacterial processes and is completely NADH biased. These *E. coli* based reactions do not include an NADPH dependent reaction step but do include several NADH dependent steps (glucose+2 NAD++2 ADP+2 Pi→2 Pyruvate+2 NADH+2H++2 ATP+2H2O; FIG. 2).

NADPH-dependent reactions in *E. coli* have been shown to quickly deplete the NADPH pool and lead to cell growth inhibition and death. This lack of NADPH capacity in *E. coli* has led previous studies to attempt to reduce NADPH dependency and the studies therefore suggest that increasing NADPH utilization would be undesirable in fermentation reactions. It was therefore surprising for the inventors to find that the carboxydotrophic Clostridia referred to herein have a relatively large capacity for NADPH-dependent reactions to proceed.

The inventors have demonstrated the relatively large capacity of the NADPH pool in carboxydotrophic Clostridia microorganisms by an experiment which monitors the acetone conversion in a bioreactor by an NADPH-dependent enzyme (see example 3). Accordingly, the inventors have shown that the use of NADPH over NADH would be favourable to drive enzymatic reactions in a fermentation process.

Thus existing strategies for *E. coli*, using NADH dependent reactions and bypassing NADPH dependent reactions (which result in a reduction in product yields and require extensive modifications) are not productive in carboxydotrophic Clostridia. The invention as described herein provides a strategy to overcome this by preferentially selecting for NADPH dependent reactions in carboxydotrophic Clostridia to achieve maximum product yields for metabolic engineering. The capacity and potential of NADPH dependent reactions is shown in example 3 as well as the difference to sugar utilizing *E. coli*. Similarly this strategy can be applied for heterologous pathways to achieve maximum product yield and flux.

Additionally, the inventors have identified that that NADPH dependent reactions proliferate in carboxydotrophic microorganisms. This enables the development of selection techniques to identify and characterise enzymes and genes that use the NADPH pool. Recombinant microorganisms that can express or over-express enzymes selected according to these techniques have utility in improving the efficiency of carboxydotrophic microorganisms and increasing the production of their desirable products.

In contrast to what is taught by the prior art in relation to sugar utilizing organisms such as *E. coli*, the inventors contemplate that NADPH dependent reactions are not an undesirable bottleneck when considering carboxydotrophic microorganisms. The inventors believe that in fact the enzymes that utilise NADPH are positively desirable as they have increased activity in its presence when compared to their activity in the presence of NADH.

The finding that NADPH-dependent enzymes can be used to drive production of desirable products has led the inventors to engineer novel recombinant microorganisms which can express or over-express these enzymes. These recombinant microorganisms enable novel pathways to be explored and desirable products to be produced. In particular embodiments, the recombinant microorganisms are carboxydotrophic microorganisms. Whereas it was previously thought that NADPH dependent enzymes should be avoided or bypassed, the inventors have surprisingly shown that utilization of these enzymes in carboxydotrophic microorganisms does not cause a decrease in microbial growth and/or production and that extensive engineering to avoid such enzymes is not necessary.

According to the first aspect of the invention, there is provided a recombinant carboxydotrophic Clostridia microorganism adapted to express one or more exogenous NADPH-dependent enzymes, and/or adapted to over-express one or more endogenous enzymes, the enzymes selected such that when the exogenous enzyme is expressed, and/or the endogenous enzyme is overexpressed, the overall utilisation of NADPH by the microorganism is increased relative to a parental microorganism.

In a further aspect, the invention also provides a method of producing a recombinant carboxydotrophic Clostridia microorganism which exhibits increased NADPH utilisation relative to a parental microorganism, the method comprising:
 a. selecting one or more exogenous and/or endogenous NADPH-dependent enzymes;
 b. transforming a parental microorganism to yield a recombinant microorganism which is adapted to express the one or more exogenous enzymes, and/or over-express the one or more endogenous enzymes.

The expression or over-expression of any one or more of the NADPH-dependent enzymes in the microorganism results in an overall increase in the utilisation of NADPH relative to a microorganism in which the one or more enzymes are not expressed or are not over-expressed.

The one or more enzymes may exist in NADH and NADPH dependent isoforms. In a particular embodiment the recombinant microorganism is adapted to express and/or overexpress the NADPH-dependent isoform. The methods of the invention are of particular utility where the utilisation of NADPH and NADH is in similar range, i.e. the activity of the isoform utilising the co-factor when it binds to an NADH co-factor is similar to the activity of an isoform when it binds to a NADPH co-factor.

In a particular embodiment, the one or more NADPH-dependent enzymes comprises hydrogenase (for example having an amino acid sequence as per Seq.ID 6, 8, 10, 12, 14, 16, 18, 20, 22, 24, 26, 28, 30, 32, YP_003781016, YP_003781017, YP_003778879, YP_003779640, YP_003779893, YP_003780193, or a functionally equivalent variant of any one thereof), formate dehydrogenase (having an amino acid sequence for example of AEI90721, AEI90723, AEI90725, YP_003779063, YP_003778871, YP_003780168, AEI90722, AEI90724, AEI90726, or a functionally equivalent variant of any one thereof) or methylene-THF-dehydrogenase (having an amino acid sequence, for example, of AEI90753, YP_003781891, AEI90771 or a functionally equivalent variant thereof).

In particular embodiments of the invention, there exists a choice of NADPH and NADH dependent reactions. The invention provides a recombinant microorganism and a method that preferentially makes use of the NADPH-dependent isoforms compared to the NADH dependent isoforms as a way of increasing the overall utilization of NADPH relative to NADPH utilization in a parental microorganism. Examples of such pathways and oxidoreductase reactions include:
 Mevalonate pathway for isoprenoid production:
 Hydroxymethylglutaryl-CoA (HMG-CoA) reductase (S. M. Ma et al., 2011):
  NADPH-dependent enzyme (EC 1.1.1.34; GO:0004420; e.g. *Saccharomyces cerevisiae*: DAA09822.1; BK006946.2:115734..118898) and NADH-dependent enzyme (EC1.1.1.88; GO:0042282; e.g. *Pseudomonas mevalonii*: P13702.1)

Butanol/PHB pathway (Bond-Watts, Bellerose, & Chang, 2011):

3-hydroxybutyryl-CoA dehydrogenase/acetoacetyl-CoA reductase/3-hydroxybutyryl-CoA hydratase:
NADPH dependent phaB (EC:1.1.1.36; GO:0018454; e.g. from *Ralstonia eutropha*:YP_725942.1, GeneID: 4249784) and
NADPH dependent phaJ (EC 4.2.1.119; e.g. from *Aeromonas punctata*: BAA21816.1)
NADH dependent hbd (EC 1.1.1.157; GO:0008691; e.g. from *C. acetobutylicum*: NP_349314.1, GeneID: 1118891)

Crotonyl-CoA reductase/crotonyl-CoA carboxylase-reductase/trans-2-enoyl-CoA reductase/butyryl-CoA dehydrogenase (Hu et al., 2012):
NADPH dependent ccr (EC 1.3.1.86; e.g. from *Streptomyces collinus*) or ccr$_{Rs}$ (EC 1.3.1.85; e.g. from *Rhodobacter sphaeroides*: YP_354044.1, Gene ID: 3720751)
NADH dependent ter (EC 1.3.1.44; GO:0050343; e.g. from *Treponema denticola*)
NADH/ferredoxin bifurcating bcd-etfAB complex (EC 1.3.8.1; GO:0004085; e.g. from *C. acetobutylicum*: NP_349317.1; GeneID:1118894) (Li et al., 2008) or
NADH/NADPH bifunctional dependent ter (EC 1.3.1.44; GO:0050343; e.g. from *Euglena gracilis*: AY741582.1) (Hoffmeister, Piotrowski, Nowitzki, & Martin, 2005)

For most oxidoreductase reactions involving dehydrogenases (e.g. alcohol dehydrogenases for ethanol or butanol, or diol dehydrogenases for butanediol) and oxidases, a choice of either NADH or NADPH dependent enzymes is available and respective enzymes can be identified using databases such as Braunschweig Enzyme database BRENDA (Scheer et al., 2011).

In a particular embodiment the microorganism is adapted to express and/or over-express an NADPH-dependent isoform while the expression of a corresponding NADH-dependent isoform is unchanged, decreases, or exhibits a comparatively smaller increase when compared to the change in expression of the NADPH-dependent isoform. In this way, the overall utilisation of NADPH is increased relative to a parental microorganism.

In a particular embodiment, the invention provides a recombinant microorganism with attenuated or zero expression of one or more NADH-dependent enzymes. In one particular embodiment, the expression of the one or more NADH-dependent isoforms has been attenuated or knocked out compared to a parental microorganism. Attenuation/knockout may be achieved by modifying a nucleic acid encoding the one or more NADH-dependent enzyme or replacing one or more nucleic acid encoding an NADH-dependent isoform with one or more nucleic acid encoding an NADPH-dependent isoform. Attenuation or knock-out of the enzyme may be achieved by transformation of a parental microorganism to arrive at the microorganisms of the invention using any number of known transformation and recombinant nucleic acid techniques. Particular methods that can achieve attenuation or knock-out in carboxydotrophic acetogens are described in Leang, Ueki, & Lovley, 2011 and further techniques are described for example in Sambrook et al, (Molecular Cloning: A laboratory manual, Cold Spring Harbor Laboratory Press, Cold Spring Harbor, N.Y., 1989). By way of general example, in the case of introducing a mutation into a gene, or otherwise disrupting or knocking out a gene, an appropriate nucleic acid construct or vector can be designed to integrate into the genome of the parental microorganism to disrupt the gene. Such constructs will typically include nucleic acid sequences (arms) homologous to a region within or flanking the gene to be disrupted, which allow for homologous recombination to occur, and the introduction of a mutation, the excision of a region of nucleic acid from the gene, or the substitution of a region of the gene with a nucleic acid on the contrast, to occur. While it is preferred that the arms on the constructs have 100% complementarity to the region in the genome which they are targeted to, this is not necessary, provided that the sequence is sufficiently complementary to allow for targeted recombination with the genetic region of interest. Typically, the arms will have a level of homology which would allow for hybridisation to a target region under stringent conditions, as defined in Sambrook et al 1989. Skilled persons will appreciate nucleic acid sequences sufficient to allow for targeted homologous recombination and integration of an exogenous nucleic acid into the genome of a parental microorganism having regard to the available sequence information for the enzymes involved in the invention as described herein.

In one embodiment, the enzyme may exhibit multiple cofactor dependence. Such enzymes may comprise a NADH/ferredoxin bifurcating enzyme or a NADH/NADPH co-dependent enzyme. In a particular embodiment, the enzyme exists in an NADH/NADPH bifurcating isoform and an NADH/Ferredoxin bifurcating isoform and the microorganism is adapted to express and/or overexpress the NADH/NADPH dependent isoform. In a particular embodiment, the NADH/NADPH dependent isoform is ter (EC 1.3.1.44; GO:0050343; from *Euglena gracilis*: AY741582.1 or a functionally equivalent variant thereof). In a further embodiment, the NADH/Fd dependent isoform is NADH/ferredoxin bifurcating bcd-etfAB complex (EC 1.3.8.1; GO:0004085; e.g. from *C. acetobutylicum*: NP_349317.1; GeneID:1118894 or a functionally equivalent variant thereof).

In a particular embodiment of the invention, the microorganism exhibits increased efficiency during a fermentation reaction when compared to a parental microorganism. Microorganisms involved in the production of fermentation products use NADPH as a co-factor to drive reactions involved in growth and production of fermentation products. If such microorganisms express enzymes with a high affinity for NADPH cofactors when compared to NADH cofactors, there exists the potential for their efficiency (see definition above) to be increased if there is an increase of the utilisation of NADPH.

Enzymes of the invention are involved in the biosynthetic pathways to produce a number of products. In particular embodiments, the pathway is the mevalonate pathway or the butanol synthesis pathway.

In one embodiment of the invention, the co-factor specificity of the one or more NADPH-dependent enzymes may be modified to increase its NADPH co-factor specificity relative to its NADH co-factor specificity.

In a particular embodiment, the invention provides a method of increasing the efficiency of a carboxydotrophic microorganism by increasing the NADPH co-factor specificity of an oxidoreductase enzyme relative to the NADH co-factor specificity of the enzyme.

The co-factor specificity of oxidoreductase enzymes may be modified from NADH to NADPH (or vice versa) by modifying the amino acid sequence, particularly in a region of the enzyme contributing to or forming a part of the respective NADH and NADPH binding pockets. The NADH/NADPH binding pocket may be modified in other ways known in the art.

Modification of the amino acid sequence may comprise the addition, deletion and/or substitution of one or more amino acid residues, or one or more other modifications that may be readily known in the art. The modification may occur in any region of an enzyme. However, in one embodiment it is in the NADH binding pocket.

In a particular embodiment, the modification of the amino acid sequence comprises the modification of particular amino acid residue(s) in NADH binding pocket as for example of a glutamic acid residue for butyryl-CoA dehydrogenase enzyme. In a particular embodiment, the glutamic acid residue is Glu75 in bcd of *C. acetobutylicum* and/or Glu80 in *T. denticola*. In one embodiment, modifications to achieve desired co-factor specificity known in the art, for example the modifications described in Hu et al (2012) may be used.

In a particular embodiment, the inventors envisage that the modification of co-factor specificity may be achieved through structural analysis of the above-mentioned Crotonyl-CoA reductase/trans-2-enoyl-CoA reductase/butyryl-CoA dehydrogenase from various species and conservation of Glu (Glu75 in bcd of *C. acetobutylicum* and Glu80 in *T. denticola*) which plays an important role in discriminating NADH against NADPH. Without wishing to be bound by theory, it is believed that this occurs by the enzyme recognizing the 2'-OH of the adenine ribose of NADH. In NADPH dependent enzymes this residue is modified (Hu et al., 2012).

Methods to achieve the modification of co-factor specificity will be known to one of skill in the art. However, by way of example, the methods used in the following examples which relate to change of co-factor specificity for various oxidoreductase enzymes may be used:

1,3-propanediol oxidoreductase (C. Ma, Zhang, Dai, & Xiu, 2010)

p-hydroxybenzoate hydroxylase (Eppink, Overkamp, Schreuder, & Van Berkel, 1999)

17β-hydroxysteroid dehydrogenase (McKeever et al., 2002)

Ketol Acid Reductoisomerase (Rane & Calvo, 1997)

Novel Bifurcating Enzyme

Electron-bifurcation is a recently discovered mechanism of coupling endergonic to exergonic redox reactions in the cytoplasm of anaerobic bacteria and Archaea. To date, only a few electron-bifurcating enzyme complexes have been identified and 4 have been characterized (Herrmann, Jayamani, Mai, & Buckel, 2008; Huang et al., 2012; Li et al., 2008; Schuchmann & Mueller, 2012; Schut & Adams, 2009; G. Wang & Wang, 1984). In 2008 it was discovered that in butyric acid forming Clostridia the exergonic reduction of crotonyl-CoA (Eo'=−10 mV) with NADH (Eo'=−320 MV) is coupled with the endergonic reduction of ferredoxin (Eo'=−400 mV) with NADH and that the coupled reaction is catalyzed by the cytoplasmic butyryl-CoA dehydrogenase-electron transfer flavoprotein complex Bcd-EtfAB (Herrmann, Jayamani, Mai, & Buckel, 2008; Li et al., 2008). It is suggested that this process is flavin-based: a protein bound flavin is reduced by NADH to the hydroquinone which is subsequently re-oxidized by crotonyl-CoA to the semi-quinone radical which has a redox potential sufficiently negative to reduce ferredoxin (Fd). To date, few electron-bifurcating enzyme complexes have been identified and 4 have been characterized (Herrmann et al., 2008; Huang et al., 2012; Li et al., 2008; Schuchmann & Mueller, 2012; Schut & Adams, 2009; G. Wang & Wang, 1984). Beside the Bcd-EtfAB complex of reaction 1, the MvhADG-HdrABC complex from methanogenic Archaea catalyzing reaction 2, the NfnAB complex from bacteria and archaea catalyzing reaction 3 and the HydABC complex from bacteria catalyzing reaction 4.

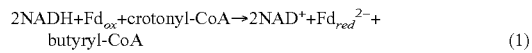

(1)

$\Delta G^{o\prime} = -44$ kJ/mol*

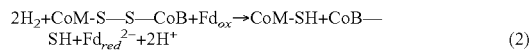

(2)

$\Delta G_o' = -50$ kJ/mol*

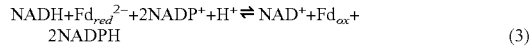

(3)

$\Delta G_o' = -16$ kJ/mol*

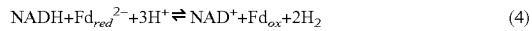

(4)

$\Delta G_o' = +21$ kJ/mol*

*Under standard conditions (1 M concentrations of substrates and products; partial pressure of gases=1 bar; pH=7) using an Eo' of −400 mV All of these complexes are NADH dependent, amongst them two a heteromeric Fe-only hydrogenase reversibly coupling the endergonic reduction of ferredoxin with $H_2$ with the exergonic reduction of NAD with $H_2$ (Schuchmann & Mueller, 2012; Schut & Adams, 2009). The inventors have identified for the first time an NADPH dependent bifurcating enzyme (reaction 5), a novel electron-bifurcating [FeFe]-hydrogenase that is NADP rather than NAD specific.

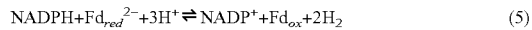

(5)

$\Delta G_o' = +21$ kJ/mol*

*Under standard conditions (1 M concentrations of substrates and products; partial pressure of gases=1 bar; pH=7) using an Eo' of −400 mV Without being bound to this theory, the role of this complex in addition to a hydrogenase is to act as formate:hydrogen lyase. In this function it represents an electron overflow valve for NADPH driven product formation by forming $H_2$ and formate by reduction of protons and $CO_2$, respectively, when the intracellular redox potential of the $Fd_{ox}/Fd_{red}^{2-}$ couple and of the NADP+/NADPH couple get too low due to CO overreduction.

Under in vivo conditions the redox potential E' of the NAD+/NADH couple is about −280 mV (Eo'=−320 mV) and E' of the NADP+/NADPH couple is about −360 mV (Eo'=−320 mV). The redox potential E' of the $Fd_{ox}/Fd_{red}^{2-}$ couple is −400 mV (Eo' from *C. pasteurianum* ferredoxin) which is considerably lower. As such, this bifurcation process aspect of the invention provides advantages such as faster reaction rates.

Figure 7:
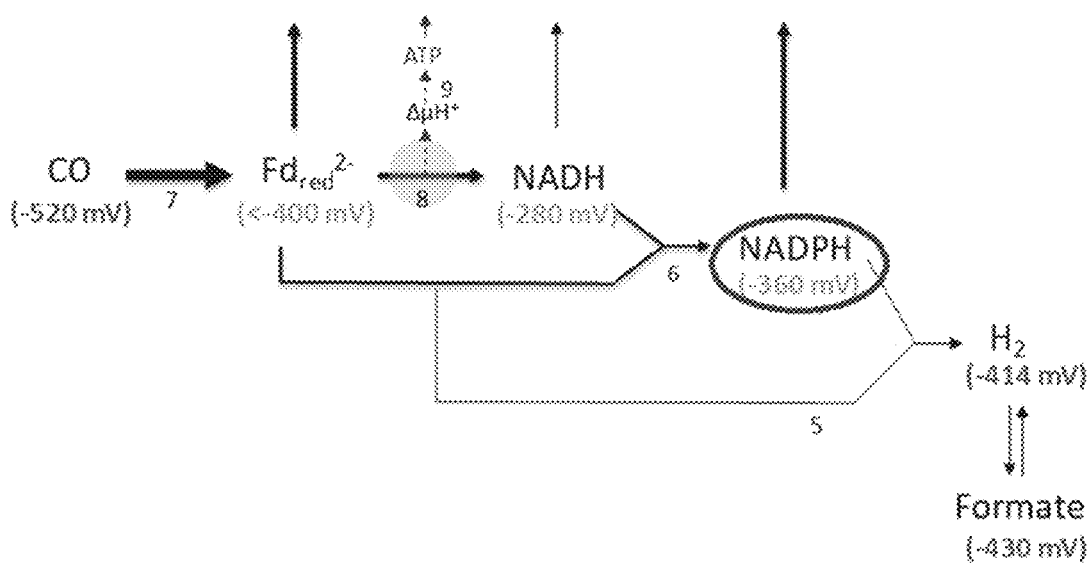
FIG. 7 shows NADPH driven product formation during growth on CO via novel electron-bifurcating NADP Fe-only hydrogenases/NADP formate dehydrogenase/formate-hydrogen lyase complexes.
Figure 8:
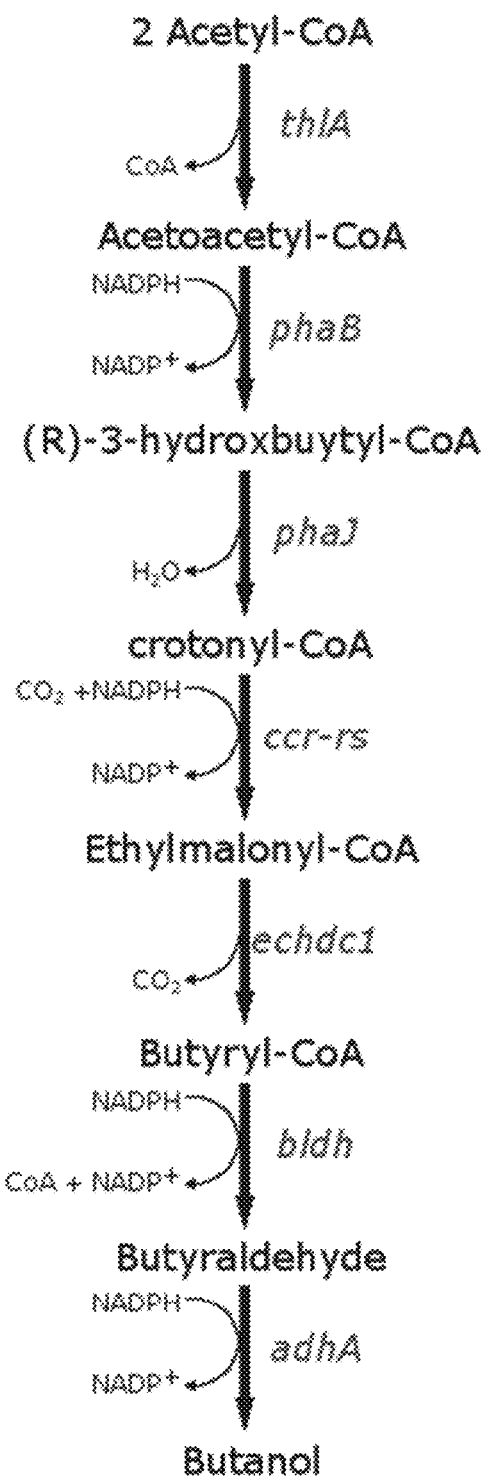
FIG. 8 shows the complete NADPH-dependent pathway for butanol biosynthesis. Each step is catalysed by and enzyme encoded in the gene annotated in italics.

Under In vivo conditions, the redox potential of ferredoxin is predicted to be near −500 mV, NADP at a redox potential near −370 mV and NAD at a redox potential near −280 mV. The redox potential difference between the $Fd_{ox}/Fd_{red}^{2-}$ couple and of the NAD+/NADH couple of about 200 mV is large enough to be coupled with electron transport phosphorylation mediated by the membrane associated Rnf complex and an $F_oF_1$ ATP synthase. It is predicted that $NAD^+$ reduction with ferredoxin is the main coupling site in the energy metabolism of *C. autoethanogenum* growing on CO. $NAD^+$ is continuously regenerated via the Nfn catalyzed reaction yielding NADPH that can then drive product formation (FIG. 7).

The inventors have identified a novel electron-bifurcating [FeFe]-hydrogenase that is NADP rather than NAD specific. The inventors have also identified that a formate dehydrogenase expressed in *C. autoethanogenum* can utilise both ferredoxin and NADPH rather than only NADPH (referred to herein as a bifurcating formate dehydrogenase).

The novel functions of these enzymes were previously unknown and are the first NADPH-dependent bifurcating NADP Fe-only hydrogenase and bifurcating NADP formate dehydrogenase enzymes to be identified. Further studies by the inventors have indicated that the NADP Fe-only hydrogenase and the NADP formate dehydrogenase form an enzyme complex, referred to herein as a formate-hydrogen lyase complex. In particular embodiments, this complex also has utility in the production of recombinant microorgansisms for achieving multiple co-factor dependence.

Accordingly, the invention provides the use of a recombinant microorganism, a polypeptide, or a polynucleotide expressing or encoding said enzyme for the purpose of utilising multiple co-factors (for example ferredoxin and NADPH) in a reaction. In a particular embodiment, the polypeptide comprises a bifurcating NADP formate dehydrogenase according to AEI90721, YP_003778871, AEI90722, or a functionally equivalent variant of any one thereof.

In a particular embodiment, the bifurcating NADP Fe-only hydrogenase is selected from the group consisting of SEQ ID NO:10, SEQ ID NO:26 and YP_003778879, and a functionally equivalent variant of any one or more thereof.

In a particular embodiment, the bifurcating formate-hydrogen lyase complex is encoded by SEQ ID NOs:65 to 67 or a functionally equivalent variant thereof.

In a particular embodiment, the polynucleotide encoding a bifurcating NADP Fe-only hydrogenase, NADP formate dehydrogenase or formate-hydrogen lyase complex, comprises one or more polynucleotides selected from the group consisting of HQ876015, CLJU_c06990, AEI90722, SEQ ID NO:9, SEQ ID NO:25, CLJU_c07070, SEQ ID NOs: 67 to 69 and a functionally equivalent variant of any one or more thereof.

Figure 3:
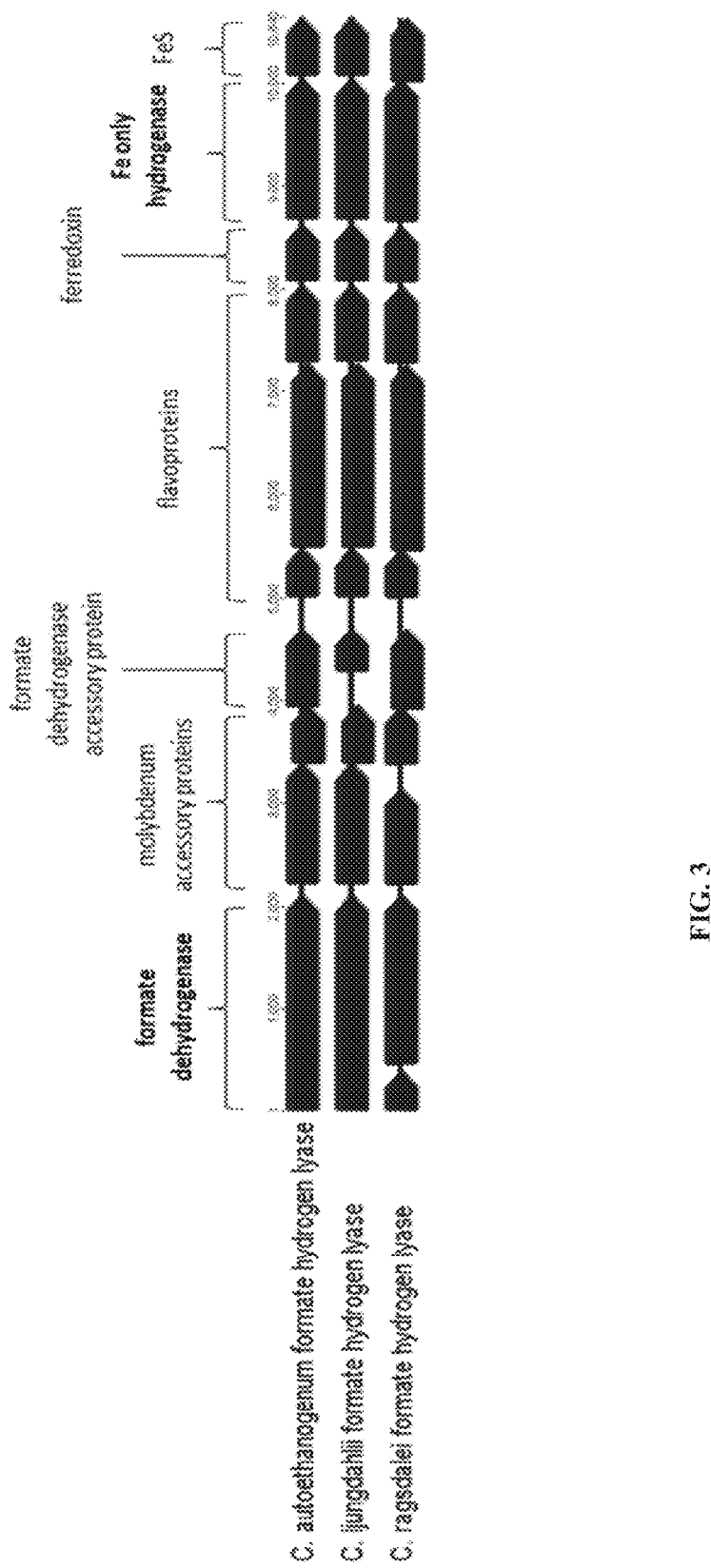
FIG. 3 Shows the organization of formate dehydrogenase and hydrogenase genes able to form a formate-hydrogen lyase complex.

The protein encoding genes for the bifurcating NADP formate dehydrogenase and the bifurcating NADP Fe-only hydrogenase were found by the inventors in a single gene cluster, along with genes for an iron-sulfur flavoprotein with a NADP binding site, iron-sulfur (FeS) proteins and a selenocysteine- and molybdopterin-containing formate dehydrogenase (FIG. 3). It is proposed by the inventors that these genes encode a functional complex which will be referred to herein as a formate hydrogen lyase (see example 1). Iron-sulfur flavoprotein, iron-sulfur (FeS) proteins and formate and molybdenum accessory proteins comprise which make up the gene cluster are encoded by the polypeptides as shown in the table 1 below:

TABLE 1

Sequences for complete formate-hydrogen lyase complex cluster of *C. autoethanogenum*: Seq ID 65, *C. ljungdahlii*: Seq ID 66, and *C. ragsdalei*: Seq. ID 67).

| | *C. autoethanogenum* | *C. ljungdahlii* | *C. ragsdalei* |
|---|---|---|---|
| Formate dehydrogenase | HQ876015; AEI90721 | CLJU_c06990; YP_003778871 | HQ876016; AEI90722 |
| Molybdenum cofactor biosynthesis protein | Seq ID 33-34 | CLJU_c07000; YP_003778872 | Seq ID 49-50 |
| Molybdopterin-guanine dinucleotide biosynthesis protein | Seq ID 35-36 | CLJU_c07010; YP_003778873 | Seq ID 51-52 |
| Formate dehydrogenase accessory protein | Seq ID 37-38 | CLJU_c07020; YP_003778874 | Seq ID 53-54 |

TABLE 1-continued

Sequences for complete formate-hydrogen lyase complex cluster of *C. autoethanogenum*: Seq ID 65, *C. ljungdahlii*: Seq ID 66, and *C. ragsdalei*: Seq. ID 67).

| | *C. autoethanogenum* | *C. ljungdahlii* | *C. ragsdalei* |
|---|---|---|---|
| Oxidoreductase Flavoprotein | Seq ID 39-40 | CLJU_c07030; YP_003778875 | Seq ID 55-56 |
| Oxidoreductase Flavoprotein | Seq ID 41-42 | CLJU_c07040; YP_003778876 | Seq ID 57-58 |
| Oxidoreductase Flavoprotein | Seq ID 43-44 | CLJU_c07050; YP_003778877 | Seq ID 59-60 |
| 4Fe—4S ferredoxin | Seq ID 45-46 | CLJU_c07060; YP_003778878 | Seq ID 61-62 |
| Fe-only hydrogenase | Seq ID 9-10 | CLJU_c07070; YP_003778879 | Seq ID 25-26 |
| FeS cluster | Seq ID 47-48 | CLJU_c07080; YP_003778880 | Seq ID 63-64 |

The invention also provides a recombinant carboxydotrophic microorganism expressing the novel bifurcating NADP Fe-only hydrogenase, bifurcating NADP formate dehydrogenase and/or a formate-hydrogen lyase, when used for the purpose of utilising multiple co-factors in a reaction. Preferably, the multiple co-factors comprise ferredoxin and NADPH.

The invention also provides a method of increasing the efficiency of the fermentation of a CO-containing substrate by using a recombinant carboxydotrophic microorganism expressing a bifurcating hydrogenase as described above. The efficiency is increased due to the bifurcating enzyme utilising both ferredoxin and NADPH rather than only NADPH. The more negative redox potential of ferredoxin compared to NADPH provides greater energetic potential to the reaction therefore increasing the reaction rate and CO substrate throughput.

In addition, the inventors have identified a novel Nfn enzyme in carboxydotrophic *Clostridium* species including *C. autoethanogenum*, *C. ljungdahlii* and *C. ragsdalei*. This Nfn enzyme is able to reduce $NADP^+$ to $NADPH+H^+$ to replenish the pool at the expense of $NADH^++H^+$ (or vice versa) (reaction 2):

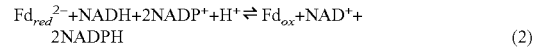

$$Fd_{red}^{2-}+NADH+2NADP^++H^+ \rightleftharpoons Fd_{ox}+NAD^++2NADPH \qquad (2)$$

This enzyme has been described for only one organism so far, *C. kluyveri* (S. Wang et al., 2010), where it is composed of two subunits NfnA and NfnB that form a complex. The inventors identified activity in cells of *C. autoethanogenum* and identified the corresponding gene (example 4). This is the first time a single Nfn gene has been identified and the first identified Nfn enzyme in carboxydotrophic organisms. Having only one subunit, rather than a complex of two subunits has advantages including in producing and modifying the enzyme.

Without being bound to this theory, the inventors believe that the two novel complexes electron-bifurcating NADP Fe-only hydrogenases/NADP formate dehydrogenase/formate-hydrogen lyase and Nfn complex play a crucial role in energy conservation and formation of reduced product from CO, which is driven by NADPH along with described ferredoxin dependent Carbon monoxide dehydrogenase (CODH), $F_oF_1$ Rnf complex (Köpke et al., 2010; Tremblay, Zhang, Dar, Leang, & Lovley, 2012) of reactions 7-9 (FIG. 7).

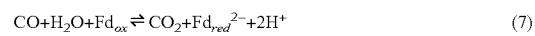

$$CO+H_2O+Fd_{ox} \rightleftharpoons CO_2+Fd_{red}^{2-}+2H^+ \qquad (7)$$

$$Fd_{red}^{2-}+NAD^++H^+ \rightleftharpoons Fd_{ox}+NADH+\Delta\mu H^+ \qquad (8)$$

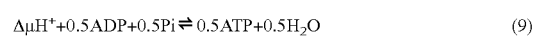

$$\Delta\mu H^++0.5ADP+0.5Pi \rightleftharpoons 0.5ATP+0.5H_2O \qquad (9)$$

Ferredoxin operates in vivo at a redox potential more negative than −400 mV, NADP at a redox potential near −360 mV and NAD at a redox potential near −280 mV. The redox potential difference between the $Fd_{ox}/Fd_{red}^{2-}$ couple and of the $NAD^+/NADH$ couple of more than 120 mV is large enough to be coupled with electron transport phosphorylation mediated by the membrane associated Rnf complex (reaction 8) and an $F_OF_1$ ATP synthase (reaction 9). $NAD^+$ is continuously regenerated via the Nfn complex catalyzed reaction 6 yielding NADPH and via other NADH dependent reactions. NADPH can then be used to drive product formation along with other NADPH dependent reactions identified (FIG. 7).

Because of the highly negative redox potential of CO (−520 mV), it is likely to over reduce ferredoxin and NADP when these electron carriers cannot be re-oxidized rapidly enough. One way to increase the rate of ferredoxin- and NADPH re-oxidation is to increase the rate of reduced product formation selecting NADPH dependent reactions.

The results in table 2 below show that carboxydotrophic microorganisms expressing the Nfn enzyme have the capacity to convert NADH to NADPH for use by NADPH-dependent enzymes.

TABLE 2

| | Reaction substrate | Enzyme activity |
|---|---|---|
| Nfn | $NADPH + NAD^+ + Fd_{ox}$ | 0.7 |
| | $NADPH + Fd_{ox}\text{-RS} + NAD^+$ | 0.3 |
| | $NADPH + NAD^+$ | 0.09 |

The Nfn enzyme was found by the inventors to be traced back to a single gene/protein (Seq. ID Nos 1 and 2 respectively in *C. autoethanogenum*), not two as in *C. kluyveri*. A similar gene encoding this enzyme is also present in *C. ljungdahlii* (YP_003781852.1; CLJU_c37240) (where it is annotated as glutamate synthase) and *C. ragsdalei* (Seq_ID Nos: 3 and 4).

The inventors envisage that upregulating the expression of the Nfn gene, or a functional variant thereof, in a recombinant microorganism will enable an increase in the efficiency of NADPH-dependent enzymes and lead to higher product output from a fermentation reaction.

Accordingly, in a particular aspect, the invention provides a method of increasing the efficiency of production of a microorganism by expressing or over-expressing an Nfn enzyme complex.

In a particular embodiment, the invention provides the use of a recombinant microorganism to convert NADH to NADPH increasing the NADPH pool size, wherein the recombinant microorganism is adapted to express and/or overexpress a single Nfn enzyme. In a particular embodiment, the Nfn enzyme comprises the amino acid sequence of SEQ_ID No. 2, 4, YP_003781852.1, CLJU_c37240 or a functionally equivalent variant of any one thereof with at least 76%, 80%, 85%, 90%, 95%, or 99% sequence identity. The Nfn enzyme converts NADH to NADPH therefore when expressed in the presence of NADH and NADPH-dependent enzymes, enzyme efficiency is increased leading to a faster reaction rate and faster regeneration rate of NADPH.

In a particular embodiment, the microorganism comprises a carboxydotrophic Clostridia microorganism. In a further embodiment, the microorganism is selected from the group of carboxydotrophic Clostridia comprising *Clostridium autoethanogenum*, *Clostridium ljungdahlii*, *Clostridium ragsdalei*.

The invention also provides the use of a polypeptide to convert NADH to NADPH, wherein the polypeptide comprises a single Nfn enzyme according to SEQ ID NO: 2, 4, YP_003781852.1, CLJU_c37240, or a functionally equivalent variant of any one thereof. Further, the invention provides the use of a polynucleotide to convert NADH to NADPH, wherein the polynucleotide encodes a single Nfn enzyme, the polynucleotide comprising SEQ ID NO: 1, 3, the sequence encoding CLJU_c37240 or YP_003781852.1, or a functionally equivalent variant thereof with at least 83%, 85%, 90%, 95%, or 99% sequence identity.

In a further aspect, the invention provides a polynucleotide according to SEQ_ID NO. 1 or 3.

In a further aspect, the invention provides a polypeptide according to SEQ_ID NO. 2 or 4. In a further aspect, the invention provides a vector and/or a recombinant microorganism comprising a novel Nfn polynucleotide, and/or a polynucleotide encoding a novel Nfn polypeptide of the invention.

In a particular embodiment, the invention provides for the optimization of NADH-dependent reactions. In this case, the respective NADPH dependent hydrogenase, formate dehydrogenase, formate-hydrogen lyase, and/or methylene-THF-dehydrogenase could be replaced with corresponding NADH-dependent enzymes, e.g. from *Moorella thermoacetica* or *A. woodii*. This would optimize flux through pathways designed and optimized for NADH. This embodiment would have particular utility where no NADPH-dependent enzyme is available or a recombinant organism comprising an NADPH-dependent enzyme cannot be effectively engineered.

In order to increase the expression of a particular enzyme, the expression of the nucleic acid encoding that enzyme is increased. Methods to increase expression of a nucleic acid encoding the desirable enzyme are outlined below. Skilled persons may readily appreciate other techniques of use.

The invention may comprise nucleic acids encoding proteins and peptides referred to herein or may use nucleic acids encoding proteins and peptides of use in the invention. In one embodiment, a nucleic acid is a nucleic acid construct or vector. In one particular embodiment, the nucleic acid construct or vector is an expression construct or vector, however other constructs and vectors, such as those used for cloning are encompassed by the invention. In one particular embodiment, the expression construct or vector is a plasmid.

It will be appreciated that an expression construct/vector of the present invention may contain any number of regulatory elements in addition to the promoter as well as additional genes suitable for expression of further proteins if desired. In one embodiment the expression construct/vector includes one promoter. In another embodiment, the expression construct/vector includes two or more promoters. In one particular embodiment, the expression construct/vector includes one promoter for each gene to be expressed. In one embodiment, the expression construct/vector includes one or more ribosomal binding sites, preferably a ribosomal binding site for each gene to be expressed.

It will be appreciated by those of skill in the art that the nucleic acid sequences and construct/vector sequences described herein may contain standard linker nucleotides such as those required for ribosome binding sites and/or restriction sites. Such linker sequences should not be interpreted as being required and do not provide a limitation on the sequences defined.

Nucleic acids and nucleic acid constructs, including expression constructs/vectors of the invention may be constructed using any number of techniques standard in the art. For example, chemical synthesis or recombinant techniques may be used. Such techniques are described, for example, in Sambrook et al (Molecular Cloning: A laboratory manual, Cold Spring Harbor Laboratory Press, Cold Spring Harbor, N.Y., 1989). Further exemplary techniques are described in the Examples section herein after. Essentially, the individual genes and regulatory elements will be operably linked to one another such that the genes can be expressed to form the desired proteins. Suitable vectors for use in the invention will be appreciated by those of ordinary skill in the art. However, by way of example, the following vectors may be suitable: pMTL80000 vectors, pIMP1, pJIR750, and the plasmids exemplified in the Examples section herein after.

It should be appreciated that nucleic acids of the invention may be in any appropriate form, including RNA, DNA, or cDNA.

The invention also provides host organisms, particularly microorganisms, and including viruses, bacteria, and yeast, comprising any one or more of the nucleic acids described herein.

Method of Producing Recombinant Microorganisms

The one or more exogenous nucleic acids may be delivered to a parental microorganism as naked nucleic acids or may be formulated with one or more agents to facilitate the transformation process (for example, liposome-conjugated nucleic acid, an organism in which the nucleic acid is contained). The one or more nucleic acids may be DNA, RNA, or combinations thereof, as is appropriate. Restriction inhibitors may be used in certain embodiments; see, for example Murray, N. E. et al. (2000) *Microbial. Molec. Biol. Rev.* 64, 412.)

The microorganisms of the invention may be prepared from a parental microorganism and one or more exogenous nucleic acids using any number of techniques known in the art for producing recombinant microorganisms. By way of example only, transformation (including transduction or transfection) may be achieved by electroporation, ultrasonication, polyethylene glycol-mediated transformation, chemical or natural competence, protoplast transformation, prophage induction or conjugation. Suitable transformation techniques are described for example in, Sambrook J, Fritsch E F, Maniatis T: Molecular Cloning: A laboratory Manual, Cold Spring Harbour Laboratory Press, Cold Spring Harbour, 1989.

Electroporation has been described for several carboxydotrophic acetogens as *C. ljungdahlii* (Köpke et al. 2010, *Poc. Nat. Acad. Sci. U.S.A.* 107: 13087-92; (Leang et al., 2011) PCT/NZ2011/000203; WO2012/053905), *C. autoethanogenum* (PCT/NZ2011/000203; WO2012/053905), *Acetobacterium woodii* (Straetz et al., 1994, *Appl. Environ. Microbiol.* 60:1033-37) or *Moorella thermoacetica* (Kita et al., 2012) and is a standard method used in many Clostridia such as *C. acetobutylicum* (Mermelstein et al., 1992, *Biotechnology*, 10, 190-195), *C. cellulolyticum* (Jennert et al., 2000, *Microbiology*, 146: 3071-3080) or *C. thermocellum* (Tyurin et al., 2004, *Appl. Environ. Microbiol.* 70: 883-890). Prophage induction has been demonstrated for carboxydotrophic acetogen as well in case of *C. scatologenes* (Prasanna Tamarapu Parthasarathy, 2010, Development of a Genetic Modification System in *Clostridium scatologenes* ATCC 25775 for Generation of Mutants, Masters Project Western Kentucky University), while conjugation has been described as method of choice for many Clostridia including *Clostridium difficile* (Herbert et al., 2003, *FEMS Microbiol. Lett.* 229: 103-110) or *C. acetobuylicum* (Williams et al., 1990, *J. Gen. Microbiol.* 136: 819-826) and could be used in a similar fashion for carboxydotrophic acetogens.

In certain embodiments, due to the restriction systems which are active in the microorganism to be transformed, it is necessary to methylate the nucleic acid to be introduced into the microorganism. This can be done using a variety of techniques, including those described below, and further exemplified in the Examples section herein after.

By way of example, in one embodiment, a recombinant microorganism of the invention is produced by a method comprises the following steps:
 a. introduction into a shuttle microorganism of (i) of an expression construct/vector as described herein and (ii) a methylation construct/vector comprising a methyltransferase gene;
 b. expression of the methyltransferase gene;
 c. isolation of one or more constructs/vectors from the shuttle microorganism; and,
 d. introduction of the one or more construct/vector into a destination microorganism.

In one embodiment, the methyltransferase gene of step B is expressed constitutively. In another embodiment, expression of the methyltransferase gene of step B is induced.

The shuttle microorganism is a microorganism, preferably a restriction negative microorganism, that facilitates the methylation of the nucleic acid sequences that make up the expression construct/vector. In a particular embodiment, the shuttle microorganism is a restriction negative *E. coli*, *Bacillus subtillis*, or *Lactococcus lactis*.

The methylation construct/vector comprises a nucleic acid sequence encoding a methyltransferase.

Once the expression construct/vector and the methylation construct/vector are introduced into the shuttle microorganism, the methyltransferase gene present on the methylation construct/vector is induced. Induction may be by any suitable promoter system although in one particular embodiment of the invention, the methylation construct/vector comprises an inducible lac promoter and is induced by addition of lactose or an analogue thereof, more preferably isopropyl-β-D-thiogalactoside (IPTG). Other suitable promoters include the ara, tet, or T7 system. In a further embodiment of the invention, the methylation construct/vector promoter is a constitutive promoter.

In a particular embodiment, the methylation construct/vector has an origin of replication specific to the identity of the shuttle microorganism so that any genes present on the methylation construct/vector are expressed in the shuttle microorganism. Preferably, the expression construct/vector has an origin of replication specific to the identity of the destination microorganism so that any genes present on the expression construct/vector are expressed in the destination microorganism.

Expression of the methyltransferase enzyme results in methylation of the genes present on the expression construct/vector. The expression construct/vector may then be isolated from the shuttle microorganism according to any one of a number of known methods. By way of example only, the methodology described in the Examples section described hereinafter may be used to isolate the expression construct/vector.

In one particular embodiment, both construct/vector are concurrently isolated.

The expression construct/vector may be introduced into the destination microorganism using any number of known methods. However, by way of example, the methodology described in the Examples section hereinafter may be used. Since the expression construct/vector is methylated, the nucleic acid sequences present on the expression construct/vector are able to be incorporated into the destination microorganism and successfully expressed.

It is envisaged that a methyltransferase gene may be introduced into a shuttle microorganism and over-expressed.

Thus, in one embodiment, the resulting methyltransferase enzyme may be collected using known methods and used in vitro to methylate an expression plasmid. The expression construct/vector may then be introduced into the destination microorganism for expression. In another embodiment, the methyltransferase gene is introduced into the genome of the shuttle microorganism followed by introduction of the expression construct/vector into the shuttle microorganism, isolation of one or more constructs/vectors from the shuttle microorganism and then introduction of the expression construct/vector into the destination microorganism.

It is envisaged that the expression construct/vector and the methylation construct/vector as defined above may be combined to provide a composition of matter. Such a composition has particular utility in circumventing restriction barrier mechanisms to produce the recombinant microorganisms of the invention.

In one particular embodiment, the expression construct/vector and/or the methylation construct/vector are plasmids.

Persons of ordinary skill in the art will appreciate a number of suitable methyltransferases of use in producing the microorganisms of the invention. However, by way of example the *Bacillus subtilis* phage ΦT1 methyltransferase and the methyltransferase described in the Examples herein after may be used. In one embodiment, the methyltransferase has been described in WO/2012/053905.

Any number of constructs/vectors adapted to allow expression of a methyltransferase gene may be used to generate the methylation construct/vector. However, by way of example, the plasmid described in the Examples section hereinafter may be used.

Methods of Production

In an embodiment of the invention, the gaseous substrate fermented by the microorganism is a gaseous substrate containing CO. The gaseous substrate may be a CO-containing waste gas obtained as a by-product of an industrial process, or from some other source such as from automobile exhaust fumes. In certain embodiments, the industrial process is selected from the group consisting of ferrous metal products manufacturing, such as a steel mill, non-ferrous products manufacturing, petroleum refining processes, gasification of coal, electric power production, carbon black production, ammonia production, methanol production and coke manufacturing. In these embodiments, the CO-containing gas may be captured from the industrial process before it is emitted into the atmosphere, using any convenient method. The CO may be a component of syngas (gas comprising carbon monoxide and hydrogen). The CO produced from industrial processes is normally flared off to produce $CO_2$ and therefore the invention has particular utility in reducing $CO_2$ greenhouse gas emissions and producing a biofuel. Depending on the composition of the gaseous CO-containing substrate, it may also be desirable to treat it to remove any undesired impurities, such as dust particles before introducing it to the fermentation. For example, the gaseous substrate may be filtered or scrubbed using known methods.

It will be appreciated that for growth of the bacteria and the production of products to occur, in addition to the CO-containing substrate gas, a suitable liquid nutrient medium will need to be fed to the bioreactor.

In particular embodiments of the method aspects, the fermentation occurs in an aqueous culture medium. In particular embodiments of the method aspects, the fermentation of the substrate takes place in a bioreactor.

The substrate and media may be fed to the bioreactor in a continuous, batch or batch fed fashion. A nutrient medium will contain vitamins and minerals sufficient to permit growth of the micro-organism used. Anaerobic media suitable for fermentation using CO are known in the art. For example, suitable media are described Biebel (2001). In one embodiment of the invention the media is as described in the Examples section herein after.

The fermentation should desirably be carried out under appropriate fermentation conditions for the production of the biofuel to occur. Reaction conditions that should be considered include pressure, temperature, gas flow rate, liquid flow rate, media pH, media redox potential, agitation rate (if using a continuous stirred tank reactor), inoculum level, maximum gas substrate concentrations to ensure that CO in the liquid phase does not become limiting, and maximum product concentrations to avoid product inhibition.

In addition, it is often desirable to increase the CO concentration of a substrate stream (or CO partial pressure in a gaseous substrate) and thus increase the efficiency of fermentation reactions where CO is a substrate. Operating at increased pressures allows a significant increase in the rate of CO transfer from the gas phase to the liquid phase where it can be taken up by the micro-organism as a carbon source for the production of fermentation. This in turn means that the retention time (defined as the liquid volume in the bioreactor divided by the input gas flow rate) can be reduced when bioreactors are maintained at elevated pressure rather than atmospheric pressure. The optimum reaction conditions will depend partly on the particular micro-organism of the invention used. However, in general, it is preferred that the fermentation be performed at pressure higher than ambient pressure. Also, since a given CO conversion rate is in part a function of the substrate retention time, and achieving a desired retention time in turn dictates the required volume of a bioreactor, the use of pressurized systems can greatly reduce the volume of the bioreactor required, and consequently the capital cost of the fermentation equipment. According to examples given in U.S. Pat. No. 5,593,886, reactor volume can be reduced in linear proportion to increases in reactor operating pressure, i.e. bioreactors operated at 10 atmospheres of pressure need only be one tenth the volume of those operated at 1 atmosphere of pressure.

By way of example, the benefits of conducting a gas-to-ethanol fermentation at elevated pressures has been described. For example, WO 02/08438 describes gas-to-ethanol fermentations performed under pressures of 30 psig and 75 psig, giving ethanol productivities of 150 g/l/day and 369 g/l/day respectively. However, example fermentations performed using similar media and input gas compositions at atmospheric pressure were found to produce between 10 and 20 times less ethanol per liter per day.

It is also desirable that the rate of introduction of the CO-containing gaseous substrate is such as to ensure that the concentration of CO in the liquid phase does not become limiting. This is because a consequence of CO-limited conditions may be that one or more product is consumed by the culture.

The composition of gas streams used to feed a fermentation reaction can have a significant impact on the efficiency and/or costs of that reaction. For example, 02 may reduce the efficiency of an anaerobic fermentation process. Processing of unwanted or unnecessary gases in stages of a fermentation process before or after fermentation can increase the burden on such stages (e.g. where the gas stream is compressed before entering a bioreactor, unnecessary energy may be used to compress gases that are not needed in the fermentation). Accordingly, it may be desirable to treat substrate streams, particularly substrate streams derived from industrial sources, to remove unwanted components and increase the concentration of desirable components.

In certain embodiments a culture of a bacterium of the invention is maintained in an aqueous culture medium. Preferably the aqueous culture medium is a minimal anaerobic microbial growth medium. Suitable media are known in the art and described for example in U.S. Pat. Nos. 5,173,429 and 5,593,886 and WO 02/08438, and as described in the Examples section herein after.

Also, if the pH of the broth was adjusted as described above to enhance adsorption of acetic acid to the activated charcoal, the pH should be re-adjusted to a similar pH to that of the broth in the fermentation bioreactor, before being returned to the bioreactor.

EXAMPLES

Example 1

All five oxidoreductase enzyme steps of the Wood-Ljungdahl pathway were assayed to determine their activity in the presence of different substrates. These enzymes can use co-factors to drive the reaction. The enzymes are involved in autotrophic growth including uptake and utilization of CO, $CO_2$, and $H_2$ gases.

The enzymes assayed and their activities are detailed in FIG. 1. All assays performed were tested using a synthetic redox dye as control, either methyl viologen (MV) or benzyl viologen (BV). Co-factors ferredoxin (Fd), NADH and NADPH or a combination thereof was tested. Enzyme assays were performed using crude extracts from a typical reactor run growing autotrophically on CO and hydrogen.

Fermentation

Fermentations with *C. autoethanogenum* DSM23693 were carried out in 1.5 L bioreactors at 37° C. and CO-containing steel mill gas as sole energy and carbon source as described below. A defined medium containing per liter: MgCl, $CaCl_2$ (0.5 mM), KCl (2 mM), $H_3PO_4$ (5 mM), Fe (100 µM), Ni, Zn (5 µM), Mn, B, W, Mo, Se (2 µM) was used for culture growth. The media was transferred into the bioreactor and autoclaved at 121° C. for 45 minutes. After autoclaving, the medium was supplemented with Thiamine, Pantothenate (0.05 mg), Biotin (0.02 mg) and reduced with 3 mM Cysteine-HCl. To achieve anaerobicity the reactor vessel was sparged with nitrogen through a 0.2 µm filter. Prior to inoculation, the gas was switched to CO-containing steel mill gas, feeding continuously to the reactor. The feed gas composition was 2% $H_2$ 42% CO 20% $CO_2$ 36% $N_2$. The pH of the culture was maintained between 5 and 5.2.

Harvesting of Cells

At the time of harvesting the cells, the gas consumption was 5 moles CO $L^{-1}$ $day^{-1}$ and 10 milimoles $H_2$ $L^{-1}$ $day^{-1}$, with the following metabolites produced: 14 g $L^{-1}$ $day^{-1}$ Acetate and 19.5 g $L^{-1}$ $day^{-1}$ Ethanol. The pH of the culture was adjusted to pH 6 with $K_2CO_3$ and the reactor chilled in ice-water bath. ~1.2 L of culture was collected on ice. The culture was divided between 2×1-L centrifuge bottles (this and all subsequent steps were carried out in an anaerobic chamber to ensure anoxic conditions to avoid inactivation of the enzymes) and cells pelleted at 5000 rpm for 10 min. The supernatant was decanted, and residual liquid removed. Each pellet resuspended in ~30 mL of 50 mM K $PO_4$ pH 7.0 with 10 mM DTT. Resuspensions transferred to pre weighed 50-mL-Falcon-tubes and cells repelleted at max speed (5000 g) for 15 min. Tubes removed from anaerobic chamber and immediately frozen on liquid $N_2$ before assaying.

Preparation of Crude Cell Extracts and Enzyme Assays

Cells were harvested from a continuous reactor under anoxic conditions. They were disrupted by three passes through a French press as described by (Huang et al., 2012).

Except where indicated, all assays were performed at 37° C. in 1.5-ml-anaerobic cuvettes closed with a rubber stopper filled with 0.8 ml reaction mixture and 0.7 ml $N_2$ or $H_2$ or CO at $1.2 \times 10^5$ Pa as described by (Huang et al., 2012).

CO dehydrogenase, formate dehydrogenase, Methylene-THF dehydrogenase, and Methylene-THF reductase were all assayed as described by (Huang et al., 2012).

CO dehydrogenase was measured using an assay mixture that contained 100 mM Tris/HCl (pH 7.5), 2 mM DTT and about 30 µM ferredoxin and/or 1 mM $NAD^+$ or 1 mM $NADP_+$. The gas phase was 100% CO.

Hydrogenase activity was measured as described, with the addition of measuring the $NADP^+$ dependent ferredoxin reduction with $H_2$. The reaction mixture was supplemented with ferredoxin (30 µM) and 1 mM NADP. The gas phase was 100% $H_2$. After the start of the reaction with enzyme ferredoxin reduction was followed at 430 nm ($\epsilon_{\Delta ox-red} \approx 13.1$ $mM^{-1}$ $cm^{-1}$).

Formate-Hydrogen lyase activity was measured in a 5-ml anaerobic serum bottle closed with a rubber stopper filled with 0.8 ml reaction mixture and 4.2 ml N2 at $1.2 \times 10^5$ Pa. The reaction mixture contained 100 mM Tris-HCl pH 7.5 and 20 mM formate. After initiating the reaction by addition of enzyme, $H_2$ production was monitored by gas chromatography. Formate-Hydrogen lyase activity for reduction of $CO_2$ with $H_2$ to formate was measured with an assay mixture containing 100 mM potassium phosphate, 2 mM DTT, and 30 mM [$^{14}C$]$K_2CO_3$ (24,000 dpm/µmol). The gas phase was 100% $H_2$. The serum bottles were continuously shaken at 200 rpm to ensure equilibration of the gas phase with the liquid phase. After start of the reaction with enzyme, 100 µl liquid samples were withdrawn every 1.5 min and added into a 1.5-ml safe seal micro tube containing 100 µl of 150 mM acetic acid to stop the reaction by acidification. The 200 µl mixture was then incubated at 40° C. for 10 min with shaking at 1,400 rpm in a Thermomixer to remove all $^{14}CO_2$ leaving behind the $^{14}C$-formate formed. Subsequently, 100 µl of the mixture was added to 5 ml of Quicksave A scintillation fluid (Zinsser Analytic, Frankfurt, Germany) and analyzed for $^{14}C$ radioactivity in a Beckman LS6500 liquid scintillation counter (Fullerton, Calif.).

Formate dehydrogenase measurement was carried out with assay mixtures containing 100 mM Tris/HCl (pH 7.5) or 100 mM potassium phosphate, 2 mM DTT, 20 mM formate and, where indicated 25 µM ferredoxin, 1 mM $NADP^+$, 1 mM $NAD^+$ and/or 10 mM methyl viologen. The gas phase was 100% $N_2$.

Methylene-$H_4F$ dehydrogenase was measured using an assay mixture containing 100 mM MOPS/KOH (pH 6.5), 50 mM 2-mercaptoethanol, 0.4 mM tetrahydrofolate, 10 mM formaldehyde and 0.5 mM $NADP^+$ or 0.5 mM $NAD^+$. The gas phase was 100% $N_2$.

Methylene-H4F reductase was assayed under the following conditions. The assay mixtures contained 100 mM Tris/HCl (pH 7.5), 20 mM ascorbate, 10 µM FAD. 20 mM benzyl viologen and 1 mM methyl-H4F. Before start of the reaction with enzyme, benzyl viologen was reduced to an $\Delta A555$ of 0.3 with sodium dithionite.

Aldehyde:ferredoxin oxidoreductase was assayed using a mixture containing 100 mM Tris/HCl (pH 7.5), 2 mM DTT, 1.1 mM acetaldehyde, and about 25 µM ferredoxin. The gas phase was 100% N2.

CoA acetylating acetaldehyde dehydrogenase was measured using a mixture contained 100 mM Tris/HCl (pH 7.5), 2 mM DTT, 1.1 mM acetaldehyde, 1 mM coenzyme A, and 1 mM NADP+ or 1 mM NAD+. The gas phase was 100% N2.

Alcohol and butanediol dehydrogenases were measured in an assay with 100 mM potassium phosphate (pH 6), 2 mM DTT, 1.1 mM acetaldehyde or acetoin respectively and 1 mM NADPH or 1 mM NADH. The gas phase was 100% N2.

Ferredoxin was purified from *C. pasteurianum* as described by (Schönheit, Wäscher, & Thauer, 1978).

Results

Hydrogenase: This enzyme is important for hydrogen uptake as an energy source and is essential for growth of carboxydotrophic microorganisms on $CO_2$. This enzyme is also able to evolve hydrogen and may act in conjunction with a formate dehydrogenase as formate hydrogen lyase.

In genome of *C. autoethanogenum* 7 hydrogenase genes (6 Fe-only hydrogenases and one NiFe hydrogenase; Seq. ID 5-20) are present. Homologues for 5 of these genes are present in genome of *C. ljungdahlii* (Kopke et al., 2010) (YP_003781016/CLJU_c26060; YP_003781017/CLJU_c26070; CLJU_c07070/YP_003778879; CLJU_c14700/YP_003779640; CLJU_c17280/YP_003779893; CLJU_c20290/YP_003780193) and could also be identified in genome of *C. ragsdalei* (Seq. ID 21-32) (Table 3).

TABLE 3

| | *C. autoethanogenum* | *C. ljungdahlii* | *C. ragsdalei* |
|---|---|---|---|
| [NiFe] hydrogenase | Seq. ID 5-8 | YP_003781016-17; CLJU_c26060-70 | Seq. ID 21-24 |
| [FeFe] hydrogenase | Seq. ID 9-10 | CLJU_c07070; YP_003778879 | Seq. ID 25-26 |
| [FeFe] hydrogenase | Seq. ID 11-12 | CLJU_c14700; YP_003779640 | Seq. ID 27-28 |
| [FeFe] hydrogenase | Seq. ID 13-14 | — | — |
| [FeFe] hydrogenase | Seq. ID 15-16 | CLJU_c20290; YP_003780193 | Seq. ID 29-30 |
| [FeFe] hydrogenase | Seq. ID 17-18 | CLJU_c17280; YP_003779893 | Seq. ID 31-32 |
| [FeFe] hydrogenase | Seq. ID 19-20 | — | — |

Using single co-factors, activity was observed with NADPH (0.2 U/mg), while zero or a much lower activity was observed with NADH (0.05 U/mg) or ferredoxin (<0.01 U/mg). This demonstrates that the hydrogenase is NADPH specific.

Highest activity was found using a combination of co-factors. With NADPH in the presence of Ferredoxin 0.68 U/mg were measured. In contrast, no measurable activity was observed with NADH (<0.01 U/mg), again confirming the high specificity of this enzyme for NADPH. This data indicates that a bifurcating hydrogenase is present as in *Thermotoga maritima* (Schut & Adams, 2009) or *Acetobaterium woodii* (Schuchmann & Mueller, 2012) or *Moorella thermoacetica* (Huang et al., 2012). However, in these other organisms, the enzyme is NADH dependent. As such, this is the first NADPH dependent bifurcating hydrogenase discovered.

Formate dehydrogenase: This enzyme catalyzes the reduction of CO2 to formate in the methyl branch of the Wood-Ljungdahl pathway and is essential for autotrophic growth on CO or $CO_2$ and $H_2$ by acetogens.

Three genes encode for seleno and non-seleno formate dehydrogenases and are present in the genomes of *C. autoethanogenum* (AEI90721, AEI90723, AEI90725; HQ876015, HQ876017, HQ876019), *C. ljungdahlii* (YP_003779063, YP_003778871, YP_003780168; CLJU_c08930, CLJU_c06990, CLJU_c20040) and *C. ragsdalei* (AEI90722, AEI90724, AEI90726; HQ876016, HQ876018, HQ876020) (Köpke et al., 2010, 2011).

Using only one co-factor, a specificity for NADPH rather than NAD was detected: 0.2 U/mg over very little 0.03 U/mg Significantly higher activity however was detected using a combination of two co-factors: with NADPH and ferredoxin 1.10 U/mg was detected, but only 0.07 with NADH instead of NADPH. This indicated the presence of a bifurcating NADP formate dehydrogenase, an enzyme that has never been described before.

Formate-hydrogen lyase: Using $H_2$ a high activity of 2.4 U/mg was detected, indicating that the bifurcating NADP formate dehydrogenase may form a formate-hydrogen complex with the NADPH bifurcating hydrogenase.

The protein encoding genes for the bifurcating NADP formate dehydrogenase (AEI90721, HQ876015; YP_003778871, CLJU_c08930; AEI90722, HQ876016) and the bifurcating NADP Fe-only hydrogenase (Seq. ID 9-10; CLJU_c07070, YP_003778879; SeqID 25-26) were found in one gene cluster, along with genes for an iron-sulfur flavoprotein with a NADP binding site, iron-sulfur (FeS) proteins and a selenocysteine- and molybdopterin-containing formate dehydrogenase (FIG. 3). Functional complex formation is reflected by the finding that the genes for the two enzymes lie side by side in the genome and could form a transcription unit.

A formate-hydrogen lyase acting in this direction from $CO_2$ and $H_2$ to formate hasn't been described before and is novel to carboxydotrophic Clostridia (FIG. 1). Reversibility of this reaction has also been demonstrated, releasing hydrogen and $CO_2$ from formate. The use of this enzyme allows capture of $CO_2$ in the form of formate using hydrogen, which can then be released again. With a purified enzyme, a formate hydrogen lyase activity of 41 U/mg for formation of formate from $CO_2+H_2$ and 40 U/mg for hydrogen formation from formate has been measured (Table 4).

TABLE 4

Reactions catalyzed by the *C. autoethanogenum* formate hydrogen lyase

| Substrates | Specific activity (U/mg) |
|---|---|
| $H_2$ + $NADHP^+$ + $Fd_{ox}$ | 32 at pH 6.5 (29.2 at pH 7.5) |
| $H_2$ + $NAD^+$ + $Fd_{ox}$ | <0.2 |
| $H_2$ + $NADP^+$ | 1.6 |
| $H_2$ + $Fd_{ox}$ | <0.2 |
| $H_2$ + $NAD^+$ | <0.1 |
| NADPH + $Fd_{red}^{2-}$ ($H_2$ formation) | 26.5 at pH 6 (8.7 at pH 7.5) |
| NADPH ($H_2$ formation) | <0.1 |
| $Fd_{red}^{2-}$ ($H_2$ formation) | 0.9 |
| Formate + $NADP^+$ + $Fd_{ox}$ | 15.2 at pH 7.5 (13 at pH 6.5) |
| Formate + $NAD^+$ + $Fd_{ox}$ | 0.2 |
| Formate + $NADP^+$ | 2 |
| Formate + $Fd_{ox}$ | 0.2 |
| Formate + $NAD^+$ | <0.1 |
| $CO_2$ + $Fd_{red}^{2-}$ + NADPH (formate formation) | 7 at pH 7.5 (see text) |
| $CO_2$ + $H_2$ (formate formation) | 41 at pH 7.0 (35 at pH 7.5) |
| $CO_2$ + $H_2$ + $Fd_{ox}$ + $NADP^+$ (formate formation) | 40 |
| Formate ($H_2$ formation) | 40 at pH 6 (23 at pH 7.5) |
| $H_2$ + MV | 18,000 at pH 7.5 |
| Formate + MV | 170 |
| NADPH + MV | 27 |
| NADH + MV | <0.1 |

With regard to Table 4, purification of the formate hydrogen lyase complex of *C. autoethanogenum* was performed under strictly anoxic conditions at room temperature. An anoxic 50 mM Tris-HCl (pH 7.6) containing 2 mM DTT, 5 µM FAD, and 5 µM FMN (Buffer A) was used through the whole process. The 150,000×g supernatant containing the cytoplasmic fraction with approximately 47 mg protein ml$^{-1}$ was fractionated with ammonium sulfate. The fraction between 40 and 55% ammonium sulfate saturation was collected by centrifugation at 30,000×g and 4° C. for 30 min. The precipitate was dissolved in 7 ml Buffer A containing 0.8 M ammonium sulfate. After removing un-dissolved proteins by centrifugation, the supernatant was loaded onto a Phenyl SEPHAROSE™ high-performance column (2.6 cm by 12 cm) equilibrated with Buffer A containing 0.8 M ammonium sulfate. Protein was eluted with a stepwise ammonium sulfate gradient (0.80, 0.64, 0.48, 0.32, 0.16, and 0 M; 100 ml each in Buffer A) at a flow rate of 5 ml min$^{-1}$. The hydrogenase activity was eluted in a peak at 0.48 M ammonium sulfate. The pooled fractions were concentrated and desalted with an AMICON™ cell with a 50-kDa-cutoff membrane. The concentrate was then applied onto a Q SEPHAROSE™ high-performance column (1.6 cm by 13 cm) equilibrated with Buffer A. The column was then washed with 90 ml Buffer A. Protein was eluted with a 0 to 1 M NaCl linear gradient at a flow rate of 5 ml min$^{-1}$. The hydrogenase activity was recovered in a single peak eluting around 0.4 M NaCl. The fraction was concentrated, desalted with a 50-kDa-cutoff AMICON™ filter, and then stored at −20° C. in Buffer A under an atmosphere of 95% N2/5% H$_2$ until used.

The activities were measured at 37° C. in 100 mM potassium phosphate at the indicated pH. When the formation of H$_2$ from formate (formate hydrogen lyase activity) was followed, the assay mixtures contained 100 mM Tris-HCl (pH 7.5) (Table 1) or 100 mM potassium phosphate (pH as indicated) (Table 3), 2 mM DTT and 20 mM sodium formate. The gas phase was 100% N$_2$. The serum bottles were continuously shaken at 200 rpm to ensure H$_2$ transfer from the liquid phase into the gas phase. Gas samples (0.2 ml) were withdrawn every 1 min, and H$_2$ was quantified by gas-chromatography. When the reduction of CO$_2$ with H$_2$ to formate was measured, the assay mixtures contained 100 mM potassium phosphate (final pH as indicated), 2 mM DTT, and 30 mM [$^{14}$C]K$_2$CO$_3$ (24,000 dpm/µmol). The gas phase was 100% H$_2$. The serum bottles were continuously shaken at 200 rpm to ensure equilibration of the gas phase with the liquid phase. After start of the reaction with enzyme, 100 µl liquid samples were withdrawn every 1.5 min and added to 1.5-ml safe-seal micro-tube containing 100 µl of 150 mM acetic acid to stop the reaction by acidification. The 200 µl mixture was then incubated at 40° C. for 10 min with shaking at 1,400 rpm in a Thermomixer (type 5436, Eppendorf, Germany) to remove all $^{14}$CO$_2$ leaving behind the $^{14}$C-formate formed. Subsequently, 100 µl of the mixture was added to 5 ml of Quicksave A scintillation fluid (Zinsser Analytic, Frankfurt, Germany) and analyzed for $^{14}$C radioactivity in a Beckman LS6500 liquid scintillation counter (Fullerton, Calif., USA). When the reduction of CO$_2$ with reduced ferredoxin and NADPH to formate was followed, the assay mixtures contained 100 mM potassium phosphate (final as indicated), 2 mM DTT, 30 mM [$^{14}$C] K$_2$CO$_3$ (24,000 dpm/µmol), 1 mM NADPH, and reduced ferredoxin-regenerating system (10 mM pyruvate, 0.1 mM thiamine pyrophosphate, 1 mM coenzyme A, 25 µM C. pasteurianum ferredoxin, 1 U pyruvate:ferredoxin oxidoreductase, and 5 U phosphotransacetylase). The gas phase was 100% N$_2$. The serum bottles were continuously shaken at 200 rpm to ensure equilibration of the gas phase with the liquid phase. After start of the reaction with enzyme, 100 µl liquid aliquots were withdrawn every 1.5 min and analyzed for formate. When the reduction of CO$_2$ with reduced ferredoxin and NADPH to formate was followed, the assay mixtures contained 100 mM potassium phosphate (final as indicated), 2 mM DTT, 30 mM [$^{14}$C]K$_2$CO$_3$ (24,000 dpm/µmol), 1 mM NADPH, and reduced ferredoxin-regenerating system (10 mM pyruvate, 0.1 mM thiamine pyrophosphate, 1 mM coenzyme A, 25 µM C. pasteurianum ferredoxin, 1 U pyruvate:ferredoxin oxidoreductase, and 5 U phosphotransacetylase). The gas phase was 100% N$_2$. The serum bottles were continuously shaken at 200 rpm to ensure equilibration of the gas phase with the liquid phase. After start of the reaction with enzyme, 100 µl liquid aliquots were withdrawn every 1.5 min and analyzed for formate as described above. Purified ferredoxin (Fd) from C. pasteurianum DSM 525 was used prepared according to Schönheit et al (Rapid procedure for purification of ferredoxin from clostridia using polyethyleneimine. FEBS Lett. 1978, 89:219-222). One unit (U) equals 2 µmol electrons transferred per min.

Methylene-THF-dehydrogenase: This enzyme catalyzes the reaction from 5,10-methylenetetrahydrofolate to 5,10-methenyltetrahydrofolate and is essential to autotrophic growth. It is part of the Wood-Ljungdahl pathway and was found to be clearly NADPH specific (1.12 U/mg with NADPH, but no detectable activity with NADH or ferredoxin).

This enzyme and respective gene has been identified in C. autoethanogenum (AEI90753; HQ876031, GI:338225353), C. ljungdahlii (YP_003781891; CLJU_c37630) and C. ragsdalei (AEI90771; HQ876032, GI:338225372) as bifunctional methylene-tetrahydrofolate dehydrogenase/formyltetrahydrofolate cyclohydrolase.

This enzyme was previously shown in Moorella thermoacetica to be NADPH-dependent, while the other reactions are NADH or ferredoxin dependent in this organism (Huang et al., 2012).

No measurable activity could be detected in the in vitro assays for the Methylene-THF reducatase with either co-factor (only with a synthetic dye). However, the inventors consider that this result can be explained by the enzyme requiring an unknown coupling site as an additional enzyme as has been proposed for other enzymes such as C. ljungdahlii or A. woodii (Köpke et al., 2010; Poehlein et al., 2012). This coupling mechanism may be NADPH dependent. The CO dehydrogenase reaction was found to be ferredoxin dependent as has been previously reported for this class of enzymes.

From all five tested oxidoreductase reactions of the Wood-Ljungdahl pathway in carboxydotrophic Clostridia Clostridium autoethanogenum, surprisingly none was found to be NADH dependent, rather the majority was found to be NADPH dependent. This is in complete contrast to for example glycolysis of sugar utilizing bacteria as E. coli (FIG. 2). Thus existing strategies for E. coli, using NADH dependent reactions and bypassing NADPH dependent reactions (which result in a reduction in product yields and require extensive modifications) are not productive in carboxydotrophic Clostridia. The invention as described herein provides a strategy to overcome this by preferentially selecting for NADPH dependent reactions in carboxydotrophic Clostridia to achieve maximum product yields for metabolic engineering. The capacity and potential of NADPH dependent reactions is shown in example 3 as well as the difference to sugar utilizing E. coli. Similarly this strategy can be applied for heterologous pathways to achieve maximum product yield and flux.

Example 2

The relative expression of over 200 genes C. autoethanogenum genes was analysed using real-time quantitative PCR to determine the genes with highest expression.

Fermentation

Fermentations with *C. autoethanogenum* DSM23693 were carried out in 1.5 L bioreactors at 37° C. and CO-containing steel mill gas as sole energy and carbon source as described below. A defined medium containing per liter: MgCl, CaCl$_2$ (0.5 mM), KCl (2 mM), H$_3$PO$_4$ (5 mM), Fe (100 µM), Ni, Zn (5 µM), Mn, B, W, Mo, Se (2 µM) was used for culture growth. The media was transferred into the bioreactor and autoclaved at 121° C. for 45 minutes. After autoclaving, the medium was supplemented with Thiamine, Pantothenate (0.05 mg), Biotin (0.02 mg) and reduced with 3 mM Cysteine-HCl. To achieve anaerobicity the reactor vessel was sparged with nitrogen through a 0.2 µm filter. Prior to inoculation, the gas was switched to CO-containing steel mill gas, feeding continuously to the reactor. The gas flow was initially set at 80 ml/min, increasing to 200 ml/min during mid-exponential phase, while the agitation was increased from 200 rpm to 350. Na$_2$S was dosed into the bioreactor at 0.25 ml/hr. Once the OD600 reached 0.5, the bioreactor was switched to a continuous mode at a rate of 1.0 ml/min (Dilution rate 0.96 d$^{-1}$). Media samples were taken to measure the biomass and metabolites and a headspace analysis of the in- and outflowing gas was performed on regular basis.

qRT-PCR

A qRT-PCR study with over 200 genes was performed using appropriate primers. Samples were taken from a typical 1.5 L fed-batch fermentation run as described above over the whole growth period (4 days). The samples were harvested by centrifugation (6,000×g, 5 min, 4° C.) and the cell pellet snap frozen in liquid nitrogen and stored at –80° C. until use. RNA was isolated by thawing the cell pellet on ice and suspending it in 100 µL of lysozyme solution (50,000 U lysozyme, 0.5 µL 10% SDS, 10 mM Tris-HCl, 0.1 mM EDTA; pH 8). After 5 min, 350 µL of lysis buffer (containing 10 µL of 2-mercaptoethanol) was added. The cell suspension was mechanistically disrupted by passing five times through an 18-21 gauge needle. RNA was then isolated using PureLink™ RNA Mini Kit (Invitrogen, Carlsbad, Calif. 92008, USA) and eluted in 100 µL of RNase-free water. The RNA was checked via PCR and gel electrophoresis and quantified spectrophotometrically, and treated with DNase I (Roche) if necessary. The reverse transcription step was carried out using SUPERSCRIPT™ III Reverse Transcriptase Kit (Invitrogen, Carlsbad, Calif. 92008, USA). RT-PCR reactions were performed in MyiQ Single Colour Real-Time PCR Detection System (Bio-Rad Laboratories, Hercules, Calif. 94547, USA) in a reaction volume of 15 µL with 25 ng of cDNA template, 67 nM of each primer, and 1×iQ SYBR Green Supermix (Bio-Rad Laboratories, Hercules, Calif. 94547, USA). Guanylate kinase (GnK) and formate tetrahydrofolate ligase (FoT4L) were used as housekeeping gene and non-template controls were included. The reaction conditions were 95° C. for 3 min, followed by 40 cycles of 95° C. for 15 s, 55° C. for 15 s and 72° C. for 30 s. A melting-curve analysis was performed immediately after completion of the qRT PCR (38 cycles of 58° C. to 95° C. at 1° C./s), for detection of primer dimerisation or other artefacts of amplification. Data on the expression level was computed in the form of threshold cycle ($C_t$) values based on PCR base line subtracted curve fit method as calculated by the Biorad iQ5 2.0 software. The raw Ct values were further analysed using Relative Expression Software Tool (REST©) 2008 V2.0.7.

Results

Figure 4:
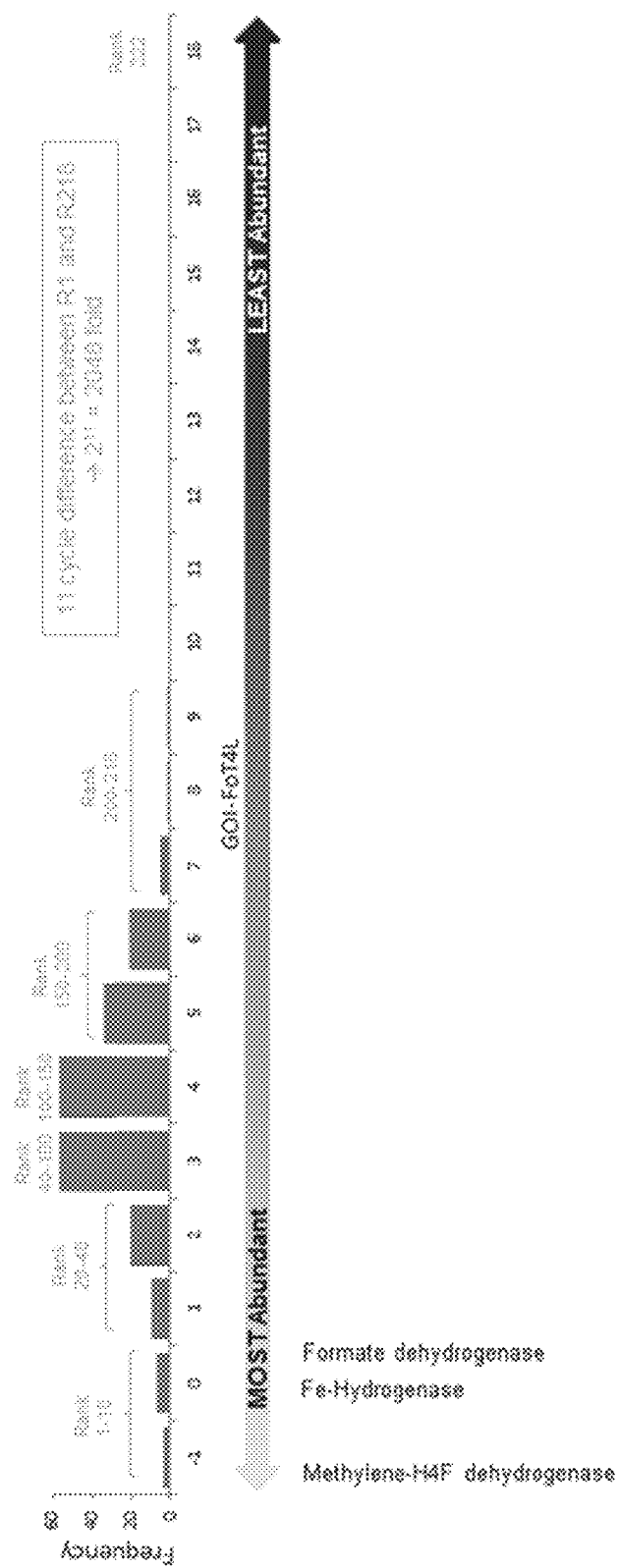
FIG. 4 shows the distribution of the qRT-PCR gene expression results, highlighting the highly expressed NADPH dependent reactions during autotrophic growth.

When growing autotrophically, carboxydotrophic microorganisms uptake gases which serve as a carbon and energy source. FIG. 4 shows the relative expression of genes expressed in *C. autoethanogenum*. The three enzymes identified were involved in autotrophic growth and gas uptake and the inventors found them to be among the most highly expressed genes in the microorganism. As shown in example 1, these same enzymes were found to exhibit high or exclusive utilization of NADPH compared to NADH. The expression of NADH-dependent enzymes was at a much lower level. Given that the enzymes that these genes encode have been found to be NADPH dependent, this indicates that the NADPH pool is extremely important (in contrast to sugar utilizing organisms as *E. coli*) and NADPH dependent reactions are not a bottleneck. For engineering pathways in a carboxydotrophic Clostridia cell, this is a big advantage as it is possible to select NADPH dependent reactions, and these reactions don't have to be avoided or bypassed. Additionally, the NADPH pool is larger so performance don't drop and extensive engineering is not necessary.

Example 3

Primary-secondary alcohol dehydrogenase (ADH) is a strictly NADPH-dependent enzyme that converts acetone to isopropanol. Its activity is demonstrated using enzyme assays with crude extract prepared from fermentation broth containing acetone as well as 0.2 mM of either NADH or NADPH (Ismaiel, Zhu, Colby, & Chen, 1993)

A reactor study with *C. autoethanogenum* was performed to demonstrate effective NADPH dependent conversion of acetone to isopropanol at high rates. In continuous mode with stable biomass and metabolite production, acetone was added to both the bioreactor and the feed medium. Acetone was spiked into the reactor to a certain level, which was then obtained by continuous feeding. Initially, 1 g/L acetone was added, once the metabolite concentrations had stabilised, the concentration was increased to 5 g/L, 15 g/l, and in a second experiment to 20 g/L.

Materials and Methods
Analysis of Metabolites

HPLC analysis of acetone, isopropanol and other metabolites was performed using an Agilent 1100 Series HPLC system equipped with a RID operated at 35° C. (Refractive Index Detector) and an Alltech IOA-2000 Organic acid column (150×6.5 mm, particle size 5 µm) kept at 60° C. Slightly acidified water was used (0.005M H$_2$SO$_4$) as mobile phase with a flow rate of 0.7 ml/min. To remove proteins and other cell residues, 400 µl samples were mixed with 100 µl of a 2% (w/v) 5-Sulfosalicylic acid and centrifuged at 14,000×g for 3 min to separate precipitated residues. 10 µl of the supernatant were then injected into the HPLC for analyses.

GC analysis of acetone, isopropanol and other metabolites was performed using an Agilent 6890N headspace GC equipped with a Supelco PDMS 100 1 cm fiber, an Alltech EC-1000 (30 m×0.25 mm×0.25 µm) column, and a flame ionization detector (FID). 5 ml samples were transferred into a Hungate tube, heated to 40° C. in a water bath and exposed to the fiber for exactly 5 min. The injector was kept at 250° C. and helium with a constant flow of 1 ml/min was used as carrier gas. The oven program was 40° C. for 5 min, followed by an increase of 10° C./min up to 200° C. The temperature was then further increased to 220° C. with a rate of 50° C./min followed by a 5 min hold this temperature, before the temperature was decreased to 40° C. with a rate of 50° C./min and a final 1 min hold. The FID was kept at 250° C. with 40 ml/min hydrogen, 450 ml/min air and 15 ml/min nitrogen as make up gas.

Headspace Analysis

Measurements were carried out on a Varian CP-4900 micro GC with two installed channels. Channel 1 was a 10 m Molsieve column running at 70° C., 200 kPa argon and a backflush time of 4.2 s, while channel 2 was a 10 m PPQ column running at 90° C., 150 kPa helium and no backflush. The injector temperature for both channels was 70° C. Runtimes were set to 120 s, but all peaks of interest would usually elute before 100 s.

Harvesting Cells

Cells from a 1.5 L bioreactor, utilizing CO and H2 having an optical density (OD) of 4 and producing ethanol, acetate and 2,3-butanediol were slowly transferred via tubings into a 2 liter bottle closed with a rubber stopper and primarily filled with $N_2$. Overpressure was released by way of a needle through the stopper. Bottles were kept at a temperature below 0° C. and the transfer of the culture was carried out slowly so as to cool down the culture to 0° C. as quickly as possible after transfer. When the transfer was finished, the bottle was placed in an anaerobic tent. The tubes were centrifuged, then the supernatant was decanted and the remaining liquid was removed with filter paper. The pellet was suspended in 50 mM anaerobic potassium phosphate pH 7 containing 10 mM dithiothreitol. The suspension of several bottles was combined, centrifuged, dried, weighed and stored on dry ice.

Enzyme Assays

Enzyme assays were conducted according to the methods outlined in Huang (Huang et al., 2012) and Ismaiel (Ismaiel et al., 1993).

Results

Figure 5:
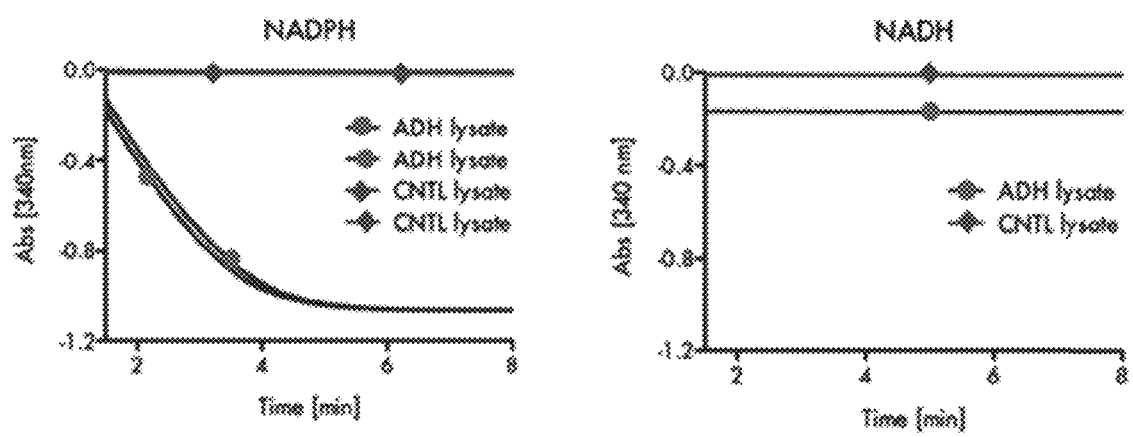
FIG. 5 shows results of enzyme assays with a secondary alcohol dehydrogenase of *C. autoethanogenum* and acetone as substrate and either NADPH or NADH as co-factor. Activity was only measured with NADPH but not NADH demonstrating that this enzyme is strictly NADPH dependent.

Reduction of acetone to isopropanol was shown to be a function of a strictly NADPH dependent secondary alcohol dehydrogenase enzyme, as shown in FIG. 5. Activity was only measured with NADPH but not NADH demonstrating that this enzyme is strictly NADPH dependent.

Figure 6:
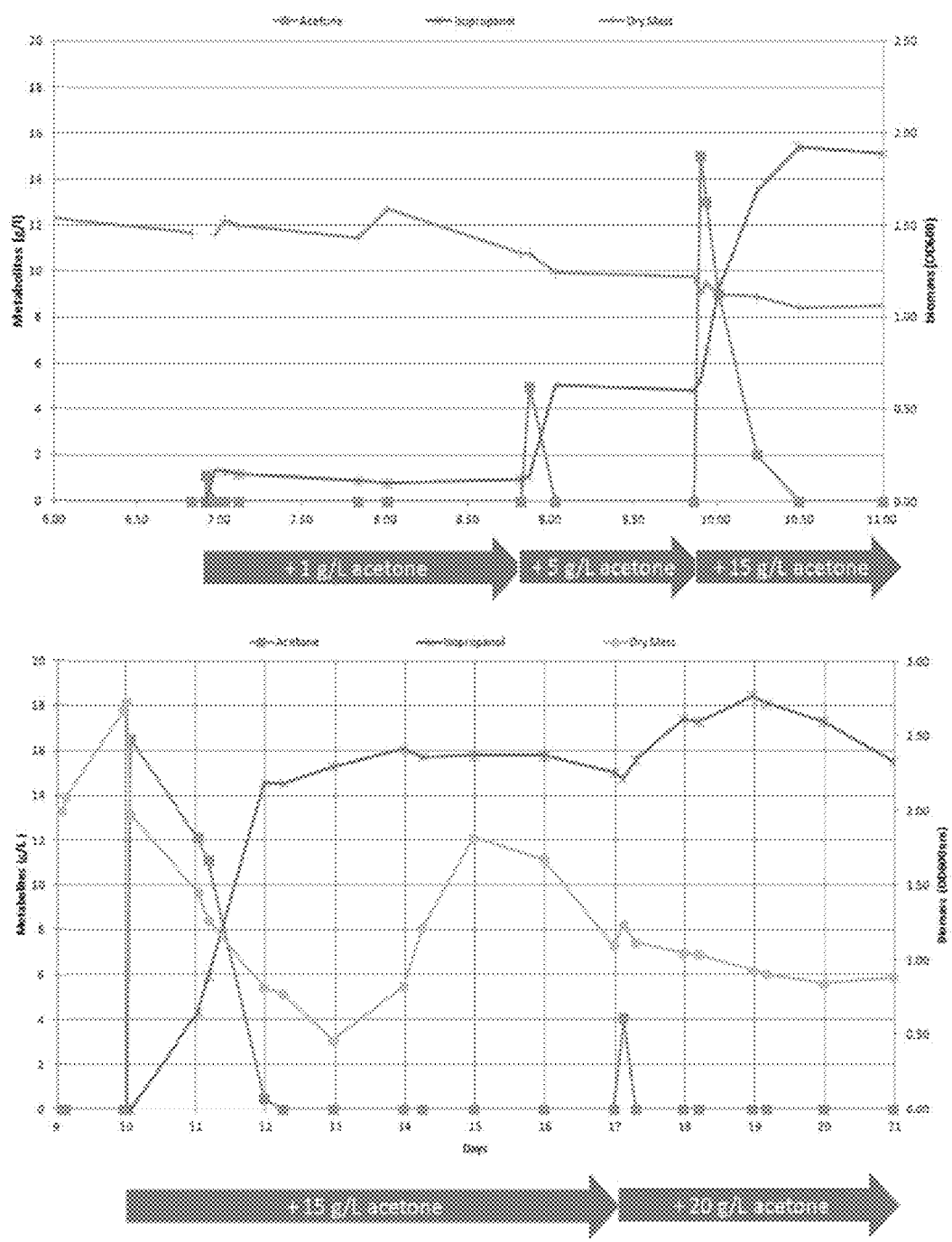
FIG. 6 shows the continuous conversion of acetone to isopropanol via an NADPH dependent secondary alcohol dehydrogenase enzyme at high rates. It can be seen that the acetone is converted into isopropanol shortly after introduction to the bioreactor. Even at high concentrations of 20 g/L the culture converted all acetone to isopropanol demonstrating that the NADPH pool is sufficient to sustain this even at high rate.

To demonstrate the capacity of NADPH pool during autotrophic growth on CO, acetone was continuously fed into a reactor growing on acetone. It was found that acetone was efficiently converted to isopropanol via this NADPH dependent secondary alcohol dehydrogenase enzyme at high rates. FIG. 6 shows that acetone is converted into isopropanol shortly after introduction to the bioreactor. Even at high concentrations of 20 g/L the culture converted all acetone to isopropanol demonstrating that the NADPH pool is sufficient to sustain this even at high rate.

This experiment demonstrates the capacity that carboxydotrophic Clostridia microorganisms have for driving sustained NADPH-dependent reactions. In *E. coli*, the NADPH capacity is considerably lower, as shown in furfural studies (E N Miller et al., 2009; Elliot N Miller et al., 2009).

Example 4

Several pathways offering the option between NADH and NADPH dependent enzymes exist, for example, the butanol pathway. Most engineering efforts so far have focused on using NADH dependent reactions while avoiding NADPH dependent reactions. This limits the choice of pathways and neglects the additional driving force provided by NADPH.

A novel, completely NADPH dependent pathway for butanol biosynthesis is designed consisting of a thiolase (EC 2.3.1.9; btkB, e.g. from *Ralstonia eutropha*: YP_725948.1, GeneID:4248815; phaA, e.g. from *Ralstonia eutropha*: YP_725941.1, Gene ID: 4249783), an NADPH dependent R-3-hydroxybutyryl-CoA dehydrogenase (EC:1.1.1.36; phaB GO:0018454; e.g. from *Ralstonia eutropha*: YP_725942.1, GeneID:4249784) and 3-hydroxybutyryl-CoA dehydrotase (EC 4.2.1.119; phaJ e.g. from *Aeromonas punctata*: BAA21816.1), an NADPH dependent crotonyl-CoA carboxylase/reductase (EC 1.3.1.86; ccr e.g. from *Streptomyces collinus*; EC 1.3.1.85; $ccr_{RS}$, e.g. from *Rhodobacter sphaeroides*:YP_354044.1, Gene ID: 3720751) and NADPH dependent ethylmalonyl-CoA decarboxylase (EC 4.1.1.41; e.g. from *Mus musculus*: NP_001103665.1, GeneID:52665) to butyryl-CoA, which then can be converted to butanol either directly through aldehyde/alcohol dehydrogenases or via buyrate via phosphotranscaetylase and butyrate kinase, aldehyde ferredoxin oxidoreduactase and alcohol dehydrogenase, an NADPH dependent butyryl-CoA reductase (EC 1.1.2.10; bldh e.g. from *Clostridium saccaroperbutylacetonicm* N1-4: AGF59413.1, GeneID: Cspa_c56880) and aldehyde reductase (EC 1.1.1.1; adhA e.g. from *Synechocystis* sp. PCC 6803: NP_443028.1, GeneID:951896) (FIG. 7) can be used.

Two molecules of acetyl-CoA are converted to crotonyl-CoA by three enzymes encoded by phaABJ from *Ralstonia eutropha*. Two acetyl-CoA are condensed to acetoacetyl-CoA by thiolase followed by reduction to R-3 hydroxybutyryl-CoA by the NADPH specific R-3-hydroxybutyryl-CoA dehydrogenase. The R-3-hydroxybutyryl-CoA is then converted to crotonyl-CoA by R-3-hydroxybutyryl-CoA dehydratase.

The combination crotonyl-CoA carboxylase/reductase from *Rhodobacter sphaeroides* (Erb et al., 2007) and ethylmalonyl-CoA decarboxylase from *Mus musculus* (mouse) (Linster et al., 2011) catalyses first the condensation of crotonyl-CoA with carbon dioxide to form ethylmalonyl-CoA with consumption of NADPH, followed by decarboxylation of ethylmalonyl-CoA to butyryl-CoA.

Butyryl-CoA reductase from *Clostridium saccharoperbutylacetonicum* NI-4 cleaves the CoA moiety from butyryl-CoA to form butyraldehyde. The enzyme is presumed NADPH dependent as a homologue from *Clostridium beijerinkii* NRRL B592 is most active with NADPH (Yan and Chen, 1990).

The aldehyde reductase of cyanobacterium *Synechocystis* sp. PCC 6803 has a strong preference for NADPH reduction of medium chain length and aromatic aldehydes to alcohols (Vidal et al., 2009). The preference for reduction of butyraldehyde to butanol relative to the oxidation of butanol is 251:1 in favour of reduction.

Example 5

In *E. coli* cells grown on glucose sugar it has been demonstrated that the pool of NADH is over 20 times larger than the NADPH pool (B. D. Bennett et al., 2009), which limits many biosynthetic reactions and bioconversions especially in fermentation processes (R Poulsen et al., 2005). NADPH and NADH pools were measured in carboxidotrophic acetogenic *Clostridium*.

Samples from a continuous fermentation with *Clostridium autoethanogenum* as described in example 2 were taken and analysed. 5 mL culture samples were rapidly pelleted by centrifugation (13000 rpm at −10° C. for 5 minutes), supernatants removed, cell pellets snap-frozen in liquid nitrogen and then stored at −80° C. until analysis. Metabolite analyses were performed on microbial pellets as described (B. D. Bennett et al., 2009; Yang et al, *Clostridium thermocellum* ATCC27405 transcriptomic, metabolomic and proteomic profiles after ethanol stress. BMC Genomics 2012, 13:336; Marcellin E, Quantitative analysis of intracellular sugar phosphates and sugar nucleotides in encapsulated streptococci using HPAEC-PAD, Biotechnol J 2009, 4, 58-63.

In contrast to *E. coli*, in *C. autoethanogenum* the NADPH pool was found to be larger than the NADH pool, with a ratio of 2.2:1 $NADPH+H^+$ and NADP to $NADH+H^+$ and NADH, respectively 36.8:1 $NADPH+H^+$ to $NADH+H^+$ demonstrating the driving force of NADPH in acetogenic carboxidotrophic Clostridia with CO as substrate.

The invention has been described herein, with reference to certain preferred embodiments, in order to enable the reader to practice the invention without undue experimentation. However, a person having ordinary skill in the art will readily recognise that many of the components and parameters may be varied or modified to a certain extent or substituted for known equivalents without departing from the scope of the invention. It should be appreciated that such modifications and equivalents are herein incorporated as if individually set forth. Titles, headings, or the like are provided to enhance the reader's comprehension of this document, and should not be read as limiting the scope of the present invention.

The entire disclosures of all applications, patents and publications, cited above and below, if any, are hereby incorporated by reference. However, the reference to any applications, patents and publications in this specification is not, and should not be taken as, an acknowledgment or any form of suggestion that they constitute valid prior art or form part of the common general knowledge in any country.

Throughout this specification and any claims which follow, unless the context requires otherwise, the words "comprise", "comprising" and the like, are to be construed in an inclusive sense as opposed to an exclusive sense, that is to say, in the sense of "including, but not limited to".

The invention claimed is:

1. A recombinant *Clostridium* bacterium adapted to express at least one exogenous nicotinamide adenine dinucleotide phosphate (NADPH)-dependent enzyme.

2. The bacterium of claim 1, wherein the NADPH-dependent enzyme is a hydrogenase, a formate dehydrogenase, a methylene-tetrahydrofolate (THF)-dehydrogenase, a hydroxymethylglutaryl (HMG)-CoA reductase, a 3-hydroxybutyryl-CoA dehydrogenase, an acetoacetyl-CoA reductase, a trans-2-enoyl-CoA reductase, a nicotinamide adenine dinucleotide (NADH)/nicotinamide adenine dinucleotide phosphate (NADPH) co-dependent enzyme, or a NADH/NADPH bifurcating enzyme.

3. The bacterium of claim 2, wherein the hydrogenase is a bifurcating nicotinamide adenine dinucleotide phosphate (NADP) Fe-only hydrogenase.

4. The bacterium of claim 2, wherein the formate dehydrogenase is a bifurcating NADP formate dehydrogenase.

5. The bacterium of claim 2, wherein the acetoacetyl-CoA reductase is phaB (EC 1.1.1.36).

6. The bacterium of claim 5, wherein the bacterium further comprises exogenous 3-hydroxybutyryl-CoA dehydratase phaJ (EC 4.2.1.119).

7. The bacterium of claim 5, wherein the bacterium further comprises exogenous NADH-dependent 3-hydroxybutyryl-CoA dehydrogenase hbd (EC 1.1.1.157).

8. The bacterium of claim 2, wherein the trans-2-enoyl-CoA reductase is a crotonyl-CoA reductase (also known as butyryl-CoA dehydrogenase).

9. The bacterium of claim 8, wherein the crotonyl-CoA reductase is ccr (EC 1.3.1.86) or $ccr_{Rs}$ (EC 1.3.1.85).

10. The bacterium of claim 9, wherein the bacterium further comprises exogenous NADH-dependent crotonyl-CoA reductase (also known as butyryl-CoA dehydrogenase) ter (EC 1.3.1.44).

11. The bacterium of claim 1, wherein bacterium has increased utilization of NADPH compared to a parental bacterium.

12. The bacterium of claim 1, wherein bacterium has increased production of at least one fermentation product compared to a parental bacterium.

13. The bacterium of claim 1, wherein a NADH-dependent isoform of the NADPH-dependent enzyme is attenuated or knocked out compared to a parental bacterium.

14. The bacterium of claim 1, wherein the bacterium is a carboxydotrophic bacterium.

15. The bacterium of claim 1, wherein the bacterium is derived from a parental bacterium selected from the group consisting of *Clostridium autoethanogenum*, *Clostridium ljungdahlii*, *Clostridium ragsdahlei*, *Clostridium carboxidivorans*, *Clostridium drakei*, *Clostridium scatologenes*, *Clostridium aceticum*, *Clostridium, formicoaceticum*, and *Clostridium magnum*.

16. The bacterium of claim 15, wherein the *Clostridium autoethanogenum* is *Clostridium autoethanogenum* DSM23693.

* * * * *

SEQUENCE LISTING

```
<160> NUMBER OF SEQ ID NOS: 67

<210> SEQ ID NO 1
<211> LENGTH: 2226
<212> TYPE: DNA
<213> ORGANISM: Unknown
<220> FEATURE:
<223> OTHER INFORMATION: Clostridium autoethanogenum

<400> SEQUENCE: 1
atggatattg aggcaccaag agttgccaag tcctgtttac caggacaatt tatcatagtc      60
aaaatggatg ataaagggga aagaatacct cttactatct gtgattatga tgcaggaaaa    120
ggaactgtta ctattgtatt tcagacatta ggagcttcaa ctaaaaaaat ggctaaatat    180
gaagtgggag aatattttga agattttgtt ggaccacttg acattgctc agaacttgta     240 gagatggatc ttaaagaact taagaagaaa aatataatgt ttgtagcagg tggtgtaggt    300
actgcaccag tttatccaca ggtaaagtgg cttcatcagc atggggtaga ggcagatgtt    360
atagttggat gtaaatcaaa agattatcta ttatttgaag atgaattaaa accaatttgt    420
gggaatttat atatagcaac ggatgatgga agttatggat ataaaggatt tgttacggat    480
cttttaaaag agcttattga caagaaagat aaagagtacg attgtgtagt tgccataggg    540
cctatgataa tgatgaagtt tataactcaa gttacgaaac aatacggaat taaaacaata    600
gtaagtttaa atactataat ggtagatgga actggaatgt gcggagcttg tagggttact    660
gtaggtggag aattaaaatt tgcctgtgta gatggtcctg aatttgatgg tcatcttgta    720
aattttgacg aagctatgag aagacaggct atgtataaaa ctgaagaagg aaagaaactt    780
ctgaaagaag aagaaggaga cacttttgat agaaaaggct gtgagtgtca caatgaagat    840
aaagctgcta ggatgaaaag agtacctata aaggaacagg atcctaaagt tagagctact    900
aattttgatg aagtttgctt gggatacact gaagaagaag ctgtaaaaga agcttcaaga    960
tgcttgaatt gtaaaaagcc tatgtgtgtt actcagtgcc ctgttacaat aactatacct   1020
aagtttgttg aacaggtaaa aaatagaaac tttgaagaag ctgctaaaat aatagcagaa   1080
tcaagtgcac ttcctgctgt atgtggaaga gtatgtcctc aggaaactca gtgtgaagga   1140
aaatgtgtac ttggcaaaaa aggtgatgct gttgctatag gtaagctgga agatttgta    1200 gcagattggt caagaaagaa taatatcgat ttatctaaga ctttacctaa aaacggcaaa   1260
aaagtagctg ttataggaag tggtccttca ggacttactt gtgcaggaga tttagcaaag   1320
cttggatatg acgttactat atttgaagca cttcatgaag caggaggagt acttgtatat   1380
ggtattccag agttcagact tccaaaggat actgtagtaa aacatgaagt tgaaaatgta   1440
aagaaattag gagtaaaaat agagacagat gtaataatag gaagaactgt tactatagat   1500
gaactagtag aaaaagaaaa atttgatgct gtatttatag gttcaggagc aggactacca   1560
aggtttatgg gaatacctgg agaaaactta aatggagtat tctctgcaaa tgaattctta   1620
```

-continued

```
acaagaagta atttaatgaa agcatatagg gatgattatg caactcctat aaaagctggt    1680
aagaaagtag ctgtagtagg aggcggaaac gtagctatgg actctgcaag gacagctcta    1740
agacttggag cagaagtata catagtatac agaagatccg aagcagaact tccagcaaga    1800
gcagaggaag tacaccatgc aaaagaggaa ggaataaagt tcaatctttt aactaatcct    1860
gtagaaatat taggagatga aaaaggttgg gttaatggaa tacgctgtat taagatggaa    1920
cttggagaac cagatgcatc tggaagaaga aaaccagttg caataaaggg ctcagaattt    1980
gatttagatg tagatactgt aattatggcc cttggtactt caccaaatcc acttatatca    2040
actacaacaa aaggacttga atgaataag cgtaaatgct taatagcaga agaagagact     2100
ggacttacta caagagaagg aatatatgca ggtggagatg cagtaacagg tgctgctact    2160
gtaatacttg cgatgggtgc aggtaaaaaa gctgctaagg ctatagatga atatctgaaa    2220
aaataa                                                               2226
```

<210> SEQ ID NO 2
<211> LENGTH: 741
<212> TYPE: PRT
<213> ORGANISM: Unknown
<220> FEATURE:
<223> OTHER INFORMATION: Clostridium autoethanogenum

<400> SEQUENCE: 2

```
Met Asp Ile Glu Ala Pro Arg Val Ala Lys Ser Cys Leu Pro Gly Gln
1               5                   10                  15

Phe Ile Ile Val Lys Met Asp Asp Lys Gly Glu Arg Ile Pro Leu Thr
                20                  25                  30

Ile Cys Asp Tyr Asp Ala Gly Lys Gly Thr Val Thr Ile Val Phe Gln
            35                  40                  45

Thr Leu Gly Ala Ser Thr Lys Lys Met Ala Lys Tyr Glu Val Gly Glu
        50                  55                  60

Tyr Phe Glu Asp Phe Val Gly Pro Leu Gly His Cys Ser Glu Leu Val
65                  70                  75                  80

Glu Met Asp Leu Lys Glu Leu Lys Lys Asn Ile Met Phe Val Ala
                85                  90                  95

Gly Gly Val Gly Thr Ala Pro Val Tyr Pro Gln Val Lys Trp Leu His
            100                 105                 110

Gln His Gly Val Glu Ala Asp Val Ile Gly Cys Lys Ser Lys Asp
        115                 120                 125

Tyr Leu Leu Phe Glu Asp Glu Leu Lys Pro Ile Cys Gly Asn Leu Tyr
130                 135                 140

Ile Ala Thr Asp Asp Gly Ser Tyr Gly Tyr Lys Gly Phe Val Thr Asp
145                 150                 155                 160

Leu Leu Lys Glu Leu Ile Asp Lys Lys Glu Tyr Asp Cys Val
                165                 170                 175

Val Ala Ile Gly Pro Met Ile Met Met Lys Phe Ile Thr Gln Val Thr
            180                 185                 190

Lys Gln Tyr Gly Ile Lys Thr Ile Val Ser Leu Asn Thr Ile Met Val
        195                 200                 205

Asp Gly Thr Gly Met Cys Gly Ala Cys Arg Val Thr Val Gly Gly Glu
    210                 215                 220

Leu Lys Phe Ala Cys Val Asp Gly Pro Glu Phe Asp Gly His Leu Val
225                 230                 235                 240

Asn Phe Asp Glu Ala Met Arg Arg Gln Ala Met Tyr Lys Thr Glu Glu
                245                 250                 255
```

```
Gly Lys Lys Leu Leu Lys Glu Glu Gly Asp Thr Phe Asp Arg Lys
            260                 265                 270

Gly Cys Glu Cys His Asn Glu Asp Lys Ala Ala Arg Met Lys Arg Val
            275                 280                 285

Pro Ile Lys Glu Gln Asp Pro Lys Val Arg Ala Thr Asn Phe Asp Glu
            290                 295                 300

Val Cys Leu Gly Tyr Thr Glu Glu Ala Val Lys Glu Ala Ser Arg
305                 310                 315                 320

Cys Leu Asn Cys Lys Lys Pro Met Cys Val Thr Gln Cys Pro Val Thr
                325                 330                 335

Ile Thr Ile Pro Lys Phe Val Gln Val Lys Asn Arg Asn Phe Glu
            340                 345                 350

Glu Ala Ala Lys Ile Ile Ala Glu Ser Ser Ala Leu Pro Ala Val Cys
                355                 360                 365

Gly Arg Val Cys Pro Gln Glu Thr Gln Cys Glu Gly Lys Cys Val Leu
            370                 375                 380

Gly Lys Lys Gly Asp Ala Val Ala Ile Gly Lys Leu Glu Arg Phe Val
385                 390                 395                 400

Ala Asp Trp Ser Arg Lys Asn Asn Ile Asp Leu Ser Lys Thr Leu Pro
                405                 410                 415

Lys Asn Gly Lys Lys Val Ala Val Ile Gly Ser Gly Pro Ser Gly Leu
            420                 425                 430

Thr Cys Ala Gly Asp Leu Ala Lys Leu Gly Tyr Asp Val Thr Ile Phe
            435                 440                 445

Glu Ala Leu His Glu Ala Gly Gly Val Leu Val Tyr Gly Ile Pro Glu
            450                 455                 460

Phe Arg Leu Pro Lys Asp Thr Val Val Lys His Glu Val Glu Asn Val
465                 470                 475                 480

Lys Lys Leu Gly Val Lys Ile Glu Thr Asp Val Ile Ile Gly Arg Thr
            485                 490                 495

Val Thr Ile Asp Glu Leu Val Glu Lys Glu Lys Phe Asp Ala Val Phe
            500                 505                 510

Ile Gly Ser Gly Ala Gly Leu Pro Arg Phe Met Gly Ile Pro Gly Glu
            515                 520                 525

Asn Leu Asn Gly Val Phe Ser Ala Asn Glu Phe Leu Thr Arg Ser Asn
            530                 535                 540

Leu Met Lys Ala Tyr Arg Asp Asp Tyr Ala Thr Pro Ile Lys Ala Gly
545                 550                 555                 560

Lys Lys Val Ala Val Val Gly Gly Gly Asn Val Ala Met Asp Ser Ala
                565                 570                 575

Arg Thr Ala Leu Arg Leu Gly Ala Glu Val Tyr Ile Val Tyr Arg Arg
            580                 585                 590

Ser Glu Ala Glu Leu Pro Ala Arg Ala Glu Glu Val His His Ala Lys
            595                 600                 605

Glu Glu Gly Ile Lys Phe Asn Leu Leu Thr Asn Pro Val Glu Ile Leu
            610                 615                 620

Gly Asp Glu Lys Gly Trp Val Asn Gly Ile Arg Cys Ile Lys Met Glu
625                 630                 635                 640

Leu Gly Glu Pro Asp Ala Ser Gly Arg Arg Lys Pro Val Ala Ile Lys
                645                 650                 655

Gly Ser Glu Phe Asp Leu Asp Val Asp Thr Val Ile Met Ala Leu Gly
            660                 665                 670
```

Thr Ser Pro Asn Pro Leu Ile Ser Thr Thr Thr Lys Gly Leu Glu Met
            675                 680                 685

Asn Lys Arg Lys Cys Leu Ile Ala Glu Glu Thr Gly Leu Thr Thr
690                 695                 700

Arg Glu Gly Ile Tyr Ala Gly Gly Asp Ala Val Thr Gly Ala Ala Thr
705                 710                 715                 720

Val Ile Leu Ala Met Gly Ala Gly Lys Lys Ala Ala Lys Ala Ile Asp
                725                 730                 735

Glu Tyr Leu Lys Lys
            740

<210> SEQ ID NO 3
<211> LENGTH: 2163
<212> TYPE: DNA
<213> ORGANISM: Unknown
<220> FEATURE:
<223> OTHER INFORMATION: Clostridium ragsdalei

<400> SEQUENCE: 3

```
atggatgata aagggaaag aatacctctt actatctgtg attatgatgc agaaaaagga      60
actgttacta ttgtatttca gacattagga gcttcaacta aaaaaatggc taaatatgaa    120
gtgggagagt attttgaaga ttttgttgga ccacttggac attgctcaga acttgtagag    180
atggatctta agaacttaa gaagaaaaat ataatgtttg tagcaggggg tgtaggtact    240
gcaccagttt atccacaggt aaaatggctt catgaacatg gagttgctgc agatgttata    300
gttggatgta atcaaaaga tcttttatta tttgaagatg aattgaaacc aatttgtgga    360
aatttatata tagcaacgga tgatgggagt tatggatata agggctttgt tacgaatctt    420
ttgaaagaac ttattgacaa gaaagataaa gaatatgatt gtgtaattgc cataggacct    480
atgataatga tgaagtttat aactcaagtt acgaaaccat atggaattaa aacaatagta    540
agtttaaata ctataatggt agatggaact ggaatgtgcg gagcttgtag ggttactgta    600
ggtggagaat taaaatttgc ctgtgtagat ggtcctgaat ttgatggtca tcttgtaaat    660
tttgatgaag ctatgagaag acaagctatg tacaagactg aagaaggaaa gaaacttctg    720
caagaagaag aagggacac tggaagtaga gaaggtaaaa agtgtagagc agaagaaaaa    780
cttgaaagaa tgaaaagagt acctataaag gaacaggatc ctaaagttag agctactaat    840
tttgatgaag tttgcttggg atacactgaa gaagaagctg taaaagaagc ttcaagatgc    900
ttgaattgta aaaagcctat gtgtgttact cagtgccctg ttacaataac tatacctaag    960
tttgttgaac aggtaaaaaa tagaaacttt gaagaagctg ctaaaataat agcagaatca  1020
agtgcacttc ctgctgtatg tggaagagta tgtcctcagg aaactcagtg tgaaggaaaa  1080
tgtgtacttg gcaaaaaagg tgatgctgtt gctataggta agctggaaag atttgtagca  1140
gattggtcaa gaaagaataa tatcgattta tctaagactt tacctaaaaa cggcaaaaaa  1200
gtagctgtta taggaagtgg tccttcagga cttacttgtg caggagattt agcaaagctt  1260
ggatatgacg ttactatatt tgaagcactt catgaagcag gaggagtact tgtatatggt  1320
attccagagt tcagacttcc aaaggatact gtagtaaaac atgaagttga aaatgtaaag  1380
aaattaggag taaaaataga gacagatgta ataataggag gaactgttac tatagatgaa  1440
ctagtagaaa agaaaaaatt tgatgctgta tttataggtt caggagcagg actaccaagg  1500
tttatgggaa tacctggaga aaacttaaat ggagtattct ctgcaaatga attcttaaca  1560
agaagtaatt taatgaaagc atataggat gattatgcaa ctcctataaa agctggtaag  1620
```

-continued

```
aaagtagctg tagtaggagg cggaaacgta gctatggact ctgcaaggac agctctaaga   1680
cttggagcag aagtatacat agtatacaga agatccgaag cagaacttcc agcaagagca   1740
gaggaagtac accatgcaaa agaggaagga ataaagttca atcttttaac taatcctgta   1800
gaaatattag gagatgaaaa aggttgggtt aatggaatac gctgtattaa gatggaactt   1860
ggagaaccag atgcatctgg aagaagaaaa ccagttgcaa taaagggatc agaatttgat   1920
ttagatgtag atactgtaat tatggcccct tggtacttca caaatccact tatatcaact   1980
acaacaaaag gacttgaaat gaataagcgt aaatgcttaa tagcagaaga agagactgga   2040
ctcactacaa gagaaggaat atatgcaggt ggagatgcag taacaggtgc tgctactgta   2100
atacttgcaa tgggtgcagg taaaaaagct gctaaggcta tagatgaata tctgaaaaaa   2160
taa                                                                2163
```

<210> SEQ ID NO 4
<211> LENGTH: 720
<212> TYPE: PRT
<213> ORGANISM: Unknown
<220> FEATURE:
<223> OTHER INFORMATION: Clostridium ragsdalei

<400> SEQUENCE: 4

```
Met Asp Asp Lys Gly Glu Arg Ile Pro Leu Thr Ile Cys Asp Tyr Asp
1               5                   10                  15

Ala Glu Lys Gly Thr Val Thr Ile Val Phe Gln Thr Leu Gly Ala Ser
            20                  25                  30

Thr Lys Lys Met Ala Lys Tyr Glu Val Gly Tyr Phe Glu Asp Phe
        35                  40                  45

Val Gly Pro Leu Gly His Cys Ser Glu Leu Val Glu Met Asp Leu Lys
    50                  55                  60

Glu Leu Lys Lys Lys Asn Ile Met Phe Val Ala Gly Val Gly Thr
65                  70                  75                  80

Ala Pro Val Tyr Pro Gln Val Lys Trp Leu His Glu His Gly Val Ala
                85                  90                  95

Ala Asp Val Ile Val Gly Cys Lys Ser Lys Asp Leu Leu Leu Phe Glu
            100                 105                 110

Asp Glu Leu Lys Pro Ile Cys Gly Asn Leu Tyr Ile Ala Thr Asp Asp
        115                 120                 125

Gly Ser Tyr Gly Tyr Lys Gly Phe Val Thr Asn Leu Leu Lys Glu Leu
    130                 135                 140

Ile Asp Lys Lys Asp Lys Glu Tyr Asp Cys Val Ile Ala Ile Gly Pro
145                 150                 155                 160

Met Ile Met Met Lys Phe Ile Thr Gln Val Thr Lys Pro Tyr Gly Ile
                165                 170                 175

Lys Thr Ile Val Ser Leu Asn Thr Ile Met Val Asp Gly Thr Gly Met
            180                 185                 190

Cys Gly Ala Cys Arg Val Thr Val Gly Gly Glu Leu Lys Phe Ala Cys
        195                 200                 205

Val Asp Gly Pro Glu Phe Asp Gly His Leu Val Asn Phe Asp Glu Ala
    210                 215                 220

Met Arg Arg Gln Ala Met Tyr Lys Thr Glu Gly Lys Lys Leu Leu
225                 230                 235                 240

Gln Glu Glu Glu Gly Asp Thr Gly Ser Arg Glu Gly Lys Lys Cys Arg
                245                 250                 255

Ala Glu Glu Lys Leu Glu Arg Met Lys Arg Val Pro Ile Lys Glu Gln
```

```
            260             265              270
Asp Pro Lys Val Arg Ala Thr Asn Phe Asp Glu Val Cys Leu Gly Tyr
        275             280             285

Thr Glu Glu Glu Ala Val Lys Glu Ala Ser Arg Cys Leu Asn Cys Lys
        290             295             300

Lys Pro Met Cys Val Thr Gln Cys Pro Val Thr Ile Thr Ile Pro Lys
305             310             315             320

Phe Val Glu Gln Val Lys Asn Arg Asn Phe Glu Glu Ala Ala Lys Ile
                325             330             335

Ile Ala Glu Ser Ser Ala Leu Pro Ala Val Cys Gly Arg Val Cys Pro
        340             345             350

Gln Glu Thr Gln Cys Glu Gly Lys Cys Val Leu Gly Lys Lys Gly Asp
        355             360             365

Ala Val Ala Ile Gly Lys Leu Glu Arg Phe Val Ala Asp Trp Ser Arg
        370             375             380

Lys Asn Asn Ile Asp Leu Ser Lys Thr Leu Pro Lys Asn Gly Lys Lys
385             390             395             400

Val Ala Val Ile Gly Ser Gly Pro Ser Gly Leu Thr Cys Ala Gly Asp
                405             410             415

Leu Ala Lys Leu Gly Tyr Asp Val Thr Ile Phe Glu Ala Leu His Glu
        420             425             430

Ala Gly Gly Val Leu Val Tyr Gly Ile Pro Glu Phe Arg Leu Pro Lys
        435             440             445

Asp Thr Val Val Lys His Glu Val Glu Asn Val Lys Lys Leu Gly Val
        450             455             460

Lys Ile Glu Thr Asp Val Ile Ile Gly Arg Thr Val Thr Ile Asp Glu
465             470             475             480

Leu Val Glu Lys Glu Lys Phe Asp Ala Val Phe Ile Gly Ser Gly Ala
                485             490             495

Gly Leu Pro Arg Phe Met Gly Ile Pro Gly Glu Asn Leu Asn Gly Val
        500             505             510

Phe Ser Ala Asn Glu Phe Leu Thr Arg Ser Asn Leu Met Lys Ala Tyr
        515             520             525

Arg Asp Asp Tyr Ala Thr Pro Ile Lys Ala Gly Lys Lys Val Ala Val
        530             535             540

Val Gly Gly Gly Asn Val Ala Met Asp Ser Ala Arg Thr Ala Leu Arg
545             550             555             560

Leu Gly Ala Glu Val Tyr Ile Val Tyr Arg Arg Ser Glu Ala Glu Leu
                565             570             575

Pro Ala Arg Ala Glu Glu Val His His Ala Lys Glu Glu Gly Ile Lys
        580             585             590

Phe Asn Leu Leu Thr Asn Pro Val Glu Ile Leu Gly Asp Glu Lys Gly
        595             600             605

Trp Val Asn Gly Ile Arg Cys Ile Lys Met Glu Leu Gly Glu Pro Asp
        610             615             620

Ala Ser Gly Arg Arg Lys Pro Val Ala Ile Lys Gly Ser Glu Phe Asp
625             630             635             640

Leu Asp Val Asp Thr Val Ile Met Ala Leu Gly Thr Ser Pro Asn Pro
                645             650             655

Leu Ile Ser Thr Thr Thr Lys Gly Leu Glu Met Asn Lys Arg Lys Cys
        660             665             670

Leu Ile Ala Glu Glu Glu Thr Gly Leu Thr Thr Arg Glu Gly Ile Tyr
        675             680             685
```

```
Ala Gly Gly Asp Ala Val Thr Gly Ala Ala Thr Val Ile Leu Ala Met
    690                 695                 700

Gly Ala Gly Lys Lys Ala Ala Lys Ala Ile Asp Glu Tyr Leu Lys Lys
705                 710                 715                 720
```

<210> SEQ ID NO 5
<211> LENGTH: 882
<212> TYPE: DNA
<213> ORGANISM: Unknown
<220> FEATURE:
<223> OTHER INFORMATION: Clostridium autoethanogenum

<400> SEQUENCE: 5

```
atgaatgctc gaagcaaggt tatatgtcct ttaatcgtag ataaggaacg cagttcaaag    60
gcttttacta gtgaagctat agatttaatt gaaaggagaa agacgaaaaa attaaatgct   120
atatggcttg aagtaacagg atgttcagga atatcatttc tttttttaaa tagtgaaaat   180
cctggactcg attatatttt ggaaaaactc attaatttaa aatacaacaa tactctaatg   240
acttcagaag gggagtatgc ctttaaacaa ttcttagata cattgaatac tgaatttata   300
ctattagtag atggagcagt atctactgcc cagaacggtt tttataatat tgttgccaat   360
tatgaaggaa accctgttac tgcacttgaa gctgtaaaaa tggcaggaga aaaagcaaag   420
catgttctct gtgtaggaac ttgtgcatcc tatggtggaa tttctgccgc aggccaaac   480
ccttcagaaa gcaaaagtgt taagaaaata ctaaatcgtg aagtcataag acttccaggc   540
tgtccatgcc acccggattg ggtagttgga actttagcac acttggttgc ttttggaaaa   600
ccacaattgg ataaagaagg aagacctctt cttttttatg gaattaccat tcatgatagt   660
tgtacaagaa gaggattttt tgataacaga atttttgcaa aaaaatttgg agaaaatgga   720
tgcatgttta aacttggatg cagggggcct gtaactaaaa cagattgtcc taggagaaag   780
tggaatgggt acgtgaactg gcctgttgaa gacaatacca actgtatagg atgtgcaaat   840
tctagatttc cagatggtat ggaaccattt gtaaggtatt ag                       882
```

<210> SEQ ID NO 6
<211> LENGTH: 293
<212> TYPE: PRT
<213> ORGANISM: Unknown
<220> FEATURE:
<223> OTHER INFORMATION: Clostridium autoethanogenum

<400> SEQUENCE: 6

```
Met Asn Ala Arg Ser Lys Val Ile Cys Pro Leu Ile Val Asp Lys Glu
1               5                   10                  15

Arg Ser Ser Lys Ala Phe Thr Ser Glu Ala Ile Asp Leu Ile Glu Arg
            20                  25                  30

Arg Lys Thr Lys Lys Leu Asn Ala Ile Trp Leu Glu Val Thr Gly Cys
        35                  40                  45

Ser Gly Asn Ile Ile Ser Phe Leu Asn Ser Glu Asn Pro Gly Leu Asp
    50                  55                  60

Tyr Ile Leu Glu Lys Leu Ile Asn Leu Lys Tyr Asn Asn Thr Leu Met
65                  70                  75                  80

Thr Ser Glu Gly Glu Tyr Ala Phe Lys Gln Phe Leu Asp Thr Leu Asn
                85                  90                  95

Thr Glu Phe Ile Leu Leu Val Asp Gly Ala Val Ser Thr Ala Gln Asn
            100                 105                 110

Gly Phe Tyr Asn Ile Val Ala Asn Tyr Glu Gly Asn Pro Val Thr Ala
```

```
                115                 120                 125
Leu Glu Ala Val Lys Met Ala Gly Glu Lys Ala Lys His Val Leu Cys
    130                 135                 140

Val Gly Thr Cys Ala Ser Tyr Gly Gly Ile Ser Ala Ala Arg Pro Asn
145                 150                 155                 160

Pro Ser Glu Ser Lys Ser Val Lys Glu Ile Leu Asn Arg Glu Val Ile
                165                 170                 175

Arg Leu Pro Gly Cys Pro Cys His Pro Asp Trp Val Val Gly Thr Leu
            180                 185                 190

Ala His Leu Val Ala Phe Gly Lys Pro Gln Leu Asp Lys Glu Gly Arg
        195                 200                 205

Pro Leu Leu Phe Tyr Gly Ile Thr Ile His Asp Ser Cys Thr Arg Arg
    210                 215                 220

Gly Phe Phe Asp Asn Arg Ile Phe Ala Lys Lys Phe Gly Glu Asn Gly
225                 230                 235                 240

Cys Met Phe Lys Leu Gly Cys Arg Gly Pro Val Thr Lys Thr Asp Cys
                245                 250                 255

Pro Arg Arg Lys Trp Asn Gly Tyr Val Asn Trp Pro Val Glu Asp Asn
            260                 265                 270

Thr Asn Cys Ile Gly Cys Ala Asn Ser Arg Phe Pro Asp Gly Met Glu
        275                 280                 285

Pro Phe Val Arg Tyr
    290

<210> SEQ ID NO 7
<211> LENGTH: 1386
<212> TYPE: DNA
<213> ORGANISM: Unknown
<220> FEATURE:
<223> OTHER INFORMATION: Clostridium autoethanogenum

<400> SEQUENCE: 7
atgaaaaaga aaattacaat tgatccaatt acgagaataa gcggttttt ggaaactaaa      60 gtgcaagtag aaaaaaatat tatagtagat gctgaaacta gtggattgct ttttagagga    120
tttgaaaaaa tgttaaagaa cagagagccg ctggatgcag tatattttac agaaagaatt    180
tgtggaatat gttcaacagc tcatgccgtg gcggctgcta cagctcttga agatgctttg    240
aagataaaaa ttagtgtaaa tgattcgtat atgcgtaatt aatacatgg ttttgaattt     300 atacaaaatc atataagaca tttttataat ttgaccatac caagttatgt gaagatgccc    360
gatataaatc ctctttcttc aaatcaatat gaagattata gattgcctta taacctaaat    420
aaaaagataa gtgaagatta tattgaaagt attaaataca gcaggttagc ccatgaaggg    480
ttggctatcc ttggaggaaa agcccccat aatcatggaa tttttgttgg aggagttacc     540
ataaatatag atccatataa actcacaaaa gttaaatcta ttatttctca aattaataaa    600
tttgtaagta gtgttatgtt agaggacatg aacataattt caaaatacta tgctgattat    660
tttaaaatgg gaggagctta tggaaacttt atgacttatg aattttttga caagtatgct    720
gatcctgaga taagttatgt aggaccttct gtattaataa atggacgaaa gtataatttc    780
aatagtaata aaattacgga aaacatactc cacacctggt atacaagcga tgatgaaacg    840
ataaatttat ctaaagaaac aggttacagc tttataaaat cgccaaccta taatggatat    900
tctatggaag taggacctct agcaagattg atactttcag gtagtatac tggtggaagt     960 tcatgtatgg acagaaatgt tgccagagta cttgaaacaa aaaagatttt agaaattatg   1020
```

-continued

```
caaggacttg cagatagaat taagcttatt ccagcagaac aaagaatata tcaaatacca    1080
gataaagcat ttggtgcagg attaattgac acaactagag gatccttggg acactggata    1140
agtatagaag ataaatttat aaagcattac aatattataa ctcctacagt gtggaatatg    1200
gggccaagaa atcaatcagg tgcgcttgga attggagaaa atctttagt tggaacgaaa     1260 ataaaagata taaagcagcc tatagaagtt gggagaatta tgagatcttt tgatccttgt    1320
gtttcctgtg caacgcatct tgtaagtgat aaatatgaac cagtggatgt acaggttata    1380
gtatga                                                               1386
```

<210> SEQ ID NO 8
<211> LENGTH: 461
<212> TYPE: PRT
<213> ORGANISM: Unknown
<220> FEATURE:
<223> OTHER INFORMATION: Clostridium autoethanogenum

<400> SEQUENCE: 8

```
Met Lys Lys Ile Thr Ile Asp Pro Ile Thr Arg Ile Ser Gly Phe
1               5                   10                  15

Leu Glu Thr Lys Val Gln Val Glu Lys Asn Ile Ile Val Asp Ala Glu
            20                  25                  30

Thr Ser Gly Leu Leu Phe Arg Gly Phe Glu Lys Met Leu Lys Asn Arg
        35                  40                  45

Glu Pro Leu Asp Ala Val Tyr Phe Thr Glu Arg Ile Cys Gly Ile Cys
    50                  55                  60

Ser Thr Ala His Ala Val Ala Ala Ala Thr Ala Leu Glu Asp Ala Leu
65                  70                  75                  80

Lys Ile Lys Ile Ser Val Asn Asp Ser Tyr Met Arg Asn Leu Ile His
                85                  90                  95

Gly Phe Glu Phe Ile Gln Asn His Ile Arg His Phe Tyr Asn Leu Thr
            100                 105                 110

Ile Pro Ser Tyr Val Lys Met Pro Asp Ile Asn Pro Leu Ser Ser Asn
        115                 120                 125

Gln Tyr Glu Asp Tyr Arg Leu Pro Tyr Asn Leu Asn Lys Lys Ile Ser
    130                 135                 140

Glu Asp Tyr Ile Glu Ser Ile Lys Tyr Ser Arg Leu Ala His Glu Gly
145                 150                 155                 160

Leu Ala Ile Leu Gly Gly Lys Ala Pro His Asn His Gly Ile Phe Val
                165                 170                 175

Gly Gly Val Thr Ile Asn Ile Asp Pro Tyr Lys Leu Thr Lys Val Lys
            180                 185                 190

Ser Ile Ile Ser Gln Ile Asn Lys Phe Val Ser Ser Val Met Leu Glu
        195                 200                 205

Asp Met Asn Ile Ile Ser Lys Tyr Tyr Ala Asp Tyr Phe Lys Met Gly
    210                 215                 220

Gly Ala Tyr Gly Asn Phe Met Thr Tyr Gly Ile Phe Asp Lys Tyr Ala
225                 230                 235                 240

Asp Pro Glu Ile Ser Tyr Val Gly Pro Ser Val Leu Ile Asn Gly Arg
                245                 250                 255

Lys Tyr Asn Phe Asn Ser Asn Lys Ile Thr Glu Asn Ile Leu His Thr
            260                 265                 270

Trp Tyr Thr Ser Asp Asp Glu Thr Ile Asn Leu Ser Lys Glu Thr Gly
        275                 280                 285

Tyr Ser Phe Ile Lys Ser Pro Thr Tyr Asn Gly Tyr Ser Met Glu Val
```

```
                290                 295                 300
Gly Pro Leu Ala Arg Leu Ile Leu Ser Gly Glu Tyr Thr Gly Gly Ser
305                 310                 315                 320

Ser Cys Met Asp Arg Asn Val Ala Arg Val Leu Glu Thr Lys Lys Ile
            325                 330                 335

Leu Glu Ile Met Gln Gly Leu Ala Asp Arg Ile Lys Leu Ile Pro Ala
        340                 345                 350

Glu Gln Arg Ile Tyr Gln Ile Pro Asp Lys Ala Phe Gly Ala Gly Leu
    355                 360                 365

Ile Asp Thr Thr Arg Gly Ser Leu Gly His Trp Ile Ser Ile Glu Asp
370                 375                 380

Lys Phe Ile Lys His Tyr Asn Ile Ile Thr Pro Thr Val Trp Asn Met
385                 390                 395                 400

Gly Pro Arg Asn Gln Ser Gly Ala Leu Gly Ile Gly Glu Lys Ser Leu
            405                 410                 415

Val Gly Thr Lys Ile Lys Asp Ile Lys Gln Pro Ile Glu Val Gly Arg
        420                 425                 430

Ile Met Arg Ser Phe Asp Pro Cys Val Ser Cys Ala Thr His Leu Val
    435                 440                 445

Ser Asp Lys Tyr Glu Pro Val Asp Val Gln Val Ile Val
450                 455                 460

<210> SEQ ID NO 9
<211> LENGTH: 1398
<212> TYPE: DNA
<213> ORGANISM: Unknown
<220> FEATURE:
<223> OTHER INFORMATION: Clostridium autoethanogenum

<400> SEQUENCE: 9
atgttaaata tgccaactag tacttctatg ataaatatag atgaagaatt atgtacaggc      60
tgcagacgat gtgcggatgt ctgccctgta gatgctatag aaggtgaaca gggtaaacct     120
cagaagataa atactgaaaa gtgtgttatg tgcggacaat gcattcaagt tgtaaaggc      180 tatcaatctg tatacgacga tgttcctact ccagttagca aaaggttatt tgatagagga     240 tgttaaagg aagtagatga accattattt gcagcatata ataaaggtca ggtaaagagt      300
gttaaagaaa ttttcaaaa caaagatgta tttaaaattg tgcaatgtgc acctgctgta      360
agagttgcta taggagagga ttttggaatg cctcttggaa ctttaagtga aggaaaaatg     420
gcagctgcac tcagaaaatt aggatttgac aaagtatatg atacaaactt tggtgcagat     480
cttactataa tggaagaagg tagtgagtta ctaaaaagag tagctgaagg cggagttttg     540
ccaatgttta cttcttgttg tccagcatgg gtaaatatg cagaacaaac atatccagaa     600
cttttacctc atctttcaag ttgtaagtct ccaaatcaga tggctggagc tatatttaaa     660
acttatggag cagagataaa taaggttaat ccggctaaaa tttataatgt atctgttatg     720
ccatgtacat gcaaggaatt tgaaagtgaa agagaagaaa tgcatgacag tggacacagg     780
gatgtagatg cagttataac tacaagggaa ttagcacaac tgttcaaaga tgctgatata     840
gattttaata ctattgaaga agaacagttt gatactcctc ttggtatgta taccggtgca     900
ggaactatat ttggtgctac aggtggagtt atggaagcag cacttagaac tggatatgaa     960
ctttatacta aaaaaactat tccaagtata gatcttacta tggtaagagg tggagaaggt    1020
tttagaactg ctgaagtaga tttaggggat attagactaa aagtaggagt agtttccggc    1080
ttaaaaaatg taaaagacgt tatggaatca gtaaaggcag gcaaatgtga tttgcacttt    1140
```

```
atagaggtta tgacctgtcc tcaaggatgt ataagtggtg gaggacaacc taaagttata    1200
cttgattcag ataagagga agcttataat aataggaaaa agggactata taatcatgac    1260
gctaatctta cttatagaaa atcacatgaa aatccagaaa taaagaaaat atatgatgag    1320
ttcttagaca aaccattagg agctaagtct catgaattat tgcacactaa atatatctca    1380
agaaaaaagg agagttaa                                                  1398
```

<210> SEQ ID NO 10
<211> LENGTH: 465
<212> TYPE: PRT
<213> ORGANISM: Unknown
<220> FEATURE:
<223> OTHER INFORMATION: Clostridium autoethanogenum

<400> SEQUENCE: 10

```
Met Leu Asn Met Pro Thr Ser Thr Ser Met Ile Asn Ile Asp Glu Glu
1               5                   10                  15

Leu Cys Thr Gly Cys Arg Arg Cys Ala Asp Val Cys Pro Val Asp Ala
            20                  25                  30

Ile Glu Gly Glu Gln Gly Lys Pro Gln Lys Ile Asn Thr Glu Lys Cys
        35                  40                  45

Val Met Cys Gly Gln Cys Ile Gln Val Cys Lys Gly Tyr Gln Ser Val
    50                  55                  60

Tyr Asp Asp Val Pro Thr Pro Val Ser Lys Arg Leu Phe Asp Arg Gly
65                  70                  75                  80

Leu Leu Lys Glu Val Asp Glu Pro Leu Phe Ala Ala Tyr Asn Lys Gly
                85                  90                  95

Gln Val Lys Ser Val Lys Glu Ile Leu Gln Asn Lys Asp Val Phe Lys
            100                 105                 110

Ile Val Gln Cys Ala Pro Ala Val Arg Val Ala Ile Gly Glu Asp Phe
        115                 120                 125

Gly Met Pro Leu Gly Thr Leu Ser Glu Gly Lys Met Ala Ala Ala Leu
    130                 135                 140

Arg Lys Leu Gly Phe Asp Lys Val Tyr Asp Thr Asn Phe Gly Ala Asp
145                 150                 155                 160

Leu Thr Ile Met Glu Glu Gly Ser Glu Leu Leu Lys Arg Val Ala Glu
                165                 170                 175

Gly Gly Val Leu Pro Met Phe Thr Ser Cys Cys Pro Ala Trp Val Lys
            180                 185                 190

Tyr Ala Glu Gln Thr Tyr Pro Glu Leu Leu Pro His Leu Ser Ser Cys
        195                 200                 205

Lys Ser Pro Asn Gln Met Ala Gly Ala Ile Phe Lys Thr Tyr Gly Ala
    210                 215                 220

Glu Ile Asn Lys Val Asn Pro Ala Lys Ile Tyr Asn Val Ser Val Met
225                 230                 235                 240

Pro Cys Thr Cys Lys Glu Phe Glu Ser Glu Arg Glu Glu Met His Asp
                245                 250                 255

Ser Gly His Arg Asp Val Asp Ala Val Ile Thr Thr Arg Glu Leu Ala
            260                 265                 270

Gln Leu Phe Lys Asp Ala Asp Ile Asp Phe Asn Thr Ile Glu Glu Glu
        275                 280                 285

Gln Phe Asp Thr Pro Leu Gly Met Tyr Thr Gly Ala Gly Thr Ile Phe
    290                 295                 300

Gly Ala Thr Gly Gly Val Met Glu Ala Ala Leu Arg Thr Gly Tyr Glu
```

```
                305                 310                 315                 320
Leu Tyr Thr Lys Lys Thr Ile Pro Ser Ile Asp Leu Thr Met Val Arg
                    325                 330                 335
Gly Gly Glu Gly Phe Arg Thr Ala Glu Val Asp Leu Gly Asp Ile Arg
                340                 345                 350
Leu Lys Val Gly Val Val Ser Gly Leu Lys Asn Val Lys Asp Val Met
            355                 360                 365
Glu Ser Val Lys Ala Gly Lys Cys Asp Leu His Phe Ile Glu Val Met
370                 375                 380
Thr Cys Pro Gln Gly Cys Ile Ser Gly Gly Gln Pro Lys Val Ile
385                 390                 395                 400
Leu Asp Ser Asp Lys Glu Ala Tyr Asn Asn Arg Lys Lys Gly Leu
                405                 410                 415
Tyr Asn His Asp Ala Asn Leu Thr Tyr Arg Lys Ser His Glu Asn Pro
                420                 425                 430
Glu Ile Lys Lys Ile Tyr Asp Glu Phe Leu Asp Lys Pro Leu Gly Ala
            435                 440                 445
Lys Ser His Glu Leu Leu His Thr Lys Tyr Ile Ser Arg Lys Lys Glu
            450                 455                 460
Ser
465

<210> SEQ ID NO 11
<211> LENGTH: 1680
<212> TYPE: DNA
<213> ORGANISM: Unknown
<220> FEATURE:
<223> OTHER INFORMATION: Clostridium autoethanogenum

<400> SEQUENCE: 11
atgagtggac aatttatgat tatagataat attcctgtag agataaatgg tgaaaaaaat      60
attcttgaac taattagaaa agctggcatt gatttaccta cattttgcta tcattcggag     120
ctttcagttt atggtgcatg ccgtatgtgc atggttgaag ataaacgcgg ccgtatgcaa     180
gctgcatgtt ctactcctcc tcaagctggt atagaaatat atacaaatac tccaagactt     240
agaaaataca gaaaaaacat tcttgagttg ttactcgcaa atcattgcag agattgtaca     300
acttgtgaaa aaaatgagca ttgcaaacta caagatttag caaagcgttt taaaataaag     360
aaagtaagat ttaaaaatac ttctataaat aaaaaaattg ataattcatc agtatgcatt     420
gtaagaaata ggagtaaatg tatcttatgc ggtgactgtg taagagtgtg tgaagaagta     480
caaaatgttg gagctattga ttttgttaaa agaggttcta atatgactgt aactactgca     540
tttgatgaac ctatagcaaa ttcgaattgt gttggatgtg gtcaatgtgc ggcagtatgc     600
cctactggtg ctattgtagt aaaggatgat acagctgaat atgggaagc acttagtgat     660
aagaatacaa aggttgtagc tcaaattgcg cccgctgtaa gagttggtct taatgaggaa     720
ttaggtgagg aaaacggcga aaacgaaatg ggtaaaatag tagctgcact agaagaatg     780
ggatttgatg aagttttga tacttcaacg gcagcagatc ttacagtttt ggaagaaaca     840
gcagaattta cttcaagact tgaaaaaaat gaaagtttac cattgtttac atcctgttgt     900
tctgcatggg taaattatgt agagaataca catccagagt aatgaaata tgtttctact     960
tgcaaatcac ctatggaaat gtttgcttct gtacttaagg agtactataa aaatagtgat    1020
aaaaaaattg tagttgtagc agttatgcct tgtacagcta aaaaatatga agcaaaacga    1080
gaagaatttt caaaaaatgg tgtacctgat gtagattatg taataactac acaggagctt    1140
```

-continued

```
ataagtatga taagacaagc aggaattgta tttcctgaat tagagcctga agcagttgat  1200
atgccatttg atcttagcag tggagctgga gttatatttg gagtaacagg tggtgttaca  1260
gaggctgtta tacgtaaagt tttagctgat aaatcaaatg ctgcattacg tgcaattgtg  1320
tttaatggtg ttaggggcat ggaaggtact aagaagcta gcattactgt tggtgatcgt  1380
gaaataaaaa tagcaatagt aagcggtctt agaaatgcag aaaatcttat acagaaaata  1440
caatctggtg aatcaaaata tgatttcgtt gaagttatgg catgtccagg tggatgcatt  1500
tctggtggtg gacaaccatt tgaaaaactt gaaggaaagc taaaacgtag tgctggaata  1560
tatcaatcag ataaaatgag cactataaaa cgtacagctg acaatccgct tatgaaatca  1620
ctgtattcag gattgttaaa aggtaaaaac cacgaactat tacatgtaaa ccgcaaatag  1680
```

<210> SEQ ID NO 12
<211> LENGTH: 559
<212> TYPE: PRT
<213> ORGANISM: Unknown
<220> FEATURE:
<223> OTHER INFORMATION: Clostridium autoethanogenum

<400> SEQUENCE: 12

```
Met Ser Gly Gln Phe Met Ile Ile Asp Asn Ile Pro Val Glu Ile Asn
1               5                   10                  15

Gly Glu Lys Asn Ile Leu Glu Leu Ile Arg Lys Ala Gly Ile Asp Leu
                20                  25                  30

Pro Thr Phe Cys Tyr His Ser Glu Leu Ser Val Tyr Gly Ala Cys Arg
            35                  40                  45

Met Cys Met Val Glu Asp Lys Arg Gly Arg Met Gln Ala Ala Cys Ser
        50                  55                  60

Thr Pro Pro Gln Ala Gly Ile Glu Ile Tyr Thr Asn Thr Pro Arg Leu
65                  70                  75                  80

Arg Lys Tyr Arg Lys Asn Ile Leu Glu Leu Leu Leu Ala Asn His Cys
                85                  90                  95

Arg Asp Cys Thr Thr Cys Glu Lys Asn Glu His Cys Lys Leu Gln Asp
            100                 105                 110

Leu Ala Lys Arg Phe Lys Ile Lys Lys Val Arg Phe Lys Asn Thr Ser
        115                 120                 125

Ile Asn Lys Lys Ile Asp Asn Ser Ser Val Cys Ile Val Arg Asn Arg
    130                 135                 140

Ser Lys Cys Ile Leu Cys Gly Asp Cys Val Arg Val Cys Glu Glu Val
145                 150                 155                 160

Gln Asn Val Gly Ala Ile Asp Phe Val Lys Arg Gly Ser Asn Met Thr
                165                 170                 175

Val Thr Thr Ala Phe Asp Glu Pro Ile Ala Asn Ser Asn Cys Val Gly
            180                 185                 190

Cys Gly Gln Cys Ala Ala Val Cys Pro Thr Gly Ala Ile Val Val Lys
        195                 200                 205

Asp Asp Thr Ala Glu Leu Trp Glu Ala Leu Ser Asp Lys Asn Thr Lys
    210                 215                 220

Val Val Ala Gln Ile Ala Pro Ala Val Arg Val Gly Leu Asn Glu Glu
225                 230                 235                 240

Leu Gly Glu Glu Asn Gly Glu Asn Glu Met Gly Lys Ile Val Ala Ala
                245                 250                 255

Leu Arg Arg Met Gly Phe Asp Glu Val Phe Asp Thr Ser Thr Ala Ala
            260                 265                 270
```

```
Asp Leu Thr Val Leu Glu Glu Thr Ala Glu Phe Thr Ser Arg Leu Glu
    275                 280                 285

Lys Asn Glu Ser Leu Pro Leu Phe Thr Ser Cys Cys Ser Ala Trp Val
    290                 295                 300

Asn Tyr Val Glu Asn Thr His Pro Glu Leu Met Lys Tyr Val Ser Thr
305                 310                 315                 320

Cys Lys Ser Pro Met Glu Met Phe Ala Ser Val Leu Lys Glu Tyr Tyr
                    325                 330                 335

Lys Asn Ser Asp Lys Lys Ile Val Val Ala Val Met Pro Cys Thr
                340                 345                 350

Ala Lys Lys Tyr Glu Ala Lys Arg Glu Glu Phe Ser Lys Asn Gly Val
                355                 360                 365

Pro Asp Val Asp Tyr Val Ile Thr Thr Gln Glu Leu Ile Ser Met Ile
    370                 375                 380

Arg Gln Ala Gly Ile Val Phe Pro Glu Leu Glu Pro Glu Ala Val Asp
385                 390                 395                 400

Met Pro Phe Asp Leu Ser Ser Gly Ala Gly Val Ile Phe Gly Val Thr
                    405                 410                 415

Gly Gly Val Thr Glu Ala Val Ile Arg Lys Val Leu Ala Asp Lys Ser
                420                 425                 430

Asn Ala Ala Leu Arg Ala Ile Val Phe Asn Gly Val Arg Gly Met Glu
                435                 440                 445

Gly Thr Lys Glu Ala Ser Ile Thr Val Gly Asp Arg Glu Ile Lys Ile
    450                 455                 460

Ala Ile Val Ser Gly Leu Arg Asn Ala Glu Asn Leu Ile Gln Lys Ile
465                 470                 475                 480

Gln Ser Gly Glu Ser Lys Tyr Asp Phe Val Glu Val Met Ala Cys Pro
                    485                 490                 495

Gly Gly Cys Ile Ser Gly Gly Gln Pro Phe Glu Lys Leu Glu Gly
                500                 505                 510

Lys Leu Lys Arg Ser Ala Gly Ile Tyr Gln Ser Asp Lys Met Ser Thr
    515                 520                 525

Ile Lys Arg Thr Ala Asp Asn Pro Leu Met Lys Ser Leu Tyr Ser Gly
530                 535                 540

Leu Leu Lys Gly Lys Asn His Glu Leu Leu His Val Asn Arg Lys
545                 550                 555

<210> SEQ ID NO 13
<211> LENGTH: 1917
<212> TYPE: DNA
<213> ORGANISM: Unknown
<220> FEATURE:
<223> OTHER INFORMATION: Clostridium autoethanogenum

<400> SEQUENCE: 13
gtgaataaaa gtcctgtaac tgttttaaaa gaaaaatgta caggttgtaa taagtgtata      60
agaacttgtc ctattcttgg tgcaaatgtt acagcaactg aaaatggtgt aagtaaggtt     120
tacatagatg aggaaagatg tattggatgc ggtgaatgtg taaaggtttg cgaacatggg     180
gctagagact taacgatag tacacaagac ttttttaagg atttgaaaaa aggcaaaaaa     240
ataacagtaa tagctgcacc atctattata gttaatatta aaattacaa gaaattttt     300 ggatatctta atctttggg agtatctata atttatgatg tttctttcgg tgcagatatt     360
actacctggg cttatctaaa agcaatgaag gagaaaaata tttcttcttt aatatcacag     420
```

```
cctgtccta tcgtggttaa ttatattgaa aaatataagc ctgaattaat agaatattta    480
gcgcctatac acagtcctat gatgtgtact gctgtttatc tgaaaaaata taagcatata    540
tgtgaagata tagcttttct gtcaccttgt attggcaagc taattgaaat caatgataag    600
aatacagatg ggtatgtgaa atataatgta acgtacaaaa agattttaga ttatttgaga    660
gataataatg tgaatttgaa caattacgat gaagttgaat ttgataatgt tcctgcttct    720
ttggggttg tttatagttt accaggtgga ttaaaagcaa atgtaaaagc tagaactgaa    780
gaactacatg ttcttcagat agaaggacac aaagaggcaa ttgagtactt gaataagtat    840
tctgatagag ttaaagctaa taacttata cctagtttac ttgatatttt aaattgcaaa    900
aatggatgta atataggtac agcttcctta gacaatttaa cggaatatga tattcaatat    960
aggtttcatg atataaaggt ggaaaagtta agagaaaaaa ctggcttgtt taagaaaaaa    1020
atcaaatcaa tagacgagta ctttgataaa aatcttaatt taaacgattt tgtaagaaag    1080
tatactgcac agaaggttaa aaaaataatt gaacctaccc aaaaagatta tgacaacata    1140
tttgatgaga tgatgaaaac tacaacattg gaaaagaat tcaattgttc cgcttgtgga    1200
tacagcactt gcaaagaaat ggtaaagatg attttttaacg gcataaattc taaggaaaat    1260
tgtatttatt atgtgaagaa aaaatcaat atggaatata gcgaactgga agaaaaaat    1320
gaagaggtca agagtctat aaacaaaata actgtactag ctgaggaaag acaacgaaaa    1380
tcagatgaaa taattaaatt tgcaaatact ctattggcag ctataaatga agtaagtaaa    1440
gggaatgagg aaagcgcatc tgcaattcaa gatatagtag aagaattaaa gtcaataatg    1500
gatatatcaa gtaagttaaa ggaaaacatt catcagataa atgaaaagtt agacaaattc    1560
acggattcat cagatagtat tgtggctatt tcagagcaga ctaatttact ttcgctaaat    1620
gccgcaatag aagcagcacg ggcaaatgaa catggaaaag gttttgcagt agtagcagat    1680
gaagtaaaga agctagcaga gcaatctaaa actaccgcac aatctactaa aaacgaagaa    1740
aatgaaatga tgcaatctat tttaaaggtt attgaagtat ctgatttact tcagaacaaa    1800
atggataata taaataacga tatattaact atatcggaaa ctatccaaga gataagtgct    1860
aagagtcagg agatagtttc tagctctgaa aagttaataa acagtgagtc acattaa    1917
```

<210> SEQ ID NO 14
<211> LENGTH: 638
<212> TYPE: PRT
<213> ORGANISM: C. autoethanogenum

<400> SEQUENCE: 14

```
Met Asn Lys Ser Pro Val Thr Val Leu Lys Glu Lys Cys Thr Gly Cys
1               5                   10                  15

Asn Lys Cys Ile Arg Thr Cys Pro Ile Leu Gly Ala Asn Val Thr Ala
            20                  25                  30

Thr Glu Asn Gly Val Ser Lys Val Tyr Ile Asp Glu Arg Cys Ile
        35                  40                  45

Gly Cys Gly Glu Cys Val Lys Val Cys Glu His Gly Ala Arg Asp Phe
    50                  55                  60

Asn Asp Ser Thr Gln Asp Phe Phe Lys Asp Leu Lys Lys Gly Lys Lys
65                  70                  75                  80

Ile Thr Val Ile Ala Ala Pro Ser Ile Val Asn Ile Lys Asn Tyr
                85                  90                  95

Lys Lys Phe Phe Gly Tyr Leu Lys Ser Leu Gly Val Ser Ile Ile Tyr
            100                 105                 110
```

-continued

Asp Val Ser Phe Gly Ala Asp Ile Thr Thr Trp Ala Tyr Leu Lys Ala
    115                 120                 125

Met Lys Glu Lys Asn Ile Ser Ser Leu Ile Ser Gln Pro Cys Pro Ile
130                 135                 140

Val Val Asn Tyr Ile Glu Lys Tyr Lys Pro Glu Leu Ile Glu Tyr Leu
145                 150                 155                 160

Ala Pro Ile His Ser Pro Met Met Cys Thr Ala Val Tyr Leu Lys Lys
                165                 170                 175

Tyr Lys His Ile Cys Glu Asp Ile Ala Phe Leu Ser Pro Cys Ile Gly
            180                 185                 190

Lys Leu Ile Glu Ile Asn Asp Lys Asn Thr Asp Gly Tyr Val Lys Tyr
        195                 200                 205

Asn Val Thr Tyr Lys Lys Ile Leu Asp Tyr Leu Arg Asp Asn Asn Val
    210                 215                 220

Asn Leu Asn Asn Tyr Asp Glu Val Glu Phe Asp Asn Val Pro Ala Ser
225                 230                 235                 240

Leu Gly Val Val Tyr Ser Leu Pro Gly Gly Leu Lys Ala Asn Val Lys
                245                 250                 255

Ala Arg Thr Glu Glu Leu His Val Leu Gln Ile Glu Gly His Lys Glu
            260                 265                 270

Ala Ile Glu Tyr Leu Asn Lys Tyr Ser Asp Arg Val Lys Ala Asn Lys
        275                 280                 285

Leu Ile Pro Ser Leu Leu Asp Ile Leu Asn Cys Lys Asn Gly Cys Asn
    290                 295                 300

Ile Gly Thr Ala Ser Leu Asp Asn Leu Thr Glu Tyr Asp Ile Gln Tyr
305                 310                 315                 320

Arg Phe His Asp Ile Lys Val Glu Lys Leu Arg Glu Lys Thr Gly Leu
                325                 330                 335

Phe Lys Lys Lys Ile Lys Ser Ile Asp Glu Tyr Phe Asp Lys Asn Leu
            340                 345                 350

Asn Leu Asn Asp Phe Val Arg Lys Tyr Thr Ala Gln Lys Val Lys Lys
        355                 360                 365

Ile Ile Glu Pro Thr Gln Lys Asp Tyr Asp Asn Ile Phe Asp Glu Met
    370                 375                 380

Met Lys Thr Thr Thr Leu Gly Lys Glu Phe Asn Cys Ser Ala Cys Gly
385                 390                 395                 400

Tyr Ser Thr Cys Lys Glu Met Val Lys Met Ile Phe Asn Gly Ile Asn
                405                 410                 415

Ser Lys Glu Asn Cys Ile Tyr Tyr Val Lys Lys Ile Asn Met Glu
            420                 425                 430

Tyr Ser Glu Leu Glu Glu Lys Asn Glu Glu Val Lys Glu Ser Ile Asn
        435                 440                 445

Lys Ile Thr Val Leu Ala Glu Glu Arg Gln Arg Lys Ser Asp Glu Ile
    450                 455                 460

Ile Lys Phe Ala Asn Thr Leu Leu Ala Ile Asn Glu Val Ser Lys
465                 470                 475                 480

Gly Asn Glu Glu Ser Ala Ser Ala Ile Gln Asp Ile Val Glu Glu Leu
                485                 490                 495

Lys Ser Ile Met Asp Ile Ser Ser Lys Leu Lys Glu Asn Ile His Gln
            500                 505                 510

Ile Asn Glu Lys Leu Asp Lys Phe Thr Asp Ser Ser Asp Ser Ile Val
        515                 520                 525

Ala Ile Ser Glu Gln Thr Asn Leu Leu Ser Leu Asn Ala Ala Ile Glu

```
    530                 535                 540

Ala Ala Arg Ala Asn Glu His Gly Lys Gly Phe Ala Val Val Ala Asp
545                 550                 555                 560

Glu Val Lys Lys Leu Ala Glu Gln Ser Lys Thr Thr Ala Gln Ser Thr
                565                 570                 575

Lys Asn Glu Glu Asn Glu Met Met Gln Ser Ile Leu Lys Val Ile Glu
            580                 585                 590

Val Ser Asp Leu Leu Gln Asn Lys Met Asp Asn Ile Asn Asn Asp Ile
        595                 600                 605

Leu Thr Ile Ser Glu Thr Ile Gln Glu Ile Ser Ala Lys Ser Gln Glu
    610                 615                 620

Ile Val Ser Ser Ser Glu Lys Leu Ile Asn Ser Glu Ser His
625                 630                 635

<210> SEQ ID NO 15
<211> LENGTH: 1347
<212> TYPE: DNA
<213> ORGANISM: Unknown
<220> FEATURE:
<223> OTHER INFORMATION: Clostridium autoethanogenum

<400> SEQUENCE: 15
ttgagagatg attataggaa tctatttaaa ttcataataa aggcatatta tagtggaaat      60
tttgaagaag aagtgatgtc atttttatta gagtctaaaa tggataaaca ggaattgtgt     120
aagattatat ctacgttgtg cggcactaat atagattata gttccaattt tatagaaaat     180
ttgaaaaaag caataaagtc ttataaacaa gaaggtaaag tagtcaataa agttagagac     240
tgttccatgg aatgtgtgga tgaaaaaggt gagatacttt gtcaaaaaac atgtcctttt     300
gatgcaattt ttatagacaa taagaaaaat tgtgcttaca tagataaaga aaaatgtacc     360
gattgtggtt tttgtgtaga tgtttgtcct actgggggaa taatggataa agttcagttc     420
attcctcttg ctgatatttt aaaaagcaaa tctccagttg tggctatagt ggctcctgcc     480
ataataggac agtttggcga agatgttact atggatcaac ttaggactgc ttttaaaaaa     540
ctgggattta ctgatatgat tgaagtggca ttttttgcag atatgcttac tttaaaggag     600
tctattgaat ttgacaatca tgtaaaagat gaaaaagatt ttatgataac ctcctgctgc     660
tgccctatgt gggtagctat ggtaaaaaag gtatacagta atttggttaa acacgtatcc     720
ccctctgtat ctccaatggt tgcaggagga agagtactta aaaagttaaa cccttactgc     780
aaggtagtgt ttataggacc atgtattgct aaaaaatctg aggcaaagga agaagacata     840
aaaggagcaa tagatttcgt acttactttt gaagaattaa gagatatatt tgatgctttt     900
catatagttc catctaaact tgaaggagat tttcctcta aatatgcgtc taggggtgga      960
agattatatg ctcgtacagg gggagtttct attgcagtaa gcgaagctgt ggaaagaatt    1020
ttccctgaaa agcataaact atttagtgca attcaggcaa atggcattag agaatgtaga    1080
gaaatgctta ccaaggtgca aaatggagaa ataaaagcta attttattga aggaatgggc    1140
tgcattggcg gatgtgtagg tggtcccaaa gcaattgtac ttaaggatga aggtagggat    1200
cgagtaaata aatttgcaca agattctgaa ataaaagttg ctgtagatag tgaatgcatg    1260
catggagtat tacatgcttt ggatatacat tctatagatg attttaagga tgagaaaaaa    1320
atagaactgt tagaacgaga attttaa                                        1347

<210> SEQ ID NO 16
<211> LENGTH: 448
```

<212> TYPE: PRT
<213> ORGANISM: Unknown
<220> FEATURE:
<223> OTHER INFORMATION: Clostridium autoethanogenum

<400> SEQUENCE: 16

```
Met Arg Asp Asp Tyr Arg Asn Leu Phe Lys Phe Ile Ile Lys Ala Tyr
1               5                   10                  15

Tyr Ser Gly Asn Phe Glu Glu Val Met Ser Phe Leu Leu Glu Ser
            20                  25                  30

Lys Met Asp Lys Gln Glu Leu Cys Lys Ile Ile Ser Thr Leu Cys Gly
            35                  40                  45

Thr Asn Ile Asp Tyr Ser Ser Asn Phe Ile Glu Asn Leu Lys Lys Ala
50                  55                  60

Ile Lys Ser Tyr Lys Gln Glu Gly Lys Val Val Asn Lys Val Arg Asp
65                  70                  75                  80

Cys Ser Met Glu Cys Val Asp Glu Lys Gly Glu Ile Leu Cys Gln Lys
                85                  90                  95

Thr Cys Pro Phe Asp Ala Ile Phe Ile Asp Asn Lys Lys Asn Cys Ala
            100                 105                 110

Tyr Ile Asp Lys Glu Lys Cys Thr Asp Cys Gly Phe Cys Val Asp Val
            115                 120                 125

Cys Pro Thr Gly Gly Ile Met Asp Lys Val Gln Phe Ile Pro Leu Ala
130                 135                 140

Asp Ile Leu Lys Ser Lys Ser Pro Val Val Ala Ile Val Ala Pro Ala
145                 150                 155                 160

Ile Ile Gly Gln Phe Gly Glu Asp Val Thr Met Asp Gln Leu Arg Thr
                165                 170                 175

Ala Phe Lys Lys Leu Gly Phe Thr Asp Met Ile Glu Val Ala Phe Phe
            180                 185                 190

Ala Asp Met Leu Thr Leu Lys Glu Ser Ile Glu Phe Asp Asn His Val
            195                 200                 205

Lys Asp Glu Lys Asp Phe Met Ile Thr Ser Cys Cys Cys Pro Met Trp
210                 215                 220

Val Ala Met Val Lys Lys Val Tyr Ser Asn Leu Val Lys His Val Ser
225                 230                 235                 240

Pro Ser Val Ser Pro Met Val Ala Gly Gly Arg Val Leu Lys Lys Leu
                245                 250                 255

Asn Pro Tyr Cys Lys Val Val Phe Ile Gly Pro Cys Ile Ala Lys Lys
            260                 265                 270

Ser Glu Ala Lys Glu Glu Asp Ile Lys Gly Ala Ile Asp Phe Val Leu
            275                 280                 285

Thr Phe Glu Glu Leu Arg Asp Ile Phe Asp Ala Phe His Ile Val Pro
290                 295                 300

Ser Lys Leu Glu Gly Asp Phe Ser Ser Lys Tyr Ala Ser Arg Gly Gly
305                 310                 315                 320

Arg Leu Tyr Ala Arg Thr Gly Gly Val Ser Ile Ala Val Ser Glu Ala
                325                 330                 335

Val Glu Arg Ile Phe Pro Glu Lys His Lys Leu Phe Ser Ala Ile Gln
            340                 345                 350

Ala Asn Gly Ile Arg Glu Cys Arg Glu Met Leu Thr Lys Val Gln Asn
            355                 360                 365

Gly Glu Ile Lys Ala Asn Phe Ile Glu Gly Met Gly Cys Ile Gly Gly
370                 375                 380
```

Cys Val Gly Gly Pro Lys Ala Ile Val Leu Lys Asp Glu Gly Arg Asp
385                 390                 395                 400

Arg Val Asn Lys Phe Ala Gln Asp Ser Glu Ile Lys Val Ala Val Asp
                405                 410                 415

Ser Glu Cys Met His Gly Val Leu His Ala Leu Asp Ile His Ser Ile
            420                 425                 430

Asp Asp Phe Lys Asp Glu Lys Lys Ile Glu Leu Leu Glu Arg Glu Phe
            435                 440                 445

<210> SEQ ID NO 17
<211> LENGTH: 1374
<212> TYPE: DNA
<213> ORGANISM: Unknown
<220> FEATURE:
<223> OTHER INFORMATION: Clostridium autoethanogenum

<400> SEQUENCE: 17

```
ttgacagtta aaagtgaagg tattgtcaaa attgataaag agttgtgtac aggatgtaga      60
cgatgtgcag atatttgtcc tgtagatgct atagaaggtg agaagggaca acctcaaaca     120
attaatactg aacgctgtgt tttgtgtggt cagtgtgtac aaatttgcag tgcttatgca     180
tctgcatttg atgaagatat tactcctcat aaggaaaaga taaagagcg taatatgctt     240
ccatctgtta aagagccctt atttgcatcc tactatagag gagatgctcc agcagtaaaa     300
gaggccttag caaattctaa acttttact atggttcaat gcgcaccagc agtacgtgtg     360
gctattgccg aagaatttgg tatgccactt ggaagtttaa caccagggaa atggcagct     420
gcgctaagag agttaggttt tgatcgaatt tatgatacta attttgctgc tgatctaact     480
attatggagg aaggcagtga acttattaaa agggttactg aaggtggagt actgccaatg     540
ttcacttcat gttgtcctgc ttgggtaaaa tttattgagc aggattatcc ggaacttatt     600
ccacatctgt cttcttgtaa atctccgcag caaatggaag gtgctctgct aaaacatat     660
ggtgcacagg ttgatggtgt agatgctggc aagatttata gtgtttcagt tatgccttgt     720
atttgcaaaa aatttgaatg tgaacgtcct gaaatgaaag acagtggata tcaggatgta     780
gatgctgtaa ttaccacacg ggaacttgca caattaatca aggatgatgg cattgatttt     840
aatggtttac ctgaaaaaga atttgacaag ccacttggaa cttattctgg tgcaggcact     900
attttctgtg ctactggtgg tgttatgaa gctgccctgc gtacggcata taaattgatt     960
actaaagaag agattccaga tgtcgatctc aaattcataa gaggaggcga aggcgcaaga    1020
agttcagaaa ttaaagtagg agatttaaca ctaaaagtag cagtagttgc tggtctgaaa    1080
aatgttgtac cagttttgga agcaattaaa actggaaaag cagatttcca tttcattgaa    1140
gtgatgacct gtccagttgg atgtgttagc gggggggcgga acctaaggt attgataccct    1200
gatgaaaaag ctgattcgta tactaatcgt acatgcagta cgtatgtaca tgatgaaaat    1260
atggaatata gaaaatcaca tgataatcct gaaatacaga aaatttataa agaattcttg    1320
gtagaagata atattcatca tttgcttcat actacgtata cgccaaggag gtaa          1374
```

<210> SEQ ID NO 18
<211> LENGTH: 457
<212> TYPE: PRT
<213> ORGANISM: Unknown
<220> FEATURE:
<223> OTHER INFORMATION: Clostridium autoethanogenum

<400> SEQUENCE: 18

Met Thr Val Lys Ser Glu Gly Ile Val Lys Ile Asp Lys Glu Leu Cys

-continued

```
1               5                   10                  15
Thr Gly Cys Arg Arg Cys Ala Asp Ile Cys Pro Val Asp Ala Ile Glu
                20                  25                  30
Gly Glu Lys Gly Gln Pro Gln Thr Ile Asn Thr Glu Arg Cys Val Leu
                35                  40                  45
Cys Gly Gln Cys Val Gln Ile Cys Ser Ala Tyr Ala Ser Ala Phe Asp
        50                  55                  60
Glu Asp Ile Thr Pro His Lys Glu Lys Ile Lys Glu Arg Asn Met Leu
65                  70                  75                  80
Pro Ser Val Lys Glu Pro Leu Phe Ala Ser Tyr Arg Gly Asp Ala
                85                  90                  95
Pro Ala Val Lys Glu Ala Leu Ala Asn Ser Lys Leu Phe Thr Met Val
                100                 105                 110
Gln Cys Ala Pro Ala Val Arg Val Ala Ile Ala Glu Glu Phe Gly Met
                115                 120                 125
Pro Leu Gly Ser Leu Thr Pro Gly Lys Met Ala Ala Ala Leu Arg Glu
        130                 135                 140
Leu Gly Phe Asp Arg Ile Tyr Asp Thr Asn Phe Ala Ala Asp Leu Thr
145                 150                 155                 160
Ile Met Glu Glu Gly Ser Glu Leu Ile Lys Arg Val Thr Glu Gly Gly
                165                 170                 175
Val Leu Pro Met Phe Thr Ser Cys Cys Pro Ala Trp Val Lys Phe Ile
                180                 185                 190
Glu Gln Asp Tyr Pro Glu Leu Ile Pro His Leu Ser Ser Cys Lys Ser
                195                 200                 205
Pro Gln Gln Met Glu Gly Ala Leu Leu Lys Thr Tyr Gly Ala Gln Val
        210                 215                 220
Asp Gly Val Asp Ala Gly Lys Ile Tyr Ser Val Ser Val Met Pro Cys
225                 230                 235                 240
Ile Cys Lys Lys Phe Glu Cys Glu Arg Pro Glu Met Lys Asp Ser Gly
                245                 250                 255
Tyr Gln Asp Val Asp Ala Val Ile Thr Thr Arg Glu Leu Ala Gln Leu
                260                 265                 270
Ile Lys Asp Asp Gly Ile Asp Phe Asn Gly Leu Pro Glu Lys Glu Phe
                275                 280                 285
Asp Lys Pro Leu Gly Thr Tyr Ser Gly Ala Gly Thr Ile Phe Cys Ala
        290                 295                 300
Thr Gly Gly Val Met Glu Ala Ala Leu Arg Thr Ala Tyr Lys Leu Ile
305                 310                 315                 320
Thr Lys Glu Glu Ile Pro Asp Val Asp Leu Lys Phe Ile Arg Gly Gly
                325                 330                 335
Glu Gly Ala Arg Ser Ser Glu Ile Lys Val Gly Asp Leu Thr Leu Lys
                340                 345                 350
Val Ala Val Ala Gly Leu Lys Asn Val Pro Val Leu Glu Ala
                355                 360                 365
Ile Lys Thr Gly Lys Ala Asp Phe His Phe Ile Glu Val Met Thr Cys
        370                 375                 380
Pro Val Gly Cys Val Ser Gly Gly Gly Gln Pro Lys Val Leu Ile Pro
385                 390                 395                 400
Asp Glu Lys Ala Asp Ser Tyr Thr Asn Arg Thr Cys Ser Thr Tyr Val
                405                 410                 415
His Asp Glu Asn Met Glu Tyr Arg Lys Ser His Asp Asn Pro Glu Ile
                420                 425                 430
```

Gln Lys Ile Tyr Lys Glu Phe Leu Val Glu Asp Asn Ile His His Leu
        435                 440                 445

Leu His Thr Thr Tyr Thr Pro Arg Arg
    450                 455

<210> SEQ ID NO 19
<211> LENGTH: 1737
<212> TYPE: DNA
<213> ORGANISM: Unknown
<220> FEATURE:
<223> OTHER INFORMATION: Clostridium autoethanogenum

<400> SEQUENCE: 19

| | | | | | | |
|---|---|---|---|---|---|---|
| atggtaaatt | taactataaa | cgatataaag | gtttctgtcc | cagaaggcac | tacaatttta | 60 |
| aacgctgcaa | aaaagtaaa | cataaatata | cctactctct | gctatcttga | tcttcacgat | 120 |
| ataaaaatgg | taaatagaac | ttcctcctgc | agagtttgtc | ttgttgaaat | tgaaggaaga | 180 |
| cgaaatcttg | caccttcatg | ttctacagaa | gctttcgagg | gtatgatagt | tagaacaaac | 240 |
| agtgccagag | ctataaaagc | aaggcgtacc | atggtagaac | ttttattatc | agatcatcct | 300 |
| accgactgcc | ttgtatgtga | aaagaatact | caatgccaac | ttcaattaat | tgctgctgaa | 360 |
| ttaggtataa | ggaaaataag | atataaaggt | gctatgtcta | attataagaa | ggattcctcc | 420 |
| agcggtgctc | tatatagaaa | tctggataag | tgcataatgt | gcagacgatg | cgaaaccatg | 480 |
| tgcaatgaag | ttcaaacctg | tcaggtttac | tctgcagtag | atagaggctt | cgaaactgta | 540 |
| gtatccctg | catttggtcg | tcctatggtt | gacacgcaat | gcacattttg | cggtcaatgt | 600 |
| gtatcagtat | gtccaaccgc | tgcattaact | caagttagta | atgtagctaa | ggtatgggaa | 660 |
| gtactaactg | atcctgataa | atatgtagta | gttcaaactg | ccctgctat | aagagttact | 720 |
| ttaggtgaaa | aattcggtat | ggaacctgga | actattgtaa | ctggcaaaat | ggttgcagcc | 780 |
| ttaagaagat | tgggttttga | taaggtatgt | gatacagact | tgcagcaga | tgtaactatt | 840 |
| ttagaagaag | ctcatgaatt | tatagataga | cttcaaaatg | gtggaagact | tccaatactc | 900 |
| acaagctgct | gtcccagctg | ggttaaattt | ataggaacatc | aatttcctga | tcttttagat | 960 |
| ataccttcaa | cttgtaaatc | tccacacata | atgtttggta | ctttagctaa | aacatatatg | 1020 |
| gcagaaaaat | taaatattga | tccatctaaa | attgtagtag | tttcagttat | gccctgtatt | 1080 |
| gcaaaaaaat | atgaaataag | cagaaaaagag | cttcaatatg | aaggtcataa | aaatgttgat | 1140 |
| cttgtggtta | ccacaagaga | gcttgcagat | atgataatgg | aagcaggaat | agattttaac | 1200 |
| aaacttcctg | atgaagattt | tgataatcca | cttggagaat | ccacaggtgc | ctctgtaata | 1260 |
| tttggaacta | ccggcggcgt | aattgaagca | gctcttagaa | ctgcttatga | atggattact | 1320 |
| ggagagactt | taaagaagt | agaatttcat | agtgtaagag | gtcttgacgg | acttaaagaa | 1380 |
| gccagtataa | atattggtgg | taaaaaata | aacatcggtg | tagcacacgg | tcttggcaac | 1440 |
| gcaagaaaac | ttcttgagga | aatagaatct | ggtgaatcaa | aatatcatgc | tatagaaata | 1500 |
| atggcctgtc | ctggaggatg | tattgacgga | ggaggtcagc | catatcactt | tggagattta | 1560 |
| gatatcgtaa | agaaaagaat | ggaagcttta | tatagagaag | atagaaacaa | acctctcaga | 1620 |
| aaatctcatg | aaaatcctga | agttcaagct | ctatataaag | aatttattgg | tgatgtaggt | 1680 |
| ggaaaaaaag | ctcatgatct | ccttcacacc | cattatataa | aaaggcaaaa | attataa | 1737 |

<210> SEQ ID NO 20
<211> LENGTH: 578
<212> TYPE: PRT

<213> ORGANISM: Unknown
<220> FEATURE:
<223> OTHER INFORMATION: Clostridium autoethanogenum

<400> SEQUENCE: 20

| | | | | | | | | | | | | | | |
|---|---|---|---|---|---|---|---|---|---|---|---|---|---|---|
| Met | Val | Asn | Leu | Thr | Ile | Asn | Asp | Ile | Lys | Val | Ser | Val | Pro | Glu | Gly |
| 1 | | | | 5 | | | | | 10 | | | | | 15 | |
| Thr | Thr | Ile | Leu | Asn | Ala | Ala | Lys | Lys | Val | Asn | Ile | Asn | Ile | Pro | Thr |
| | | | 20 | | | | | 25 | | | | | 30 | | |
| Leu | Cys | Tyr | Leu | Asp | Leu | His | Asp | Ile | Lys | Met | Val | Asn | Arg | Thr | Ser |
| | | | 35 | | | | | 40 | | | | | 45 | | |
| Ser | Cys | Arg | Val | Cys | Leu | Val | Glu | Ile | Glu | Gly | Arg | Arg | Asn | Leu | Ala |
| | 50 | | | | | 55 | | | | | 60 | | | | |
| Pro | Ser | Cys | Ser | Thr | Glu | Ala | Phe | Glu | Gly | Met | Ile | Val | Arg | Thr | Asn |
| 65 | | | | | 70 | | | | | 75 | | | | | 80 |
| Ser | Ala | Arg | Ala | Ile | Lys | Ala | Arg | Arg | Thr | Met | Val | Glu | Leu | Leu | Leu |
| | | | | 85 | | | | | 90 | | | | | 95 | |
| Ser | Asp | His | Pro | Thr | Asp | Cys | Leu | Val | Cys | Glu | Lys | Asn | Thr | Gln | Cys |
| | | | 100 | | | | | 105 | | | | | 110 | | |
| Gln | Leu | Gln | Leu | Ile | Ala | Ala | Glu | Leu | Gly | Ile | Arg | Lys | Ile | Arg | Tyr |
| | | | 115 | | | | | 120 | | | | | 125 | | |
| Lys | Gly | Ala | Met | Ser | Asn | Tyr | Lys | Lys | Asp | Ser | Ser | Gly | Ala | Leu | |
| | 130 | | | | | 135 | | | | | 140 | | | | |
| Tyr | Arg | Asn | Leu | Asp | Lys | Cys | Ile | Met | Cys | Arg | Arg | Cys | Glu | Thr | Met |
| 145 | | | | | 150 | | | | | 155 | | | | | 160 |
| Cys | Asn | Glu | Val | Gln | Thr | Cys | Gln | Val | Tyr | Ser | Ala | Val | Asp | Arg | Gly |
| | | | | 165 | | | | | 170 | | | | | 175 | |
| Phe | Glu | Thr | Val | Val | Ser | Pro | Ala | Phe | Gly | Arg | Pro | Met | Val | Asp | Thr |
| | | | 180 | | | | | 185 | | | | | 190 | | |
| Gln | Cys | Thr | Phe | Cys | Gly | Gln | Cys | Val | Ser | Val | Cys | Pro | Thr | Ala | Ala |
| | | | 195 | | | | | 200 | | | | | 205 | | |
| Leu | Thr | Gln | Val | Ser | Asn | Val | Ala | Lys | Val | Trp | Glu | Val | Leu | Thr | Asp |
| | 210 | | | | | 215 | | | | | 220 | | | | |
| Pro | Asp | Lys | Tyr | Val | Val | Val | Gln | Thr | Ala | Pro | Ala | Ile | Arg | Val | Thr |
| 225 | | | | | 230 | | | | | 235 | | | | | 240 |
| Leu | Gly | Glu | Lys | Phe | Gly | Met | Glu | Pro | Gly | Thr | Ile | Val | Thr | Gly | Lys |
| | | | | 245 | | | | | 250 | | | | | 255 | |
| Met | Val | Ala | Ala | Leu | Arg | Arg | Leu | Gly | Phe | Asp | Lys | Val | Cys | Asp | Thr |
| | | | 260 | | | | | 265 | | | | | 270 | | |
| Asp | Phe | Ala | Ala | Asp | Val | Thr | Ile | Leu | Glu | Glu | Ala | His | Glu | Phe | Ile |
| | | | 275 | | | | | 280 | | | | | 285 | | |
| Asp | Arg | Leu | Gln | Asn | Gly | Gly | Arg | Leu | Pro | Ile | Leu | Thr | Ser | Cys | Cys |
| | 290 | | | | | 295 | | | | | 300 | | | | |
| Pro | Ser | Trp | Val | Lys | Phe | Ile | Glu | His | Gln | Phe | Pro | Asp | Leu | Leu | Asp |
| 305 | | | | | 310 | | | | | 315 | | | | | 320 |
| Ile | Pro | Ser | Thr | Cys | Lys | Ser | Pro | His | Ile | Met | Phe | Gly | Thr | Leu | Ala |
| | | | | 325 | | | | | 330 | | | | | 335 | |
| Lys | Thr | Tyr | Met | Ala | Glu | Lys | Leu | Asn | Ile | Asp | Pro | Ser | Lys | Ile | Val |
| | | | 340 | | | | | 345 | | | | | 350 | | |
| Val | Val | Ser | Val | Met | Pro | Cys | Ile | Ala | Lys | Lys | Tyr | Glu | Ile | Ser | Arg |
| | | | 355 | | | | | 360 | | | | | 365 | | |
| Lys | Glu | Leu | Gln | Tyr | Glu | Gly | His | Lys | Asn | Val | Asp | Leu | Val | Val | Thr |
| | 370 | | | | | 375 | | | | | 380 | | | | |
| Thr | Arg | Glu | Leu | Ala | Asp | Met | Ile | Met | Glu | Ala | Gly | Ile | Asp | Phe | Asn |

Lys Leu Pro Asp Glu Asp Phe Asp Asn Pro Leu Gly Glu Ser Thr Gly
            385                 390                 395                 400

Ala Ser Val Ile Phe Gly Thr Thr Gly Val Ile Glu Ala Ala Leu
        405                 410                 415

Arg Thr Ala Tyr Glu Trp Ile Thr Gly Glu Thr Leu Lys Glu Val Glu
420                 425                 430

Phe His Ser Val Arg Gly Leu Asp Gly Leu Lys Glu Ala Ser Ile Asn
            435                 440                 445

Ile Gly Gly Lys Lys Ile Asn Ile Gly Val Ala His Gly Leu Gly Asn
450                 455                 460

Ala Arg Lys Leu Leu Glu Ile Glu Ser Glu Ser Lys Tyr His
465                 470                 475                 480

Ala Ile Glu Ile Met Ala Cys Pro Gly Gly Cys Ile Asp Gly Gly Gly
            485                 490                 495

Gln Pro Tyr His Phe Gly Asp Leu Asp Ile Val Lys Lys Arg Met Glu
500                 505                 510

Ala Leu Tyr Arg Glu Asp Arg Asn Lys Pro Leu Arg Lys Ser His Glu
            515                 520                 525

Asn Pro Glu Val Gln Ala Leu Tyr Lys Glu Phe Ile Gly Asp Val Gly
530                 535                 540

Gly Lys Lys Ala His Asp Leu Leu His Thr His Tyr Ile Lys Arg Gln
545                 550                 555                 560

Lys Leu
            565                 570                 575

<210> SEQ ID NO 21
<211> LENGTH: 882
<212> TYPE: DNA
<213> ORGANISM: Unknown
<220> FEATURE:
<223> OTHER INFORMATION: Clostridium ragsdalei

<400> SEQUENCE: 21
atgaatgttc gaaacaaggg tatatgtcct ttaatcgtag ataaggaacg cagttcaaag      60
gcttttacta gtgaagctat agatttaatt aaaagggaa agacgaaaaa attaaatgct     120
atatggcttg aagtaacagg atgttcagga atattatt cttttttaaa tagtgaaaat     180
cctggactcg attatattt agaaaaactc attaatttaa atacaacaa tactctaatg     240
acttcagaag gtgagtatgc ttttaaacaa ttcttagata cattggatac tgaattata     300
ctactagtag atggagcggt atctactgct caaaatggtt tttataatat tgttgccaat     360
tatgaaggaa aacctgttac tgcacttgaa gctgtaaaaa tggcaggaga aaaagcaaag     420
tatgttctct gtgtaggaac ttgtgcatcc tatggtggaa tttctgccgc aggccaaac     480
ccatcagaaa gcaaaagtgt taaagaaata ctaaatcgtg aagtcataag acttccaggc     540
tgtccatgcc atccggattg ggtagttgga actttagcac atttagttgc ttttggcaaa     600
ccgcaattgg atgaagatgg aagacctctt ctttttttatg gaattaccat tcatgatagg     660
tgtacaagaa ggggattttt tgataacaga atttttgcaa aaaatttgg agaagatgga     720
tgtatgttta aacttggatg caggggggcct gtaactaaaa cagattgtcc taggagaaag     780
tggaatggat atgtgaactg gcctgttgaa gacaatacca actgtataagg atgtgcaaat     840
tctagatttc cagatggtat ggaaccattt gtaaggtatt ag                         882

<210> SEQ ID NO 22

<211> LENGTH: 293
<212> TYPE: PRT
<213> ORGANISM: Unknown
<220> FEATURE:
<223> OTHER INFORMATION: Clostridium ragsdalei

<400> SEQUENCE: 22

Met Asn Val Arg Asn Lys Gly Ile Cys Pro Leu Ile Val Asp Lys Glu
1               5                   10                  15

Arg Ser Ser Lys Ala Phe Thr Ser Glu Ala Ile Asp Leu Ile Lys Arg
            20                  25                  30

Gly Lys Thr Lys Lys Leu Asn Ala Ile Trp Leu Glu Val Thr Gly Cys
        35                  40                  45

Ser Gly Asn Ile Ile Ser Phe Leu Asn Ser Glu Asn Pro Gly Leu Asp
    50                  55                  60

Tyr Ile Leu Glu Lys Leu Ile Asn Leu Lys Tyr Asn Asn Thr Leu Met
65                  70                  75                  80

Thr Ser Glu Gly Glu Tyr Ala Phe Lys Gln Phe Leu Asp Thr Leu Asp
                85                  90                  95

Thr Glu Phe Ile Leu Leu Val Asp Gly Ala Val Ser Thr Ala Gln Asn
            100                 105                 110

Gly Phe Tyr Asn Ile Val Ala Asn Tyr Glu Gly Lys Pro Val Thr Ala
        115                 120                 125

Leu Glu Ala Val Lys Met Ala Gly Glu Lys Ala Lys Tyr Val Leu Cys
    130                 135                 140

Val Gly Thr Cys Ala Ser Tyr Gly Gly Ile Ser Ala Ala Arg Pro Asn
145                 150                 155                 160

Pro Ser Glu Ser Lys Ser Val Lys Glu Ile Leu Asn Arg Glu Val Ile
                165                 170                 175

Arg Leu Pro Gly Cys Pro Cys His Pro Asp Trp Val Val Gly Thr Leu
            180                 185                 190

Ala His Leu Val Ala Phe Gly Lys Pro Gln Leu Asp Glu Asp Gly Arg
        195                 200                 205

Pro Leu Leu Phe Tyr Gly Ile Thr Ile His Asp Arg Cys Thr Arg Arg
    210                 215                 220

Gly Phe Phe Asp Asn Arg Ile Phe Ala Lys Lys Phe Gly Glu Asp Gly
225                 230                 235                 240

Cys Met Phe Lys Leu Gly Cys Arg Gly Pro Val Thr Lys Thr Asp Cys
                245                 250                 255

Pro Arg Arg Lys Trp Asn Gly Tyr Val Asn Trp Pro Val Glu Asp Asn
            260                 265                 270

Thr Asn Cys Ile Gly Cys Ala Asn Ser Arg Phe Pro Asp Gly Met Glu
        275                 280                 285

Pro Phe Val Arg Tyr
        290

<210> SEQ ID NO 23
<211> LENGTH: 1386
<212> TYPE: DNA
<213> ORGANISM: Unknown
<220> FEATURE:
<223> OTHER INFORMATION: Clostridium ragsdalei

<400> SEQUENCE: 23
atgaaaaaga aaattaccat tgatccaatt acgagaataa gtggttttt ggaaactaaa      60 gtgcaagtag aaaaaaatat tatagtagat gctgaaacta gtggattgct tttagagga     120

-continued

```
tttgaaaaaa tgttaaaaaa cagacagccg ctggatgcag tatattttac agaaagaatt    180
tgtgggatat gttcaacagc tcatgctgtg gcagctgcta cagctcttga agatgctttg    240
aagataaaaa ttagtgtaaa tgattcgtat atgcgtaatt taatacatgg ttttgaattt    300
atacaaaatc atataagaca tttttataat ttgactatac caagttatgt gaagatgccc    360
aatataaatc ctcttttttc agatcaatat gaagattata gattacctta taacttaaat    420
aaaaagataa gtgaagatta tattgaaagt attaaataca gtaggttagc ccatgaagga    480
ttggctactc ttggaggaaa ggctccccat aatcacggaa ttttgttgg aggagttacc     540
ataaatatag atccatataa acttacaaaa gttaaatcta ttatttctca aattaatgaa    600
ttcgtaagta gtgttatgtt agaggacatg aacataattt caaaatacta tgctgattat    660
tttaaaatgg gaaaagccta tggaaacttt atgacttatg aattttttga taagtatgct    720
gatcctgaga taagttatgt aggaccttct gtcttaataa atggacaaaa gcataacttt    780
aatagtaata aaattacaga gaatatactt tacacctggt acatgaatga tgatgaaaca    840
ataaatttat ctaaagaaac aggttacagc tttataaaat cgccaactta tgatggctat    900
tctatggaag taggacctct agcaagattg atactttcag gtgagtatac tggtggaagt    960
tcatgtatgg acagaaatgt tgccagagta cttgaaacaa aaagattttt agaaattatg   1020
caaggacttg cagatagaat taagcttatt ccagcagaac aaagaatata tgaaatccca   1080
gataaagcat ttggtgcagg attaattgac acaactagag gatccttggg acactggata   1140
agtatagaag ataaatttat aaagcattac aatattataa ctcctacagt gtggaacatg   1200
gggccaagaa atcaatcagg tgcgcttgga attggagaaa atctttact tggaacgaaa    1260
ataaaagata taaagcagcc tatagaagtt gggagaatta tgaggtcctt tgatccttgt   1320
gtttcctgtg caactcattt gataagtgat gcatatgaac cagtggacgt acaggttata   1380
gtatga                                                              1386
```

<210> SEQ ID NO 24
<211> LENGTH: 461
<212> TYPE: PRT
<213> ORGANISM: Unknown
<220> FEATURE:
<223> OTHER INFORMATION: Clostridium ragsdalei

<400> SEQUENCE: 24

```
Met Lys Lys Lys Ile Thr Ile Asp Pro Ile Thr Arg Ile Ser Gly Phe
1               5                   10                  15

Leu Glu Thr Lys Val Gln Val Glu Lys Asn Ile Ile Val Asp Ala Glu
            20                  25                  30

Thr Ser Gly Leu Leu Phe Arg Gly Phe Glu Lys Met Leu Lys Asn Arg
        35                  40                  45

Gln Pro Leu Asp Ala Val Tyr Phe Thr Glu Arg Ile Cys Gly Ile Cys
    50                  55                  60

Ser Thr Ala His Ala Val Ala Ala Thr Ala Leu Glu Asp Ala Leu
65                  70                  75                  80

Lys Ile Lys Ile Ser Val Asn Asp Ser Tyr Met Arg Asn Leu Ile His
                85                  90                  95

Gly Phe Glu Phe Ile Gln Asn His Ile Arg His Phe Tyr Asn Leu Thr
            100                 105                 110

Ile Pro Ser Tyr Val Lys Met Pro Asn Ile Asn Pro Leu Phe Ser Asp
        115                 120                 125

Gln Tyr Glu Asp Tyr Arg Leu Pro Tyr Asn Leu Asn Lys Lys Ile Ser
```

```
                130              135                140
Glu Asp Tyr Ile Glu Ser Ile Lys Tyr Ser Arg Leu Ala His Glu Gly
145                 150                 155                 160

Leu Ala Thr Leu Gly Gly Lys Ala Pro His Asn His Gly Ile Phe Val
                165                 170                 175

Gly Gly Val Thr Ile Asn Ile Asp Pro Tyr Lys Leu Thr Lys Val Lys
            180                 185                 190

Ser Ile Ile Ser Gln Ile Asn Glu Phe Val Ser Val Met Leu Glu
            195                 200                 205

Asp Met Asn Ile Ile Ser Lys Tyr Tyr Ala Asp Tyr Phe Lys Met Gly
    210                 215                 220

Lys Ala Tyr Gly Asn Phe Met Thr Tyr Gly Ile Phe Asp Lys Tyr Ala
225                 230                 235                 240

Asp Pro Glu Ile Ser Tyr Val Gly Pro Ser Val Leu Ile Asn Gly Gln
                245                 250                 255

Lys His Asn Phe Asn Ser Asn Lys Ile Thr Glu Asn Ile Leu Tyr Thr
            260                 265                 270

Trp Tyr Met Asn Asp Asp Glu Thr Ile Asn Leu Ser Lys Glu Thr Gly
        275                 280                 285

Tyr Ser Phe Ile Lys Ser Pro Thr Tyr Asp Gly Tyr Ser Met Glu Val
290                 295                 300

Gly Pro Leu Ala Arg Leu Ile Leu Ser Gly Tyr Thr Gly Gly Ser
305                 310                 315                 320

Ser Cys Met Asp Arg Asn Val Ala Arg Val Leu Glu Thr Lys Lys Ile
                325                 330                 335

Leu Glu Ile Met Gln Gly Leu Ala Asp Arg Ile Lys Leu Ile Pro Ala
            340                 345                 350

Glu Gln Arg Ile Tyr Glu Ile Pro Asp Lys Ala Phe Gly Ala Gly Leu
        355                 360                 365

Ile Asp Thr Thr Arg Gly Ser Leu Gly His Trp Ile Ser Ile Glu Asp
370                 375                 380

Lys Phe Ile Lys His Tyr Asn Ile Ile Thr Pro Thr Val Trp Asn Met
385                 390                 395                 400

Gly Pro Arg Asn Gln Ser Gly Ala Leu Gly Ile Gly Glu Lys Ser Leu
                405                 410                 415

Leu Gly Thr Lys Ile Lys Asp Ile Lys Gln Pro Ile Glu Val Gly Arg
            420                 425                 430

Ile Met Arg Ser Phe Asp Pro Cys Val Ser Cys Ala Thr His Leu Ile
        435                 440                 445

Ser Asp Ala Tyr Glu Pro Val Asp Val Gln Val Ile Val
450                 455                 460

<210> SEQ ID NO 25
<211> LENGTH: 1398
<212> TYPE: DNA
<213> ORGANISM: Unknown
<220> FEATURE:
<223> OTHER INFORMATION: Clostridium ragsdalei

<400> SEQUENCE: 25
atgttaaata tgccaactag tacttctatg ataaatatag atgaagaatt atgtacaggc      60
tgcagacgat gtgcggatgt ctgccctgta gatgctatag aaggtgaaca gggtaaacct     120
cagaagataa atactgaaaa gtgtgttatg tgcggacaat gcattcaagt ttgtaaaggc     180
tatcaatctg tatacgatga tattcctact ccagttagca aaaggttatt tgatagagga     240
```

```
ttgttaaagg aagtagatga accattattt gcagcatata ataaaggtca ggcaaagaga    300
gttaaagaaa ttttacaaaa caaagatgta tttaaaattg tgcaatgtgc acctgctgta    360
agagttgcta taggagagga ttttggaatg cctcttggaa ctttaagtga aggaaaaatg    420
gcagctgcac tcagaaaatt aggatttgac aaagtatatg atacaaactt tggtgcagat    480
cttactataa tggaagaagg tagtgagtta ctaaaaagag tagctgaagg tggagttttg    540
ccaatgttta cttcttgttg tccagcatgg gtaaatatg cagaacaaac atatccagaa    600
cttttacctc atctttcaag ttgtaagtct ccaaatcaga tggctggagc tatatttaaa    660
acttatggag cagagataaa taaggttaat ccggctaaaa tttataatgt atctgttatg    720
ccatgtacat gcaaggaatt tgaaagtgaa agagaagaaa tgcatgacag tggacacaga    780
gatgtagatg cagttataac tacaagggaa ttagcacaac tgttcaaaga tgctgatata    840
gattttaata ctattgaaga agaacagttt gatactcctc ttggtatgta tactggtgca    900
ggaactatat ttggtgctac aggtggagtt atggaagcag cacttagaac tggatatgaa    960
ctttatacta aaaaaactat tccaagtata gatcttacta tggtaagagg tggagaaggt    1020
tttagaactg ctgaagtaga tttaggagat attagactaa aagtaggagt agtttccggc    1080
ttaaaaaatg taaagatgt tatggaatca gtaaaggcag gtaaatgtga tttacacttt    1140
atagaggtta tgacttgtcc tcaaggatgt ataagtggtg gaggacaacc taaggttata    1200
cttgattcag ataaagaaga agcttataat aataggaaaa agggactata taatcatgac    1260
gctaatctta cttatagaaa atcacatgaa aatccagaaa taagaaaaat atatgatgag    1320
ttcttagaca aaccattagg agctaagtct catgaattat tgcacactaa atatatctca    1380
agaaaaaagg agagttaa                                                  1398

<210> SEQ ID NO 26
<211> LENGTH: 465
<212> TYPE: PRT
<213> ORGANISM: Unknown
<220> FEATURE:
<223> OTHER INFORMATION: Clostridium ragsdalei

<400> SEQUENCE: 26

Met Leu Asn Met Pro Thr Ser Thr Ser Met Ile Asn Ile Asp Glu Glu
1               5                   10                  15

Leu Cys Thr Gly Cys Arg Arg Cys Ala Asp Val Cys Pro Val Asp Ala
                20                  25                  30

Ile Glu Gly Glu Gln Gly Lys Pro Gln Lys Ile Asn Thr Glu Lys Cys
            35                  40                  45

Val Met Cys Gly Gln Cys Ile Gln Val Cys Lys Gly Tyr Gln Ser Val
        50                  55                  60

Tyr Asp Asp Ile Pro Thr Pro Val Ser Lys Arg Leu Phe Asp Arg Gly
65                  70                  75                  80

Leu Leu Lys Glu Val Asp Glu Pro Leu Phe Ala Ala Tyr Asn Lys Gly
                85                  90                  95

Gln Ala Lys Arg Val Lys Glu Ile Leu Gln Asn Lys Asp Val Phe Lys
            100                 105                 110

Ile Val Gln Cys Ala Pro Ala Val Arg Val Ala Ile Gly Glu Asp Phe
        115                 120                 125

Gly Met Pro Leu Gly Thr Leu Ser Glu Gly Lys Met Ala Ala Ala Leu
    130                 135                 140

Arg Lys Leu Gly Phe Asp Lys Val Tyr Asp Thr Asn Phe Gly Ala Asp
```

```
            145                 150                 155                 160
Leu Thr Ile Met Glu Glu Gly Ser Glu Leu Leu Lys Arg Val Ala Glu
                    165                 170                 175

Gly Gly Val Leu Pro Met Phe Thr Ser Cys Cys Pro Ala Trp Val Lys
                180                 185                 190

Tyr Ala Glu Gln Thr Tyr Pro Glu Leu Leu Pro His Leu Ser Ser Cys
            195                 200                 205

Lys Ser Pro Asn Gln Met Ala Gly Ala Ile Phe Lys Thr Tyr Gly Ala
        210                 215                 220

Glu Ile Asn Lys Val Asn Pro Ala Lys Ile Tyr Asn Val Ser Val Met
225                 230                 235                 240

Pro Cys Thr Cys Lys Glu Phe Glu Ser Glu Arg Glu Met His Asp
                    245                 250                 255

Ser Gly His Arg Asp Val Asp Ala Val Ile Thr Thr Arg Glu Leu Ala
                260                 265                 270

Gln Leu Phe Lys Asp Ala Asp Ile Asp Phe Asn Thr Ile Glu Glu Glu
            275                 280                 285

Gln Phe Asp Thr Pro Leu Gly Met Tyr Thr Gly Ala Gly Thr Ile Phe
        290                 295                 300

Gly Ala Thr Gly Gly Val Met Glu Ala Ala Leu Arg Thr Gly Tyr Glu
305                 310                 315                 320

Leu Tyr Thr Lys Lys Thr Ile Pro Ser Ile Asp Leu Thr Met Val Arg
                    325                 330                 335

Gly Gly Glu Gly Phe Arg Thr Ala Glu Val Asp Leu Gly Asp Ile Arg
                340                 345                 350

Leu Lys Val Gly Val Val Ser Gly Leu Lys Asn Val Lys Asp Val Met
            355                 360                 365

Glu Ser Val Lys Ala Gly Lys Cys Asp Leu His Phe Ile Glu Val Met
        370                 375                 380

Thr Cys Pro Gln Gly Cys Ile Ser Gly Gly Gly Gln Pro Lys Val Ile
385                 390                 395                 400

Leu Asp Ser Asp Lys Glu Glu Ala Tyr Asn Asn Arg Lys Lys Gly Leu
                    405                 410                 415

Tyr Asn His Asp Ala Asn Leu Thr Tyr Arg Lys Ser His Glu Asn Pro
                420                 425                 430

Glu Ile Lys Lys Ile Tyr Asp Glu Phe Leu Asp Lys Pro Leu Gly Ala
            435                 440                 445

Lys Ser His Glu Leu Leu His Thr Lys Tyr Ile Ser Arg Lys Lys Glu
        450                 455                 460

Ser
465

<210> SEQ ID NO 27
<211> LENGTH: 1737
<212> TYPE: DNA
<213> ORGANISM: C. ragsdalei

<400> SEQUENCE: 27
atggtaaatt taactataaa cgatataaag gtttctgtcc cagaaggcac tacaatttta      60
aacgctgcaa aaaagtaaa cataaatata cctactctct gctatcttga tcttcacgat    120
ataaaaatgg taaataggac ttcctcctgc agagtctgcc ttgttgaaat tgaaggcagg   180
cgaaatcttg caccttcatg ttctacagaa gctttcgaag gtatgatagt tagaacaaat    240
agtgccagag ctataaaagc aaggcgtact atggtagaac ttttattatc agatcatcct   300
```

```
accgactgcc ttgtatgtga aagaatact caatgtcaac ttcaattaat cgctgctgaa    360
ttaggtataa gaaaaataag atataaaggt gctatgtcta attacaaaaa ggattcatca    420
agtggtgcta tatatagaaa tcttgataaa tgtataatgt gcagacgatg tgaaaccatg    480
tgcaatgaag ttcaaacctg tcaggtttac tctgcagtag atagaggctt cgaaactgta    540
gtatcccctg catttggtcg tcccatggtt gacacgcaat gcacattttg cggtcaatgt    600
gtatccgtat gcccaactgc tgcattaact caagttagta atgtagctaa ggtatgggaa    660
gtactaactg atcctgataa atatgtagta gttcaaactg cccctgctat aagagttact    720
ttaggtgaaa aattcggtat ggaacctgga actattgtaa ctggcaaaat ggtatctgct    780
cttagaagat gggctttga taaggtatgt gataccgatt ttgcagcaga tgtaactatt    840
ttagaagaag ctcatgaatt tatagataga cttcaaaacg gcggaagact tccaatactc    900
acaagctgct gtcccagctg ggttaaattt atagaacatc aatttcctga tcttttagat    960
ataccttcaa cttgtaagtc tccacacata atgtttggta ctttagctaa acatatatg   1020
gcagaaaaat taaatattga tccatctaaa attgtaatag tttcagttat gccatgtatt   1080
gcaaaaaaat atgaagtaag cagaaaagaa cttcaatatg aaggtcataa aaatgttgat   1140
cttgtagtta ccacaagaga gcttgcagat atgataatgg aagcaggaat agatttaat   1200
aaacttcctg atgaagactt tgataaacct tttggagaat ccacaggtgc ttctgtaata   1260
tttggaacta ccggcggtgt aattgaagca gctcttagaa ctgcttatga atggattact   1320
ggagagactt taaagaagt agaatttcat ggtgtaagag gacttgatgg acttaaagaa   1380
gccagtataa atattggtgg taagaaata aacattggcg tagctcacgg tcttggcaac   1440
gcaagaaaac ttcttgagga atagaatct ggtgaatcaa aatatcacgc tatagaaata   1500
atggcatgtc ctggaggatg tattgacgga ggaggtcagc cgtatcattt tggagattta   1560
gatattgtaa agaaaagaat ggacgcttta tatagagaag atagaaacaa acctctcaga   1620
aaatctcatg agaatcctga agttcaagct ctatataaag aatttattgg agatgtaggc   1680
ggaaaaaaag ctcatgatct ccttcacact cattatataa aaggcaaaa gttataa     1737
```

<210> SEQ ID NO 28
<211> LENGTH: 578
<212> TYPE: PRT
<213> ORGANISM: C. ragsdalei

<400> SEQUENCE: 28

```
Met Val Asn Leu Thr Ile Asn Asp Ile Lys Val Ser Val Pro Glu Gly
1               5                   10                  15

Thr Thr Ile Leu Asn Ala Ala Lys Lys Val Asn Ile Asn Ile Pro Thr
                20                  25                  30

Leu Cys Tyr Leu Asp Leu His Asp Ile Lys Met Val Asn Arg Thr Ser
            35                  40                  45

Ser Cys Arg Val Cys Leu Val Glu Ile Glu Gly Arg Arg Asn Leu Ala
        50                  55                  60

Pro Ser Cys Ser Thr Glu Ala Phe Glu Gly Met Ile Val Arg Thr Asn
65                  70                  75                  80

Ser Ala Arg Ala Ile Lys Ala Arg Arg Thr Met Val Glu Leu Leu Leu
                85                  90                  95

Ser Asp His Pro Thr Asp Cys Leu Val Cys Glu Lys Asn Thr Gln Cys
            100                 105                 110

Gln Leu Gln Leu Ile Ala Ala Glu Leu Gly Ile Arg Lys Ile Arg Tyr
```

```
              115                 120                 125
Lys Gly Ala Met Ser Asn Tyr Lys Lys Asp Ser Ser Gly Ala Ile
130                 135                 140

Tyr Arg Asn Leu Asp Lys Cys Ile Met Cys Arg Arg Cys Glu Thr Met
145                 150                 155                 160

Cys Asn Glu Val Gln Thr Cys Gln Val Tyr Ser Ala Val Asp Arg Gly
                165                 170                 175

Phe Glu Thr Val Val Ser Pro Ala Phe Gly Arg Pro Met Val Asp Thr
                180                 185                 190

Gln Cys Thr Phe Cys Gly Gln Cys Val Ser Val Cys Pro Thr Ala Ala
                195                 200                 205

Leu Thr Gln Val Ser Asn Val Ala Lys Val Trp Glu Val Leu Thr Asp
210                 215                 220

Pro Asp Lys Tyr Val Val Gln Thr Ala Pro Ala Ile Arg Val Thr
225                 230                 235                 240

Leu Gly Glu Lys Phe Gly Met Glu Pro Gly Thr Ile Val Thr Gly Lys
                245                 250                 255

Met Val Ser Ala Leu Arg Arg Leu Gly Phe Asp Lys Val Cys Asp Thr
                260                 265                 270

Asp Phe Ala Ala Asp Val Thr Ile Leu Glu Glu Ala His Glu Phe Ile
                275                 280                 285

Asp Arg Leu Gln Asn Gly Gly Arg Leu Pro Ile Leu Thr Ser Cys Cys
290                 295                 300

Pro Ser Trp Val Lys Phe Ile Glu His Gln Phe Pro Asp Leu Leu Asp
305                 310                 315                 320

Ile Pro Ser Thr Cys Lys Ser Pro His Ile Met Phe Gly Thr Leu Ala
                325                 330                 335

Lys Thr Tyr Met Ala Glu Lys Leu Asn Ile Asp Pro Ser Lys Ile Val
                340                 345                 350

Ile Val Ser Val Met Pro Cys Ile Ala Lys Lys Tyr Glu Val Ser Arg
                355                 360                 365

Lys Glu Leu Gln Tyr Glu Gly His Lys Asn Val Asp Leu Val Val Thr
370                 375                 380

Thr Arg Glu Leu Ala Asp Met Ile Met Glu Ala Gly Ile Asp Phe Asn
385                 390                 395                 400

Lys Leu Pro Asp Glu Asp Phe Asp Lys Pro Phe Gly Glu Ser Thr Gly
                405                 410                 415

Ala Ser Val Ile Phe Gly Thr Thr Gly Gly Val Ile Glu Ala Ala Leu
                420                 425                 430

Arg Thr Ala Tyr Glu Trp Ile Thr Gly Glu Thr Leu Lys Glu Val Glu
                435                 440                 445

Phe His Gly Val Arg Gly Leu Asp Gly Leu Lys Glu Ala Ser Ile Asn
                450                 455                 460

Ile Gly Gly Lys Glu Ile Asn Ile Gly Val Ala His Gly Leu Gly Asn
465                 470                 475                 480

Ala Arg Lys Leu Leu Glu Glu Ile Glu Ser Glu Ser Lys Tyr His
                485                 490                 495

Ala Ile Glu Ile Met Ala Cys Pro Gly Gly Cys Ile Gly Gly Gly
                500                 505                 510

Gln Pro Tyr His Phe Gly Asp Leu Asp Ile Val Lys Lys Arg Met Asp
                515                 520                 525

Ala Leu Tyr Arg Glu Asp Arg Asn Lys Pro Leu Arg Lys Ser His Glu
530                 535                 540
```

Asn Pro Glu Val Gln Ala Leu Tyr Lys Glu Phe Ile Gly Asp Val Gly
545                 550                 555                 560

Gly Lys Lys Ala His Asp Leu Leu His Thr His Tyr Ile Lys Arg Gln
            565                 570                 575

Lys Leu

<210> SEQ ID NO 29
<211> LENGTH: 1101
<212> TYPE: DNA
<213> ORGANISM: Unknown
<220> FEATURE:
<223> OTHER INFORMATION: Clostridium ragsdalei

<400> SEQUENCE: 29

```
atggaatgtg tggatgaaaa aggtgagata ctatgtcaaa aaacatgtcc ttttgatgca      60
attttatag  acaataagaa aaattgtgct tacatagata agaaaagtg  taccgattgt     120
ggtttgtgtg tagatgtttg ccctactggg ggaataatgg ataaagttca gttcattcct     180
attttggata ttttaaaaag taaatctcca gttgtggcta tagtggctcc tgccataata     240
ggacagtttg gggaagatgt tactatggat caacttagga ccgcttttaa aaaactggga     300
tttactgata tgattgaagt ggcattttt  gcagatatgc ttactttaaa ggaatctatt     360
gaatttgaca atcatgtaaa agatgaaaaa gatttttatga taacttcctg ctgttgtcct    420
atgtgggtgg ctatggtaaa aaaggtatac agtaacttgg ttaaacatgt atctccctct    480
gtatctccga tggttgcagg aggaagagta cttaaaaagt taagtcctta ctgcaaggta    540
gtgtttatag gcccatgtat tgctaaaaaa tctgaggcaa aggaagaaga tataaaagga    600
gcaatagatt ttgtacttac ttttgaagaa ttaagagata tatttgatgc ttttcatata    660
gttccatcta aacttgaagg agattttca  tctaaatatg cttctagagg tggaagatta    720
tatgcccgta caggtggagt ttctattgca gtaagcgaag ctgtggaaaa gattttttcct   780
gaaaagcata aactatttag tgcaattcag gcaaatggca ttagagaatg taaagaaatg    840
cttaccaagg tgcaaaatgg agaaataaaa gctaattta  ttgaaggaat gggctgtatt    900
ggtggatgtg taggtggtcc caaagcaatt gcatctaagg atgaaggtag ggatcgagta    960
aataaatttg cacaagattc tgaaataaaa gttgctgtag atagtgaatg tatgcatgga   1020
gtattacatg ctttggatat acattctata gatgatttta aggatgagaa aaaaatagaa   1080
ctgttagaac gagaattta  a                                             1101
```

<210> SEQ ID NO 30
<211> LENGTH: 366
<212> TYPE: PRT
<213> ORGANISM: Unknown
<220> FEATURE:
<223> OTHER INFORMATION: Clostridium ragsdalei

<400> SEQUENCE: 30

Met Glu Cys Val Asp Glu Lys Gly Glu Ile Leu Cys Gln Lys Thr Cys
1               5                   10                  15

Pro Phe Asp Ala Ile Phe Ile Asp Asn Lys Lys Asn Cys Ala Tyr Ile
                20                  25                  30

Asp Lys Glu Lys Cys Thr Asp Cys Gly Leu Cys Val Asp Val Cys Pro
            35                  40                  45

Thr Gly Gly Ile Met Asp Lys Val Gln Phe Ile Pro Ile Leu Asp Ile
        50                  55                  60

```
Leu Lys Ser Lys Ser Pro Val Val Ala Ile Val Ala Pro Ala Ile Ile
 65                  70                  75                  80

Gly Gln Phe Gly Glu Asp Val Thr Met Asp Gln Leu Arg Thr Ala Phe
                 85                  90                  95

Lys Lys Leu Gly Phe Thr Asp Met Ile Glu Val Ala Phe Phe Ala Asp
            100                 105                 110

Met Leu Thr Leu Lys Glu Ser Ile Glu Phe Asp Asn His Val Lys Asp
        115                 120                 125

Glu Lys Asp Phe Met Ile Thr Ser Cys Cys Pro Met Trp Val Ala
    130                 135                 140

Met Val Lys Lys Val Tyr Ser Asn Leu Val Lys His Val Ser Pro Ser
145                 150                 155                 160

Val Ser Pro Met Val Ala Gly Arg Val Leu Lys Lys Leu Ser Pro
                165                 170                 175

Tyr Cys Lys Val Val Phe Ile Gly Pro Cys Ile Ala Lys Lys Ser Glu
            180                 185                 190

Ala Lys Glu Glu Asp Ile Lys Gly Ala Ile Asp Phe Val Leu Thr Phe
        195                 200                 205

Glu Glu Leu Arg Asp Ile Phe Asp Ala Phe His Ile Val Pro Ser Lys
210                 215                 220

Leu Glu Gly Asp Phe Ser Ser Lys Tyr Ala Ser Arg Gly Gly Arg Leu
225                 230                 235                 240

Tyr Ala Arg Thr Gly Val Ser Ile Ala Val Ser Glu Ala Val Glu
                245                 250                 255

Lys Ile Phe Pro Glu Lys His Lys Leu Phe Ser Ala Ile Gln Ala Asn
            260                 265                 270

Gly Ile Arg Glu Cys Lys Glu Met Leu Thr Lys Val Gln Asn Gly Glu
        275                 280                 285

Ile Lys Ala Asn Phe Ile Glu Gly Met Gly Cys Ile Gly Gly Cys Val
    290                 295                 300

Gly Gly Pro Lys Ala Ile Ala Ser Lys Asp Glu Gly Arg Asp Arg Val
305                 310                 315                 320

Asn Lys Phe Ala Gln Asp Ser Glu Ile Lys Val Ala Val Asp Ser Glu
                325                 330                 335

Cys Met His Gly Val Leu His Ala Leu Asp Ile His Ser Ile Asp Asp
            340                 345                 350

Phe Lys Asp Glu Lys Lys Ile Glu Leu Leu Glu Arg Glu Phe
        355                 360                 365

<210> SEQ ID NO 31
<211> LENGTH: 1374
<212> TYPE: DNA
<213> ORGANISM: Unknown
<220> FEATURE:
<223> OTHER INFORMATION: Clostridium ragsdalei

<400> SEQUENCE: 31
ttgacagtta agactgaagg tattgtcaaa attgataaag agttgtgtac aggatgtagg      60
cgatgtgcag atgttttgtcc tgtagatgct atagaaggtg aaaaaggaca acctcaaaaa    120
attaatactg aacgttgtgt tttgtgtggt cagtgtgtac aaatttgcag tgcttatgca     180
tctgcatttg atgaagatat tactcctcgt gagcaaaaga taaagagcg taatatgctc     240 ccctctgtta aagagccctt atttgcatcc tactatacag gccatgccat agaagtaaaa    300
gaggccttag caaattctaa actttttact atggttcaat gtgcaccagc agtacgtgta    360
```

```
gctattgctg aagaatttgg tatgccactt ggaagtttaa caccagggaa aatggcagct    420
gcactaagag agctaggttt tgatcgaatt tatgatacta attttgctgc tgatctcact    480
attatggagg aaggtaatga acttattaaa agggttactg aaggtggagt gctgcccatg    540
ttcacttcat gttgtcctgc ttgggtaaaa tttattgagc aggattatcc ggagcttatt    600
cctcatctgt cttcttgtaa atctccacaa caaatggaag gtgctctgct aaaacatat     660 ggtgcacagg ttgatggtgt agatgctggc aagatttata gtgtttcagt tatgccttgt    720
atttgcaaaa aatttgaatg tgaacgtcct gaaatgaaag acagtggata tcaggatgta    780
gattctgtaa ttaccacacg ggaacttgga caattaatca aagatgctgg cattgatttt    840
aatgctttac ctgaaaatga atttgacaag ccacttggga cttattctgg ggcaggtact    900
attttttgcg ctactggagg tgttatgaa gctgccctgc gtacggcata taaattgatt    960
actaaagaag agattccaga tgtcaatctc aaatttataa gaggcggcga aggagtaaga   1020
agttcagaaa ttaaagtagg agatctgaca ttaaaagtag cagtagttgc tggtctgaaa   1080
aatgttgtac cagttttgga agcaattaaa gctggaaaag cagatttcca tttcattgaa   1140
gtgatgacct gtccagttgg atgtgttagt ggaggggac aacctaagat attgatacct     1200
gatgaaaaaa ctgatgctta tactaatcgt acgtgcagta cgtatgtaca tgatgaaaat   1260
atggaatata gaaaatcaca tgataatcct gagatacaga aaatttataa agaattcttg   1320
gtagaagata tattcatca tttgcttcat actacgtata caccaaggag gtaa           1374
```

<210> SEQ ID NO 32
<211> LENGTH: 457
<212> TYPE: PRT
<213> ORGANISM: Unknown
<220> FEATURE:
<223> OTHER INFORMATION: Clostridium ragsdalei

<400> SEQUENCE: 32

```
Met Thr Val Lys Thr Glu Gly Ile Val Lys Ile Asp Lys Glu Leu Cys
1               5                   10                  15

Thr Gly Cys Arg Arg Cys Ala Asp Val Cys Pro Val Asp Ala Ile Glu
            20                  25                  30

Gly Glu Lys Gly Gln Pro Gln Lys Ile Asn Thr Glu Arg Cys Val Leu
        35                  40                  45

Cys Gly Gln Cys Val Gln Ile Cys Ser Ala Tyr Ala Ser Ala Phe Asp
    50                  55                  60

Glu Asp Ile Thr Pro Arg Glu Gln Lys Ile Lys Glu Arg Asn Met Leu
65                  70                  75                  80

Pro Ser Val Lys Glu Pro Leu Phe Ala Ser Tyr Tyr Thr Gly His Ala
                85                  90                  95

Ile Glu Val Lys Glu Ala Leu Ala Asn Ser Lys Leu Phe Thr Met Val
            100                 105                 110

Gln Cys Ala Pro Ala Val Arg Val Ala Ile Ala Glu Glu Phe Gly Met
        115                 120                 125

Pro Leu Gly Ser Leu Thr Pro Gly Lys Met Ala Ala Ala Leu Arg Glu
    130                 135                 140

Leu Gly Phe Asp Arg Ile Tyr Asp Thr Asn Phe Ala Ala Asp Leu Thr
145                 150                 155                 160

Ile Met Glu Glu Gly Asn Glu Leu Ile Lys Arg Val Thr Glu Gly Gly
                165                 170                 175

Val Leu Pro Met Phe Thr Ser Cys Cys Pro Ala Trp Val Lys Phe Ile
            180                 185                 190
```

Glu Gln Asp Tyr Pro Glu Leu Ile Pro His Leu Ser Ser Cys Lys Ser
            195                 200                 205

Pro Gln Gln Met Glu Gly Ala Leu Leu Lys Thr Tyr Gly Ala Gln Val
    210                 215                 220

Asp Gly Val Asp Ala Gly Lys Ile Tyr Ser Val Ser Val Met Pro Cys
225                 230                 235                 240

Ile Cys Lys Lys Phe Glu Cys Glu Arg Pro Glu Met Lys Asp Ser Gly
                245                 250                 255

Tyr Gln Asp Val Asp Ser Val Ile Thr Thr Arg Glu Leu Gly Gln Leu
            260                 265                 270

Ile Lys Asp Ala Gly Ile Asp Phe Asn Ala Leu Pro Glu Asn Glu Phe
        275                 280                 285

Asp Lys Pro Leu Gly Thr Tyr Ser Gly Ala Gly Thr Ile Phe Cys Ala
    290                 295                 300

Thr Gly Gly Val Met Glu Ala Ala Leu Arg Thr Ala Tyr Lys Leu Ile
305                 310                 315                 320

Thr Lys Glu Glu Ile Pro Asp Val Asn Leu Lys Phe Ile Arg Gly Gly
                325                 330                 335

Glu Gly Val Arg Ser Ser Glu Val Lys Val Gly Asp Leu Thr Leu Lys
            340                 345                 350

Val Ala Val Ala Gly Leu Lys Asn Val Val Pro Val Leu Glu Ala
        355                 360                 365

Ile Lys Ala Gly Lys Ala Asp Phe His Phe Ile Glu Val Met Thr Cys
    370                 375                 380

Pro Val Gly Cys Val Ser Gly Gly Gly Gln Pro Lys Ile Leu Ile Pro
385                 390                 395                 400

Asp Glu Lys Thr Asp Ala Tyr Thr Asn Arg Thr Cys Ser Thr Tyr Val
                405                 410                 415

His Asp Glu Asn Met Glu Tyr Arg Lys Ser His Asp Asn Pro Glu Ile
            420                 425                 430

Gln Lys Ile Tyr Lys Glu Phe Leu Val Glu Asp Asn Ile His His Leu
        435                 440                 445

Leu His Thr Thr Tyr Thr Pro Arg Arg
    450                 455

<210> SEQ ID NO 33
<211> LENGTH: 1200
<212> TYPE: DNA
<213> ORGANISM: Unknown
<220> FEATURE:
<223> OTHER INFORMATION: Clostridium autoethanogenum

<400> SEQUENCE: 33
gtgatagacg tacatgaagc attcaatata gtaatgaata acacaaaact gcttaaaggt    60
gaagatatat cgttgataaa ttctcttaac agggtattgg cagaggatat aagctcaaaa   120
gataatcttc ccccatttga caaatcctgt atggatgggt atgctttaaa aagtgaagat   180
actaaggaaa aaatgtcaaa atttcgaatt aagggaagca taaggcgggg agattttcct   240
gatatagtat tgaaaaatgg tgaagccata aaaataatga caggagctcc agtaccaaaa   300
ggtgcagatg cagttattca aatagaaaaa gtaaagtag aaggaaaaga acttcatgta   360
ttagaaaata tatctcctgg aaccaacata tttaaaactg gtgaggagat aaaaattggt   420
gatgttgctt taagaaaagg aaagatttg agacctgcag aaatagggt attggcatca   480 ctaggttata ctaaaataaa atgttataaa gcccctaaaa ttataataat aaatactggg   540

```
gatgaactta taaatataga tcaaaactta atgcaaggta aaataaggaa ttgtaatgaa    600
tatacattaa ttgcccttat taaaaattta aatgcagaag ttaaatcata tgggataata    660
agagatgata aggataagat ttttaatgct ataaaaactg catttgaaga gggagatata    720
atcataacta ctggaggagc atctgtaggt gattacgatt ttatagaaga tgttcttcag    780
aaaataggaa cagatataaa gtttacttcg gtagctatta aaccaggaaa accagttgtt    840
tttgcaactt ttaaagataa attgttcttt ggacttccag gaaatccgct ttcggtaata    900
aattcatttg aaagttttgt agcaccatct attaaaaaaa tgattggaag agatgatgcg    960
tttcctgaag aatttcctgt aactttaaaa gatgatttta aatcaggaaa agaaagagac   1020
tgctatatgt atgtaaacat aaaaaaggaa gataaccgtt attatgccta tgatgtagga   1080
agacaagatt ccaatgggct ttttacgctt actaagtcaa atggagtcgt catcatggaa   1140
aagggaacta gtatagcaaa agctggagat attttaaatg gaaaatttat attcaaataa   1200
```

<210> SEQ ID NO 34
<211> LENGTH: 399
<212> TYPE: PRT
<213> ORGANISM: Unknown
<220> FEATURE:
<223> OTHER INFORMATION: Clostridium autoethanogenum

<400> SEQUENCE: 34

```
Val Ile Asp Val His Glu Ala Phe Asn Ile Val Met Asn Asn Thr Lys
 1               5                  10                  15

Leu Leu Lys Gly Glu Asp Ile Ser Leu Ile Asn Ser Leu Asn Arg Val
            20                  25                  30

Leu Ala Glu Asp Ile Ser Ser Lys Asp Asn Leu Pro Pro Phe Asp Lys
        35                  40                  45

Ser Cys Met Asp Gly Tyr Ala Leu Lys Ser Glu Asp Thr Lys Glu Lys
    50                  55                  60

Met Ser Lys Phe Arg Ile Lys Gly Ser Ile Lys Ala Gly Asp Phe Ser
65                  70                  75                  80

Asp Ile Val Leu Lys Asn Gly Glu Ala Ile Lys Ile Met Thr Gly Ala
                85                  90                  95

Pro Val Pro Lys Gly Ala Asp Ala Val Ile Gln Ile Glu Lys Val Lys
           100                 105                 110

Val Glu Gly Lys Glu Leu His Val Leu Glu Asn Ile Ser Pro Gly Thr
       115                 120                 125

Asn Ile Phe Lys Thr Gly Glu Glu Ile Lys Ile Gly Asp Val Ala Leu
   130                 135                 140

Arg Lys Gly Lys Ile Leu Arg Pro Ala Glu Ile Gly Leu Leu Ala Ser
145                 150                 155                 160

Leu Gly Tyr Thr Lys Ile Lys Cys Tyr Lys Ala Pro Lys Ile Ile Ile
                165                 170                 175

Ile Asn Thr Gly Asp Glu Leu Ile Asn Ile Asp Gln Asn Leu Met Gln
            180                 185                 190

Gly Lys Ile Arg Asn Cys Asn Glu Tyr Thr Leu Ile Ala Leu Ile Lys
        195                 200                 205

Asn Leu Asn Ala Glu Val Lys Ser Tyr Gly Ile Ile Arg Asp Asp Lys
    210                 215                 220

Asp Lys Ile Phe Asn Ala Ile Lys Thr Ala Phe Glu Glu Gly Asp Ile
225                 230                 235                 240

Ile Ile Thr Thr Gly Gly Ala Ser Val Gly Asp Tyr Asp Phe Ile Glu
```

```
                245                 250                 255
Asp Val Leu Gln Lys Ile Gly Thr Asp Ile Lys Phe Thr Ser Val Ala
            260                 265                 270

Ile Lys Pro Gly Lys Pro Val Val Phe Ala Thr Phe Lys Asp Lys Leu
        275                 280                 285

Phe Phe Gly Leu Pro Gly Asn Pro Leu Ser Val Ile Asn Ser Phe Glu
        290                 295                 300

Ser Phe Val Ala Pro Ser Ile Lys Lys Met Ile Gly Arg Asp Asp Ala
305                 310                 315                 320

Phe Pro Glu Glu Phe Pro Val Thr Leu Lys Asp Asp Phe Lys Ser Gly
                325                 330                 335

Lys Glu Arg Asp Cys Tyr Met Tyr Val Asn Ile Lys Lys Glu Asp Asn
            340                 345                 350

Arg Tyr Tyr Ala Tyr Asp Val Gly Arg Gln Asp Ser Asn Gly Leu Phe
        355                 360                 365

Thr Leu Thr Lys Ser Asn Gly Val Val Ile Met Glu Lys Gly Thr Ser
        370                 375                 380

Ile Ala Lys Ala Gly Asp Ile Leu Asn Gly Lys Phe Ile Phe Lys
385                 390                 395

<210> SEQ ID NO 35
<211> LENGTH: 570
<212> TYPE: DNA
<213> ORGANISM: Unknown
<220> FEATURE:
<223> OTHER INFORMATION: Clostridium autoethanogenum

<400> SEQUENCE: 35
atggaaaatt tatattcaaa taagaggtca gtaatttcta ttatttcatc tagttcaaat      60
tcgggtaaga ctaccttgat agaaggaata ataagaattc taaaaagcag aggatataag     120
gttggtgcaa taaagaatga tgctcataag ttacagatag attacccagg aaaagacagc     180
tttagattta cagaggcagg tgcggacaat gttgttattg catcggataa tacagtggct     240
atgataaaaa aagtaagtgg acccaaaagt atagaagaac tactgttgct ttttcaagat     300
gtagatattg taatagtgga aggcttcaag ggtaacgaat tcctaaaaat agaagtatac     360
aggaaaaatg caagcaaatg tttactttac aaaaattcta aatataattt tcaaaatttt     420
gtagctattg taaccaatga aaacttaata actgatattc ctgtatttga tataaatgat     480
acaaaaaaaa tagctgattt tattgagaac gactttatag gaggtaacaa aaatggagaa     540
aaccatggaa cttcatgtag tcaaatatga                                      570

<210> SEQ ID NO 36
<211> LENGTH: 189
<212> TYPE: PRT
<213> ORGANISM: Unknown
<220> FEATURE:
<223> OTHER INFORMATION: Clostridium autoethanogenum

<400> SEQUENCE: 36

Met Glu Asn Leu Tyr Ser Asn Lys Arg Ser Val Ile Ser Ile Ser
1               5                   10                  15

Ser Ser Ser Asn Ser Gly Lys Thr Thr Leu Ile Glu Gly Ile Ile Arg
            20                  25                  30

Ile Leu Lys Ser Arg Gly Tyr Lys Val Gly Ala Ile Lys Asn Asp Ala
        35                  40                  45

His Lys Leu Gln Ile Asp Tyr Pro Gly Lys Asp Ser Phe Arg Phe Thr
```

```
                50                  55                  60
Glu Ala Gly Ala Asp Asn Val Ile Ala Ser Asp Asn Thr Val Ala
 65                  70                  75                  80

Met Ile Lys Lys Val Ser Gly Pro Lys Ser Ile Glu Glu Leu Leu Leu
                 85                  90                  95

Leu Phe Gln Asp Val Asp Ile Val Ile Val Glu Gly Phe Lys Gly Asn
                100                 105                 110

Glu Phe Pro Lys Ile Glu Val Tyr Arg Lys Asn Ala Ser Lys Cys Leu
                115                 120                 125

Leu Tyr Lys Asn Ser Lys Tyr Asn Phe Gln Asn Phe Val Ala Ile Val
            130                 135                 140

Thr Asn Glu Asn Leu Ile Thr Asp Ile Pro Val Phe Asp Ile Asn Asp
145                 150                 155                 160

Thr Lys Lys Ile Ala Asp Phe Ile Glu Asn Asp Phe Ile Gly Gly Asn
                165                 170                 175

Lys Asn Gly Glu Asn His Gly Thr Ser Cys Ser Gln Ile
            180                 185
```

<210> SEQ ID NO 37
<211> LENGTH: 777
<212> TYPE: DNA
<213> ORGANISM: Unknown
<220> FEATURE:
<223> OTHER INFORMATION: Clostridium autoethanogenum

<400> SEQUENCE: 37

```
atggaacttc atgtagtcaa atatgacaaa gaatgtaaaa agacagtaga ggaatcaact      60
atttgtgaat atcctttaaa tgtatttgta aatggtgaac atttgacagt actcttatgt     120
acgcctgaaa agcttaagga attaacaata ggtttcttga cctttagagg tgttataaaa     180
tctctagatg aaataaaatc tctagagata gatgaaaaaa gtggagcgtc cagggtaact     240
ttgaaaaata gccaatttaa taagagttg tattcaaagc aagtgcttcc tataacattt      300
agtgaaaatg agaaagtaa gttcttttcg tatattattg attccatgga aattagtata      360
atcaacaatg ataatgttta cattcatgtc gataaaatct atgatctaat gatggacaat     420
cttggatatt ccaagacgtt taaactcact ggaggaacac attgtgcagc tctttgtgat     480
gaagataaag taatatctat ttgtgaggat gtggctagac acaatgctgt agacaagctt     540
ataggtgagg catttataaa aaatatttat ttaaaggata aaataatatt tgtgagcagc     600
agagtatctt ttgaaatggt atataaaatt gctaggctag ggtacctat aataatatct       660
aaatctgcac ctacaagtct ttctatagaa tttgcaaaag ctttaaatgt tacattaatt     720
ggatttgtaa ggggagaaag aatgaatgta tatacaaatc cacagagaat aatatag        777
```

<210> SEQ ID NO 38
<211> LENGTH: 258
<212> TYPE: PRT
<213> ORGANISM: Unknown
<220> FEATURE:
<223> OTHER INFORMATION: Clostridium autoethanogenum

<400> SEQUENCE: 38

```
Met Glu Leu His Val Val Lys Tyr Asp Lys Glu Cys Lys Lys Thr Val
  1               5                  10                  15

Glu Glu Ser Thr Ile Cys Glu Tyr Pro Leu Asn Val Phe Val Asn Gly
             20                  25                  30

Glu His Leu Thr Val Leu Leu Cys Thr Pro Glu Lys Leu Lys Glu Leu
```

```
                35                  40                  45
Thr Ile Gly Phe Leu Thr Phe Arg Gly Val Ile Lys Ser Leu Asp Glu
 50                  55                  60

Ile Lys Ser Leu Glu Ile Asp Glu Lys Ser Gly Ala Ser Arg Val Thr
 65                  70                  75                  80

Leu Lys Asn Ser Gln Phe Asn Lys Glu Leu Tyr Ser Lys Gln Val Leu
                 85                  90                  95

Pro Ile Thr Phe Ser Glu Asn Gly Lys Ser Lys Phe Phe Ser Tyr Ile
                100                 105                 110

Ile Asp Ser Met Glu Ile Ser Ile Ile Asn Asn Asp Asn Val Tyr Ile
                115                 120                 125

His Val Asp Lys Ile Tyr Asp Leu Met Met Asp Asn Leu Gly Tyr Ser
            130                 135                 140

Lys Thr Phe Lys Leu Thr Gly Gly Thr His Cys Ala Ala Leu Cys Asp
145                 150                 155                 160

Glu Asp Lys Val Ile Ser Ile Cys Glu Asp Val Ala Arg His Asn Ala
                165                 170                 175

Val Asp Lys Leu Ile Gly Glu Ala Phe Ile Lys Asn Ile Tyr Leu Lys
            180                 185                 190

Asp Lys Ile Ile Phe Val Ser Ser Arg Val Ser Phe Glu Met Val Tyr
        195                 200                 205

Lys Ile Ala Arg Leu Gly Val Pro Ile Ile Ser Lys Ser Ala Pro
210                 215                 220

Thr Ser Leu Ser Ile Glu Phe Ala Lys Ala Leu Asn Val Thr Leu Ile
225                 230                 235                 240

Gly Phe Val Arg Gly Glu Arg Met Asn Val Tyr Thr Asn Pro Gln Arg
                245                 250                 255

Ile Ile

<210> SEQ ID NO 39
<211> LENGTH: 486
<212> TYPE: DNA
<213> ORGANISM: Unknown
<220> FEATURE:
<223> OTHER INFORMATION: Clostridium autoethanogenum

<400> SEQUENCE: 39
atgttaacta acagcaaaa tgaagacctg tctggacaag atgtaattga aaaatatcct    60
aaagagcaga gatttactct tgctatacta caggatatac agagaaagta caaatatata   120
ccaagagaag cactggagaa tttagctaag tatttggaca cgcctgtaag tagactgtat   180
ggtatggcta ctttttataa ggcattgagc cttactccaa aaggggaaaa cataataact   240
gtatgtgatg gaaccgcttg ccatgttgct ggttctatgg ttgtaatgga tgaacttgaa   300
aaggcaatag gaattaaacc aggtgaaact acagaggatc tcaaattttc aataaataca   360
gttaactgta taggatgctg tgcaatagct cctgtcatga tgataaatga caaatattat   420
ggaaatttaa cacctaaact ggttgaagaa attcttagtg agtataggag tgagagtgat   480
gagtga                                                              486

<210> SEQ ID NO 40
<211> LENGTH: 161
<212> TYPE: PRT
<213> ORGANISM: Unknown
<220> FEATURE:
<223> OTHER INFORMATION: Clostridium autoethanogenum
```

<400> SEQUENCE: 40

```
Met Leu Thr Lys Gln Gln Asn Glu Asp Leu Ser Gly Gln Asp Val Ile
1               5                   10                  15

Glu Lys Tyr Pro Lys Glu Gln Arg Phe Thr Leu Ala Ile Leu Gln Asp
            20                  25                  30

Ile Gln Arg Lys Tyr Lys Tyr Ile Pro Arg Glu Ala Leu Glu Asn Leu
        35                  40                  45

Ala Lys Tyr Leu Asp Thr Pro Val Ser Arg Leu Tyr Gly Met Ala Thr
    50                  55                  60

Phe Tyr Lys Ala Leu Ser Leu Thr Pro Lys Gly Glu Asn Ile Ile Thr
65                  70                  75                  80

Val Cys Asp Gly Thr Ala Cys His Val Ala Gly Ser Met Val Val Met
                    85                  90                  95

Asp Glu Leu Glu Lys Ala Ile Gly Ile Lys Pro Gly Glu Thr Thr Glu
                100                 105                 110

Asp Leu Lys Phe Ser Ile Asn Thr Val Asn Cys Ile Gly Cys Cys Ala
            115                 120                 125

Ile Ala Pro Val Met Met Ile Asn Asp Lys Tyr Tyr Gly Asn Leu Thr
        130                 135                 140

Pro Lys Leu Val Glu Glu Ile Leu Ser Glu Tyr Arg Ser Glu Ser Asp
145                 150                 155                 160

Glu
```

<210> SEQ ID NO 41
<211> LENGTH: 1800
<212> TYPE: DNA
<213> ORGANISM: Unknown
<220> FEATURE:
<223> OTHER INFORMATION: Clostridium autoethanogenum

<400> SEQUENCE: 41

```
atgagtgata aaaaaactgt caatatatgt tgtgggacag gttgtttagc taaaggcagt      60
atggaagtat atgaagaaat gaaggcacaa atagctaaat taggggcaaa tgcagaagta     120
aatgttaaat taaaagcaac aggttgcgat ggattgtgtg agaaaggtcc tgtactgaaa     180
atatatccag atgacattgc atattttaaa gttaaagtag aagatgtaga agacgtagta     240
aaaaagacat tgatgaatgg ggaaataatt gaaaaattat tatattttga gactgctaca     300
aaacagagat taagaaatca taagaaagt gaattttgta aaagacaata caaaattgct     360
ctcagaaatg ttggtgaaat agatccaata agtttggaag attatgttga agaggcgga     420
tacaaagctc ttaaaaaagc aataagcagc atgaaacctg aagatgtgct tgaagaaata     480
acaaaatcag gtcttagagg aagaggtgga gcaggattcc caacaggacg taaatggaaa     540
actgctgcag atattgatac atcacctata tatgtagtat gtaatggtga tgaaggagat     600
cctggagcat ttatggatag aagtataatg gagggagatc ctaacagtgt tatagaaggt     660
atgacattat gtgcttatgc agtaggaggt acaaatggaa ttgcttatat aagagatgaa     720
tatggacttg ctgtagaaaa tatgcagaaa gctattaata agcaaaaga tgaaaattta     780
ttaggtaata atatattagg aactgatttt tccttcgata tacagatagt aagaggtgga     840
ggagcttttg tatgtggtga atctactgca cttatgtcgt ctatagaagg tatggtaggt     900
gaacctagag ctaaatatat acacactaca gaaaaaggat tgtggggaca acctacagtt     960
ttaaataatg tagaaacttg ggccaatgta cctataataa ttgaaaaagg cggagattgg    1020
tatcatgcta taggaactat ggagaagagt aagggaacaa aggtattctc attagttgga    1080
```

-continued

```
aaagttaaga atactggact tgtagaagta cctatgggaa ctactcttag agaaataata   1140
tatgatattg gcggtggagt attaaatgat agaaagttta aggcagttca aataggtgga   1200
ccttcaggtg gatgtttacc agctgaatat ttagatttgc cagtagatta tgatactttg   1260
gttaaagcag attccatgat gggttcaggc ggaatgatcg taatggatga tagaacctgt   1320
atggtagatg taactagata ttacctgagc ttcttggctg aagaatcttg tggaaagtgt   1380
gtaccttgta gagaaggcgt aaagaggatg cttgaaatac tcactgacat atgcaatggt   1440
gatggaaaag aaggagacat agaagagctt ctcgaaatat gttccatgac aagcaaggca   1500
tctctgtgca gtcttggtaa gagtgctcca aatccagtaa ttgcttctat aagatatttt   1560
agagatgaat ttgaagagca tataaagaat aagagatgta gagcaggagt ttgtaagaaa   1620
cttactacat ttggtataga cgaggataaa tgtaagggat gcgatatgtg taaaaagaat   1680
tgtccagctg attgtataac agggaaatt aagaaaccac atacaataga tgctgataag   1740
tgcttgagat gcggtaactg catgaacatc tgtaagtttg atgctgttaa ggttctatag   1800
```

<210> SEQ ID NO 42
<211> LENGTH: 599
<212> TYPE: PRT
<213> ORGANISM: Unknown
<220> FEATURE:
<223> OTHER INFORMATION: Clostridium autoethanogenum

<400> SEQUENCE: 42

```
Met Ser Asp Lys Lys Thr Val Asn Ile Cys Cys Gly Thr Gly Cys Leu
1               5                   10                  15

Ala Lys Gly Ser Met Glu Val Tyr Glu Glu Met Lys Ala Gln Ile Ala
            20                  25                  30

Lys Leu Gly Ala Asn Ala Glu Val Asn Val Lys Leu Lys Ala Thr Gly
        35                  40                  45

Cys Asp Gly Leu Cys Glu Lys Gly Pro Val Leu Lys Ile Tyr Pro Asp
    50                  55                  60

Asp Ile Ala Tyr Phe Lys Val Lys Val Glu Asp Val Glu Asp Val Val
65                  70                  75                  80

Lys Lys Thr Leu Met Asn Gly Glu Ile Ile Glu Lys Leu Leu Tyr Phe
                85                  90                  95

Glu Thr Ala Thr Lys Gln Arg Leu Arg Asn His Lys Glu Ser Glu Phe
            100                 105                 110

Cys Lys Arg Gln Tyr Lys Ile Ala Leu Arg Asn Val Gly Glu Ile Asp
        115                 120                 125

Pro Ile Ser Leu Glu Asp Tyr Val Glu Arg Gly Gly Tyr Lys Ala Leu
    130                 135                 140

Lys Lys Ala Ile Ser Ser Met Lys Pro Glu Asp Val Leu Glu Glu Ile
145                 150                 155                 160

Thr Lys Ser Gly Leu Arg Gly Arg Gly Ala Gly Phe Pro Thr Gly
                165                 170                 175

Arg Lys Trp Lys Thr Ala Ala Asp Ile Asp Thr Ser Pro Ile Tyr Val
            180                 185                 190

Val Cys Asn Gly Asp Glu Gly Asp Pro Gly Ala Phe Met Asp Arg Ser
        195                 200                 205

Ile Met Glu Gly Asp Pro Asn Ser Val Ile Glu Gly Met Thr Leu Cys
    210                 215                 220

Ala Tyr Ala Val Gly Gly Thr Asn Gly Phe Ala Tyr Ile Arg Asp Glu
225                 230                 235                 240
```

Tyr Gly Leu Ala Val Glu Asn Met Gln Lys Ala Ile Asn Lys Ala Lys
              245                 250                 255

Asp Glu Asn Leu Leu Gly Asn Asn Ile Leu Gly Thr Asp Phe Ser Phe
            260                 265                 270

Asp Ile Gln Ile Val Arg Gly Gly Ala Phe Val Cys Gly Glu Ser
        275                 280                 285

Thr Ala Leu Met Ser Ser Ile Glu Gly Met Val Gly Glu Pro Arg Ala
    290                 295                 300

Lys Tyr Ile His Thr Thr Glu Lys Gly Leu Trp Gly Gln Pro Thr Val
305                 310                 315                 320

Leu Asn Asn Val Glu Thr Trp Ala Asn Val Pro Ile Ile Glu Lys
                325                 330                 335

Gly Gly Asp Trp Tyr His Ala Ile Gly Thr Met Glu Lys Ser Lys Gly
            340                 345                 350

Thr Lys Val Phe Ser Leu Val Gly Lys Val Lys Asn Thr Gly Leu Val
        355                 360                 365

Glu Val Pro Met Gly Thr Thr Leu Arg Glu Ile Ile Tyr Asp Ile Gly
    370                 375                 380

Gly Gly Val Leu Asn Asp Arg Lys Phe Lys Ala Val Gln Ile Gly Gly
385                 390                 395                 400

Pro Ser Gly Gly Cys Leu Pro Ala Glu Tyr Leu Asp Leu Pro Val Asp
                405                 410                 415

Tyr Asp Thr Leu Val Lys Ala Asp Ser Met Met Gly Ser Gly Gly Met
            420                 425                 430

Ile Val Met Asp Asp Arg Thr Cys Met Val Asp Val Thr Arg Tyr Tyr
        435                 440                 445

Leu Ser Phe Leu Ala Glu Glu Ser Cys Gly Lys Cys Val Pro Cys Arg
    450                 455                 460

Glu Gly Val Lys Arg Met Leu Glu Ile Leu Thr Asp Ile Cys Asn Gly
465                 470                 475                 480

Asp Gly Lys Glu Gly Asp Ile Glu Val Leu Leu Glu Ile Cys Ser Met
                485                 490                 495

Thr Ser Lys Ala Ser Leu Cys Ser Leu Gly Lys Ser Ala Pro Asn Pro
            500                 505                 510

Val Ile Ala Ser Ile Arg Tyr Phe Arg Asp Glu Phe Glu Glu His Ile
        515                 520                 525

Lys Asn Lys Arg Cys Arg Ala Gly Val Cys Lys Leu Thr Thr Phe
530                 535                 540

Gly Ile Asp Glu Asp Lys Cys Lys Gly Cys Asp Met Cys Lys Lys Asn
545                 550                 555                 560

Cys Pro Ala Asp Cys Ile Thr Gly Glu Ile Lys Pro His Thr Ile
                565                 570                 575

Asp Ala Asp Lys Cys Leu Arg Cys Gly Asn Cys Met Asn Ile Cys Lys
            580                 585                 590

Phe Asp Ala Val Lys Val Leu
        595

<210> SEQ ID NO 43
<211> LENGTH: 768
<212> TYPE: DNA
<213> ORGANISM: Unknown
<220> FEATURE:
<223> OTHER INFORMATION: Clostridium autoethanogenum

<400> SEQUENCE: 43

-continued

```
gtgaatgtag atatgaaaat tacaatagat ggaaaagctt gtgaagctga aaaggagaa      60 ttcatattac aaatagcaag aagaaataac atatatatac ctacattatg tcacagcgat    120
gcattgcctg ggcttgctag ctgtagacta tgtatagtta aagtagtaga taggggacgt    180
gcaaagatag taacttcctg tatattccct gtaagtaagg aagtagaagt tataactaat    240
gacgatgaaa taaagagaat gagaaaaaac atagttatgc ttttaaaagt aagatgccct    300
gaaaataaag aggtaaatga attagctaaa gcctttggag tagaggaaaa gagagtaaag    360
aggttcaaat tggatccaga acaaaattgt gttttgtgcg gactttgtgc aaaagcttgc    420
aaggaattag gtactggagc aatttcaaca gttaataggg gtatgtataa agaagtagca    480
actccatatc acgaatcttc accggaatgt ataggatgtg cttcctgtgc aaatgtttgt    540
ccaactaatg caataaaagt tgtggataaa gatggagaaa gagaaatatg gggcaaaaaa    600
ttcaagatgg ttaagtgtga tttgtgcgga gaatattttg ctacagaaga acatgtaaaa    660
tatgcttaca ataggcttgg aaaagagcag ccagaaaaac ttatgtgtag cagctgcaag    720
aagaaagtta cagccaaaga tgtcaaaaat atttttgaga acgtgtga                 768
```

<210> SEQ ID NO 44
<211> LENGTH: 255
<212> TYPE: PRT
<213> ORGANISM: Unknown
<220> FEATURE:
<223> OTHER INFORMATION: Clostridium autoethanogenum

<400> SEQUENCE: 44

```
Val Asn Val Asp Met Lys Ile Thr Ile Asp Gly Lys Ala Cys Glu Ala
1               5                   10                  15

Glu Lys Gly Glu Phe Ile Leu Gln Ile Ala Arg Arg Asn Asn Ile Tyr
            20                  25                  30

Ile Pro Thr Leu Cys His Ser Asp Ala Leu Pro Gly Leu Ala Ser Cys
        35                  40                  45

Arg Leu Cys Ile Val Lys Val Asp Arg Gly Arg Ala Lys Ile Val
    50                  55                  60

Thr Ser Cys Ile Phe Pro Val Ser Lys Glu Val Glu Val Ile Thr Asn
65                  70                  75                  80

Asp Asp Glu Ile Lys Arg Met Arg Lys Asn Ile Val Met Leu Leu Lys
                85                  90                  95

Val Arg Cys Pro Glu Asn Lys Glu Val Asn Glu Leu Ala Lys Ala Phe
            100                 105                 110

Gly Val Glu Glu Lys Arg Val Lys Arg Phe Lys Leu Asp Pro Glu Gln
        115                 120                 125

Asn Cys Val Leu Cys Gly Leu Cys Ala Lys Ala Cys Lys Glu Leu Gly
    130                 135                 140

Thr Gly Ala Ile Ser Thr Val Asn Arg Gly Met Tyr Lys Glu Val Ala
145                 150                 155                 160

Thr Pro Tyr His Glu Ser Ser Pro Glu Cys Ile Gly Cys Ala Ser Cys
                165                 170                 175

Ala Asn Val Cys Pro Thr Asn Ala Ile Lys Val Val Asp Lys Asp Gly
            180                 185                 190

Glu Arg Glu Ile Trp Gly Lys Lys Phe Lys Met Val Lys Cys Asp Leu
        195                 200                 205

Cys Gly Glu Tyr Phe Ala Thr Glu Glu His Val Lys Tyr Ala Tyr Asn
    210                 215                 220
```

Arg Leu Gly Lys Glu Gln Pro Glu Lys Leu Met Cys Ser Ser Cys Lys
225                 230                 235                 240

Lys Lys Val Thr Ala Lys Asp Val Lys Asn Ile Phe Glu Asn Val
            245                 250                 255

<210> SEQ ID NO 45
<211> LENGTH: 555
<212> TYPE: DNA
<213> ORGANISM: Unknown
<220> FEATURE:
<223> OTHER INFORMATION: Clostridium autoethanogenum

<400> SEQUENCE: 45

```
atgaaaccag agtttaattc ttttgtaata gccgatcctg acaagtgcat aggctgtaga       60
tcttgtgaga ttgcctgtgc tgcaaaacat agagaagata ctcaaggaaa aaccattgga      120
actatgaata ataaagttac tccaaggtta ttctttgtta aaaataaagg aaatgtaatg      180
ccagtacaat gcagacattg tgaggatgca ccatgtctaa atgcctgccc agttaatgct      240
atagttgaaa aagatggaag tatcattata atgaaagtg catgtatagg atgtcagacc       300
tgtacaatag tatgtccggt aggtgctgta agtttactgc ctagaactca aggtaaagta      360
gttacaggag gaattcaggt taaagtaaga gcagcagctt ataaatgtga tttatgtaag      420
gaagagggag gagaacctgc ttgcgtcaaa gaatgtccaa agaggccttt gaggttagta      480
gatcctagag aagataaaaa agatcgtagt gtgaaagctg ctatggaact gttaaatata      540
aacgcaaatc tctaa                                                       555
```

<210> SEQ ID NO 46
<211> LENGTH: 184
<212> TYPE: PRT
<213> ORGANISM: Unknown
<220> FEATURE:
<223> OTHER INFORMATION: Clostridium autoethanogenum

<400> SEQUENCE: 46

Met Lys Pro Glu Phe Asn Ser Phe Val Ile Ala Asp Pro Asp Lys Cys
1               5                   10                  15

Ile Gly Cys Arg Ser Cys Glu Ile Ala Cys Ala Ala Lys His Arg Glu
            20                  25                  30

Asp Thr Gln Gly Lys Thr Ile Gly Thr Met Asn Asn Lys Val Thr Pro
        35                  40                  45

Arg Leu Phe Phe Val Lys Asn Lys Gly Asn Val Met Pro Val Gln Cys
    50                  55                  60

Arg His Cys Glu Asp Ala Pro Cys Leu Asn Ala Cys Pro Val Asn Ala
65                  70                  75                  80

Ile Val Glu Lys Asp Gly Ser Ile Ile Ile Asn Glu Ser Ala Cys Ile
                85                  90                  95

Gly Cys Gln Thr Cys Thr Ile Val Cys Pro Val Gly Ala Val Ser Leu
            100                 105                 110

Leu Pro Arg Thr Gln Gly Lys Val Val Thr Gly Gly Ile Gln Val Lys
        115                 120                 125

Val Arg Ala Ala Ala Tyr Lys Cys Asp Leu Cys Lys Glu Glu Gly Gly
    130                 135                 140

Glu Pro Ala Cys Val Lys Glu Cys Pro Lys Glu Ala Leu Arg Leu Val
145                 150                 155                 160

Asp Pro Arg Glu Asp Lys Lys Asp Arg Ser Val Lys Ala Ala Met Glu
                165                 170                 175

Leu Leu Asn Ile Asn Ala Asn Leu
            180

<210> SEQ ID NO 47
<211> LENGTH: 567
<212> TYPE: DNA
<213> ORGANISM: Unknown
<220> FEATURE:
<223> OTHER INFORMATION: Clostridium autoethanogenum

<400> SEQUENCE: 47

```
atgaagaatt gcctcgtagt agcagatcct aataaatgca taggatgtag gacttgtgaa      60
gcagcttgtg gtattgcaca ttcaggaggg gactttttta acacaaatgt atccaagatt     120
aattttaatc ctcgcttaaa tgtgataaaa actgctaaag taagtgctcc tgttcaatgc     180
agacaatgcg aagatgcacc ttgtggtaaa gcttgtccag ttaacgctat ttcaaatgaa     240
aatggttatg ttagtgtaaa taaagatgta tgtgttggat gtaaaatctg catgttagct     300
tgtcctttg gagctattga attagcttct caatataggg atggagaagt tgtagaccaa      360
aagggactta agatgagtga ggaaggtaat cctactgtga atggaaaagg aagagtggta     420
gcaaataagt gtgatctctg ccaggatagg gatggagggc ctgcttgtat agaagtttgt     480
cctacaaaat ctctcaaact agttacttat gatgacaata ataatatagt tgaaaaaaaa     540
gatgacgacg aacgtgaagt aagctaa                                         567
```

<210> SEQ ID NO 48
<211> LENGTH: 188
<212> TYPE: PRT
<213> ORGANISM: Unknown
<220> FEATURE:
<223> OTHER INFORMATION: Clostridium autoethanogenum

<400> SEQUENCE: 48

Met Lys Asn Cys Leu Val Val Ala Asp Pro Asn Lys Cys Ile Gly Cys
1               5                   10                  15

Arg Thr Cys Glu Ala Ala Cys Gly Ile Ala His Ser Gly Gly Asp Phe
            20                  25                  30

Phe Asn Thr Asn Val Ser Lys Ile Asn Phe Asn Pro Arg Leu Asn Val
        35                  40                  45

Ile Lys Thr Ala Lys Val Ser Ala Pro Val Gln Cys Arg Gln Cys Glu
    50                  55                  60

Asp Ala Pro Cys Gly Lys Ala Cys Pro Val Asn Ala Ile Ser Asn Glu
65                  70                  75                  80

Asn Gly Tyr Val Ser Val Asn Lys Asp Val Cys Val Gly Cys Lys Ile
                85                  90                  95

Cys Met Leu Ala Cys Pro Phe Gly Ala Ile Glu Leu Ala Ser Gln Tyr
            100                 105                 110

Arg Asp Gly Glu Val Val Asp Gln Lys Gly Leu Lys Met Ser Glu Glu
        115                 120                 125

Gly Asn Pro Thr Val Asn Gly Lys Gly Arg Val Val Ala Asn Lys Cys
    130                 135                 140

Asp Leu Cys Gln Asp Arg Asp Gly Gly Pro Ala Cys Ile Glu Val Cys
145                 150                 155                 160

Pro Thr Lys Ser Leu Lys Leu Val Thr Tyr Asp Asp Asn Asn Asn Ile
                165                 170                 175

Val Glu Lys Asp Asp Asp Glu Arg Glu Val Ser
            180                 185

<210> SEQ ID NO 49
<211> LENGTH: 957
<212> TYPE: DNA
<213> ORGANISM: Unknown
<220> FEATURE:
<223> OTHER INFORMATION: Clostridium ragsdalei

<400> SEQUENCE: 49

```
gtgatagacg tacatgaagc attcaatata gtaatgaata atacaaaact gcttaaaagt     60
gaagatatgt ccctgataaa ttctcttaac agggtattgg cagaggatat aagctcaaaa    120
gataatcttc ccccatttga caaatcctgt atggatgggt atgctttaaa aagtgaagat    180
actaaggaaa aaatgtcaaa atttcaaatt aagggaagca taaaggcggg agatttttct    240
gatatagtat taaaaaatgg tgaagccata aaaataatga caggagctcc agtaccaaaa    300
ggtgcagatg caattattca aatagaaaaa gtaaaagtag aaggaaaaga acttcatgta    360
ttggaaaagg tatctcctgg aaccaacata tttaaaactg gtgaggagat aaaaattggt    420
gatgttgctt taaaaaaggg aaaaatcgta agacctgcag aaatagggtt attggcatca    480
ctaggttata ctaaaataaa atgctacaaa gtccctaaaa ttataataat aaatacaggg    540
gatgaactta taaatataga tcaaaactta atgcaaggta aaataagaaa ttgtaatgaa    600
tacacattaa ttgcccttat taaaaattta aatgcagaag ttaaatcgta tgggataata    660
agagatgata agaataaaat ttttaatgct ataaaaactg catttgaaga gggagatata    720
atcataacta ctggaggagc atctgtgggt gattacgatt ttatagaaga tgttcttaag    780
gaaataggaa cagatataaa atttacttcg gtagctatta aaccaggaaa accagttgtt    840
tttgcaactt ttaaagataa attattcttt ggacttccag gaaatccact ttcagtaata    900
aattcatttg aaagttttgt agcaccatct attaaaaaaa atgattggaa gagatga       957
```

<210> SEQ ID NO 50
<211> LENGTH: 318
<212> TYPE: PRT
<213> ORGANISM: Unknown
<220> FEATURE:
<223> OTHER INFORMATION: Clostridium ragsdalei

<400> SEQUENCE: 50

```
Met Ile Asp Val His Glu Ala Phe Asn Ile Val Met Asn Asn Thr Lys
1               5                   10                  15

Leu Leu Lys Ser Glu Asp Met Ser Leu Ile Asn Ser Leu Asn Arg Val
            20                  25                  30

Leu Ala Glu Asp Ile Ser Ser Lys Asp Asn Leu Pro Pro Phe Asp Lys
        35                  40                  45

Ser Cys Met Asp Gly Tyr Ala Leu Lys Ser Glu Asp Thr Lys Glu Lys
    50                  55                  60

Met Ser Lys Phe Gln Ile Lys Gly Ser Ile Lys Ala Gly Asp Phe Ser
65                  70                  75                  80

Asp Ile Val Leu Lys Asn Gly Glu Ala Ile Lys Ile Met Thr Gly Ala
                85                  90                  95

Pro Val Pro Lys Gly Ala Asp Ala Ile Ile Gln Ile Glu Lys Val Lys
            100                 105                 110

Val Glu Gly Lys Glu Leu His Val Leu Glu Lys Val Ser Pro Gly Thr
        115                 120                 125

Asn Ile Phe Lys Thr Gly Glu Glu Ile Lys Ile Gly Asp Val Ala Leu
    130                 135                 140
```

```
Lys Lys Gly Lys Ile Val Arg Pro Ala Glu Ile Gly Leu Leu Ala Ser
145                 150                 155                 160

Leu Gly Tyr Thr Lys Ile Lys Cys Tyr Lys Val Pro Lys Ile Ile Ile
                165                 170                 175

Ile Asn Thr Gly Asp Glu Leu Ile Asn Ile Asp Gln Asn Leu Met Gln
            180                 185                 190

Gly Lys Ile Arg Asn Cys Asn Glu Tyr Thr Leu Ile Ala Leu Ile Lys
        195                 200                 205

Asn Leu Asn Ala Glu Val Lys Ser Tyr Gly Ile Ile Arg Asp Asp Lys
    210                 215                 220

Asn Lys Ile Phe Asn Ala Ile Lys Thr Ala Phe Glu Glu Gly Asp Ile
225                 230                 235                 240

Ile Ile Thr Thr Gly Gly Ala Ser Val Gly Asp Tyr Asp Phe Ile Glu
                245                 250                 255

Asp Val Leu Lys Glu Ile Gly Thr Asp Ile Lys Phe Thr Ser Val Ala
            260                 265                 270

Ile Lys Pro Gly Lys Pro Val Val Phe Ala Thr Phe Lys Asp Lys Leu
        275                 280                 285

Phe Phe Gly Leu Pro Gly Asn Pro Leu Ser Val Ile Asn Ser Phe Glu
    290                 295                 300

Ser Phe Val Ala Pro Ser Ile Lys Lys Asn Asp Trp Lys Arg
305                 310                 315

<210> SEQ ID NO 51
<211> LENGTH: 570
<212> TYPE: DNA
<213> ORGANISM: Unknown
<220> FEATURE:
<223> OTHER INFORMATION: Clostridium ragsdalei

<400> SEQUENCE: 51
atggaaaatt tatattcaaa taagaggtca gtaatttcta ttatttcatc tagttcaaat      60
tcaggtaaga ctaccttaat agaaggaata ataagaattt taaaaagcag aggatataag     120
gttggtgcaa taaagaatga tgctcataag ttacagatag attatccagg aaaagacagc     180
tttagattta cagaggcagg tgcagacaat gttgttattg catcggataa tacagtggct     240
atgataaaaa aagtaagtgg accaaaaagt atagaagaat tgctgttgct ttttcaggat     300
gtagatattg taatagtgga aggttttaag ggcaacgaat ttcctaaaat agaagtatac     360
aggaaaaatg caagtaaatg tttactctac aaaaattctg aatataattt tcaaaatttt     420
gtagctattg taaccaatga aaatttaata actgatattc ctgtatttga tataaatgat     480
acaaaaaaag tagctgattt tattgaaagc aactttatag gaggtaacaa aaatggagaa     540
aaccatggaa cttcatgtag tcaaatatga                                      570

<210> SEQ ID NO 52
<211> LENGTH: 189
<212> TYPE: PRT
<213> ORGANISM: Unknown
<220> FEATURE:
<223> OTHER INFORMATION: Clostridium ragsdalei

<400> SEQUENCE: 52

Met Glu Asn Leu Tyr Ser Asn Lys Arg Ser Val Ile Ser Ile Ile Ser
1               5                   10                  15

Ser Ser Ser Asn Ser Gly Lys Thr Thr Leu Ile Glu Gly Ile Ile Arg
            20                  25                  30
```

```
Ile Leu Lys Ser Arg Gly Tyr Lys Val Gly Ala Ile Lys Asn Asp Ala
            35                  40                  45

His Lys Leu Gln Ile Asp Tyr Pro Gly Lys Ser Phe Arg Phe Thr
 50                  55                  60

Glu Ala Gly Ala Asp Asn Val Val Ile Ala Ser Asp Asn Thr Val Ala
 65                  70                  75                  80

Met Ile Lys Lys Val Ser Gly Pro Lys Ser Ile Glu Glu Leu Leu Leu
                 85                  90                  95

Leu Phe Gln Asp Val Asp Ile Val Ile Val Glu Gly Phe Lys Gly Asn
                100                 105                 110

Glu Phe Pro Lys Ile Glu Val Tyr Arg Lys Asn Ala Ser Lys Cys Leu
            115                 120                 125

Leu Tyr Lys Asn Ser Glu Tyr Asn Phe Gln Asn Phe Val Ala Ile Val
130                 135                 140

Thr Asn Glu Asn Leu Ile Thr Asp Ile Pro Val Phe Asp Ile Asn Asp
145                 150                 155                 160

Thr Lys Lys Val Ala Asp Phe Ile Glu Ser Asn Phe Ile Gly Gly Asn
                165                 170                 175

Lys Asn Gly Glu Asn His Gly Thr Ser Cys Ser Gln Ile
            180                 185
```

<210> SEQ ID NO 53
<211> LENGTH: 789
<212> TYPE: DNA
<213> ORGANISM: Unknown
<220> FEATURE:
<223> OTHER INFORMATION: Clostridium ragsdalei

<400> SEQUENCE: 53

| | | | | | |
|---|---|---|---|---|---|
| atggagaaaa | ccatggaact | tcatgtagtc | aaatatgaca | agaatgtaa | aaagacagtg | 60 |
| gaggaatcaa | ctatttgcga | atatccttta | aatgtatttg | taaatggtga | acatttgaca | 120 |
| gtgctcttat | gtactcctga | aaagcttaag | gaattaacaa | taggtttctt | ggtctttaaa | 180 |
| ggtattataa | aatctctaga | tgaaataaaa | tctttagaga | tagatgaaaa | aagtggagcg | 240 |
| tccagggtaa | tcttgaaaaa | tagacaattt | aataaagagt | tgtattcaaa | gcaagtactt | 300 |
| cctacaacat | ttaatgaaaa | tgaaaaaagt | aaattctttt | catatattat | tgattccatg | 360 |
| aaaattagtc | taatcaataa | tgataatgtt | tacatacatg | ttgataaaat | ctatggctta | 420 |
| atgatggaca | atcttggata | ttccaagact | tttaaactca | ctggaggagc | acattgtgca | 480 |
| gctctttgtg | atgaagataa | agtaatatct | atttgtgagg | atgtggccag | acacaatgct | 540 |
| gtagacaagc | ttataggtga | ggcatttata | aaaaatattt | gtttaaaaga | taaaataata | 600 |
| tttgtgagta | gcagggtatc | ttttgaaatg | gtatataaaa | ttgctagact | tggggtacct | 660 |
| ataataatat | ctaaatctgc | acctacaaat | ctttctatag | aatttgcaaa | agctttaaat | 720 |
| gttacattaa | ttggatttgt | aaggggagaa | agaatgaatg | tatatacaaa | tccacagaga | 780 |
| ataatatag | | | | | | 789 |

<210> SEQ ID NO 54
<211> LENGTH: 262
<212> TYPE: PRT
<213> ORGANISM: Unknown
<220> FEATURE:
<223> OTHER INFORMATION: Clostridium ragsdalei

<400> SEQUENCE: 54

Met Glu Lys Thr Met Glu Leu His Val Val Lys Tyr Asp Lys Glu Cys

```
 1               5                   10                  15
Lys Lys Thr Val Glu Glu Ser Thr Ile Cys Glu Tyr Pro Leu Asn Val
                20                  25                  30
Phe Val Asn Gly Glu His Leu Thr Val Leu Leu Cys Thr Pro Glu Lys
                35                  40                  45
Leu Lys Glu Leu Thr Ile Gly Phe Leu Val Phe Lys Gly Ile Ile Lys
 50                 55                  60
Ser Leu Asp Glu Ile Lys Ser Leu Glu Ile Asp Glu Lys Ser Gly Ala
 65                 70                  75                  80
Ser Arg Val Ile Leu Lys Asn Arg Gln Phe Asn Lys Glu Leu Tyr Ser
                85                  90                  95
Lys Gln Val Leu Pro Thr Thr Phe Asn Glu Asn Glu Lys Ser Lys Phe
                100                 105                 110
Phe Ser Tyr Ile Ile Asp Ser Met Lys Ile Ser Leu Ile Asn Asn Asp
                115                 120                 125
Asn Val Tyr Ile His Val Asp Lys Ile Tyr Gly Leu Met Met Asp Asn
 130                135                 140
Leu Gly Tyr Ser Lys Thr Phe Lys Leu Thr Gly Gly Ala His Cys Ala
 145                150                 155                 160
Ala Leu Cys Asp Glu Asp Lys Val Ile Ser Ile Cys Glu Asp Val Ala
                165                 170                 175
Arg His Asn Ala Val Asp Lys Leu Ile Gly Glu Ala Phe Ile Lys Asn
                180                 185                 190
Ile Cys Leu Lys Asp Lys Ile Ile Phe Val Ser Ser Arg Val Ser Phe
                195                 200                 205
Glu Met Val Tyr Lys Ile Ala Arg Leu Gly Val Pro Ile Ile Ile Ser
 210                215                 220
Lys Ser Ala Pro Thr Asn Leu Ser Ile Glu Phe Ala Lys Ala Leu Asn
 225                230                 235                 240
Val Thr Leu Ile Gly Phe Val Arg Gly Glu Arg Met Asn Val Tyr Thr
                245                 250                 255
Asn Pro Gln Arg Ile Ile
                260
```

<210> SEQ ID NO 55
<211> LENGTH: 486
<212> TYPE: DNA
<213> ORGANISM: Unknown
<220> FEATURE:
<223> OTHER INFORMATION: Clostridium ragsdalei

<400> SEQUENCE: 55

```
atgttaacta acagcaaaa tgaagacctg tctggacaag atgtaattga aaaatatcct      60
aaagagcaga gatttactct tgctatacta caggatatac agagaaagta caaatatata     120
cccagagaag cactggagaa tttagctaag tatttggaca cgcctgtaag tagactgtat     180
ggtatggcta cttttatata ggcattgagc cttactccaa aggggaaaa cataataact      240
gtatgtgatg gaaccgcttg ccatgttgct ggttctatgg ttgtaatgga tgaacttgaa     300
aaggcaatag gaattaaacc aggtgaaact acagaagatc ttaaattttc aataaataca     360
gttaactgta taggatgctg tgcaatagct cctgtcatga tgataaatga caaatatttt     420
ggaaatttaa cacctaaact ggttgaagaa attcttagtg agtataggag tgaaagccat     480
gagtga                                                                486
```

<210> SEQ ID NO 56
<211> LENGTH: 161
<212> TYPE: PRT
<213> ORGANISM: Unknown
<220> FEATURE:
<223> OTHER INFORMATION: Clostridium ragsdalei

<400> SEQUENCE: 56

```
Met Leu Thr Lys Gln Gln Asn Glu Asp Leu Ser Gly Gln Asp Val Ile
1               5                   10                  15

Glu Lys Tyr Pro Lys Glu Gln Arg Phe Thr Leu Ala Ile Leu Gln Asp
            20                  25                  30

Ile Gln Arg Lys Tyr Lys Tyr Ile Pro Arg Glu Ala Leu Glu Asn Leu
        35                  40                  45

Ala Lys Tyr Leu Asp Thr Pro Val Ser Arg Leu Tyr Gly Met Ala Thr
    50                  55                  60

Phe Tyr Lys Ala Leu Ser Leu Thr Pro Lys Gly Glu Asn Ile Ile Thr
65                  70                  75                  80

Val Cys Asp Gly Thr Ala Cys His Val Ala Gly Ser Met Val Val Met
                85                  90                  95

Asp Glu Leu Glu Lys Ala Ile Gly Ile Lys Pro Gly Glu Thr Thr Glu
            100                 105                 110

Asp Leu Lys Phe Ser Ile Asn Thr Val Asn Cys Ile Gly Cys Cys Ala
        115                 120                 125

Ile Ala Pro Val Met Met Ile Asn Asp Lys Tyr Phe Gly Asn Leu Thr
    130                 135                 140

Pro Lys Leu Val Glu Glu Ile Leu Ser Glu Tyr Arg Ser Glu Ser His
145                 150                 155                 160

Glu
```

<210> SEQ ID NO 57
<211> LENGTH: 1821
<212> TYPE: DNA
<213> ORGANISM: Unknown
<220> FEATURE:
<223> OTHER INFORMATION: Clostridium ragsdalei

<400> SEQUENCE: 57

```
gtgagtatag gagtgaaagc catgagtgat aaaaaaattg tcaatatatg ttgtggaaca     60
ggttgcttag ctaaaggcag caaggaagta tatgaagaaa tgaaggcaca aatagctaaa    120
ttaggggcaa atgcagaagt aaatgttaaa ttaaaagcaa caggttgcga tggattgtgt    180
gagaaaggtc ctgtactgaa aatatatcca gatgacattg catattttaa agttaaagta    240
gaagatgtag aagacgtagt aaaaaagaca ttgatgaatg gggaaataat tgaaaaatta    300
ttatattttg aaactgctac aaaacagaga ttaagaaatc ataaagaaag tgaattttgt    360
aaaagacaat acaaaattgc tctcagaaat gttggtgaaa tagatccaat aagtttggaa    420
gattatgttg aaagaggcgg atataaagct cttaaaaaag caataagcag catgaaacct    480
gaagatgtgc ttgaagaaat aacaaaatca ggtcttagag gaagaggtgg agcaggattc    540
ccaacaggac gtaaatggaa aactgctgca gatattgata catcacctat atatgtagta    600
tgcaatggtg atgagggaga tcctggagca tttatggata gaagtataat ggagggagat    660
cctaacagtg ttatagaagg tatgacattg tgtgcctatg cagtaggagg tacaaacggc    720
tttgcttata taagagatga atatggactt gctgtagaaa atatgcagaa agctattaat    780
aaagcaaaag atgaaaattt attaggtaat aatatattag gaactgactt ttccttcgat    840
```

-continued

```
atacagatag taagaggtgg aggagctttt gtatgtggtg agtctactgc acttatgtca    900
tctatagaag gtatggtagg agaacctaga gctaaatata tacacactac agaaaaagga    960
ttgtggggac aacctactgt tttaaataat gtagaaactt gggccaatgt acctataata   1020
attgaaaaag gtggagattg gtatcatgct ataggaacta tggagaagag taagggaaca   1080
aaagtattct cattagttgg aaaagttaag aatactggac ttgtagaagt acctatggga   1140
actactctta gagaaataat atatgatatt ggcggtggag tattaaacga cagaaagttt   1200
aaggcagttc aaataggtgg accttcagga ggatgtttac catctgaata tttagacttg   1260
ccagtagatt atgatacttt ggttaaagcg gattctatga tgggttccgg cggaatgatc   1320
gtaatggatg atagaacctg tatggtagat gtaactagat attacttgag tttcttagct   1380
gaagaatctt gtggaaagtg tgtaccttgt agagaaggcg taagagaat gcttgaaata   1440
ctcactgata tatgcaatgg tgatggaaaa gaaggagaca tagaagagct tcttgaaata   1500
tgttccatga caagcaaggc atctctgtgc agtcttggta agagtgctcc aaatccagta   1560
aaagcagcta agatatttt tagagatgaa tttgaagaac atataaagaa taagagatgt   1620
agagcaggag tttgtaagaa acttactaca tttggtatag atcaagataa atgtaaggga   1680
tgcgatatgt gtaaaaagaa ttgtccagct gattgtataa caggggaaat taagaaacca   1740
catacaatag atgctgataa gtgcttgaga tgcggtaact gcatgaacat ctgtaagttt   1800
gatgctgtta aggttttata g                                             1821
```

<210> SEQ ID NO 58
<211> LENGTH: 606
<212> TYPE: PRT
<213> ORGANISM: Unknown
<220> FEATURE:
<223> OTHER INFORMATION: Clostridium ragsdalei

<400> SEQUENCE: 58

```
Met Ser Ile Gly Val Lys Ala Met Ser Asp Lys Lys Ile Val Asn Ile
1               5                   10                  15

Cys Cys Gly Thr Gly Cys Leu Ala Lys Gly Ser Lys Glu Val Tyr Glu
            20                  25                  30

Glu Met Lys Ala Gln Ile Ala Lys Leu Gly Ala Asn Ala Glu Val Asn
        35                  40                  45

Val Lys Leu Lys Ala Thr Gly Cys Asp Gly Leu Cys Glu Lys Gly Pro
    50                  55                  60

Val Leu Lys Ile Tyr Pro Asp Asp Ile Ala Tyr Phe Lys Val Lys Val
65                  70                  75                  80

Glu Asp Val Glu Asp Val Val Lys Lys Thr Leu Met Asn Gly Glu Ile
                85                  90                  95

Ile Glu Lys Leu Leu Tyr Phe Glu Thr Ala Thr Lys Gln Arg Leu Arg
            100                 105                 110

Asn His Lys Glu Ser Glu Phe Cys Lys Arg Gln Tyr Lys Ile Ala Leu
        115                 120                 125

Arg Asn Val Gly Glu Ile Asp Pro Ile Ser Leu Glu Asp Tyr Val Glu
    130                 135                 140

Arg Gly Gly Tyr Lys Ala Leu Lys Ala Ile Ser Ser Met Lys Pro
145                 150                 155                 160

Glu Asp Val Leu Glu Glu Ile Thr Lys Ser Gly Leu Arg Gly Arg Gly
                165                 170                 175

Gly Ala Gly Phe Pro Thr Gly Arg Lys Trp Lys Thr Ala Ala Asp Ile
            180                 185                 190
```

-continued

```
Asp Thr Ser Pro Ile Tyr Val Val Cys Asn Gly Asp Glu Gly Asp Pro
            195                 200                 205

Gly Ala Phe Met Asp Arg Ser Ile Met Glu Gly Asp Pro Asn Ser Val
        210                 215                 220

Ile Glu Gly Met Thr Leu Cys Ala Tyr Ala Val Gly Gly Thr Asn Gly
225                 230                 235                 240

Phe Ala Tyr Ile Arg Asp Glu Tyr Gly Leu Ala Val Glu Asn Met Gln
                245                 250                 255

Lys Ala Ile Asn Lys Ala Lys Asp Glu Asn Leu Leu Gly Asn Asn Ile
            260                 265                 270

Leu Gly Thr Asp Phe Ser Phe Asp Ile Gln Ile Val Arg Gly Gly Gly
        275                 280                 285

Ala Phe Val Cys Gly Glu Ser Thr Ala Leu Met Ser Ser Ile Glu Gly
    290                 295                 300

Met Val Gly Glu Pro Arg Ala Lys Tyr Ile His Thr Thr Glu Lys Gly
305                 310                 315                 320

Leu Trp Gly Gln Pro Thr Val Leu Asn Asn Val Glu Thr Trp Ala Asn
                325                 330                 335

Val Pro Ile Ile Glu Lys Gly Gly Asp Trp Tyr His Ala Ile Gly
            340                 345                 350

Thr Met Glu Lys Ser Lys Gly Thr Lys Val Phe Ser Leu Val Gly Lys
        355                 360                 365

Val Lys Asn Thr Gly Leu Val Glu Val Pro Met Gly Thr Thr Leu Arg
    370                 375                 380

Glu Ile Ile Tyr Asp Ile Gly Gly Val Leu Asn Asp Arg Lys Phe
385                 390                 395                 400

Lys Ala Val Gln Ile Gly Gly Pro Ser Gly Gly Cys Leu Pro Ser Glu
                405                 410                 415

Tyr Leu Asp Leu Pro Val Asp Tyr Asp Thr Leu Val Lys Ala Asp Ser
            420                 425                 430

Met Met Gly Ser Gly Gly Met Ile Val Met Asp Asp Arg Thr Cys Met
        435                 440                 445

Val Asp Val Thr Arg Tyr Tyr Leu Ser Phe Leu Ala Glu Glu Ser Cys
    450                 455                 460

Gly Lys Cys Val Pro Cys Arg Glu Gly Val Lys Arg Met Leu Glu Ile
465                 470                 475                 480

Leu Thr Asp Ile Cys Asn Gly Asp Gly Lys Glu Gly Asp Ile Glu Glu
                485                 490                 495

Leu Leu Glu Ile Cys Ser Met Thr Ser Lys Ala Ser Leu Cys Ser Leu
            500                 505                 510

Gly Lys Ser Ala Pro Asn Pro Val Lys Ala Ala Ile Arg Tyr Phe Arg
        515                 520                 525

Asp Glu Phe Glu Glu His Ile Lys Asn Lys Arg Cys Arg Ala Gly Val
    530                 535                 540

Cys Lys Lys Leu Thr Thr Phe Gly Ile Asp Gln Asp Lys Cys Lys Gly
545                 550                 555                 560

Cys Asp Met Cys Lys Lys Asn Cys Pro Ala Asp Cys Ile Thr Gly Glu
                565                 570                 575

Ile Lys Lys Pro His Thr Ile Asp Ala Asp Lys Cys Leu Arg Cys Gly
            580                 585                 590

Asn Cys Met Asn Ile Cys Lys Phe Asp Ala Val Lys Val Leu
        595                 600                 605
```

<210> SEQ ID NO 59
<211> LENGTH: 768
<212> TYPE: DNA
<213> ORGANISM: Unknown
<220> FEATURE:
<223> OTHER INFORMATION: Clostridium ragsdalei

<400> SEQUENCE: 59

```
gtgaatgtag atatgaaaat tacaatagat ggaaaagctt gtgaagctga aaaaggagaa 60
ttcatattac aaatagcaag aagaaataat atatatatac ctacactgtg ccacagtgat 120
gcattgcctg gcttgctag ctgtagactg tgtatagtta aagtagtaga taggggacgt 180
gcaaagatag taacttcctg tatattccct gtaagtaagg aagtagaagt tataactaat 240
gacgatgaaa taaagagaat gagaaaaaac atagttatgc ttttaaaagt aagatgccct 300
gaaaataaag aagtaaatga attagctaaa gcctttggag tagaggaaaa gagagtaaag 360
aggttcaaat tggatccaga acaaaattgt gttttgtgcg gactttgtgc aaaagcttgc 420
aaggaattag gtactggagc aatctcaaca gttaataggg gtatgtataa agaagtagca 480
actccatatc acgaatcttc accagaatgt ataggatgtg cttcctgtgc aaatgtttgt 540
ccaactaatg caataaaagt tgtggataaa gatggagaaa gagaaatatg gggcaaaaaa 600
ttcaagatgg ttaaatgtga tttgtgcgga gaatattttg ctacagaaga acacgtaaaa 660
tatgcttaca ataggcttgg aaaagagcag ccagaaaagc ttatgtgcag cagctgcaag 720
aagaaagtta cagccaaaga tgtcaaaaat atttttgaga acgtgtga 768
```

<210> SEQ ID NO 60
<211> LENGTH: 255
<212> TYPE: PRT
<213> ORGANISM: Unknown
<220> FEATURE:
<223> OTHER INFORMATION: Clostridium ragsdalei

<400> SEQUENCE: 60

```
Met Asn Val Asp Met Lys Ile Thr Ile Asp Gly Lys Ala Cys Glu Ala
1 5 10 15

Glu Lys Gly Glu Phe Ile Leu Gln Ile Ala Arg Arg Asn Asn Ile Tyr
20 25 30

Ile Pro Thr Leu Cys His Ser Asp Ala Leu Pro Gly Leu Ala Ser Cys
35 40 45

Arg Leu Cys Ile Val Lys Val Val Asp Arg Gly Arg Ala Lys Ile Val
50 55 60

Thr Ser Cys Ile Phe Pro Val Ser Lys Glu Val Glu Val Ile Thr Asn
65 70 75 80

Asp Asp Glu Ile Lys Arg Met Arg Lys Asn Ile Val Met Leu Leu Lys
85 90 95

Val Arg Cys Pro Glu Asn Lys Glu Val Asn Glu Leu Ala Lys Ala Phe
100 105 110

Gly Val Glu Glu Lys Arg Val Lys Arg Phe Lys Leu Asp Pro Glu Gln
115 120 125

Asn Cys Val Leu Cys Gly Leu Cys Ala Lys Ala Cys Lys Glu Leu Gly
130 135 140

Thr Gly Ala Ile Ser Thr Val Asn Arg Gly Met Tyr Lys Glu Val Ala
145 150 155 160

Thr Pro Tyr His Glu Ser Ser Pro Glu Cys Ile Gly Cys Ala Ser Cys
165 170 175
```

-continued

```
Ala Asn Val Cys Pro Thr Asn Ala Ile Lys Val Val Asp Lys Asp Gly
            180                 185                 190

Glu Arg Glu Ile Trp Gly Lys Lys Phe Lys Met Val Lys Cys Asp Leu
        195                 200                 205

Cys Gly Glu Tyr Phe Ala Thr Glu Glu His Val Lys Tyr Ala Tyr Asn
    210                 215                 220

Arg Leu Gly Lys Glu Gln Pro Glu Lys Leu Met Cys Ser Ser Cys Lys
225                 230                 235                 240

Lys Lys Val Thr Ala Lys Asp Val Lys Asn Ile Phe Glu Asn Val
                245                 250                 255

<210> SEQ ID NO 61
<211> LENGTH: 555
<212> TYPE: DNA
<213> ORGANISM: Unknown
<220> FEATURE:
<223> OTHER INFORMATION: Clostridium ragsdalei
<400> SEQUENCE: 61
atgaaaccag agtttaattc ttttgtaata gccgatcctg acaagtgcat aggctgtaga      60
tcttgtgaga ttgcctgtgc tgcaaaacat agagaagata ctcaaggaaa aactattgga     120
actatgaata ataaagttac tccaaggtta ttctttgtta aaaataaagg aaatgtaatg     180
ccggtacaat gcagacattg tgaggatgca ccatgtctaa atgcctgccc agttaatgct     240
atagttgaaa aagatggaag tatcattata aatgaaagtg catgtatagg gtgtcagacc     300
tgtacaatag tatgtccggt aggtgctgta agtttacttc ctagaactca aggtaaagta     360
gttacaggag gaattcaggt taaagtaaga gcagcagctt ataaatgtga tttatgtaag     420
gaagagggag gagaacctgc ctgcgtcaaa gaatgtccaa aagaggcctt aaggttagta     480
gatcctagag aagataaaaa agatcgtagt gtgaaagctg ctatggaact gttaaatata     540
aacgcaaatc tctaa                                                      555

<210> SEQ ID NO 62
<211> LENGTH: 184
<212> TYPE: PRT
<213> ORGANISM: Unknown
<220> FEATURE:
<223> OTHER INFORMATION: Clostridium ragsdalei

<400> SEQUENCE: 62

Met Lys Pro Glu Phe Asn Ser Phe Val Ile Ala Asp Pro Asp Lys Cys
1               5                   10                  15

Ile Gly Cys Arg Ser Cys Glu Ile Ala Cys Ala Ala Lys His Arg Glu
            20                  25                  30

Asp Thr Gln Gly Lys Thr Ile Gly Thr Met Asn Asn Lys Val Thr Pro
        35                  40                  45

Arg Leu Phe Phe Val Lys Asn Lys Gly Asn Val Met Pro Val Gln Cys
    50                  55                  60

Arg His Cys Glu Asp Ala Pro Cys Leu Asn Ala Cys Pro Val Asn Ala
65                  70                  75                  80

Ile Val Glu Lys Asp Gly Ser Ile Ile Ile Asn Glu Ser Ala Cys Ile
                85                  90                  95

Gly Cys Gln Thr Cys Thr Ile Val Cys Pro Val Gly Ala Val Ser Leu
            100                 105                 110

Leu Pro Arg Thr Gln Gly Lys Val Val Thr Gly Gly Ile Gln Val Lys
        115                 120                 125
```

```
Val Arg Ala Ala Ala Tyr Lys Cys Asp Leu Cys Lys Glu Glu Gly Gly
    130                 135                 140

Glu Pro Ala Cys Val Lys Glu Cys Pro Lys Glu Ala Leu Arg Leu Val
145                 150                 155                 160

Asp Pro Arg Glu Asp Lys Lys Asp Arg Ser Val Lys Ala Ala Met Glu
                165                 170                 175

Leu Leu Asn Ile Asn Ala Asn Leu
            180
```

```
<210> SEQ ID NO 63
<211> LENGTH: 618
<212> TYPE: DNA
<213> ORGANISM: Unknown
<220> FEATURE:
<223> OTHER INFORMATION: Clostridium ragsdalei

<400> SEQUENCE: 63
atgaattatt gcacactaaa tatatctcaa gaaaaaagga gagttaataa aatgaagaat     60
tgcctcgtag tagcagatcc taataaatgc ataggatgta ggacttgtga agcagcttgt    120
ggtattgcac attcaggagg ggactttttt aatacaaatg tatccaaaat taattttaat    180
cctcgcttaa atgtgataaa aactgctaaa gtaagtgctc ctgttcaatg cagacaatgc    240
gaagatgcac cttgtggtaa agcttgtcca gttaacgcta tttcaaatga aaatggttat    300
gttagtgtag ataaagatgt atgtgttgga tgtaaaatct gcatgttagc ttgtcctttt    360
ggagctattg aattagcttc tcaatataag gatggagaag ttgtagacca aaagggactt    420
aagatgagtg aggaaggtaa tcctactgta aatggaaaag gaagagtggt agcaaataag    480
tgtgatcttt gccaggatag ggatggagga cctgcttgca tagaagtttg tcctacaaaa    540
tctctcaaat tagttactta tgatgacaat aataatatag ttgaaaaaaa agatgacgac    600
gaacgtgaag taggctaa                                                  618
```

```
<210> SEQ ID NO 64
<211> LENGTH: 205
<212> TYPE: PRT
<213> ORGANISM: Unknown
<220> FEATURE:
<223> OTHER INFORMATION: Clostridium ragsdalei

<400> SEQUENCE: 64

Met Asn Tyr Cys Thr Leu Asn Ile Ser Gln Glu Lys Arg Arg Val Asn
1               5                   10                  15

Lys Met Lys Asn Cys Leu Val Val Ala Asp Pro Asn Lys Cys Ile Gly
            20                  25                  30

Cys Arg Thr Cys Glu Ala Ala Cys Gly Ile Ala His Ser Gly Gly Asp
        35                  40                  45

Phe Phe Asn Thr Asn Val Ser Lys Ile Asn Phe Asn Pro Arg Leu Asn
    50                  55                  60

Val Ile Lys Thr Ala Lys Val Ser Ala Pro Val Gln Cys Arg Gln Cys
65                  70                  75                  80

Glu Asp Ala Pro Cys Gly Lys Ala Cys Pro Val Asn Ala Ile Ser Asn
                85                  90                  95

Glu Asn Gly Tyr Val Ser Val Asp Lys Asp Val Cys Val Gly Cys Lys
            100                 105                 110

Ile Cys Met Leu Ala Cys Pro Phe Gly Ala Ile Glu Leu Ala Ser Gln
        115                 120                 125

Tyr Lys Asp Gly Glu Val Val Asp Gln Lys Gly Leu Lys Met Ser Glu
```

```
                130              135              140
Glu Gly Asn Pro Thr Val Asn Gly Lys Gly Arg Val Val Ala Asn Lys
145                 150                 155                 160

Cys Asp Leu Cys Gln Asp Arg Asp Gly Gly Pro Ala Cys Ile Glu Val
                165                 170                 175

Cys Pro Thr Lys Ser Leu Lys Leu Val Thr Tyr Asp Asp Asn Asn Asn
                180                 185                 190

Ile Val Glu Lys Lys Asp Asp Asp Glu Arg Glu Val Gly
                195                 200                 205

<210> SEQ ID NO 65
<211> LENGTH: 10640
<212> TYPE: DNA
<213> ORGANISM: Unknown
<220> FEATURE:
<223> OTHER INFORMATION: Clostridium autoethanogenum

<400> SEQUENCE: 65
```

| | | | | | |
|---|---|---|---|---|---|
| atggataaaa | aagtttttaac | tgtttgtcct | tactgtggcg | ctggttgtaa | tttatacttg | 60 |
| catgtaaaga | atggcaaaat | aattaaagca | gagcctgcta | atggtaggac | aaatgaagga | 120 |
| tcactgtgtt | taaaaggaca | ctttggttgg | gattttttaa | acgatcctaa | aatattgaca | 180 |
| tctagaatta | aacatccgat | gataagaaaa | acggagagc | tagaagaggt | aagctgggat | 240 |
| gaagctatta | gttttacggc | ttcaagattg | tcacaaataa | aagagaaata | tggacctgat | 300 |
| tccataatgg | gaacaggatg | tgctaggggt | tctggaaacg | aagcaaacta | cataatgcaa | 360 |
| aagttttatga | gggcggttat | tggaaccaat | aacgtagatc | actgtgccag | agtttgacat | 420 |
| gctccttctg | tagccggtct | ggcttacgtt | ttaggaaatg | gtgctatgtc | aaatggtata | 480 |
| catgaaaatag | atgatacaga | tttactactt | atttttggat | ataatggagc | agcttcgcat | 540 |
| ccaatagttg | ctaagagaat | agttagggca | aaacaaaagg | gtgcaaaggt | aatagttgta | 600 |
| gatccacgta | taacagagtc | tggtaggata | gcagatttat | ggctccctat | aaaaaatgga | 660 |
| acaaatatgg | ttcttgtaaa | tactttttgcc | aacatactta | taaataaaca | gttttataac | 720 |
| aaacaatatg | tagaagatca | tactgttggt | tttgaagaat | atagatctat | agttgaaaat | 780 |
| tatactcctg | aatatgcaga | aaaagttact | ggcatacctt | cagaggatat | agtagaagct | 840 |
| atgaaaatgt | actcaggtgc | taaaaatgcc | atgatattat | atggtatggg | agtatgtcaa | 900 |
| tttgctcaag | ctgtagatgt | agttaaggga | ctagcttcta | tagcattatt | aactggtaat | 960 |
| tttggaagac | taatgtagg | ataggaccta | gtaagaggcc | agaacaatgt | tcaaggtgct | 1020 |
| tgtgatatgg | gagcacttcc | taatgtatac | ccaggttatc | aaagtgtaac | tgacgatgca | 1080 |
| attaggcaaa | aatttgaaaa | agcttggggt | gttaaacttc | aaacaaagt | tggttatcac | 1140 |
| ctgacacaag | ttcctgaatt | aacgcttaaa | gaggataaaa | taaaggcata | ttatataatg | 1200 |
| ggtgaagatc | cagttcaaag | tgatcctgat | tctaatgaaa | tgagagagac | actggataaa | 1260 |
| atggaacttg | taatagttca | ggatatattt | atgaataaaa | ctgcactcca | tgcagatgta | 1320 |
| attttacctt | ccacgtcttg | gggagaacat | gaaggagtct | ttagttctgc | agatagagga | 1380 |
| ttccagagat | ttagaaaagc | tgtagaacct | aagggagatg | ttaaaccaga | ttgggaaata | 1440 |
| atttcaaaaa | ttgcctgtgc | tatgggttat | aatatgcatt | ataacaatac | tgaggaaata | 1500 |
| tggaatgaac | ttataaattt | atgtccaaat | ttcaaaggag | caacttataa | gagactcgaa | 1560 |
| gaattaggag | gaatccaatg | gccttgtcca | tctgaaaatc | atcctggaac | ttcttatctc | 1620 |
| tacaaaggta | ataaatttaa | tacacctact | ggaaaagcaa | acttatttgc | agcagaatgg | 1680 |

```
agacctcctg tagagcagac agataaagat tatccactcg ttctttctac agttagagaa    1740
gtaggacatt attctgtaag aacaatgaca ggaaactgta gggcacttca gcagttagcc    1800
gatgaaccag gatatgtaca agttaatcca atggatgcaa aggctaaggg aataatagat    1860
ggtgagctta tgagaataag ttcacgaaga ggttctgtgg ttgcccgtgc acttattact    1920
gaaagggcaa ataaaggagc agtctatatg acctatcaat ggtgggtagg cgcatgtaat    1980
gaacttacat ctaataatct agatccagta tcaaaaactc ctgaattaaa gtattgtgca    2040
gtaaaaatag aagctataaa agatcagaaa gaagctgaaa agtttataaa agatcaatat    2100
gatcttttaa agaaaaagat gaatgtttaa tattttaata taaagatggc taaaaagacc    2160
ttgattaaga ggtcttttag ccaaaagctt taaatcaata ggagttgata gactgtgata    2220
gacgtacatg aagcattcaa tatagtaatg aataacacaa aactgcttaa aggtgaagat    2280
atatcgttga taaattctct aacagggta ttggcagagg atataagctc aaaagataat    2340
cttcccccat ttgacaaatc ctgtatggat gggtatgctt taaaaagtga agatactaag    2400
gaaaaaatgt caaaatttcg aattaaggga agcataaagg cgggagattt ttctgatata    2460
gtattgaaaa atggtgaagc cataaaaata atgacaggag ctccagtacc aaaaggtgca    2520
gatgcagtta ttcaaataga aaaagtaaaa gtagaaggaa aagaacttca tgtattagaa    2580
aatatatctc ctggaaccaa catatttaaa actggtgagg agataaaaat tggtgatgtt    2640
gctttaagaa aaggaaagat tttgagacct gcagaaatag ggttattggc atcactaggt    2700
tatactaaaa taaaatgtta taaagcccct aaaattataa taataaatac tggggatgaa    2760
cttataaata tagatcaaaa cttaatgcaa ggtaaaataa ggaattgtaa tgaatataca    2820
ttaattgccc ttattaaaaa tttaaatgca gaagttaaat catatgggat aataagagat    2880
gataaggata agattttaa tgctataaaa actgcatttg aagagggaga tataatcata    2940
actactggag gagcatctgt aggtgattac gattttatag aagatgttct tcagaaaata    3000
ggaacagata taaagtttac ttcggtagct attaaaccag gaaaaccagt tgttttttgca    3060 acttttaaag ataaattgtt cttttggactt ccaggaaatc cgctttcggt aataaattca    3120
tttgaaagtt ttgtagcacc atctattaaa aaaatgattg gaagagatga tgcgtttcct    3180
gaagaatttc ctgtaacttt aaaagatgat tttaaatcag gaaaagaaag agactgctat    3240
atgtatgtaa acataaaaa ggaagataac cgttattatg cctatgatgt aggaagacaa    3300
gattccaatg ggctttttac gcttactaag tcaaatggag tcgtcatcat ggaaaaggga    3360
actagtatag caaaagctgg agatattta aatggaaaat ttatattcaa ataagaggtc    3420
agtaatttct attattcat ctagttcaaa ttcgggtaag actaccttga tagaaggaat    3480
aataagaatt ctaaaaagca gaggatataa ggttggtgca ataagaatg atgctcataa    3540 gttacagata gattacccag gaaaagacag ctttagattt acagaggcag gtgcggacaa    3600
tgttgttatt gcatcggata atacagtggc tatgataaaa aaagtaagtg gacccaaaag    3660
tatagaagaa ctactgttgc ttttttcaaga tgtagatatt gtaatagtgg aaggcttcaa    3720
gggtaacgaa tttcctaaaa tagaagtata caggaaaaat gcaagcaaat gtttacttta    3780
caaaaattct aaatataatt ttcaaaattt tgtagctatt gtaaccaatg aaaacttaat    3840
aactgatatt cctgtatttg atataaatga tacaaaaaaa atagctgatt ttattgagaa    3900
cgactttata ggaggtaaca aaaatggaga aaaccatgga acttcatgta gtcaaatatg    3960
acaaagaatg taaaaagaca gtagaggaat caactatttg tgaatatcct ttaaatgtat    4020
```

```
ttgtaaatgg tgaacatttg acagtactct tatgtacgcc tgaaaagctt aaggaattaa    4080
caataggttt cttgaccttt agaggtgtta taaaatctct agatgaaata aaatctctag    4140
agatagatga aaaaagtgga gcgtccaggg taactttgaa aaatagccaa tttaataaag    4200
agttgtattc aaagcaagtg cttcctataa catttagtga aaatgagaaa agtaagttct    4260
tttcgtatat tattgattcc atggaaatta gtataatcaa caatgataat gtttacattc    4320
atgtcgataa atctatgat ctaatgatgg acaatcttgg atattccaag acgtttaaac    4380
tcactggagg aacacattgt gcagctcttt gtgatgaaga taaagtaata tctatttgtg    4440
aggatgtggc tagacacaat gctgtagaca agcttatagg tgaggcattt ataaaaaata    4500
tttatttaaa ggataaaata atatttgtga gcagcagagt atcttttgaa atggtatata    4560
aaattgctag gctaggggta cctataataa tatctaaatc tgcacctaca agtcttttcta    4620 tagaatttgc aaaagcttta aatgttacat taattggatt tgtaagggga gaaagaatga    4680
atgtatatac aaatccacag agaataatat agtaatttct gttaacatat ttttgaatat    4740
aatcttaaaa aattaatcat atagttatat aaaaataata taatatttaa tgttaataat    4800
tagtccctaa ttaaatagga ctaagtttat attttaattt ttaaataagg taattaaaat    4860
aattttaaat taaatgtgtt atatgtttta aaattatttc ttaagtatag aggctcaaat    4920
ctttggttta gagctaatat cttattcctt ctaatatttt aaggggaaaa tcaattataa    4980
tattcaaatg ggagggtgaa gtatttaatg ttaactaaac agcaaaatga agacctgtct    5040
ggacaagatg taattgaaaa atatcctaaa gagcagagat ttactcttgc tatactacag    5100
gatatacaga gaaagtacaa atatatacca agagaagcac tggagaattt agctaagtat    5160
ttggacacgc ctgtaagtag actgtatggt atggctactt tttataaggc attgagcctt    5220
actccaaaag gggaaaacat aataactgta tgtgatggaa ccgcttgcca tgttgctggt    5280
tctatggttg taatggatga acttgaaaag gcaataggaa ttaaaccagg tgaaactaca    5340
gaggatctca aattttcaat aaatacagtt aactgtatag gatgctgtgc aatagctcct    5400
gtcatgatga taaatgacaa atattatgga aatttaacac ctaaactggt tgaagaaatt    5460
cttagtgagt ataggagtga gagtgatgag tgataaaaaa actgtcaata tatgttgtgg    5520
gacaggttgt ttagctaaag gcagtatgga agtatatgaa gaaatgaagg cacaaatagc    5580
taaattaggg gcaaatgcag aagtaaatgt taaattaaaa gcaacaggtt gcgatggatt    5640
gtgtgagaaa ggtcctgtac tgaaaatata tccagatgac attgcatatt ttaaagttaa    5700
agtagaagat gtagaagacg tagtaaaaaa gacattgatg aatggggaaa taattgaaaa    5760
attattatat tttgagactg ctacaaaaca gagattaaga aatcataaag aaagtgaatt    5820
ttgtaaaaga caatacaaaa ttgctctcag aaatgttggt gaaatagatc caataagttt    5880
ggaagattat gttgaaagag gcggatacaa agctcttaaa aaagcaataa gcagcatgaa    5940
acctgaagat gtgcttgaag aaataacaaa atcaggtctt agaggaagag gtggagcagg    6000
attcccaaca ggacgtaaat ggaaaactgc tgcagatatt gatacatcac ctatatatgt    6060
agtatgtaat ggtgatgaag gagatcctgg agcatttatg gatagaagta taatggaggg    6120
agatcctaac agtgttatag aaggtatgac attatgtgct tatgcagtag gaggtacaaa    6180
tggatttgct tatataagag atgaatatgg acttgctgta gaaaatatgc agaaagctat    6240
taataaagca aaagatgaaa atttattagg taataatata ttaggaactg attttttcctt    6300 cgatatacag atagtaagag gtggaggagc ttttgtatgt ggtgaatcta ctgcacttat    6360
gtcgtctata gaaggtatgg taggtgaacc tagagctaaa tatatacaca ctacagaaaa    6420
```

```
aggattgtgg ggacaaccta cagttttaaa taatgtagaa acttgggcca atgtacctat   6480
aataattgaa aaaggcggag attggtatca tgctataggc actatggaga agagtaaggg   6540
aacaaaggta ttctcattag ttggaaaagt taagaatact ggacttgtag aagtacctat   6600
gggaactact cttagagaaa taatatatga tattggcggt ggagtattaa atgatagaaa   6660
gtttaaggca gttcaaatag gtggaccttc aggtggatgt ttaccagctg aatatttaga   6720
tttgccagta gattatgata ctttggttaa agcagattcc atgatgggtt caggcggaat   6780
gatcgtaatg gatgatagaa cctgtatggt agatgtaact agatattacc tgagcttctt   6840
ggctgaagaa tcttgtggaa agtgtgtacc ttgtagagaa ggcgtaaaga ggatgcttga   6900
aatactcact gacatatgca atggtgatgg aaaagaagga gacatagaag agcttctcga   6960
aatatgttcc atgacaagca aggcatctct gtgcagtctt ggtaagagtg ctccaaatcc   7020
agtaattgct tctataagat atttttagaga tgaatttgaa gagcatataa agaataagag   7080
atgtagagca ggagtttgta agaaacttac tacatttggt atagacgagg ataaatgtaa   7140
gggatgcgat atgtgtaaaa agaattgtcc agctgattgt ataacagggg aaattaagaa   7200
accacataca atagatgctg ataagtgctt gagatgcggt aactgcatga acatctgtaa   7260
gtttgatgct gttaaggttc tatagggagg tgaatgtaga tatgaaaatt acaatagatg   7320
gaaaagcttg tgaagctgaa aaaggagaat tcatattaca aatagcaaga gaaataaca   7380 tatatatacc tacattatgt cacagcgatg cattgcctgg gcttgctagc tgtagactat   7440
gtatagttaa agtagtagat aggggacgtg caaagatagt aacttcctgt atattccctg   7500
taagtaagga agtagaagtt ataactaatg acgatgaaat aaagagaatg agaaaaaaca   7560
tagttatgct tttaaaagta agatgccctg aaaataaaga ggtaaatgaa ttagctaaag   7620
cctttggagt agaggaaaag agagtaaaga ggttcaaatt ggatccagaa caaaattgtg   7680
ttttgtgcgg actttgtgca aaagcttgca aggaattagg tactggagca atttcaacag   7740 ttaataggg tatgtataaa gaagtagcaa ctccatatca cgaatcttca ccggaatgta   7800
taggatgtgc ttcctgtgca aatgtttgtc caactaatgc aataaaagtt gtggataaag   7860
atggagaaag agaaatatgg ggcaaaaaat tcaagatggt taagtgtgat ttgtgcggag   7920
aatattttgc tacagaagaa catgtaaaat atgcttacaa taggcttgga aaagagcagc   7980
cagaaaaact tatgtgtagc agctgcaaga agaaagttac agccaaagat gtcaaaaata   8040
tttttgagaa cgtgtgaaaa ttaaagagg ggtggtaatt taaatgaaac cagagtttaa   8100
ttcttttgta atagccgatc ctgacaagtg cataggctgt agatcttgtg agattgcctg   8160
tgctgcaaaa catagagaag atactcaagg aaaaaccatt ggaactatga ataataaagt   8220
tactccaagg ttattctttg ttaaaaataa aggaaatgta atgccagtac aatgcagaca   8280
ttgtgaggat gcaccatgtc taaatgcctg cccagttaat gctatagttg aaaaagatgg   8340
aagtatcatt ataaatgaaa gtgcatgtat aggatgtcag acctgtacaa tagtatgtcc   8400
ggtaggtgct gtaagtttac tgcctagaac tcaaggtaaa gtagttacag gaggaattca   8460
ggttaaagta agagcagcag cttataaatg tgatttatgt aaggaagagg gaggagaacc   8520
tgcttgcgtc aaagaatgtc caaagaggc cttgaggtta gtagatccta gagaagataa   8580 aaagatcgt agtgtgaaag ctgctatgga actgttaaat ataaacgcaa atctctaatt   8640
tataagttat aaaaatccgg aaaagaaagg aatgttaaat atgccaacta gtacttctat   8700
gataaatata gatgaagaat tatgtacagg ctgcagacga tgtgcggatg tctgccctgt   8760
```

```
agatgctata gaaggtgaac agggtaaacc tcagaagata aatactgaaa agtgtgttat    8820
gtgcggacaa tgcattcaag tttgtaaagg ctatcaatct gtatacgacg atgttcctac    8880
tccagttagc aaaaggttat ttgatagagg attgttaaag gaagtagatg aaccattatt    8940
tgcagcatat aataaaggtc aggtaaagag tgttaaagaa attttacaaa acaaagatgt    9000
atttaaaatt gtgcaatgtg cacctgctgt aagagttgct ataggagagg attttggaat    9060
gcctcttgga actttaagtg aaggaaaaat ggcagctgca ctcagaaaat taggatttga    9120
caaagtatat gatacaaact tggtgcaga tcttactata atggaagaag gtagtgagtt    9180
actaaaaaga gtagctgaag gcggagtttt gccaatgttt acttcttgtt gtccagcatg    9240
ggtaaaatat gcagaacaaa catatccaga acttttacct catctttcaa gttgtaagtc    9300
tccaaatcag atggctggag ctatatttaa aacttatgga gcagagataa ataaggttaa    9360
tccggctaaa atttataatg tatctgttat gccatgtaca tgcaaggaat ttgaaagtga    9420
aagagaagaa atgcatgaca gtggacacag ggatgtagat gcagttataa ctacaaggga    9480
attagcacaa ctgttcaaag atgctgatat agattttaat actattgaag aagaacagtt    9540
tgatactcct cttggtatgt ataccggtgc aggaactata tttggtgcta caggtggagt    9600
tatggaagca gcacttagaa ctggatatga actttatact aaaaaaacta ttccaagtat    9660
agatcttact atggtaagag gtggagaagg ttttagaact gctgaagtag atttagggga    9720
tattagacta aaagtaggag tagttttccgg cttaaaaaat gtaaagacg ttatggaatc    9780 agtaaaggca ggcaaatgtg atttgcactt tatagaggtt atgacctgtc ctcaaggatg    9840
tataagtggt ggaggacaac ctaaagttat acttgattca gataaagagg aagcttataa    9900
taataggaaa aagggactat ataatcatga cgctaatctt acttatagaa aatcacatga    9960
aaatccagaa ataagaaaaa tatatgatga gttcttagac aaaccattag gagctaagtc   10020
tcatgaatta ttgcacacta aatatatctc aagaaaaaag gagagttaat aaaatgaaga   10080
attgcctcgt agtagcagat cctaataaat gcataggatg taggacttgt gaagcagctt   10140
gtggtattgc acattcagga ggggactttt ttaacacaaa tgtatccaag attaatttta   10200
atcctcgctt aaatgtgata aaaactgcta aagtaagtgc tcctgttcaa tgcagacaat   10260
gcgaagatgc accttgtggt aaagcttgtc cagttaacgc tatttcaaat gaaaatggtt   10320
atgttagtgt aaataaagat gtatgtgttg gatgtaaaat ctgcatgtta gcttgtcctt   10380
ttggagctat tgaattagct tctcaatata gggatggaga agttgtagac caaaagggac   10440
ttaagatgag tgaggaaggt aatcctactg tgaatgaaaa aggaagagtg gtagcaaata   10500
agtgtgatct ctgccaggat agggatggag ggcctgcttg tatagaagtt tgtcctacaa   10560
aatctctcaa actagttact tatgatgaca ataataatat agttgaaaaa aagatgacg   10620 acgaacgtga agtaagctaa                                                10640

<210> SEQ ID NO 66
<211> LENGTH: 10640
<212> TYPE: DNA
<213> ORGANISM: Unknown
<220> FEATURE:
<223> OTHER INFORMATION: Clostridium ljungdahlii

<400> SEQUENCE: 66
atggataaaa aagttttaac tgtttgtcct tactgtggcg ctggttgtaa tttatacttg      60
catgtaaaga atggcaaaat aattaaagca gagcctgcta atggtaggac aaatgaagga     120
tcactgtgtt taaaaggaca ctttggttgg gattttttaa acgatcctaa aatattgaca     180
```

```
tctagaatta aacatccgat gataagaaaa aacggagagc tagaagaggt aagctgggat    240
gaagctatta gttttacggc ttcaagattg tcacaaataa aagagaaata tggacctgat    300
tccataatgg gaacaggatg tgctaggggt tctggaaacg aagcaaacta cataatgcaa    360
aagtttatga gggcggttat tggaaccaat aacgtagatc actgtgccag agtttgacat    420
gctccttctg tagccggtct ggcttacgtt ttaggaaatg gtgctatgtc aaatggtata    480 catgaaaatag atgatacaga tttactactt attttggat ataatggagc agcttcgcat    540
ccaatagttg ctaagagaat agttagggca aaacaaaagg gtgcaaaggt aatagttgta    600
gatccacgta aacagagtc tggtaggata gcagatttat ggctccctat aaaaaatgga    660
acaaatatgg ttcttgtaaa tacttttgcc aacatactta taaataaaca gttttataac    720
aaacaatatg tagaagatca tactgttggt tttgaagaat atagatctat agttgaaaat    780
tatactcctg aatatgcaga aaagttact ggcataccct cagaggatat agtagaagct    840
atgaaaatgt actcaggtgc taaaaatgcc atgatattat atggtatggg agtatgtcaa    900
tttgctcaag ctgtagatgt agttaaggga ctagcttcta tagcattatt aactggtaat    960
tttgaaagac taatgtagg tataggacct gtaagaggcc agaacaatgt tcaaggtgct    1020
tgtgatatgg gagcacttcc taatgtatac ccaggttatc aaagtgtaac tgacgatgca    1080
attaggaaaa aatttgaaaa agcttggggt gttaaacttc caaacaaagt tggttatcac    1140
ctgacacaag ttcctgaatt aacgcttaaa gaggataaaa taaaggcata ttatataatg    1200
ggtgaagatc cagttcaaag tgatcctgat tctaatgaaa tgagagagac actggataaa    1260
atggaacttg taatagttca ggatatattt atgaataaaa ctgcactcca tgcagatgta    1320 attttaccctt ccacgtcttg gggagaacat gaaggagtct ttagttctgc agatagagga    1380
ttccagagat ttagaaaagc tgtagaacct aagggagatg ttaaaccaga ttgggaaata    1440
atttcaaaaa ttgcctgtgc tatgggttat aatatgcatt ataacaatac tgaggaaata    1500
tggaatgaac ttataaattt atgtccaaat ttcaaggag caacttataa gagactcgaa    1560
gaattaggag aatccaatg gccttgtcca tctgaaaatc atcctggaac ttcttatctc    1620
tacaaaggta ataaatttaa tacacctact ggaaaagcaa acttatttgc agcagaatgg    1680
agacctcctg tagagcagac agataaagat tatccacttg ttctttctac agttagagaa    1740
gtaggacatt attctgtaag aacaatgaca ggaaactgta gggcacttca gcagttagcc    1800
gatgaaccag atatgtaca agttaatcca atggatgcaa aggctaaggg aataatagat    1860
ggtgagctta tgagaataag ttcacgaaga ggttctgtgg ttgcccgtgc acttattact    1920
gaaagggcaa ataaaggagc agtctatatg acctatcaat ggtgggtagg cgcatgtaat    1980
gaacttacat ctaataatct agatccagta tcaaaaactc ctgaattaaa gtattgtgca    2040
gtaaaaatag aagctataaa agatcagaaa gaagctgaaa agtttataaa agatcaatat    2100
gatcttttaa agaaaagat gaatgtttaa tatttaata taaagatggc taaaaagacc    2160
ttgattaaga ggtctttag ccaaaagctt taaatcaata ggagttgata gactgtgata    2220
gacgtacatg aagcattcaa tatagtaatg aataacacaa aactgcttaa aggtgaagat    2280
atatcgttga taaattctct taacagggta ttggcagagg atataagctc aaaagataat    2340
cttcccccat ttgacaaatc ctgtatggat gggtatgctt taaaaagtga agatactaag    2400
gaaaaaatgt caaatttcg aattaaggga agcataaagg cgggagattt ttctgatata    2460
gtattgaaaa atggtgaagc cataaaaata atgacaggag ctccagtacc aaaaggtgca    2520
```

```
gatgcagtta ttcaaataga aaaagtaaaa gtagaaggaa agaaacttca tgtattagaa    2580
aatgtatctc ctggaaccaa catatttaaa actggtgagg agataaaaat tggtgatgtt    2640
gctttaagaa aaggaaagat tttgagacct gcagaaatag ggttattggc atcactaggt    2700
tatactaaaa taaaatgtta taaagcccct aaaattataa taataaatac tggggatgaa    2760
cttataaata tagatcaaaa cttaatgcaa ggtaaaataa ggaattgtaa tgaatataca    2820
ttaattgccc ttattaaaaa tttaaatgca gaagttaaat catatgggat aataagagat    2880
gataaggata agatttttaa tgctataaaa actgcatttg aagagggaga tataatcata    2940
actactggag gagcatctgt aggtgattac gattttatag aagatgttct tcagaaaata    3000
ggaacagata taaagtttac ttcggtagct attaaaccag gaaaaccagt tgtttttgca    3060
acttttaaag ataaattgtt ctttggactt ccaggaaatc cgctttcggt aataaattca    3120
tttgaaagtt ttgtagcacc atctattaaa aaaatgattg aagagatga tgcgtttcct    3180 gaagaatttc ctgtaacttt aaaagatgat tttaaatcag gaaaagaaag agactgctat    3240
atgtatgtaa acataaaaaa ggaagataac cgttattatg cctatgatgt aggaagacaa    3300
gattccaatg ggcttttttac gcttactaag tcaaatggag tcgtcatcat ggaaaaggga    3360
actagtatag caaaagctgg agatatttta aatggaaaat ttatattcaa ataagaggtc    3420
agtaatttct attatttcat ctagttcaaa ttcgggtaag actaccttga tagaaggaat    3480
aataagaatt ctaaaaagca gaggatataa ggttggtgca ataagaatg atgctcataa    3540 gttacagata gattacccag gaaaagacag ctttagattt acagaggcag gtgcggacaa    3600
tgttgttatt gcatcggata atacagtggc tatgataaaa aaagtaagtg acccaaaag    3660 tatagaagaa ctactgttgc tttttcaaga tgtagatatt gtaatagtgg aaggcttcaa    3720
gggtaacgaa tttcctaaaa tagaagtata caggaaaaat acaagcaaat gtttactta    3780 caaaaattct aaatataatt ttcaaaattt tgtagctatt gtaaccaatg aaaacttaat    3840
aactgatatt cctgtatttg atataaatga tacaaaaaaa atagctgatt ttattgagaa    3900
cgactttata ggaggtaaca aaaatggaga aaaccatgga acttcatgta gtcaaatatg    3960
acaaagaatg taaaaagaca gtagaggaat caactatttg tgaatatcct ttaaatgtat    4020
ttgtaaatgg tgaacatttg acagtactct tatgtacgcc tgaaaagctt aaggaattaa    4080 caataggtttt cttgaccttt agaggtgtta taaaatctct agatgaaata aaatctctag    4140
agatagatga aaaagtgga gcgtccaggg taactttgaa aaatagccaa tttaataaag    4200
agttgtattc aaagcaagtg cttcctataa catttaatga aaatgagaaa agtaagttct    4260
tttcgtatat tattgattcc atggaaatta gtataatcaa caatgataat gtttacattc    4320
atgtcgataa aatctatgat ctaatgatgg acaatcttgg atattccaag acgtttaaac    4380
tcactggagg aacacattgt gcagctcttt gtgatgaaga taaagtaata tctatttgtg    4440
aggatgtggc tagacacaat gctgtagaca agcttatagg tgaggcattt ataaaaaata    4500
tttatttaaa ggataaaata atatttgtga gcagcagagt atcttttgaa atggtatata    4560
aaattgctag gctagggagta cctataataa tatctaaatc tgcacctaca agtctttcta    4620
tagaatttgc aaaagcttta aatgttacat taattggatt tgtaagggga gaaagaatga    4680
atgtatatac aaatccacag agaataatat agtaatttct gttaacatat ttttgaatat    4740
aatcttaaaa aattaatcat atagttatat aaaaataata taatatttaa tgttaataat    4800
tagtccctaa ttaaataggga ctaagtttat attttaattt ttaaataagg taattaaaat    4860
aattttaaat taaatgtgtt atatgtttta aaattatttc ttaagtatag aggctcaaat    4920
```

```
ctttggttta gagctaatat cttattcctt ctaatatttt aagggggaaa tcaattataa      4980
tattcaaatg ggagggtgaa gtatttaatg ttaactaaac agcaaaatga agacctgtct      5040
ggacaagatg taattgaaaa atatcctaaa gagcagagat ttactcttgc tatactacag      5100
gatatacaga gaaagtacaa atatatacca agagaagcac tggagaattt agctaagtat      5160
ttggacacgc ctgtaagtag actgtatggt atggctactt tttataaggc attgagcctt      5220
actccaaaag gggaaaacat aataactgta tgtgatggaa ccgcttgcca tgttgctggt      5280
tctatggttg taatggatga acttgaaaag gcaataggaa ttaaaccagg tgaaactaca      5340
gaggatctca aattttcaat aaatacagtt aactgtatag gatgctgtgc aatagctcct      5400
gtcatgatga taaatgacaa atattatgga aatttaacac ctaaactggt tgaagaaatt      5460
cttagtgagt ataggagtga gagtgatgag tgataaaaaa actgtcaata tatgttgtgg      5520
gacaggttgt ttagctaaag gcagtatgga agtatatgaa gaaatgaagg cacaaatagc      5580
taaattaggg gcaaatgcag aagtaaatgt taaattaaaa gcaacaggtt gcgatggatt      5640
gtgtgagaaa ggtcctgtac tgaaaatata tccagatgac attgcatatt ttaaagttaa      5700
agtagaagat gtagaagacg tagtaaaaaa gacattgatg aatggggaaa taattgaaaa      5760
attattatat tttgagactg ctacaaaaca gagattaaga aatcataaag aaagtgaatt      5820
ttgtaaaaga caatacaaaa ttgctctcag aaatgttggt gaaatagatc caataagttt      5880
ggaagattat gttgaaagag gcggatacaa agctcttaaa aaagcaataa gcagcatgaa      5940
acctgaagat gtgcttgaag aaataacaaa atcaggtctt agaggaagag gtggagcagg      6000
attcccaaca ggacgtaaat ggaaaactgc tgcagatatt gatacatcac ctatatatgt      6060
agtatgtaat ggtgatgaag gagatcctgg agcatttatg gatagaagta taatggaggg      6120
agatcctaac agtgttatag aaggtatgac attatgtgct tatgcagtag gaggtacaaa      6180
tggatttgct tatataagag atgaaatatg gacttgctgta gaaaatatgc agaaagctat      6240
taataaagca aaagatgaaa atttattagg taataatata ttaggaactg attttttcctt      6300 cgatatacag atagtaagag gtggaggagc ttttgtatgt ggtgaatcta ctgcacttat      6360
gtcgtctata gaaggtatgg taggtgaacc tagagctaaa tatatacaca ctacagaaaa      6420
aggattgtgg ggacaaccta cagtttttaaa taatgtagaa acttgggcca atgtacctat      6480
aataattgaa aaaggcggag attggtatca tgctatagga actatggaga agagtaaggg      6540
aacaaaggta ttctcattag ttggaaaagt taagaatact ggacttgtag aagtaccta t      6600 gggaactact cttagagaaa taatatatga tattggcggt ggagtattaa atgatagaaa      6660
gtttaaggca gttcaaatag gtggaccttc aggtggatgt ttaccagctg aatatttaga      6720
tttgccagta gattatgata ctttggttaa gcagattcc atgatgggtt caggcggaat      6780
gatcgtaatg gatgatagaa cctgtatggt agatgtaact agatattact tgagcttctt      6840
ggctgaagaa tcttgtggaa agtgtgtacc ttgtagagaa ggcgtaaaga ggatgcttga      6900
aatactcact gacatatgca atggtgatgg aaaagaagga gacatagaag agcttcttga      6960
aatatgttcc atgacaagca aggcatctct gtgcagtctt ggtaagagtg ctccaaatcc      7020
agtaattgct tctataagat atttagaga tgagtttgaa gagcatataa agaataagag      7080
atgtagagca ggagtttgta agaaacttac tacatttggt atagacgagg ataaatgtaa      7140
gggatgcgat atgtgtaaaa agaattgtcc agctgattgt ataacagggg aaattaagaa      7200
accacataca atagatgctg ataagtgctt gagatgcggt aactgcatga acatctgtaa      7260
```

```
gtttgatgct gttaaggttc tatagggagg tgaatgtaga tatgaaaatt acaatagatg    7320
gaaaagcttg tgaagctgaa aaaggagaat tcatattaca aatagcaaga agaaataaca    7380
tatatatacc tacattatgt cacagcgatg cattgcctgg gcttgctagc tgtagactat    7440
gtatagttaa agtagtagat aggggacgtg caaagatagt aacttcctgt atattccctg    7500
taagtaagga agtagaagtt ataactaatg acgatgaaat aaagagaatg agaaaaaaca    7560
tagttatgct tttaaaagta agatgccctg aaaataaaga ggtaaatgaa ttagctaaag    7620
cctttggagt agaggaaaag agagtaaaga ggttcaaatt ggatccagaa caaaattgtg    7680
ttttgtgcgg actttgtgca aaagcttgca aggaattagg tactggagca atttcaacag    7740
ttaatagggg tatgtataaa gaagtagcaa ctccatatca cgaatcttca ccggaatgta    7800
taggatgtgc ttcctgtgca aatgtttgtc caactaatgc aataaaagtt gtggataaag    7860
atggagaaag agaaatatgg ggcaaaaaat tcaagatggt taagtgtgat ttgtgcggag    7920
aatattttgc tacagaagaa catgtaaaat atgcttacaa taggcttgga aaagagcagc    7980
cagaaaaact tatgtgcagc agctgcaaga agaaaattac agccaaagat gtcaaaaata    8040
tttttgagaa cgtgtgaaaa ttaaagagg ggtggtaatt taaatgaaac cagagtttaa    8100
ttcttttgta ataggccgatc ctgacaagtg cataggctgt agatcttgtg agattgcctg    8160
tgctgcaaaa catagagaag atactcaagg aaaaaccatt ggaactatga ataataaagt    8220
tactccaagg ttattctttg ttaaaaataa aggaaatgta atgccagtac aatgcagaca    8280
ttgtgaggat gcaccatgtc taaatgcctg cccagttaat gctatagttg aaaaagatgg    8340
aagtatcatt ataaatgaaa gtgcatgtat aggatgccag acctgtacaa tagtatgtcc    8400
ggtaggtgct gtaagtttac tgcctagaac tcaaggtaaa gtagttacag gaggaattca    8460
ggttaaagta agagcagcag cttataaatg tgatttatgt aaggaagagg gaggagaacc    8520
tgcttgcgtc aaagaatgtc caaagaggc cttgaggtta gtagatccta gagaagataa    8580
aaaagatcgt agtgtgaaag ctgctatgga actgttaaat ataaacgcaa atctctaatt    8640
tataagttat aaaaatccgg aaaagaaagg aatgttaaat atgccaacta gtacttctat    8700
gataaatata gatgaagaat tatgtacagg ctgcagacga tgtgcggatg tctgccctgt    8760
agatgctata gaaggtgaac agggtaaacc tcagaagata aatactgaaa agtgtgttat    8820
gtgcggacaa tgcattcaag tttgtaaagg ctatcaatct gtatacgacg atgttcctac    8880
tccagttagc aaaaggttat ttgatagagg attgttaaag gaagtagatg aaccattatt    8940
tgcagcatat aataaaggtc aggcaaagag tgttaaagaa attttacaaa acaaagatgt    9000
atttaaaatt gtgcaatgtg cacctgctgt aagagttgct ataggagagg attttggaat    9060
gcctcttgga actttaagtg aaggaaaaat ggcagctgca ctcagaaaat taggatttga    9120
caaagtatat gatacaaact tggtgcagga tcttactata atggaagaag gtagtgagtt    9180
actaaaaaga gtagctgaag gcggagtttt gccaatgttt acttcttgtt gtccagcatg    9240 ggtaaaaatat gcagaacaaa catatccaga acttttacct catctttcaa gttgtaagtc    9300
tccaaatcag atggctggag ctatatttaa aacttatgga gcagagataa ataaggttaa    9360
tccggctaaa atttataatg tatctgttat gccatgtaca tgcaaggaat ttgaaagtga    9420
aagagaagaa atgcatgaca gtggacacag ggatgtagat gcagttataa ctacaaggga    9480
attagcacaa ctgttcaaag atgctgtatat agattttaat actattgaag aagaacagtt    9540
tgatactcct cttggtatgt ataccggtgc aggaactata tttggtgcta caggtggagt    9600
tatggaagca gcacttagaa ctggatatga acttttatact aaaaaaacta ttccaagtat    9660
```

-continued

```
agatcttact atggtaagag gtggagaagg ttttagaact gctgaagtag atttagggga        9720
tattagacta aaagtaggag tagtttccgg cttaaaaaat gtaaagacg ttatggaatc         9780 agtaaaggca ggcaaatgtg atttgcactt tatagaggtt atgacctgtc ctcaaggatg        9840
tataagtggt ggaggacaac ctaaagttat acttgattca gataaagagg aagcttataa       9900
taataggaaa aagggactat ataatcatga cgctaatctt acttatagaa aatcacatga        9960
aaatccagaa ataagaaaaa tatatgatga gttcttagac aaaccattag gagctaagtc       10020
tcatgaatta ttgcacacta aatatatctc aagaaaaaag gagagttaat aaaatgaaga      10080
attgcctcgt agtagcagat cctaataaat gcataggatg taggacttgt gaagcagctt      10140
gtggtattgc acattcagga ggggactttt ttaacacaaa tgtatccaag attaatttta     10200
atcctcgctt aaatgtgata aaaactgcta agtaagtgc tcctgttcaa tgcagacaat      10260
gcgaagatgc accttgtggt aaagcttgtc cagttaacgc tatttcaaat gaaaatggtt     10320
atgttagtgt aaataaagat gtatgtgttg atgtaaaat ctgcatgtta gcttgtcctt      10380
ttggagctat tgaattagct tctcaatata gggatggaga agttgtagac caaaagggac      10440
ttaagatgag tgaggaaggt aatcctactg tgaatgaaa aggaagagtg gtagcaaata      10500
agtgtgatct ctgccaggat agggatggag ggcctgcttg tatagaagtt tgtcctacaa     10560
aatctctcaa actagttact tatgatgaca ataataatat agttgaaaaa aaagatgacg      10620
acgaacgtga agtaagctaa                                                   10640
```

<210> SEQ ID NO 67
<211> LENGTH: 10633
<212> TYPE: DNA
<213> ORGANISM: Unknown
<220> FEATURE:
<223> OTHER INFORMATION: Clostridium ragsdalei

<400> SEQUENCE: 67

```
atggataaaa aagttttaac tgtttgtcct tactgcggtg ctggttgtaa gttatacttg         60
catgtaaagg atggcaagat aattaaagca gagcctgcta atggtaggac aaatgaaggg       120
tccttgtgtt taaaaggacg atttggctgg gattttctaa atgatcctaa atattgaca       180 tctagaatta aacatccaat gataagaaaa aatggagagt tagaagaggt aagttgggat      240
gaagctatta gttttacggc ttcaaaattg tcacaaataa aagagaaata tggacctgat     300
tctataatgg gaacaggatg tgctagggt tctggaaatg aagcaaacta cgtaatgcaa       360 aagttatga gggcggttat tggaaccaat aacgtagatc actgtgccag agtttgacat       420
gctccttctg tagccggtct ggcttacgtt ttaggaaatg gtgctatgtc aaatggtata      480
catgaaatag atgatacaga tttactactt atttttggat ataatggagc agcttcgcat     540
ccaatagttg ctaagagaat agttagggca aaacaaaaag gtgcaaaggt aatagttgta      600
gatccacgta aacagagtc tggtaggata gcagatttat ggctccctat aaaaaatgga      660
acaaatatgg ttcttgtaaa tacttttgcc aatatactta taaacaagca atttatgac      720 aaacaatatg tagaagatca tactgttggt tttgaagaat ataaatctat agttgaggat      780
tatacgcctg aatatgcaga aaagttact ggtatacctg cagaggatat agtagaagct       840
atgaaaatgt actccagtgc taaaaatgct atgatattgt acggtatggg agtatgtcag      900
tttgctcaag ctgtagatgt agtaaaaggg ttagcttcaa tagctttatt aactggtaat      960
tttggaagac ctaatgtagg cataggacct gtaagaggcc agaacaatgt gcaaggtgcc     1020
```

```
tgcgatatgg gagcacttcc taatgtatac ccaggttatc aaagtgtaac tgacgatgca   1080
attagagaaa aatttgaaaa agcttgggga gttaaacttt caaacaaagt tggttatcac   1140
ctgacacgag ttcctgaatt aacgcttaaa gaggataaaa taaaagcata ttatataatg   1200
ggcgaagatc cagctcaaag tgatcctgat tctaatgaaa tgagggaaac acttgataaa   1260
atggaacttg taatagttca agatatattt atgaataaaa ctgcactcca tgcagatgta   1320
attttacctt ctacgtcttg gggagaacat gaaggagtct tcagttctgc tgatagagga   1380
ttccagagat ttagaaaagc tgtagaacct aagggcgatg ttaaaccaga ttgggagata   1440
atttcagaaa ttgcatgtgc tatgggttat gatatgcatt ataacaatac tgaggaaata   1500
tgggatgaac ttataaattt atgcccaaat ttcaaaggag caacttataa gagattggat   1560
gaattaggag gaattcaatg gccttgtcca tctgaagatc atccaggaac ttcttatctc   1620
tacaaaggaa ataaatttaa tacacctact ggaaaagcaa atttatttgc agcagaatgg   1680
agacctccta tagagaagac agatgaagaa tatccacttg ttctttctac agttagagaa   1740
gtagggcatt actccgtaag aacaatgaca ggaaactgta gggcactcca gcagttagct   1800
gatgaaccag atatgtaca aattaatcca gtggatgcaa aggctaaaaa aataatagat   1860
ggtgagctta tgagagtaag ttcacgaaga ggttctgtag ttgcccgtgc acttgttact   1920
gaaagggcaa ataaaggagc agtttatatg acctatcaat ggtgggtagg tgcatgtaat   1980
gagcttacag ctaataattt agatccagta tcaaaaactc ctgaattaaa gtattgtgca   2040
gtgaaggtag aagctataga agatcagaaa gaagctgaaa agtttataaa agatcaatat   2100
gcttcaataa agaaaaagat gaatgtttaa tataaagatg gctaaaaaga ccttgattaa   2160
aaggtctttt agccaaaagc tttaaatcaa taggagttga tagactgtga tagacgtaca   2220
tgaagcattc aatatagtaa tgaataatac aaaactgctt aaaagtgaag atatgtccct   2280
gataaattct cttaacaggg tattggcaga ggatataagc tcaaaagata atcttccccc   2340
atttgacaaa tcctgtatgg atgggtatgc tttaaaaagt gaagatacta aggaaaaaat   2400
gtcaaaattt caaattaagg gaagcataaa ggcgggagat ttttctgata tagtattaaa   2460
aaatggtgaa gccataaaaa taatgacagg agctccagta ccaaaaggtg cagatgcaat   2520
tattcaaata gaaaaagtaa agtagaagg aaaagaactt catgtattgg aaaaggtatc   2580
tcctggaacc aacatattta aaactggtga ggagataaaa attggtgatg ttgctttaaa   2640
aaagggaaaa atcgtaagac ctgcagaaat agggttattg gcatcactag ttatactaa   2700 aataaaatgc tacaaagtcc ctaaaattat aataataaat acaggggatg aacttataaa   2760
tatagatcaa aacttaatgc aaggtaaaat aagaaattgt aatgaataca cattaattgc   2820
ccttattaaa aatttaaatg cagaagttaa atcgtatggg ataataagag atgataagaa   2880
taaaattttt aatgctataa aaactgcatt tgaagaggga gatataatca taactactgg   2940
aggagcatct gtgggtgatt acgattttat agaagatgtt cttaaggaaa taggaacaga   3000
tataaaattt acttcggtag ctattaaacc aggaaaacca gttgttttg caacttttaa   3060 agataaatta ttctttggac ttccaggaaa tccactttca gtaataaatt catttgaaag   3120
ttttgtagca ccatctatta aaaaaaatga ttggaagaga tgatgcattt cctgaagaat   3180
ttcctgtaac tttaaaagat gattttaagt caggaaaaga aagagactgt tatatgtatg   3240
tagatataaa aaaggaagat aaccattatt atgcttatga tgtaggaaga caagattcca   3300
atggcctttt tacacttact aagtcaaatg gcgtggttat catgaaaaag ggaactagta   3360
tagcaaaagc tggagatatt ttaaatggaa aatttatatt caaataagag gtcagtaatt   3420
```

```
tctattattt catctagttc aaattcaggt aagactacct taatagaagg aataataaga    3480
attttaaaaa gcagaggata taaggttggt gcaataaaga atgatgctca taagttacag    3540
atagattatc caggaaaaga cagctttaga tttacagagg caggtgcaga caatgttgtt    3600
attgcatcgg ataatacagt ggctatgata aaaaaagtaa gtggaccaaa aagtatagaa    3660
gaattgctgt tgcttttca ggatgtagat attgtaatag tggaaggttt taagggcaac    3720
gaatttccta aaatagaagt atacaggaaa aatgcaagta aatgtttact ctacaaaaat    3780
tctgaatata attttcaaaa ttttgtagct attgtaacca atgaaaattt aataactgat    3840
attcctgtat ttgatataaa tgatacaaaa aagtagctg atttattga aagcaacttt    3900 ataggaggta acaaaaatgg agaaaaccat ggaacttcat gtagtcaaat atgacaaaga    3960
atgtaaaaag acagtggagg aatcaactat ttgcgaatat cctttaaatg tatttgtaaa    4020
tggtgaacat ttgacagtgc tcttatgtac tcctgaaaag cttaaggaat taacaatagg    4080
tttcttggtc tttaaaggta ttataaaatc tctagatgaa ataaaatctt tagagataga    4140 tgaaaaagt ggagcgtcca gggtaatctt gaaaaataga caatttaata aagagttgta    4200
ttcaaagcaa gtacttccta caacatttaa tgaaaatgaa aaaagtaaat tcttttcata    4260
tattattgat tccatgaaaa ttagtctaat caataatgat aatgtttaca tacatgttga    4320
taaaatctat ggcttaatga tggacaatct tggatattcc aagactttta aactcactgg    4380
aggagcacat tgtgcagctc tttgtgatga agataaagta tatctatttt gtgaggatgt    4440
ggccagacac aatgctgtag acaagcttat aggtgaggca tttataaaaa atatttgttt    4500
aaaagataaa ataatatttg tgagtagcag ggtatctttt gaaatggtat ataaaattgc    4560
tagacttggg gtacctataa taatatctaa atctgcacct acaaatcttt ctatagaatt    4620
tgcaaaagct ttaaatgtta cattaattgg atttgtaagg ggagaaagaa tgaatgtata    4680
tacaaatcca cagagaataa tatagtaatt tctgataata catttttgaa tataatctta    4740
aaaaattagt catatagtta tataaaaata atataatatt taatgttgat aattagttct    4800
taattaaata ggactaaatt tatattttaa ttttaaata aggtaattaa aataatttta    4860
aattaaatat gttatatgtt ttaaaattat ttcttaagca tagaggctca aatctttgat    4920
ttagagctaa tatcttattc cttctaatat tttaaggggg aaatcaatta taatattcaa    4980
atgggagggt gaagtattta atgttaacta aacagcaaaa tgaagacctg tctgacaag    5040 atgtaattga aaatatcct aaagagcaga gatttactct tgctatacta caggatatac    5100
agagaaagta caaatatata cccagagaag cactggagaa tttagctaag tatttggaca    5160
cgcctgtaag tagactgtat ggtatggcta cttttaataa ggcattgagc cttactccaa    5220 aagggggaaaa cataataact gtatgtgatg gaaccgcttg ccatgttgct ggttctatgg    5280
ttgtaatgga tgaacttgaa aaggcaatag gaattaaacc aggtgaaact acagaagatc    5340
ttaaattttc aataaataca gttaactgta taggatgctg tgcaatagct cctgtcatga    5400
tgataaatga caaatatttt ggaaatttaa cacctaaact ggttgaagaa attcttagtg    5460
agtataggag tgaaagccat gagtgataaa aaaattgtca atatatgttg tggaacaggt    5520
tgcttagcta aaggcagcaa ggaagtatat gaagaaatga aggcacaaat agctaaatta    5580
ggggcaaatg cagaagtaaa tgttaaatta aaagcaacag gttgcgatgg attgtgtgag    5640
aaaggtcctg tactgaaaat atatccagat gacattgcat attttaaagt taagtagaaa    5700
gatgtagaag acgtagtaaa aaagacattg atgaatgggg aataattga aaaattatta    5760
```

```
tattttgaaa ctgctacaaa acagagatta agaaatcata agaaagtga attttgtaaa      5820 agacaataca aaattgctct cagaaatgtt ggtgaaatag atccaataag tttggaagat      5880
tatgttgaaa gaggcggata taaagctctt aaaaaagcaa taagcagcat gaaacctgaa      5940
gatgtgcttg aagaaataac aaaatcaggt cttagaggaa gaggtggagc aggattccca      6000
acaggacgta aatggaaaac tgctgcagat attgatacat cacctatata tgtagtatgc      6060
aatggtgatg agggagatcc tggagcattt atggataaga gtataatgga gggagatcct      6120
aacagtgtta tagaaggtat gacattgtgt gcctatgcag taggaggtac aaacggcttt      6180
gcttatataa gagatgaata tggacttgct gtagaaaata tgcagaaagc tattaataaa      6240
gcaaaagatg aaaatttatt aggtaataat atattaggaa ctgactttc cttcgatata      6300 cagatagtaa gaggtggagg agcttttgta tgtggtgagt ctactgcact tatgtcatct      6360
atagaaggta tggtaggaga acctagagct aaatatatac acactacaga aaaggattg      6420 tggggacaac ctactgtttt aaataatgta gaaacttggg ccaatgtacc tataataatt      6480 gaaaaggtg gagattggta tcatgctata ggaactatgg agaagagtaa gggaacaaaa      6540
gtattctcat tagttggaaa agttaagaat actggacttg taagagtacc tatgggaact      6600
actcttagag aaataatata tgatattggc ggtgagtat aaacgacag aaagtttaag      6660 gcagttcaaa taggtggacc ttcaggagga tgtttaccat ctgaatattt agacttgcca      6720
gtagattatg atactttggt taaagcggat tctatgatgg gttccggcgg aatgatcgta      6780
atggatgata aacctgtat ggtagatgta actagatatt acttgagttt cttagctgaa      6840
gaatcttgtg gaaagtgtgt accttgtaga gaaggcgtaa agagaatgct tgaaatactc      6900
actgatatat gcaatggtga tggaaaagaa ggagacatag aagagcttct tgaaatatgt      6960
tccatgacaa gcaaggcatc tctgtgcagt cttggtaaga gtgctccaaa tccagtaaaa      7020
gcagctataa gatattttag agatgaattt gaagaacata taaagaataa gagatgtaga      7080
gcaggagttt gtaagaaact tactacattt ggtatagatc aagataaatg taagggatgc      7140
gatatgtgta aaaagaattg tccagctgat tgtataacag gggaaattaa gaaaccacat      7200
acaatagatg ctgataagtg cttgagatgc ggtaactgca tgaacatctg taagtttgat      7260
gctgttaagg tttataggg aggtgaatgt agatatgaaa attacaatag atggaaaagc      7320
ttgtgaagct gaaaaaggag aattcatatt acaaatagca agaagaaata atatatatat      7380
acctacactg tgccacagtg atgcattgcc tgggcttgct agctgtagac tgtgtatagt      7440
taaagtagta gataggggac gtgcaaagat agtaacttcc tgtatattcc ctgtaagtaa      7500
ggaagtagaa gttataacta atgacgatga aataaagaga atgagaaaaa acatagttat      7560
gcttttaaaa gtaagatgcc ctgaaaataa agaagtaaat gaattagcta aagcctttgg      7620
agtagaggaa aagagagtaa agaggttcaa attggatcca gaacaaaatt gtgttttgtg      7680
cggactttgt gcaaaagctt gcaaggaatt aggtactgga gcaatctcaa cagttaatag      7740
gggtatgtat aaagaagtag caactccata tcacgaatct tcaccagaat gtataggatg      7800
tgcttcctgt gcaatgtttt gtccaactaa tgcaataaaa gttgtggata agatggaga      7860 aagagaaata tggggcaaaa aattcaagat ggttaaatgt gatttgtgcg gagaatattt      7920
tgctacagaa gaacacgtaa aatatgctta caataggctt ggaaaagagc agccagaaaa      7980
gcttatgtgc agcagctgca agaagaaagt tacagccaaa gatgtcaaaa atattttga      8040 gaacgtgtga aaattaaaag aggggtggta atttaaatga aaccagagtt taattctttt      8100
gtaatagccg atcctgacaa gtgcataggc tgtagatctt gtgagattgc ctgtgctgca      8160
```

```
aaacatagag aagatactca aggaaaaact attggaacta tgaataataa agttactcca   8220
aggttattct ttgttaaaaa taaaggaaat gtaatgccgg tacaatgcag acattgtgag   8280
gatgcaccat gtctaaatgc ctgcccagtt aatgctatag ttgaaaaaga tggaagtatc   8340
attataaatg aaagtgcatg tataggggtgt cagacctgta caatagtatg tccggtaggt   8400
gctgtaagtt tacttcctag aactcaaggt aaagtagtta caggaggaat tcaggttaaa   8460
gtaagagcag cagcttataa atgtgattta tgtaaggaag agggaggaga acctgcctgc   8520
gtcaaagaat gtccaaaaga ggccttaagg ttagtagatc ctagagaaga taaaaaagat   8580
cgtagtgtga aagctgctat ggaactgtta aatataaacg caaatctcta atttataagt   8640
tataaaaatc cggaaaagaa aggaatgtta aatatgccaa ctagtacttc tatgataaat   8700
atagatgaag aattatgtac aggctgcaga cgatgtgcgg atgtctgccc tgtagatgct   8760
atagaaggtg aacagggtaa acctcagaag ataaatactg aaaagtgtgt tatgtgcgga   8820
caatgcattc aagtttgtaa aggctatcaa tctgtatacg atgatattcc tactccagtt   8880
agcaaaaggt tatttgatag aggattgtta aaggaagtag atgaaccatt atttgcagca   8940
tataataaag gtcaggcaaa gagagttaaa gaaattttac aaaacaaaga tgtatttaaa   9000
attgtgcaat gtgcacctgc tgtaagagtt gctataggag aggattttgg aatgcctctt   9060
ggaactttaa gtgaaggaaa aatggcagct gcactcagaa aattaggatt tgacaaagta   9120
tatgatacaa actttggtgc agatcttact ataatggaag aaggtagtga gttactaaaa   9180
agagtagctg aagtggagt tttgccaatg tttacttctt gttgtccagc atgggtaaaa   9240
tatgcagaac aaacatatcc agaactttta cctcatcttt caagttgtaa gtctccaaat   9300
cagatggctg gagctatatt taaaacttat ggagcagaga taaataaggt taatccggct   9360
aaaatttata atgtatctgt tatgccatgt acatgcaagg aatttgaaag tgaaagagaa   9420
gaaatgcatg acagtggaca cagagatgta gatgcagtta taactacaag ggaattagca   9480
caactgttca aagatgctga tatagatttt aatactattg aagaagaaca gtttgatact   9540
cctcttggta tgtatactgg tgcaggaact atatttggtg ctacaggtgg agttatggaa   9600
gcagcactta gaactggata tgaactttat actaaaaaaa ctattccaag tatagatctt   9660
actatggtaa gaggtggaga aggttttaga actgctgaag tagatttagg agatattaga   9720
ctaaaagtag gagtagtttc cggcttaaaa aatgtaaaag atgttatgga atcagtaaag   9780
gcaggtaaat gtgatttaca ctttatagag gttatgactt gtcctcaagg atgtataagt   9840
ggtggaggac aacctaaggt tatacttgat tcagataaag aagaagctta taataatagg   9900
aaaaagggac tatataatca tgacgctaat cttacttata gaaaatcaca tgaaaatcca   9960
gaaataaaga aaatatatga tgagttctta gacaaaccat taggagctaa gtctcatgaa  10020
ttattgcaca ctaaatatat ctcaagaaaa aaggagagtt aataaaatga agaattgcct  10080
cgtagtagca gatcctaata aatgcatagg atgtaggact tgtgaagcag cttgtggtat  10140
tgcacattca ggaggggact ttttaatac aaatgtatcc aaaattaatt ttaatcctcg  10200
cttaaatgtg ataaaaactg ctaaagtaag tgctcctgtt caatgcagac aatgcgaaga  10260
tgcaccttgt ggtaaagctt gtccagttaa cgctatttca aatgaaaatg gttatgttag  10320
tgtagataaa gatgtatgtg ttggatgtaa aatctgcatg ttagcttgtc cttttggagc  10380
tattgaatta gcttctcaat ataaggatgg agaagttgta gaccaaaagg gacttaagat  10440
gagtgaggaa ggtaatccta ctgtaaatgg aaaaggaaga gtggtagcaa ataagtgtga  10500
```

```
tctttgccag gatagggatg gaggacctgc ttgcatagaa gtttgtccta caaaatctct   10560
caaattagtt acttatgatg acaataataa tatagttgaa aaaaaagatg acgacgaacg   10620
tgaagtaggc taa                                                      10633
```